United States Patent
Duffy

(10) Patent No.: US 10,471,046 B2
(45) Date of Patent: Nov. 12, 2019

(54) METHOD FOR TREATING, PREVENTING, OR REDUCING THE RISK OF SKIN INFECTION

(71) Applicant: Melinta Subsidiary Corp., New Haven, CT (US)

(72) Inventor: Erin M. Duffy, Deep River, CT (US)

(73) Assignee: MELINTA SUBSIDARY CORP., Morristown, NJ (US)

( * ) Notice: Subject to any disclaimer, the term of this patent is extended or adjusted under 35 U.S.C. 154(b) by 0 days.

(21) Appl. No.: 14/942,021

(22) Filed: Nov. 16, 2015

(65) Prior Publication Data

US 2016/0136137 A1 May 19, 2016

Related U.S. Application Data

(60) Provisional application No. 62/080,212, filed on Nov. 14, 2014.

(51) Int. Cl.
| | |
|---|---|
| *A61K 31/42* | (2006.01) |
| *A61K 31/422* | (2006.01) |
| *A61K 9/00* | (2006.01) |
| *A61K 47/10* | (2017.01) |
| *A61K 9/06* | (2006.01) |
| *A61K 9/08* | (2006.01) |
| *A61K 9/20* | (2006.01) |
| *A61K 9/48* | (2006.01) |
| *A61P 31/04* | (2006.01) |

(52) U.S. Cl.
CPC .......... *A61K 31/422* (2013.01); *A61K 9/0014* (2013.01); *A61K 9/0019* (2013.01); *A61K 9/0053* (2013.01); *A61K 9/06* (2013.01); *A61K 9/08* (2013.01); *A61K 9/2054* (2013.01); *A61K 9/4866* (2013.01); *A61K 47/10* (2013.01); *A61P 31/04* (2018.01)

(58) Field of Classification Search
CPC .................................................... A61K 31/422
USPC ......................................................... 514/376
See application file for complete search history.

(56) References Cited

U.S. PATENT DOCUMENTS

| | | | |
|---|---|---|---|
| 3,410,645 | A | 11/1968 | Schwartzman |
| 3,418,055 | A | 12/1968 | Schwartzman |
| 3,535,422 | A | 10/1970 | Cox et al. |
| 3,669,323 | A | 6/1972 | Harker et al. |

(Continued)

FOREIGN PATENT DOCUMENTS

| | | |
|---|---|---|
| GB | 1185685 A | 3/1970 |
| GB | 1407937 A | 10/1975 |

(Continued)

OTHER PUBLICATIONS

Mathur et al. "Activity of RBx 11760, a novel biaryl oxazolidinone, against Clostrium difficile," J. Antimicrob Chemother. 2011, vol. 66, pp. 1087-1095.*

(Continued)

*Primary Examiner* — Shengjun Wang
(74) *Attorney, Agent, or Firm* — Wilmer Cutler Pickering Hale and Dorr LLP

(57) ABSTRACT

The present invention relates to methods for treating acne and other skin infections caused or mediated by *Propionibacterium acnes, Gardnerella vaginalis,* or *Staphylococcus aureus* in a patient with a safe and effective amount of a topically applied oxazolidinone antibiotic compound.

20 Claims, 9 Drawing Sheets

(56) References Cited

U.S. PATENT DOCUMENTS

| | | | |
|---|---|---|---|
| 4,254,105 | A | 3/1981 | Fukuda |
| 4,522,811 | A | 6/1985 | Eppstein et al. |
| 4,620,648 | A | 11/1986 | Schwartzman |
| 4,693,623 | A | 9/1987 | Schwartzman |
| 4,800,197 | A | 1/1989 | Kowcz et al. |
| 4,891,227 | A | 1/1990 | Thaman et al. |
| 4,891,228 | A | 1/1990 | Thaman et al. |
| 4,919,934 | A | 4/1990 | Deckner et al. |
| 4,937,370 | A | 6/1990 | Sabatelli |
| 4,960,764 | A | 10/1990 | Figueroa, Jr. et al. |
| 4,985,459 | A | 1/1991 | Sunshine et al. |
| 4,999,186 | A | 3/1991 | Sabatelli et al. |
| 5,073,371 | A | 12/1991 | Turner et al. |
| 5,073,372 | A | 12/1991 | Turner et al. |
| 5,087,445 | A | 2/1992 | Haffey et al. |
| 5,654,435 | A | 8/1997 | Barbachyn et al. |
| 5,688,792 | A | 11/1997 | Barbachyn et al. |
| 5,763,263 | A | 6/1998 | Dehlinger |
| 5,998,436 | A | 12/1999 | Yazaki et al. |
| 6,133,284 | A | 10/2000 | Yazaki et al. |
| 6,156,903 | A | 12/2000 | Yazaki et al. |
| 6,413,981 | B1 | 7/2002 | Paget et al. |
| 6,559,303 | B1 | 5/2003 | Cook |
| 6,969,726 | B2 | 11/2005 | Lou et al. |
| 7,091,196 | B2 | 8/2006 | Wang et al. |
| 7,129,259 | B2 | 10/2006 | Chen et al. |
| 7,148,219 | B2 | 12/2006 | Lou et al. |
| 7,456,206 | B2 * | 11/2008 | Zhou .................. C07D 263/20 514/376 |
| 2005/0043317 | A1 | 2/2005 | Zhou et al. |
| 2005/0153971 | A1 | 7/2005 | Chen et al. |
| 2005/0203147 | A1 | 9/2005 | Zhou et al. |
| 2013/0059774 | A1 * | 3/2013 | Patel .................. A61K 45/06 514/2.9 |

FOREIGN PATENT DOCUMENTS

| | | | |
|---|---|---|---|
| WO | WO-199711068 | A1 | 3/1997 |
| WO | WO-2001094342 | A1 | 12/2001 |
| WO | WO-2003/030906 | A1 | 4/2003 |
| WO | WO-2004029066 | A2 | 4/2004 |
| WO | WO-2004078770 | A1 | 9/2004 |
| WO | WO-2005012270 | A2 | 2/2005 |
| WO | WO-2005012271 | A2 | 2/2005 |
| WO | WO-2005019211 | A2 | 3/2005 |
| WO | WO-2005061468 | A1 | 7/2005 |
| WO | WO-2005070904 | A2 | 8/2005 |
| WO | WO-2006015194 | A2 | 2/2006 |
| WO | WO-2006022794 | A1 | 3/2006 |
| WO | WO-2006042034 | A2 | 4/2006 |
| WO | WO-2006110815 | A1 | 10/2006 |
| WO | WO-2006133397 | A2 | 12/2006 |
| WO | WO-2007025089 | A2 | 3/2007 |
| WO | WO-2007025098 | A2 | 3/2007 |
| WO | WO-2007025284 | A1 | 3/2007 |
| WO | WO-2011/139832 | A2 | 11/2011 |

OTHER PUBLICATIONS

Backer et al. "Antibiotic susceptibility of Atopobium vaginae," BMC Infectious Diseases, Mar. 16, 2006, vol. 6, pp. 1-6.*

Farrell et al. "Potency of radezolid (RX-1741) and torezolid (DA-7157) tested against a collection of linezolid-non-susceptible strains with genetically defined resistant mechantisms," 21st annual European Congress of Clinical Microbiology and Infectious Diseases (ECCMID), May 7-10, 2011, Milan, Italy.*

Aubin et al. "Propionibacterium acnes, an emerging pathogen: From acne toimplant-infections, from phylotype to resistance," Medecine et Maladies lnfectieuses, Mar. 20, 2014, vol. 44, pp. 241-250.*

Jabes "Antibiotic R&D pipeline: an update", Current Opinion in Microbiology, 2011, vol. 14, pp. 565-569. (Year: 2011).*

Lemaire, et al., "Cellular Pharmacodynamics of the Novel Biaryloxazolidinone Radezolid: Studies with Infected Phagocytic and Nonphagocytic cells, Using *Staphylococcus aureus*, *Staphylococcus epidermidis*, Listeria monocytogenes, and Legionella pneumophila," Antimicrob. Agents Chemother., vol. 54(6), pp. 2549-2559 (2010).

Shaikh, W., "The Changing Face of Antihistamines and Cardiac Adverse Drug Reactions: A Clinical Perspective," J. Indian Medical Association, vol. 98, No. 7, pp. 397-399 (Jul. 2000).

Nguyen, et al., "Chiral Drugs: An Overview," International Journal of Biomedical Science, vol. 2, pp. 85-100 (2006).

Zyvox (linezolid) label, Pharmacia & Upjohn Company, Division of Pfizer Inc., LAB-0139-20.0, Jun. 2010, pp. 1-35.

Bayston, R. et al., "Antibiotics for the eradication of Propionibacterium acnes biofilms in surgical infection," Journal of Antimicrobial Chemotherapy, vol. 60, pp. 1298-1301 (Oct. 24, 2007).

Mory, F., et al., "In vitro activities of cefotaxime, vancomycin, quinupristin/dalfopristin, linezolid and other antibiotics alone and in combination against Propionibacterium acnes isolates from central nervous system infections," Journal of Antimicrobial Chemotherapy, vol. 55, pp. 265-268 (Dec. 8, 2004).

Ager, S. and Gould, K., "Clinical update on linezolid in the treatment of Gram-positive bacterial infections," Infection and Drug Resistance, vol. 5, pp. 87-102 (2012).

Michalska, K., et al., "Recent development of potent analogues of oxazolidinone antibacterial agents," Bioorganic and Medicinal Chemistry, vol. 21, pp. 577-591 (2013).

Shaw, K.J., et al., "The oxazolidinones: past, present, and future," Ann. N.Y. Acad. Sci.—Issue: Antimicrobial Therapeutics Review, vol. 1241, pp. 48-70 (2011).

Hymes, S.R., et al., "DNase Inhibits Gardnerella vaginalis Biofilms In Vitro and In Vivo," JID, vol. 207, pp. 1491-1497 (May 15, 2013).

Skripkin, E., et al., "$R_x$-01, a New Family of Oxazolidinones That Overcome Ribosome-Based Linezolid Resistance," Antimicrobial Agents and Chemotherapy, vol. 52, No. 10, pp. 3550-3557 (Oct. 2008).

Lawrence, L., et al., "In Vitro Activities of the $R_x$-01 Oxazolidinones against Hospital and Community Pathogens," Antimicrobial Agents and Chemotherapy, vol. 52, No. 5, pp. 1653-1662 (May 2008).

Brook, I., et al., "Anaerobic and Aerobic Bacteriology of Acute Conjunctivitis," Annals of Ophthalmology, pp. 389-393 (Mar. 1979).

* cited by examiner

METHOD FOR TREATING, PREVENTING, OR REDUCING THE RISK OF SKIN INFECTION

RELATED APPLICATIONS

This application claims the benefit of priority under 35 U.S.C. § 119(e) of U.S. Provisional Application No. 62/080,212, filed Nov. 14, 2014, the contents of which are hereby incorporated in their entirety.

FIELD OF THE INVENTION

The present invention relates to methods for treating, preventing, or reducing the risk of acne and other skin infections caused or mediated by *Propionibacterium acnes*, *Gardnerella vaginalis*, or *Staphylococcus aureus* in a patient by administering a safe and effective amount of an antibiotic compound.

BACKGROUND

Acne is a common inflammatory pilosebaceous disease characterized by comedones, papules, pustules, inflamed nodules, superficial pus-filled cysts, and in extreme cases, sinus formation and deep inflammation, sometimes associated with purulent sacs.

The pathogenesis of acne is complex. An interaction between hormones, keratinization, sebum, and bacteria somehow determines the course and severity of the disease. Acne usually begins at puberty when the increase of androgens causes an increase in the size and activity of the pilosebaceous glands. The earliest microscopic change is intrafollicular hyperkeratosis, which leads to restriction of the pilosebaceous follicle with consequent formation of the comedone composed of sebum, keratin, and microorganisms, particularly *Propionibacterium acnes*. Lipases from *Propionibacterium acnes* break down triglycerides in the sebum to form free fatty acids (FFA), which irritate the follicular wall. Retention of sebaceous secretions and dilation of the follicle may lead to cyst formation. Rupture of the follicle with release of the contents into the tissues induces an inflammatory reaction which heals with scarring in severe cases.

Acne tends to appear during puberty and to fade away again, usually spontaneously when growth has stopped. Occasionally it is still to be found in older adults. The face, back, and shoulders are the predominant areas affected. Particularly with the face, severe cases can cause alterations resulting in considerable disfigurement with significant psychological burdens for the afflicted person.

Over the years, many compositions have been developed for the treatment or prevention of acne. For example, acne can be treated by topical application of various lotions, salves, and the like or by, for example, localized treatment with sulfur, resorcinol, salicylic acid, benzoyl peroxide, vitamin A acids, retinoic acid, antibiotics such as erythromycin, and the like. Acne has also been treated orally with antibiotics and tretinoin. However, the effectiveness, reliability, and convenience of current treatments have not always met with patient expectations.

Salicylic acid is a long-known anti-acne active ingredient which is believed to cause a reduction in intercellular cohesion of the corneocytes (see C. Huber et al., *Arch. Derm. Res.* 257, pp. 293-297, 1977). It has also been postulated that salicylic acid works by dissolving the existing keratin plugs, as well as by preventing the formation of new ones. In order to best exert its skin benefits, the ideal anti-acne composition should deliver and retain optimal concentrations of salicylic acid in the stratum corneum with less penetration through the skin and into the general circulation. Also, compliance by the user to a regimen of treatment involving repeated applications is important. However, salicylic acid tends to be somewhat drying and irritating and can often cause peeling, thereby causing individuals to refrain from using salicylic acid products as frequently and copiously as is necessary to obtain an optimum benefit. Thus, user compliance with current salicylic acid compositions is less than ideal.

Benzoyl peroxide has been used as a keratolytic agent and an antibacterial agent in the topical treatment of skin lesions such as acne. See e.g., Levine et al., Ohio State Med. J., 65, 492 (1969); U.S. Pat. No. 3,535,422, to Cox et al., issued Oct. 20, 1970; British Patent Application Nos. 1,185,685, to Fisher, published Mar. 25, 1970; 1,163,004, to Stiefel Laboratories, Inc., published Sep. 4, 1969; and 1,407,937, to Stiefel Laboratories, Inc. published Oct. 1, 1975. The topical application of benzoyl peroxide for skin lesion therapy is thoroughly detailed in the medical literature. See Brogdne et al., *Drugs*, 4, 417 (1974); Poole et al., *Arch Derm.*, 102, 400 (1972); Eaglstein, *Arch Derm.*, 97, 527 (1968); Pace, *Can. Med. Assoc. J.*, 93,252 (1965); Vasarinsh, *Arch. Derm.*, 98, 183 (1968); Mysliborski et al., *AFP*, 15, 86 (1977); Nare, *Br. J. Clin. Prac*, 29, 63 (1975); Fulton et al., *Arch. Derm.*, 1, 10, 83 (1974); and Wilkinson et al., *Can. Med. Assoc. J.*, 95, 28 (1966).

While benzoyl peroxide can be a useful topical treatment of skin lesions from acne, seborrhea, and other conditions, it has the undesirable side effect of being a contact irritant. The irritation associated with benzoyl peroxide therapy has also been detailed in the medical literature cited in the previous paragraph. Additionally, the redness induced by benzoyl peroxide may impair a patient's ability to perceive the improvement in acne condition initially. Accordingly, some patients are denied the benefits of benzoyl peroxide therapy because of the irritation problem. When used in the treatment of acne, benzoyl peroxide produces dryness, exfoliation, increased redness and a decrease in bacterial flora.

Other agents, such as retinoic acid, are used for the treatment of acne. However, retinoic acid can be extremely drying and irritating when applied topically and can adversely affect the structure of the skin. Also, retinoic acid can be administered orally. However, retinoic acid can be teratogenic and have other undesired side effects.

Antibiotic agents, such as erythromycin, clindamycin, tetracycline, and beta lactams have also been used both orally and topically in the treatment of acne. However, as is a problem with the use of most antibiotic agents in general, bacteria can become resistant making the underlying condition more difficult to treat. Resistant strains of *Propionibacterium acnes, Staphylococcus aureus, Propionibacterium granulosum, Gardnerella vaginalis* and other bacteria involved in acne have begun to emerge. See, e.g., Eady E. A., et al. The effects of acne treatment with a combination of benzoyl peroxide and erythromycin on skin carriage of erythromycin-resistant propionibacteria. *Br. J. Dermatol.* 1996; 134:107-113; McLean, N. W.; McGroarty, J. A. *Appl. Environ. Microbiol.* 1996, 62(3), 1089-1092; Nagaraja, P. *Indian J. Med. Microbiol.* 2008, 26(2), 155-157; Tomusiak, A. et al. *Ginekol. Pol.* 2011, 82(12), 900-904; Eschenbach, D. A. *Clin. Infectious Dis.* 2007, 44(2), 220-221. Furthermore, bacteria, including resistant strains of bacteria, can also cause further complications such as skin infections, eye infections, bone and joint infections, central nervous system infections, and endocarditis. Therefore, with antibiotic treatments for acne, it would be highly desirable to have effective treatments which are also useful against resistant bacteria. See Tan, A. W. and Tan, H. H., "Acne vulgaris,: a review of antibiotic therapy", *Expert Opin. Pharmacother.*, 2005 Mar. 6(3), 409-418; Oprica, C. et al., "European surveillance study on the antibiotic susceptibility of *Propionibacterium acnes*", Clinical Microbiology and Infection, Volume 11, Number 3, March 2005, pp. 204-312; and Goldstein, E., et al., "Comparative In Vitro Activities of retapamulin (SB-275833) against 141 Clinical isolates of *propionibacterium* spp., Including 117 *P. acnes* Isolates", Antimicrobial Agents and Chemotherapy, Jan. 2006, p. 379-381, vol. 50, no. 1.

From the foregoing, and especially in view of the development of resistant strains of bacteria, it is seen that there is a continuing need for safe, effective, and convenient means for treating, preventing, or reducing the risk of acne and other skin infections caused or mediated by *Propionibacterium acnes, Staphylococcus aureus,* or *Gardneralla vaginalis.*

Bacterial vaginosis (BV) is one of the most common vaginal diseases in women of reproductive age. Since BV is caused by an imbalance of normal vaginal microorganisms, there are multiple risk factors, including the use of intrauterine devices, the use of douches, and new sexual partners. *Gardnerella vaginalis* is a causative agent of BV. BV may present with a burning sensation when urinating and white or gray discharge with a fish-like odor. Additionally, BV can increase the risk of contracting sexually transmitted diseases, including HIV/AIDS. Treatment of BV with current antibiotics has high rates of failure and recurrence. Thus, it is important for there to be safe, effective, and convenient alternatives for treating, preventing, or reducing the risk of BV.

The present invention provides methods for treating, preventing, and reducing the risk of acne and other skin infections caused or mediated by *Propionibacterium acnes, Gardnerella vaginalis,* or *Staphylococcus aureus,* in a patient by administering a safe and effective amount of an antibiotic compound, e.g., a topically applied oxazolidinone compound.

SUMMARY OF THE INVENTION

The present invention relates to methods for treating, preventing, or reducing the risk of acne and other skin infections caused or mediated by *Propionibacterium acnes, Gardnerella vaginalis,* or *Staphylococcus aureus* by administering to a patient in need thereof a safe and effective amount of an antibiotic compound, e.g., an oxazolidinone compound.

The present invention relates to compounds for use in methods for treating, preventing, or reducing the risk of acne and other skin infections caused or mediated by *Propionibacterium acnes, Gardnerella vaginalis,* or *Staphylococcus aureus* in a patient in need thereof. For example, the compounds for use are administered in a safe and effective amount. The compound can be, e.g., an oxazolidinone compound.

In addition, the present invention provides formulations useful in the present invention and provides the use of an antibiotic compound in the manufacture of a medicament useful for topically treating, preventing, or reducing the risk of acne and other skin infections caused or mediated by *Propionibacterium acnes, Gardnerella vaginalis,* or *Staphylococcus aureus.*

In one aspect, disclosed herein is a method of treating, preventing, or reducing the risk of a skin infection caused or mediated by *Propionibacterium acnes, Gardnerella vaginalis,* or *Staphylococcus aureus* in a patient, the method comprising administering a pharmaceutically effective amount of a compound having the formula:

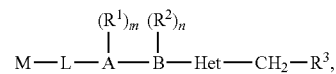

or a pharmaceutically acceptable tautomer, salt, ester, or prodrug thereof, wherein:

A is selected from the group consisting of:
  phenyl, pyridyl, pyrazinyl, pyrimidinyl, and pyridazinyl;
B is selected from the group consisting of:
  phenyl, pyridyl, pyrazinyl, pyrimidinyl, and pyridazinyl;
Het-CH$_2$—R$^3$ is selected from the group consisting of:

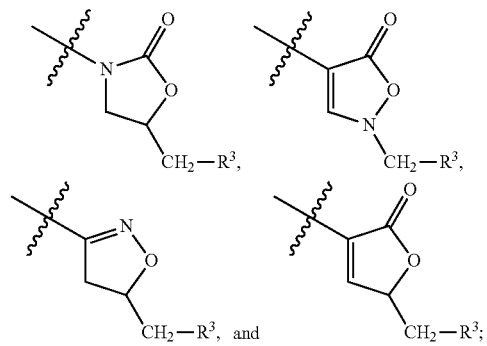

M is selected from the group consisting of:
  a) saturated, unsaturated, or aromatic C$_{3-14}$ carbocycle, and b) saturated, unsaturated, or aromatic 3-14 membered heterocycle containing one or more heteroatoms selected from the group consisting of nitrogen, oxygen, and sulfur,
    wherein a) or b) optionally is substituted with one or more R$^5$ groups;
M-L is selected from the group consisting of:
  a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X-X—, i) M-L$^1$-X-X—, j) M-X-X-L$^2$, and k) M-L$^1$-X-X-L$^2$,
  wherein
X, at each occurrence, independently is selected from the group consisting of:
  a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N═, i) ═N—NR$^4$—, j) —O—N═, k) ═N—O—, l) —N═, m) ═N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and s)

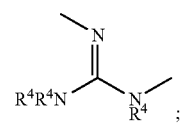

$L^1$ is selected from the group consisting of:
  a) $C_{1-6}$ alkyl, b) $C_{2-6}$ alkenyl, and c) $C_{2-6}$ alkynyl, wherein any of a)-c) optionally is substituted with one or more $R^5$ groups; and
$L^2$ is selected from the group consisting of:
  a) $C_{1-6}$ alkyl, b) $C_{2-6}$ alkenyl, and c) $C_{2-6}$ alkynyl, wherein any of a)-c) optionally is substituted with one or more $R^5$ groups;
$R^1$, at each occurrence, independently is selected from the group consisting of:
  a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)R^4$, bb) —$SO_2NR^4R^4$, and cc) $R^4$;
$R^2$, at each occurrence, independently is selected from the group consisting of:
  a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)R^4$, bb) —$SO_2NR^4R^4$, and cc) $R^4$;
$R^3$ is selected from the group consisting of:
  a) —$OR^4$, b) —$NR^4R^4$, c) —$C(O)R^4$, d) —$C(O)OR^4$, e) —$OC(O)R^4$, f) —$C(O)NR^4R^4$, g) —$NR^4C(O)R^4$, h) —$OC(O)NR^4R^4$, i) —$NR^4C(O)OR^4$, j) —$NR^4C(O)NR^4R^4$, k) —$C(S)R^4$, l) —$C(S)OR^4$, m) —$OC(S)R^4$, n) —$C(S)NR^4R^4$, o) —$NR^4C(S)R^4$, p) —$OC(S)NR^4R^4$, q) —$NR^4C(S)OR^4$, r) —$NR^4C(S)NR^4R^4$, s) —$NR^4C(NR^4)NR^4R^4$, t) —$S(O)_pR^4$, u) —$SO_2NR^4R^4$, and v) $R^4$;
$R^4$, at each occurrence, independently is selected from the group consisting of:
  a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —$C(O)$—$C_{1-6}$ alkyl, h) —$C(O)$—$C_{2-6}$ alkenyl, i) —$C(O)$—$C_{2-6}$ alkynyl, j) —$C(O)$—$C_{3-14}$ saturated, unsaturated, or aromatic carbocycle, k) —$C(O)$-3-14 membered saturated, unsaturated, or aromatic heterocycle comprising one or more heteroatoms selected from the group consisting of nitrogen, oxygen, and sulfur, l) —$C(O)O$—$C_{1-6}$ alkyl, m) —$C(O)O$—$C_{2-6}$ alkenyl, n) —$C(O)O$—$C_{2-6}$ alkynyl, o) —$C(O)O$—$C_{3-14}$ saturated, unsaturated, or aromatic carbocycle, and p) —$C(O)O$-3-14 membered saturated, unsaturated, or aromatic heterocycle comprising one or more heteroatoms selected from the group consisting of nitrogen, oxygen, and sulfur, wherein any of b)-p) optionally is substituted with one or more $R^5$ groups;
$R^5$, at each occurrence, is independently selected from the group consisting of:
  a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —$C(O)R^6$, p) —$C(O)OR^6$, q) —$OC(O)R^6$, r) —$C(O)NR^6R^6$, s) —$NR^6C(O)R^6$, t) —$OC(O)NR^6R^6$, u) —$NR^6C(O)OR^6$, v) —$NR^6C(O)NR^6R^6$, w) —$C(S)R^6$, x) —$C(S)OR^6$, y) —$OC(S)R^6$, z) —$C(S)NR^6R^6$, aa) —$NR^6C(S)R^6$, bb) —$OC(S)NR^6R^6$, cc) —$NR^6C(S)OR^6$, dd) —$NR^6C(S)NR^6R^6$, ee) —$NR^6C(NR^6)NR^6R^6$, ff) —$S(O)_pR^6$, gg) —$SO_2NR^6R^6$, and hh) $R^6$;
$R^6$, at each occurrence, independently is selected from the group consisting of:
  a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —$C(O)$—$C_{1-6}$ alkyl, h) —$C(O)$—$C_{2-6}$ alkenyl, i) —$C(O)$—$C_{2-6}$ alkynyl, j) —$C(O)$—$C_{3-14}$ saturated, unsaturated, or aromatic carbocycle, k) —$C(O)$-3-14 membered saturated, unsaturated, or aromatic heterocycle comprising one or more heteroatoms selected from the group consisting of nitrogen, oxygen, and sulfur, l) —$C(O)O$—$C_{1-6}$ alkyl, m) —$C(O)O$—$C_{2-6}$ alkenyl, n) —$C(O)O$—$C_{2-6}$ alkynyl, o) —$C(O)O$—$C_{3-14}$ saturated, unsaturated, or aromatic carbocycle, and p) —$C(O)O$-3-14 membered saturated, unsaturated, or aromatic heterocycle comprising one or more heteroatoms selected from the group consisting of nitrogen, oxygen, and sulfur, wherein any of b)-p) optionally is substituted with one or more $R^7$ groups;
$R^7$, at each occurrence, independently is selected from the group consisting of:
  a) F, b) Cl, c) Br, d) I, e) =O, f) =S, g) =$NR^8$, h) =$NOR^8$, i) =N—$NR^8R^8$, j) —$CF_3$, k) —$OR^8$, l) —CN, m) —$NO_2$, n) —$NR^8R^8$, o) —$C(O)R^8$, p) —$C(O)OR^8$, q) —$OC(O)R^8$, r) —$C(O)NR^8R^8$, s) —$NR^8C(O)R^8$, t) —$OC(O)NR^8R^8$, u) —$NR^8C(O)OR^8$, v) —$NR^8C(O)NR^8R^8$, w) —$C(S)R^8$, x) —$C(S)OR^8$, y) —$OC(S)R^8$, z) —$C(S)NR^8R^8$, aa) —$NR^8C(S)R^8$, bb) —$OC(S)NR^8R^8$, cc) —$NR^8C(S)OR^8$, dd) —$NR^8C(S)NR^8R^8$, ee) —$NR^8C(NR^8)NR^8R^8$, ff) —$S(O)_pR^8$, gg) —$SO_2NR^8R^8$, hh) $C_{1-6}$ alkyl, ii) $C_{2-6}$ alkenyl, jj) $C_{2-6}$ alkynyl, kk) $C_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur, wherein any of hh)-ll) optionally is substituted with one or more moieties selected from the group consisting of $R^8$, F, Cl, Br, I, —$CF_3$, —$OR^8$, —$SR^8$, —CN, —$NO_2$, —$NR^8R^8$, —$C(O)R^8$, —$C(O)OR^8$, —$OC(O)R^8$, —$C(O)NR^8R^8$, —$NR^8C(O)R^8$, —$OC(O)NR^8R^8$, —$NR^8C(O)OR^8$, —$NR^8C(O)NR^8R^8$, —$C(S)R^8$, —$C(S)OR^8$, —$OC(S)R^8$, —$C(S)NR^8R^8$, —$NR^8C(S)R^8$, —$OC(S)NR^8R^8$, —$NR^8C(S)OR^8$, —$NR^8C(S)NR^8R^8$, —$NR^8C(NR^8)NR^8R^8$, —$SO_2NR^8R^8$, and —$S(O)_pR^8$;
$R^8$, at each occurrence, independently is selected from the group consisting of:
  a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —CF$_3$, —OH, —OCH$_3$, —SH, —SCH$_3$, —CN, —NO$_2$, —NH$_2$, —NHCH$_3$, —N(CH$_3$)$_2$, —C(O)CH$_3$, —C(O)OCH$_3$, —C(O)NH$_2$, —NHC(O)CH$_3$, —SO$_2$NH$_2$, —SO$_2$NHCH$_3$, —SO$_2$N(CH$_3$)$_2$, and —S(O)$_p$CH$_3$;

m, at each occurrence, independently is 0, 1, 2, 3, or 4;
n, at each occurrence, independently is 0, 1, 2, 3, or 4; and
p, at each occurrence, independently is 0, 1, or 2.

In another aspect, disclosed herein is a method of treating, preventing, or reducing the risk of a skin infection caused or mediated by *Propionibacterium acnes, Gardnerella vaginalis,* or *Staphylococcus aureus* in a patient, the method comprising administering a pharmaceutically effective amount of a compound having the formula:

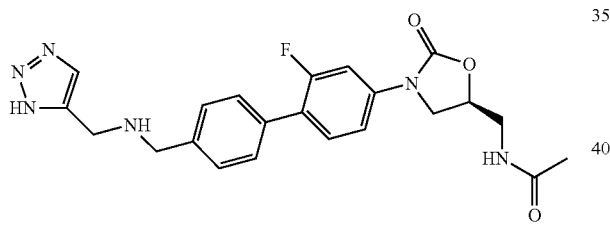

or a pharmaceutically acceptable tautomer, salt, ester, or prodrug thereof.

In another aspect, disclosed herein is a topical formulation for use in treating, preventing, or reducing the risk of a skin infection caused or mediated by *Propionibacterium acnes, Gardnerella vaginalis,* or *Staphylococcus aureus* in a patient, the formulation comprising one or more dermatologically acceptable carriers and one or more compounds having the formula:

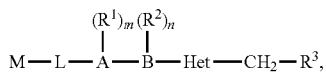

or a pharmaceutically acceptable tautomer, salt, ester, or prodrug thereof, wherein:

A is selected from the group consisting of:
  phenyl, pyridyl, pyrazinyl, pyrimidinyl, and pyridazinyl;
B is selected from the group consisting of:
  phenyl, pyridyl, pyrazinyl, pyrimidinyl, and pyridazinyl;

Het-CH$_2$—R$^3$ is selected from the group consisting of:

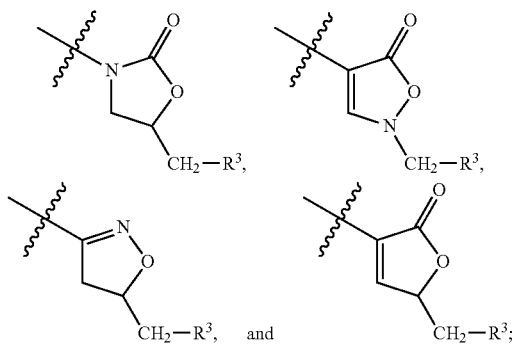

M is selected from the group consisting of:
  a) saturated, unsaturated, or aromatic C$_{3-14}$ carbocycle, and b) saturated, unsaturated, or aromatic 3-14 membered heterocycle containing one or more heteroatoms selected from the group consisting of nitrogen, oxygen, and sulfur,
    wherein a) or b) optionally is substituted with one or more R$^5$ groups;

M-L is selected from the group consisting of:
  a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X-X—, i) M-L$^1$-X-X—, j) M-X-X-L$^2$, and k) M-L$^1$-X-X-L$^2$, wherein X, at each occurrence, independently is selected from the group consisting of:
  a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N═, i) ═N—NR$^4$—, j) —O—N═, k) ═N—O—, l) —N═, m) ═N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and s)

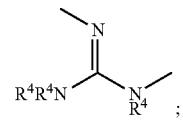

L$^1$ is selected from the group consisting of:
  a) C$_{1-6}$ alkyl, b) C$_{2-6}$ alkenyl, and c) C$_{2-6}$ alkynyl, wherein any of a)-c) optionally is substituted with one or more R$^5$ groups; and
L$^2$ is selected from the group consisting of:
  a) C$_{1-6}$ alkyl, b) C$_{2-6}$ alkenyl, and c) C$_{2-6}$ alkynyl, wherein any of a)-c) optionally is substituted with one or more R$^5$ groups;

R$^1$, at each occurrence, independently is selected from the group consisting of:
  a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;

$R^2$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)_pR^4$, bb) —$SO_2NR^4R^4$, and cc) $R^4$;

$R^3$ is selected from the group consisting of:
a) —$OR^4$, b) —$NR^4R^4$, c) —$C(O)R^4$, d) —$C(O)OR^4$, e) —$OC(O)R^4$, f) —$C(O)NR^4R^4$, g) —$NR^4C(O)R^4$, h) —$OC(O)NR^4R^4$, i) —$NR^4C(O)OR^4$, j) —$NR^4C(O)NR^4R^4$, k) —$C(S)R^4$, l) —$C(S)OR^4$, m) —$OC(S)R^4$, n) —$C(S)NR^4R^4$, o) —$NR^4C(S)R^4$, p) —$OC(S)NR^4R^4$, q —$NR^4C(S)OR^4$, r) —$NR^4C(S)NR^4R^4$, s) —$NR^4C(NR^4)NR^4R^4$, t) —$S(O)_pR^4$, u) —$SO_2NR^4R^4$, and v) $R^4$;

$R^4$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated,
unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl,
m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more $R^5$ groups;

$R^5$, at each occurrence, is independently selected from the group consisting of:
a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —$C(O)R^6$, p) —$C(O)OR^6$, q) —$OC(O)R^6$, r) —$C(O)NR^6R^6$, s) —$NR^6C(O)R^6$, t) —$OC(O)NR^6R^6$, u) —$NR^6C(O)OR^6$, v) —$NR^6C(O)NR^6R^6$, w) —$C(S)R^6$, x) —$C(S)OR^6$, y) —$OC(S)R^6$, z) —$C(S)NR^6R^6$, aa) —$NR^6C(S)R^6$, bb) —$OC(S)NR^6R^6$, cc) —$NR^6C(S)OR^6$, dd) —$NR^6C(S)NR^6R^6$, ee) —$NR^6C(NR^6)NR^6R^6$, ff) —$S(O)_pR^6$, gg) —$SO_2NR^6R^6$, and hh) $R^6$;

$R^6$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated,
unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl,
m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more $R^7$ groups;

$R^7$, at each occurrence, independently is selected from the group consisting of:
a) F, b) Cl, c) Br, d) I, e) =O, f) =S, g) =$NR^8$, h) =$NOR^8$, i) =N—$NR^8R^8$, j) —$CF_3$, k) —$OR^8$, l) —CN, m) —$NO_2$, n) —$NR^8R^8$, o) —$C(O)R^8$, p) —$C(O)OR^8$, q) —$OC(O)R^8$, r) —$C(O)NR^8R^8$, s) —$NR^8C(O)R^8$, t) —$OC(O)NR^8R^8$, u) —$NR^8C(O)OR^8$, v) —$NR^8C(O)NR^8R^8$, w) —$C(S)R^8$, x) —$C(S)OR^8$, y) —$OC(S)R^8$, z) —$C(S)NR^8R^8$, aa) —$NR^8C(S)R^8$, bb) —$OC(S)NR^8R^8$, cc) —$NR^8C(S)OR^8$, dd) —$NR^8C(S)NR^8R^8$, ee) —$NR^8C(NR^8)NR^8R^8$, ff) —$S(O)_pR^8$, gg) —$SO_2NR^8R^8$, hh) $C_{1-6}$ alkyl, ii) $C_{2-6}$ alkenyl, jj) $C_{2-6}$ alkynyl, kk) $C_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur, wherein any of hh)-ll) optionally is substituted with one or more moieties selected from the group consisting of $R^8$, F, Cl, Br, I, —$CF_3$, —$OR^8$, —$SR^8$, —CN, —$NO_2$, —$NR^8R^8$, —$C(O)R^8$, —$C(O)OR^8$, —$OC(O)R^8$, —$C(O)NR^8R^8$, —$NR^8C(O)R^8$, —$OC(O)NR^8R^8$, —$NR^8C(O)OR^8$, —$NR^8C(O)NR^8R^8$, —$C(S)R^8$, —$C(S)OR^8$, —$OC(S)R^8$, —$C(S)NR^8R^8$, —$NR^8C(S)R^8$, —$OC(S)NR^8R^8$, —$NR^8C(S)OR^8$, —$NR^8C(S)NR^8R^8$, —$NR^8C(NR^8)NR^8R^8$, —$SO_2NR^8R^8$, and —$S(O)_p R^8$;

$R^8$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated,
unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl,
m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —$CF_3$, —OH, —$OCH_3$, —SH, —$SCH_3$, —CN, —$NO_2$, —$NH_2$, —$NHCH_3$, —$N(CH_3)_2$, —$C(O)CH_3$, —C(O)

OCH$_3$, —C(O)NH$_2$, —NHC(O)CH$_3$, —SO$_2$NH$_2$, —SO$_2$NHCH$_3$, —SO$_2$N(CH$_3$)$_2$, and —S(O)$_p$CH$_3$;

m, at each occurrence, independently is 0, 1, 2, 3, or 4;

n, at each occurrence, independently is 0, 1, 2, 3, or 4; and p, at each occurrence, independently is 0, 1, or 2.

In another aspect, disclosed herein is a topical formulation for use in treating, preventing, or reducing the risk of a skin infection caused or mediated by *Propionibacterium acnes, Gardnerella vaginalis*, or *Staphylococcus aureus* in a patient, the formulation comprising one or more dermatologically acceptable carriers and one or more compounds having the formula:

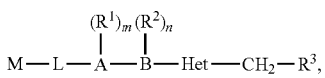

or a pharmaceutically acceptable tautomer, salt, ester, or prodrug thereof, wherein:

A is a phenyl;

B is a phenyl;

Het-CH$_2$—R$^3$ is:

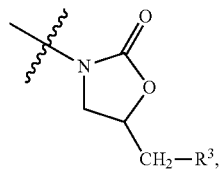

M is a 5-membered unsaturated heterocycle containing one or more nitrogen heteroatoms optionally substituted with one or more R$^5$ groups, wherein the heterocycle contains only nitrogen atoms;

M-L is M-L$^1$-X-L$^2$, wherein

X, at each occurrence, independently is selected from the group consisting of:
a) —NR$^4$—, b) —SO$_2$NR$^4$—

L$^1$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups; and L$^2$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups;

R$^1$, at each occurrence, independently is selected from the group consisting of:
a) F, b) Cl, c) Br, d);

R$^2$, at each occurrence, independently is selected from the group consisting of:
a) F, b) Cl, c) Br, d);

R$^3$ is —NR$^4$C(O)R$^4$;

R$^4$, at each occurrence, independently is selected from the group consisting of:
a) H, b) C$_{1-6}$ alkyl;

R$^5$, at each occurrence, is independently selected from the group consisting of:
a) F, b) Cl, c) Br, d) I, e) =O, f) =S, g) —CF$_3$, h) —CN, i) —NO$_2$, j) —NR$^6$R$^6$, k) —C(O)R$^6$, l) —C(O)NR$^6$R$^6$, m) —S(O)$_p$R$^6$, and n) R$^6$;

R$^6$, at each occurrence, independently is selected from the group consisting of:
a) H, b) C$_{1-6}$ alkyl, c) C$_{2-6}$ alkenyl, d) C$_{2-6}$ alkynyl, wherein any of b)-d) optionally is substituted with one or more R$^7$ groups;

R$^7$, at each occurrence, independently is selected from the group consisting of:
a) F, b) Cl, c) Br, d) I, e) =NR$^8$, f) —CF$_3$, g) —OR$^8$, h) —CN, i) —NO$_2$, j) —NR$^8$R$^8$, k) —C(O)R$^8$, and l) —C(O)OR$^8$;

R$^8$, at each occurrence, independently is selected from the group consisting of:
a) H, b) C$_{1-6}$ alkyl, c) C$_{2-6}$ alkenyl, d) C$_{2-6}$ alkynyl, wherein any of b)-d) optionally is substituted with one or more moieties selected from the group consisting of F, Cl, Br, I, —CF$_3$, and —OH;

m is 0, 1, 2, 3, or 4;

n is 0, 1, 2, 3, or 4; and p, at each occurrence, independently is 0, 1, or 2.

In another aspect, disclosed herein is a topical formulation for use in treating, preventing, or reducing the risk of a skin infection caused or mediated by *Propionibacterium acnes, Gardnerella vaginalis*, or *Staphylococcus aureus* in a patient, the formulation comprising one or more dermatologically acceptable carriers and a compound having the formula:

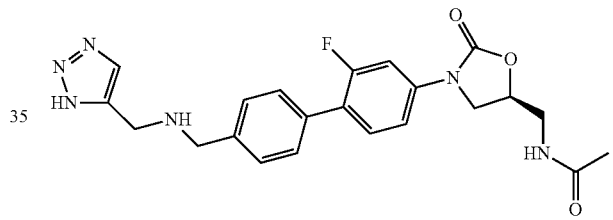

or a pharmaceutically acceptable tautomer, salt, ester, or prodrug thereof.

In another aspect, disclosed herein is a method of treating, preventing, or reducing the risk of a skin infection caused or mediated by *Propionibacterium acnes, Gardnerella vaginalis*, or *Staphylococcus aureus* in a patient, the method comprising administering a pharmaceutically effective amount of the topical formulation according to any one of claims 32 through 39.

In another aspect, disclosed herein is a use of a compound having the formula:

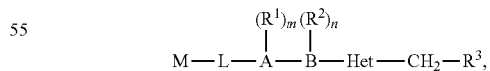

or a pharmaceutically acceptable tautomer, salt, ester, or prodrug thereof, wherein:

A is selected from the group consisting of:
phenyl, pyridyl, pyrazinyl, pyrimidinyl, and pyridazinyl;

B is selected from the group consisting of:
phenyl, pyridyl, pyrazinyl, pyrimidinyl, and pyridazinyl;

Het-CH$_2$—R$^3$ is selected from the group consisting of:

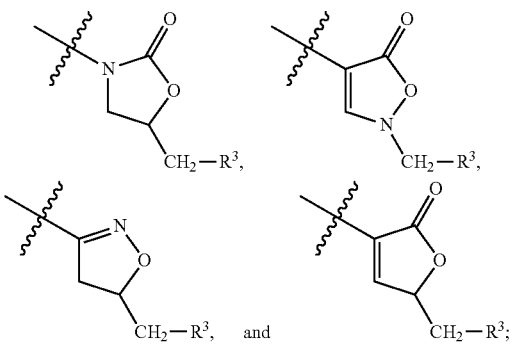

M is selected from the group consisting of:
  a) saturated, unsaturated, or aromatic C$_{3-14}$ carbocycle, and b) saturated, unsaturated, or aromatic 3-14 membered heterocycle containing one or more heteroatoms selected from the group consisting of nitrogen, oxygen, and sulfur,
    wherein a) or b) optionally is substituted with one or more R$^5$ groups;

M-L is selected from the group consisting of:
  a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X-X—, i) M-L$^1$-X-X—, j) M-X-X-L$^2$, and k) M-L$^1$-X-X-L$^2$, wherein X, at each occurrence, independently is selected from the group consisting of:
  a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N═, i) ═N—NR$^4$—, j) —O—N═, k) ═N—O—, l) —N═, m) ═N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and s)

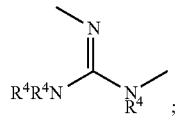

L$^1$ is selected from the group consisting of:
  a) C$_{1-6}$ alkyl, b) C$_{2-6}$ alkenyl, and c) C$_{2-6}$ alkynyl, wherein any of a)-c) optionally is substituted with one or more R$^5$ groups; and L$^2$ is selected from the group consisting of:
  a) C$_{1-6}$ alkyl, b) C$_{2-6}$ alkenyl, and c) C$_{2-6}$ alkynyl, wherein any of a)-c) optionally is substituted with one or more R$^5$ groups;

R$^1$, at each occurrence, independently is selected from the group consisting of:
  a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;

R$^2$, at each occurrence, independently is selected from the group consisting of:
  a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;

R$^3$ is selected from the group consisting of:
  a) —OR$^4$, b) —NR$^4$R$^4$, c) —C(O)R$^4$, d) —C(O)OR$^4$, e) —OC(O)R$^4$, f) —C(O)NR$^4$R$^4$, g) —NR$^4$C(O)R$^4$, h) —OC(O)NR$^4$R$^4$, i) —NR$^4$C(O)OR$^4$, j) —NR$^4$C(O)NR$^4$R$^4$, k) —C(S)R$^4$, l) —C(S)OR$^4$, m) —OC(S)R$^4$, n) —C(S)NR$^4$R$^4$, o) —NR$^4$C(S)R$^4$, p) —OC(S)NR$^4$R$^4$, q) —NR$^4$C(S)OR$^4$, r) —NR$^4$C(S)NR$^4$R$^4$, s) —NR$^4$C(NR$^4$)NR$^4$R$^4$, t) —S(O)$_p$R$^4$, u) —SO$_2$NR$^4$R$^4$, and v) R$^4$;

R$^4$, at each occurrence, independently is selected from the group consisting of:
  a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R$^5$ groups;

R$^5$, at each occurrence, is independently selected from the group consisting of:
  a) F, b) Cl, c) Br, d) I, e) ═O, f) ═S, g) ═NR$^6$, h) ═NOR$^6$, i) ═N—NR$^6$R$^6$, j) —CF$_3$, k) —OR$^6$, l) —CN, m) —NO$_2$, n) —NR$^6$R$^6$, o) —C(O)R$^6$, p) —C(O)OR$^6$, q) —OC(O)R$^6$, r) —C(O)NR$^6$R$^6$, s) —NR$^6$C(O)R$^6$, t) —OC(O)NR$^6$R$^6$, u) —NR$^6$C(O)OR$^6$, v) —NR$^6$C(O)NR$^6$R$^6$, w) —C(S)R$^6$, x) —C(S)OR$^6$, y) —OC(S)R$^6$, z) —C(S)NR$^6$R$^6$, aa) —NR$^6$C(S)R$^6$, bb) —OC(S)NR$^6$R$^6$, cc) —NR$^6$C(S)OR$^6$, dd) —NR$^6$C(S)NR$^6$R$^6$, ee) —NR$^6$C(NR$^6$)NR$^6$R$^6$, ff) —S(O)$_p$R$^6$, gg) —SO$_2$NR$^6$R$^6$, and hh) R$^6$;

R$^6$, at each occurrence, independently is selected from the group consisting of:
  a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl,
m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R$^7$ groups;

R$^7$, at each occurrence, independently is selected from the group consisting of:
a) F, b) Cl, c) Br, d) I, e) =O, f) =S, g) =NR$^8$, h) =NOR$^8$, i) =N—NR$^8$R$^8$, j) —CF$_3$, k) —OR$^8$, l) —CN, m) —NO$_2$, n) —NR$^8$R$^8$, o) —C(O)R$^8$, p) —C(O)OR$^8$, q) —OC(O)R$^8$, r) —C(O)NR$^8$R$^8$, s) —NR$^8$C(O)R$^8$, t) —OC(O)NR$^8$R$^8$, u) —NR$^8$C(O)OR$^8$, v) —NR$^8$C(O)NR$^8$R$^8$, w) —C(S)R$^8$, x) —C(S)OR$^8$, y) —OC(S)R$^8$, z) —C(S)NR$^8$R$^8$, aa) —NR$^8$C(S)R$^8$, bb) —OC(S)NR$^8$R$^8$, cc) —NR$^8$C(S)OR$^8$, dd) —NR$^8$C(S)NR$^8$R$^8$, ee) —NR$^8$C(NR$^8$)NR$^8$R$^8$, ff) —S(O)$_p$R$^8$, gg) —SO$_2$NR$^8$R$^8$, hh) C$_{1-6}$ alkyl, ii) C$_{2-6}$ alkenyl, jj) C$_{2-6}$ alkynyl, kk) C$_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur, wherein any of hh)-ll) optionally is substituted with one or more moieties selected from the group consisting of R$^8$, F, Cl, Br, I, —CF$_3$, —OR$^8$, —SR$^8$, —CN, —NO$_2$, —NR$^8$R$^8$, —C(O)R$^8$, —C(O)OR$^8$, —OC(O)R$^8$, —C(O)NR$^8$R$^8$, —NR$^8$C(O)R$^8$, —OC(O)NR$^8$R$^8$, —NR$^8$C(O)OR$^8$, —NR$^8$C(O)NR$^8$R$^8$, —C(S)R$^8$, —C(S)OR$^8$, —OC(S)R$^8$, —C(S)NR$^8$R$^8$, —NR$^8$C(S)R$^8$, —OC(S)NR$^8$R$^8$, —NR$^8$C(S)OR$^8$, —NR$^8$C(S) NR$^8$R$^8$, —NR$^8$C(NR$^8$)NR$^8$R$^8$, —SO$_2$NR$^8$R$^8$, and —S(O)$_p$ R$^8$;

R$^8$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated,
unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl,
m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —CF$_3$, —OH, —OCH$_3$, —SH, —SCH$_3$, —CN, —NO$_2$, —NH$_2$, —NHCH$_3$, —N(CH$_3$)$_2$, —C(O)CH$_3$, —C(O) OCH$_3$, —C(O)NH$_2$, —NHC(O)CH$_3$, —SO$_2$NH$_2$, —SO$_2$NHCH$_3$, —SO$_2$N(CH$_3$)$_2$, and —S(O)$_p$ CH$_3$;

m, at each occurrence, independently is 0, 1, 2, 3, or 4;
n, at each occurrence, independently is 0, 1, 2, 3, or 4; and
p, at each occurrence, independently is 0, 1, or 2,
in the manufacture of a medicament for treating, preventing, or reducing the risk of a skin infection caused or mediated by *Propionibacterium acnes, Gardnerella vaginalis*, or *Staphylococcus aureus* in a patient.

In another aspect, disclosed herein is a use of a compound having the formula:

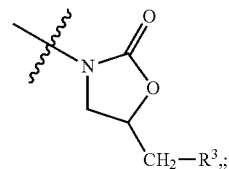

or a pharmaceutically acceptable tautomer, salt, ester, or prodrug thereof, wherein:
A is a phenyl;
B is a phenyl;
Het-CH$_2$—R$^3$ is:

M is a 5-membered unsaturated heterocycle containing one or more nitrogen heteroatoms optionally substituted with one or more R$^5$ groups, wherein the heterocycle contains only nitrogen atoms;
M-L is M-L$^1$-X-L$^2$, wherein
X, at each occurrence, independently is selected from the group consisting of:
a) —NR$^4$—, b) —SO$_2$NR$^4$—
L$^1$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups; and
L$^2$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups;
R$^1$, at each occurrence, independently is selected from the group consisting of:
a) F, b) Cl, c) Br, d);
R$^2$, at each occurrence, independently is selected from the group consisting of:
a) F, b) Cl, c) Br, d);
R$^3$ is —NR$^4$C(O)R$^4$;
R$^4$, at each occurrence, independently is selected from the group consisting of:
a) H, b) C$_{1-6}$ alkyl;
R$^5$, at each occurrence, is independently selected from the group consisting of:
a) F, b) Cl, c) Br, d) I, e) =O, f) =S, g) —CF$_3$, h) —CN, i) —NO$_2$, j) —NR$^6$R$^6$, k) —C(O)R$^6$, l) —C(O)NR$^6$R$^6$, m) —S(O)$_p$R$^6$, and n) R$^6$;

$R^6$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more $R^7$ groups;

$R^7$, at each occurrence, independently is selected from the group consisting of:
a) F, b) Cl, c) Br, d) I, e) =$NR^8$, f) —$CF_3$, g) —$OR^8$, h) —CN, i) —$NO_2$, j) —$NR^8R^8$, k) —C(O)$R^8$, and l) —C(O)$OR^8$;

$R^8$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more moieties selected from the group consisting of F, Cl, Br, I, —$CF_3$, and —OH;

m is 0, 1, 2, 3, or 4;
n is 0, 1, 2, 3, or 4; and
p, at each occurrence, independently is 0, 1, or 2,
in the manufacture of a medicament for treating, preventing, or reducing the risk of a skin infection caused or mediated by *Propionibacterium acnes, Gardnerella vaginalis,* or *Staphylococcus aureus* in a patient comprising.

In another aspect, disclosed herein is a use of a compound having the formula:

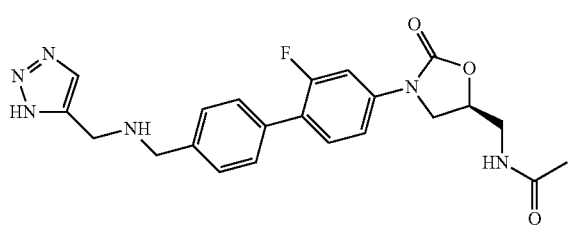 [SMILES: CC(=O)NC[C@H]1CN(c2ccc(-c3ccc(CNCc4cnn[nH]4)cc3)c(F)c2)C(=O)O1]

or a pharmaceutically acceptable tautomer, salt, ester, or prodrug thereof, in the manufacture of a medicament for treating, preventing, or reducing the risk of a skin infection caused or mediated by *Propionibacterium acnes, Gardnerella vaginalis,* or *Staphylococcus aureus* in a patient.

In another aspect, disclosed herein is a use of a compound having the formula:

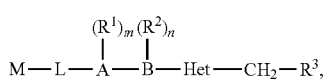

or a pharmaceutically acceptable tautomer, salt, ester, or prodrug thereof, wherein:

A is selected from the group consisting of:
phenyl, pyridyl, pyrazinyl, pyrimidinyl, and pyridazinyl;

B is selected from the group consisting of:
phenyl, pyridyl, pyrazinyl, pyrimidinyl, and pyridazinyl;

Het-$CH_2$—$R^3$ is selected from the group consisting of:

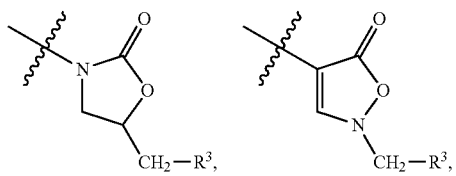

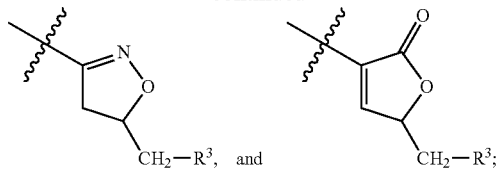

M is selected from the group consisting of:
a) saturated, unsaturated, or aromatic $C_{3-14}$ carbocycle, and b) saturated, unsaturated, or aromatic 3-14 membered heterocycle containing one or more heteroatoms selected from the group consisting of nitrogen, oxygen, and sulfur,
wherein a) or b) optionally is substituted with one or more $R^5$ groups;

M-L is selected from the group consisting of:
a) M-X, b) $M-L^1$, c) $M-L^1$-X, d) $M-X-L^2$, e) $M-L^1-X-L^2$, f) $M-X-L^1-X-L^2$, g) $M-L^1-X-L^2-X$, h) M-X-X—, i) $M-L^1-X-X$—, j) $M-X-X-L^2$, and k) $M-L^1-X-X-L^2$,
wherein X, at each occurrence, independently is selected from the group consisting of:
a) —O—, b) —$NR^4$—, c) —N(O)—, d) —N($OR^4$)—, e) —S(O)$_p$—, f) —$SO_2NR^4$—, g) —$NR^4SO_2$—, h) —$NR^4$—N=, i) =N—$NR^4$—, j) —O—N=, k) =N—O—, l) —N=, m) =N—, n) —$NR^4$—$NR^4$—, o) —$NR^4$C(O)O—, p) —OC(O)$NR^4$—, q) —$NR^4$C(O)$NR^4$— r) —$NR^4$C($NR^4$)$NR^4$—, and s)

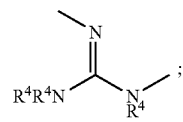

$L^1$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups; and $L^2$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups;

$R^1$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —C(O)$R^4$, k) —C(O)$OR^4$, l) —OC(O)$R^4$, m) —C(O)$NR^4R^4$, n) —$NR^4$C(O)$R^4$, o) —OC(O)$NR^4R^4$, p) —$NR^4$C(O)$OR^4$, q) —$NR^4$C(O)$NR^4R^4$, r) —C(S)$R^4$, s) —C(S)$OR^4$, t) —OC(S)$R^4$, u) —C(S)$NR^4R^4$, v) —$NR^4$C(S)$R^4$, w) —OC(S)$NR^4R^4$, x) —$NR^4$C(S)$OR^4$, y) —$NR^4$C(S)$NR^4R^4$, z) —$NR^4$C($NR^4$)$NR^4R^4$, aa) —S(O)$_pR^4$, bb) —$SO_2NR^4R^4$, and cc) $R^4$;

$R^2$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —C(O)$R^4$, k) —C(O)$OR^4$, l) —OC(O)$R^4$, m) —C(O)$NR^4R^4$, n) —$NR^4$C(O)$R^4$, o) —OC(O)$NR^4R^4$, p) —$NR^4$C(O)$OR^4$, q) —$NR^4$C(O)$NR^4R^4$, r) —C(S)$R^4$, s) —C(S)$OR^4$, t) —OC(S)$R^4$, u) —C(S)$NR^4R^4$, v) —$NR^4$C(S)$R^4$, w) —OC(S)$NR^4R^4$, x) —$NR^4$C(S)$OR^4$, y) —$NR^4$C(S)$NR^4R^4$, z)

—NR⁴C(NR⁴)NR⁴R⁴, aa) —S(O)$_p$R⁴, bb) —SO₂NR⁴R⁴, and cc) R⁴;

R³ is selected from the group consisting of:
 a) —OR⁴, b) —NR⁴R⁴, c) —C(O)R⁴, d) —C(O)OR⁴, e) —OC(O)R⁴, f) —C(O)NR⁴R⁴, g) —NR⁴C(O)R⁴, h) —OC(O)NR⁴R⁴, i) —NR⁴C(O)OR⁴, j) —NR⁴C(O)NR⁴R⁴, k) —C(S)R⁴, l) —C(S)OR⁴, m) —OC(S)R⁴, n) —C(S)NR⁴R⁴, o) —NR⁴C(S)R⁴, p) —OC(S)NR⁴R⁴, q) —NR⁴C(S)OR⁴, r) —NR⁴C(S)NR⁴R⁴, s) —NR⁴C(NR⁴)NR⁴R⁴, t) —S(O)$_p$R⁴, u) —SO₂NR⁴R⁴, and v) R⁴;

R⁴, at each occurrence, independently is selected from the group consisting of:
 a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl,
 m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R⁵ groups;

R⁵, at each occurrence, is independently selected from the group consisting of:
 a) F, b) Cl, c) Br, d) I, e) =O, f) =S, g) =NR⁶, h) =NOR⁶, i) =N—NR⁶R⁶, j) —CF₃, k) —OR⁶, l) —CN, m) —NO₂, n) —NR⁶R⁶, o) —C(O)R⁶, p) —C(O)OR⁶, q) —OC(O)R⁶, r) —C(O)NR⁶R⁶, s) —NR⁶C(O)R⁶, t) —OC(O)NR⁶R⁶, u) —NR⁶C(O)OR⁶, v) —NR⁶C(O)NR⁶R⁶, w) —C(S)R⁶, x) —C(S)OR⁶, y) —OC(S)R⁶, z) —C(S)NR⁶R⁶, aa) —NR⁶C(S)R⁶, bb) —OC(S)NR⁶R⁶, cc) —NR⁶C(S)OR⁶, dd) —NR⁶C(S)NR⁶R⁶, ee) —NR⁶C(NR⁶)NR⁶R⁶, ff) —S(O)$_p$R⁶, gg) —SO₂NR⁶R⁶, and hh) R⁶;

R⁶, at each occurrence, independently is selected from the group consisting of:
 a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl,
 m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R⁷ groups;

R⁷, at each occurrence, independently is selected from the group consisting of:
 a) F, b) Cl, c) Br, d) I, e) =O, f) =S, g) =NR⁸, h) =NOR⁸, i) =N—NR⁸R⁸, j) —CF₃, k) —OR⁸, l) —CN, m) —NO₂, n) —NR⁸R⁸, o) —C(O)R⁸, p) —C(O)OR⁸, q) —OC(O)R⁸, r) —C(O)NR⁸R⁸, s) —NR⁸C(O)R⁸, t) —OC(O)NR⁸R⁸, u) —NR⁸C(O)OR⁸, v) —NR⁸C(O)NR⁸R⁸, w) —C(S)R⁸, x) —C(S)OR⁸, y) —OC(S)R⁸, z) —C(S)NR⁸R⁸, aa) —NR⁸C(S)R⁸, bb) —OC(S)NR⁸R⁸, cc) —NR⁸C(S)OR⁸, dd) —NR⁸C(S)NR⁸R⁸, ee) —NR⁸C(NR⁸)NR⁸R⁸, ff) —S(O)$_p$R⁸, gg) —SO₂NR⁸R⁸, hh) $C_{1-6}$ alkyl, ii) $C_{2-6}$ alkenyl, jj) $C_{2-6}$ alkynyl, kk) $C_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur, wherein any of hh)-ll) optionally is substituted with one or more moieties selected from the group consisting of R⁸, F, Cl, Br, I, —CF₃, —OR⁸, —SR⁸, —CN, —NO₂, —NR⁸R⁸, —C(O)R⁸, —C(O)OR⁸, —OC(O)R⁸, —C(O)NR⁸R⁸, —NR⁸C(O)R⁸, —OC(O)NR⁸R⁸, —NR⁸C(O)OR⁸, —NR⁸C(O)NR⁸R⁸, —C(S)R⁸, —C(S)OR⁸, —OC(S)R⁸, —C(S)NR⁸R⁸, —NR⁸C(S)R⁸, —OC(S)NR⁸R⁸, —NR⁸C(S)OR⁸, —NR⁸C(S) NR⁸R⁸, —NR⁸C(NR⁸)NR⁸R⁸, —SO₂NR⁸R⁸, and —S(O)$_p$ R⁸;

R⁸, at each occurrence, independently is selected from the group consisting of:
 a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl,
 m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —CF₃, —OH, —OCH₃, —SH, —SCH₃, —CN, —NO₂, —NH₂, —NHCH₃, —N(CH₃)₂, —C(O)CH₃, —C(O)OCH₃, —C(O)NH₂, —NHC(O)CH₃, —SO₂NH₂, —SO₂NHCH₃, —SO₂N(CH₃)₂, and —S(O)$_p$ CH₃;

m, at each occurrence, independently is 0, 1, 2, 3, or 4;
n, at each occurrence, independently is 0, 1, 2, 3, or 4; and
p, at each occurrence, independently is 0, 1, or 2, for treating, preventing, or reducing the risk of a skin infection caused or mediated by *Propionibacterium acnes*, *Gardnerella vaginalis*, or *Staphylococcus aureus* in a patient.

In another aspect, disclosed herein is a use of a compound having the formula:

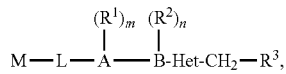

or a pharmaceutically acceptable tautomer, salt, ester, or prodrug thereof, wherein:
A is a phenyl;
B is a phenyl;
Het-CH$_2$—R$^3$ is:

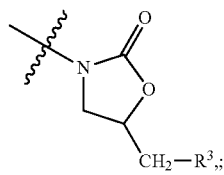

M is a 5-membered unsaturated heterocycle containing one or more nitrogen heteroatoms optionally substituted with one or more R$^5$ groups, wherein the heterocycle contains only nitrogen atoms;
M-L is M-L$^1$-X-L$^2$, wherein
  X, at each occurrence, independently is selected from the group consisting of:
    a) —NR$^4$—, b) —SO$_2$NR$^4$—
  L$^1$ is selected from the group consisting of:
    a) C$_{1-6}$ alkyl, b) C$_{2-6}$ alkenyl, and c) C$_{2-6}$ alkynyl, wherein any of a)-c) optionally is substituted with one or more R$^5$ groups; and
  L$^2$ is selected from the group consisting of:
    a) C$_{1-6}$ alkyl, b) C$_{2-6}$ alkenyl, and c) C$_{2-6}$ alkynyl, wherein any of a)-c) optionally is substituted with one or more R$^5$ groups;
R$^1$, at each occurrence, independently is selected from the group consisting of:
    a) F, b) Cl, c) Br, d) I;
R$^2$, at each occurrence, independently is selected from the group consisting of:
    a) F, b) Cl, c) Br, d) I;
R$^3$ is —NR$^4$C(O)R$^4$;
R$^4$, at each occurrence, independently is selected from the group consisting of:
    a) H, b) C$_{1-6}$ alkyl;
R$^5$, at each occurrence, is independently selected from the group consisting of:
    a) F, b) Cl, c) Br, d) I, e) =O, f) =S, g) —CF$_3$, h) —CN, i) —NO$_2$, j) —NR$^6$R$^6$, k) —C(O)R$^6$, l) —C(O)NR$^6$R$^6$, m) —S(O)$_p$R$^6$, and n) R$^6$;
R$^6$, at each occurrence, independently is selected from the group consisting of:
    a) H, b) C$_{1-6}$ alkyl, c) C$_{2-6}$ alkenyl, d) C$_{2-6}$ alkynyl, wherein any of b)-d) optionally is substituted with one or more R$^7$ groups;
R$^7$, at each occurrence, independently is selected from the group consisting of:
    a) F, b) Cl, c) Br, d) I, e) =NR$^8$, f) —CF$_3$, g) —OR$^8$, h) —CN, i) —NO$_2$, j) —NR$^8$R$^8$, k) —C(O)R$^8$, and l) —C(O)OR$^8$;
R$^8$, at each occurrence, independently is selected from the group consisting of:
    a) H, b) C$_{1-6}$ alkyl, c) C$_{2-6}$ alkenyl, d) C$_{2-6}$ alkynyl,
    wherein any of b)-d) optionally is substituted with one or more moieties selected from the group consisting of F, Cl, Br, I, —CF$_3$, and —OH;
m is 0, 1, 2, 3, or 4;
n is 0, 1, 2, 3, or 4; and
p, at each occurrence, independently is 0, 1, or 2,
for treating, preventing, or reducing the risk of a skin infection caused or mediated by *Propionibacterium acnes*, *Gardnerella vaginalis*, or *Staphylococcus aureus* in a patient.

In another aspect, disclosed herein is a use of a compound having the formula:

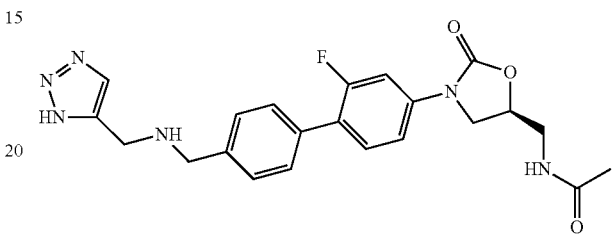

or a pharmaceutically acceptable tautomer, salt, ester, or prodrug thereof, for treating, preventing, or reducing the risk of a skin infection caused or mediated by *Propionibacterium acnes*, *Gardnerella vaginalis*, or *Staphylococcus aureus* in a patient.

The foregoing and other aspects and embodiments of the present invention can be more fully understood by reference to the following detailed description and claims.

DETAILED DESCRIPTION OF THE INVENTION

Figure 1:
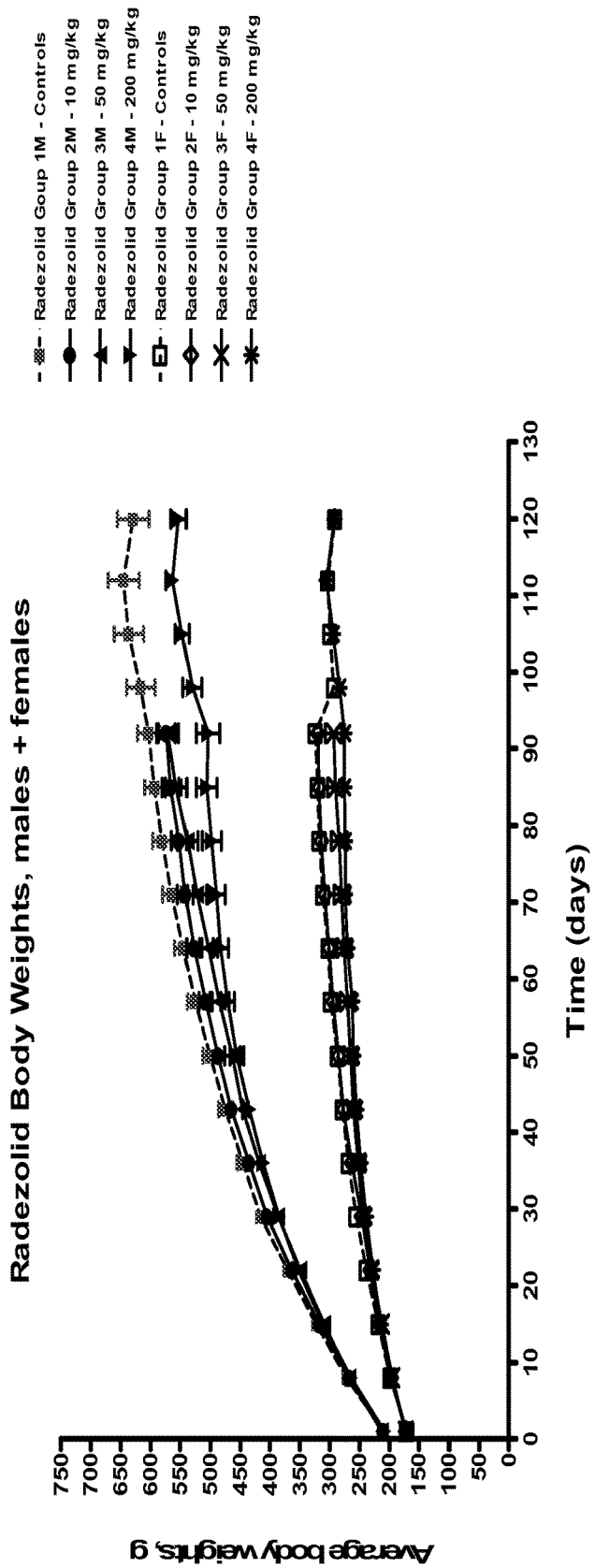
FIG. 1. shows radezolid safety in a long-term rat study, as indicated by average body weight over time.

The present invention relates to methods for treating, preventing, or reducing the risk of acne and other skin infections caused or mediated by *Propionibacterium acnes, Gardnerella vaginalis*, or *Staphylococcus aureus* in a patient a safe and effective amount of an antibiotic, i.e., an antimicrobial compound such as, e.g., an oxazolidinone compound as described herein.

1. Definitions

The term "patient," as used herein, means the human or animal (in the case of an animal, more typically a mammal) subject that would be considered to be in need of the methods of treating, preventing, or reducing the risk of acne or a pilosebaceous disorder.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "treating," as used herein, means to cure an already present acne outbreak or other undesirable other skin infection caused or mediated by *Propionibacterium acnes, Gardnerella vaginalis*, or *Staphylococcus aureus* in a patient or subject.

The term "preventing," as used herein means, to completely or almost completely stop an acne outbreak or other undesirable pilosebaceous disorder from occurring in a patient or subject, especially when the patient or subject is predisposed to such. Preventing can also include inhibiting, i.e., arresting the development of, an acne outbreak or other undesirable pilosebaceous disorder, and relieving or ameliorating, i.e., causing regression of the acne outbreak or pilosebaceous disorder.

The term "reducing the risk of," as used herein, means to lower the likelihood or probability of an acne outbreak or other undesirable pilosebaceous disorder from occurring, especially when the patient or subject is predisposed to such occurrence.

As used herein, the term "pharmaceutically effective amount" refers to an amount of a compound, or a combination of compounds, of the present invention effective when administered alone or in combination with other active ingredients useful to treat, prevent, or reduce the risk of acne or a pilosebaceous disorder. For example, a pharmaceutically effective amount refers to an amount of the compound present in a formulation or on a medical device given to a recipient patient or subject sufficient to elicit biological activity, for example, activity against acne or other undesirable pilosebaceous disorder. The combination of compounds optionally is a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-proliferative and/or anti-infective effect, or some other beneficial effect of the combination compared with the individual components.

The term "prophylactically effective amount" means an effective amount of a compound or compounds, of the present invention that is administered to prevent or reduce the risk of an acne outbreak or other undesirable pilosebaceous disorder. In other words, an amount that can be administered to provide a preventative or prophylactic effect.

As used herein, "topically applying" and "topical administration" means that compounds of the present invention are applied to the skin of the patient directly laying or spreading said compound or compounds on the outer skin, scalp, hair, fur, feathers, scales, shells, eyes, or ears of the patient, e.g., by use of the hands or an applicator such as a wipe, roller, or spray.

As used herein, "dermatologically acceptable" means that the ingredients the term describes are suitable for use in contact with tissues (e.g., the skin or hair) without undue toxicity, incompatibility, instability, irritation, allergic response, or the like.

With respect to the antibiotic compounds useful in the present invention, the following terms can be applicable, however, it should be kept in mind that more specific definitions are also given in the references referred to and incorporated by reference herein:

The chemical compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separated isomeric forms. All chiral, diastereomeric, racemic, and geometric isomeric forms of a structure are intended, unless the specific stereochemistry or isomeric form is specifically indicated. All processes used to prepare compounds of the present invention and intermediates made therein are, where appropriate, considered to be part of the present invention. All tautomers of shown or described compounds are also, where appropriate, considered to be part of the present invention.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The compounds of the present invention can also be prepared as esters, for example pharmaceutically acceptable esters. For example a carboxylic acid functional group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation, and as appropriate, purification from a reaction mixture, and formulation into an efficacious therapeutic agent.

As used herein, "skin infection" includes but is not limited to acne vulgaris, rosacea, impetigo, otitis externa, bacterial conjunctivitis, and bacterial vaginosis.

As used herein, "treating acne" refers to a mitigating, reducing, preventing, improving, or eliminating the presence or signs of disorders resulting from the actions of hormones and other substances on the sebaceous glands and hair follicles, typically leading to clogged pores and the formation of inflammatory or non-inflammatory lesions on the skin. Specifically, it relates to the treatment or prevention of blemishes, lesions, or pimples, pre-emergent pimples, blackheads, and/or whiteheads.

As used herein, "treating bacterial vaginosis" refers to mitigating, reducing, preventing, improving, or eliminating the presence or signs of disorders resulting from the actions of *Gardnerella vaginalis* in the vagina.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

2. Methods of the Invention

The present invention relates to methods for treating acne and other skin infections caused or mediated by *Propionibacterium acnes, Gardnerella vaginalis*, or *Staphylococcus aureus* in a patient in need thereof a safe and effective amount of an antibiotic.

The present invention relates to methods for preventing acne and other skin infections caused or mediated by *Propionibacterium acnes, Gardnerella vaginalis*, or *Staphylococcus aureus* in a patient in need thereof a safe and effective amount of an antibiotic compound.

The present invention relates to methods for reducing the risk of acne and other skin infections caused or mediated by *Propionibacterium acnes, Gardnerella vaginalis*, or *Staphylococcus aureus* in a patient with a safe and prophylactically effective amount of an antibiotic compound.

As discussed above, acne and other skin infections can be caused or mediated by *Propionibacterium acnes, Gardnerella vaginalis*, or *Staphylococcus aureus*. It has been found that the antibiotic compounds of the present invention are useful for treating, preventing, or reducing the risk of these microbial infections and the associated acne or other skin infections caused or mediated by *Propionibacterium acnes, Gardnerella vaginalis*, or *Staphylococcus aureus*.

The methods of the present invention can be usefully applied to patients, whether human or animal.

As discussed above, bacterial vaginosis can be caused or mediated by *Gardnerella vaginalis*. It has been found that the antibiotic compounds of the present invention are useful for treating, preventing, or reducing the risk of bacterial vaginosis caused or mediated by *Gardnerella vaginalis*. The methods of the present invention can be usefully applied to patients, whether human or animal.

In practicing the methods of the present invention, it is desired that the tissue level, or sometimes the blood level in the patient or subject, of the compound used to provide the effect be of an appropriate level for a sufficient time interval. Also, because it often takes a finite amount of time to achieve such blood or tissue levels, it is important that the compound is administered at some appropriate time. The appropriate time for administration of the compound will depend upon the pharmacokinetic profile of the compound and its formulation, route of administration, time required for completing administration, patient characteristics, desired clinical outcome, etc.

The compounds used in the methods of the present invention are generally provided to the patient or subject by topical administration, including, but not limited to administration to the skin, hair, fur, feathers, ears, or eyes.

3. Antibiotic Compounds Useful in the Present Invention

The antibiotic, i.e. antimicrobial, compounds or antibiotic agents useful herein are those that are particularly effective against bacteria that cause or mediate or are involved in acne and other undesirable skin infections caused or mediated by *Propionibacterium acnes*, *Gardnerella vaginalis*, or *Staphylococcus aureus*, and that are especially effective against resistant strains of such bacteria.

A wide range of antibiotic compounds can be used in the methods, compositions, and uses of the present invention. These antibiotic compounds can provide their therapeutic effect by a variety of biochemical or biophysical mechanisms. Antibiotic compounds useful in the present invention can include those which bind to or modulate ribosomal RNA, for example bacterial ribosomal RNA. Antibiotic compounds also useful in the present invention can include those which bind to or modulate the large ribosomal subunit, for example the large ribosomal subunit of a bacterial organism. Nonlimiting classes of antibiotic compounds useful herein include oxazolidinone antibiotics and antibiotics. Oxazolidinone antibiotics are characterized in having an oxazolidinone ring. Antibiotics are characterized in having a macrocyclic ring, typically a 13-16-membered macrocyclic ring, more typically a 14-15-membered macrocyclic ring.

The antibiotic compounds useful in the present invention can include their pharmaceutically acceptable salts, esters, or prodrugs thereof. The invention further provides methods for synthesizing any one of the antibiotic compounds of the present invention. The invention also provides pharmaceutical compositions comprising an effective amount of one or more of the antibiotic compounds of the present invention and a pharmaceutically acceptable carrier. The present invention further provides methods for making these pharmaceutical compositions.

Nonlimiting examples of antibiotic compounds useful herein and their pharmaceutically acceptable salts, esters, tautomers, and prodrugs thereof are disclosed and incorporated by reference here in the following Table 1.

TABLE 1

References Disclosing Antibiotic Compounds of the Present Invention

| PCT Publication No., U.S. patent or Publication No., or U.S. application Serial No. | Applicant or Assignee | Title | Publication or Issue Date | International or U.S. Filing Date |
| --- | --- | --- | --- | --- |
| WO 2004/029066 | Rib-X Pharmaceuticals, Inc. | Bifunctional Heterocyclic Compounds and Methods of Making and Using Same | Apr. 8, 2004 | Sep. 25, 2003 |
| WO 2004/078770 | Rib-X Pharmaceuticals, Inc. | Bifunctional Heterocyclic Compounds and Methods of Making and Using the Same | Sep. 16, 2004 | Mar. 5, 2004 |
| WO 2007/025284 | Rib-X Pharmaceuticals, Inc. | Triazole Compounds and Methods of Making and Using the Same | Mar. 1, 2007 | Aug. 24, 2006 |
| WO 2007/025098 | Rib-X Pharmaceuticals, Inc. | Triazole Compounds and Methods of Making and Using the Same | Mar. 1, 2007 | Aug. 24, 2006 |
| WO 2007/025089 | Rib-X Pharmaceuticals, Inc. | Triazole Compounds and Methods of Making and Using the Same | Mar. 1, 2007 | Aug. 24, 2006 |
| WO 2006/133397 | Rib-X Pharmaceuticals, Inc. | Process for the Synthesis of Triazoles | Dec. 14, 2006 | Jun. 8, 2006 |
| 7,148,219 B2 | Rib-X Pharmaceuticals, Inc. | Biaryl Heterocyclic Compounds and Methods of Making and Using The Same | Dec. 12, 2006 | Apr. 29, 2005 |
| 7,129,259, B2 and its Certificate of Correction of Mar. 6, 2007 | Rib-X Pharmaceuticals, Inc. | Halogenated Biaryl Heterocyclic Compounds and Methods of Making and Using the Same | Oct. 31, 2006 | Dec. 1, 2004 |

TABLE 1-continued

References Disclosing Antibiotic Compounds of the Present Invention

| PCT Publication No., U.S. patent or Publication No., or U.S. application Serial No. | Applicant or Assignee | Title | Publication or Issue Date | International or U.S. Filing Date |
|---|---|---|---|---|
| 7,091,196 B2 | Rib-X Pharmaceuticals, Inc. | Bifunctional Heterocyclic Compounds and Methods of Making and Using Same | Aug. 15, 2006 | Sep. 25, 2003 |
| 6,969,726 B2 and its Certificate of Correction of Feb. 27, 2007 | Melinta Therapeutics, Inc. | Biaryl Heterocyclic Compounds and Methods of Making and Using The Same | Nov. 29, 2005 | Jun. 2, 2004 |
| US 2005/0043317 A1 | Rib-X Pharmaceuticals, Inc. | Biaryl Heterocyclic Compounds and Methods of Making and Using The Same | Feb. 24, 2005 | Jun. 2, 2004 |
| US 2005/0203147 A1 | Rib-X Pharmaceuticals, Inc. | Biaryl Heterocyclic Compounds and Methods of Making and Using The Same | Sep. 15, 2005 | Jun. 2, 2004 |
| US 2005/0153971 A1 | Rib-X Pharmaceuticals, Inc. | Halogenated Biaryl Heterocyclic Compounds and Methods of Making and Using The Same | Jul. 14, 2005 | Dec. 1, 2004 |
| WO 2005/019211 | Rib-X Pharmaceuticals, Inc. | Biaryl Heterocyclic Compounds and Methods of Making and Using The Same | Mar. 3, 2005 | Jun. 2, 2004 |
| WO 2006/022794 | Rib-X Pharmaceuticals, Inc. | Biaryl Heterocyclic Compounds and Methods of Making and Using The Same | Mar. 2, 2006 | Dec. 1, 2004 |
| WO 2005/061468 | Rib-X Pharmaceuticals, Inc. | Halogenated Biaryl Heterocyclic Compounds and Methods of Making and Using The Same | Jul. 7, 2005 | Dec. 1, 2004 |
| WO 2005/070904 | Rib-X Pharmaceuticals, Inc. | Sulfonamide Compounds and Methods of Making and Using The Same | Aug. 4, 2005 | Jun. 2, 2004 |
| WO 2005/012270 | Rib-X Pharmaceuticals, Inc. | Biaryl Heterocyclic Amides, Amides, and Sulfur-Containing Compounds and Methods of Making and Using the Same | Feb. 10, 2005 | Jul. 28, 2004 |
| WO 2005/012271 | Rib-X Pharmaceuticals, Inc. | Process for the Synthesis of Biaryl Oxazolidinones | Feb. 10, 2005 | Jul. 28, 2004 |
| U.S. Pat. No. 6,559,303 B1 | Pharmacia & Upjohn Company | Linezolid-Crystal Form II | May 6, 2003 | May 23, 2002 |
| U.S. Pat. No. 5,688,792 | Pharmacia & Upjohn Company | Substituted Oxazine and Thiazine Oxazolidinone Antimicrobials | Nov. 18, 1997 | § 371 Date Mar. 5, 1996 |
| U.S. Pat. No. 5,654,435 | Pharmacia & Upjohn Company | Substituted Arylphenyloxazolidinones | Aug. 5, 1997 | Jun. 6, 1995 |
| WO 2001/094342 | Dong A Pharm. Co., Ltd. | Novel Oxazolidinone Derivatives and a Process for the Preparation Thereof | Dec. 13, 2001 | May 18, 2001 |
| WO 01/081350 | AstraZeneca AB and AstraZeneca UK Limited | Oxazolidinone Derivatives with Antibiotic Activity | Nov. 1, 2001 | Apr. 23, 2001 |
| U.S. Pat. No. 6,133,284 | Wakunaga Pharmaceutical Co., Ltd. | Pyridone Carboxylic Acid Derivatives or their Salts, and Antibacterial Agents Containing the Same as Their Effective Components | Oct. 17, 2000 | Jun. 10, 1999 |
| U.S. Pat. No. 5,998,436 and its certificate of correction of Dec. 17, 2002 | Wakunaga Pharmaceutical Co., Ltd. | Pyridone Carboxylic Acid Derivatives or their Salts and Antibacterial Agent Comprising the Same as the Active Ingredient | Dec. 7, 1999 | PCT Filed Sep. 20, 1996 |
| U.S. Pat. No. 6,156,903 | Wakunaga Pharmaceutical Co., Ltd. | Pyridone Carboxylic Acid Derivatives or their Salts, and Antibacterial Agents Containing the Same as Their Effective Components | Dec. 5, 2000 | Jun. 10, 1999 |

TABLE 1-continued

References Disclosing Antibiotic Compounds of the Present Invention

| PCT Publication No., U.S. patent or Publication No., or U.S. application Serial No. | Applicant or Assignee | Title | Publication or Issue Date | International or U.S. Filing Date |
|---|---|---|---|---|
| WO 1997/11068 | Wakunaga Pharmaceutical Co., Ltd. | Novel Pyridone Carboxylic Acid Derivatives or their Salts and Antibacterial Agent Comprising the Same as the Active Ingredient | Mar. 27, 1997 | Sep. 20, 1996 |
| WO 2006/015194 | Abbott Laboratories | Preparation of Pyridone Carboxylic Acid Antibacterials | Feb. 9, 2006 | Jul. 29, 2005 |
| WO 2006/042034 | Abbott Laboratories | Salt and Crystalline Forms Thereof of a Drug | Apr. 20, 2006 | Oct. 9, 2005 |
| WO 2006/110815 | Abbott Laboratories | Pharmaceutical Compositions Having Improved Dissolution Profiles for Poorly Soluble Drugs | Oct. 19, 2006 | Apr. 11, 2006 |

Exemplary compounds in accordance with the invention are listed in Table 2 with their minimum inhibitory concentrations (MICs) (μg/mL) for *S. aureus*:

TABLE 2

| Compound Number | Structure | MICs |
|---|---|---|
| 1001 | 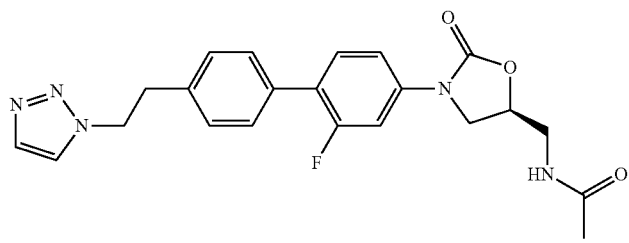 [SMILES: CC(=O)NC[C@H]1CN(c2ccc(-c3ccc(CCn4ccnn4)cc3)c(F)c2)C(=O)O1]<br>N-{3-[2-Fluoro-4'-(2-[1,2,3]triazol-1-yl-ethyl)-biphenyl-4-yl]-2-oxo-oxazolidin-5-(S)-ylmethyl}-acetamide | 2 |
| 1002 | 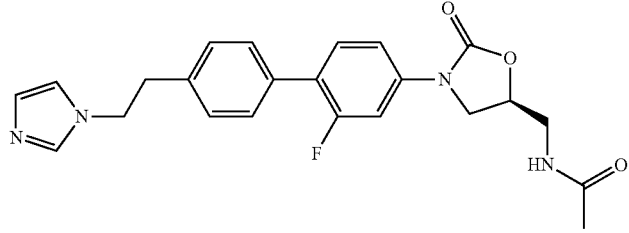 [SMILES: CC(=O)NC[C@H]1CN(c2ccc(-c3ccc(CCn4ccnc4)cc3)c(F)c2)C(=O)O1]<br>N-{3-[2-Fluoro-4'-(2-imidazol-1-yl-ethyl)-biphenyl-4-yl]-2-oxo-oxazolidin-5-(S)-ylmethyl}-acetamide | 2 |

TABLE 2-continued

| Compound Number | Structure | MICs |
|---|---|---|
| 1003 | 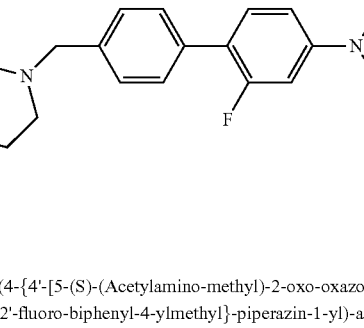<br>2-(4-{4'-[5-(S)-(Acetylamino-methyl)-2-oxo-oxazolidin-3-yl]-2'-fluoro-biphenyl-4-ylmethyl}-piperazin-1-yl)-acetamide | 2 |
| 1004 | 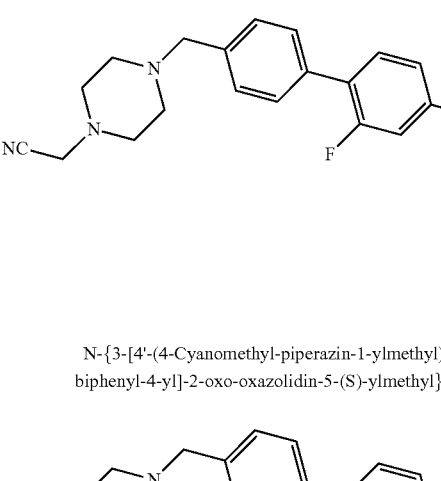<br>N-{3-[4'-(4-Cyanomethyl-piperazin-1-ylmethyl)-2-fluoro-biphenyl-4-yl]-2-oxo-oxazolidin-5-(S)-ylmethyl}-acetamide | 2 |
| 1005 | 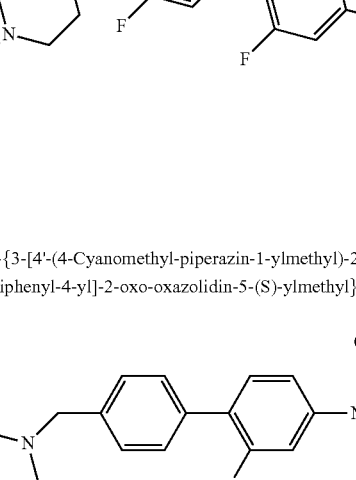<br>N-{3-[4'-(4-Cyanomethyl-piperazin-1-ylmethyl)-2,3'-difluoro-biphenyl-4-yl]-2-oxo-oxazolidin-5-(S)-ylmethyl}-acetamide | 2 |
| 1006 | 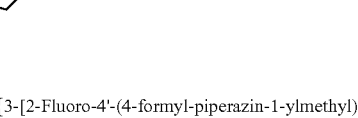<br>N-{3-[2-Fluoro-4'-(4-formyl-piperazin-1-ylmethyl)-biphenyl-4-yl]-2-oxo-oxazolidin-5-(S)-ylmethyl}-acetamide | 0.5 |

TABLE 2-continued

| Compound Number | Structure | MICs |
|---|---|---|
| 1007 | N-{3-[2-Fluoro-4'-(1H-tetrazol-5-(S)-ylmethyl)-biphenyl-4-yl]-2-oxo-oxazolidin-5-(S)-ylmethyl}-acetamide | 8 |
| 1008 | N-[3-(2-Fluoro-4'-imidazol-1-ylmethyl-biphenyl-4-yl)-2-oxo-oxazolidin-5-(S)-ylmethyl]-acetamide | 0.5 |
| 1009 | N-[3-(2,3'-Difluoro-4'-[1,2,3]triazol-1-ylmethyl-biphenyl-4-yl)-2-oxo-oxazolidin-5-(S)-ylmethyl]-acetamide | 0.25 |
| 1010 | N-[3-(2,3'-Difluoro-4'-imidazol-1-ylmethyl-biphenyl-4-yl)-2-oxo-oxazolidin-5-(S)-ylmethyl]-acetamide | 1 |

TABLE 2-continued

| Compound Number | Structure | MICs |
|---|---|---|
| 1011 | N-{3-[4'-(4-Aminomethyl-[1,2,3]triazol-1-ylmethyl)-2-fluoro-biphenyl-4-yl]-2-oxo-oxazolidin-5-(S)-ylmethyl}-acetamide | 1 |
| 1012 | N-{3-[2-Fluoro-4'-(4-methylaminomethyl-[1,2,3]triazol-1-ylmethyl)-biphenyl-4-yl]-2-oxo-oxazolidin-5-(S)-ylmethyl}-acetamide | 2 |
| 1013 | N-{3-[4'-(4-Dimethylaminomethyl-[1,2,3]triazol-1-ylmethyl)-2-fluoro-biphenyl-4-yl]-2-oxo-oxazolidin-5-(S)-ylmethyl}-acetamide | 4 |
| 1014 | N-(1-{4'-[5-(S)-(Acetylamino-methyl)-2-oxo-oxazolidin-3-yl]-2'-fluoro-biphenyl-4-ylmethyl}-1H-[1,2,3]triazol-4-ylmethyl)-2-amino-acetamide | 8 |

TABLE 2-continued

| Compound Number | Structure | MICs |
|---|---|---|
| 1015 | N-[3-(2-Fluoro-4'-[1,2,3]triazol-1-ylmethyl-biphenyl-4-yl)-2-oxo-oxazolidin-5-(S)-ylmethyl]-acetamide | 0.25 |
| 1016 | N-{3-[2-Fluoro-4'-(5-(S)-oxo-2,5-(S)-dihydro-[1,2,4]oxadiazol-3-ylmethyl)-biphenyl-4-yl]-2-oxo-oxazolidin-5-(S)-ylmethyl}-acetamide | 4 |
| 1017 | N-{3-[2-Fluoro-4'-(5-(S)-methyl-[1,2,4]oxadiazol-3-ylmethyl)-biphenyl-4-yl]-2-oxo-oxazolidin-5-(S)-ylmethyl}-acetamide | 1 |
| 1018 | N-{3-[2,6-Difluoro-4'-(4-hydroxymethyl-[1,2,3]triazol-1-ylmethyl)-biphenyl-4-yl]-2-oxo-oxazolidin-5-(S)-ylmethyl}-acetamide | 1 |

TABLE 2-continued

| Compound Number | Structure | MICs |
|---|---|---|
| 1019 | N-{3-[4'-(4-Dimethylaminomethyl-[1,2,3]triazol-1-ylmethyl)-2,6-difluoro-biphenyl-4-yl]-2-oxo-oxazolidin-5-(S)-ylmethyl}-acetamide | 2 |
| 1020 | N-[3-(2-Fluoro-4'-{2-[(tetrahydro-furan-2-ylmethyl)-amino]-thiazol-4-ylmethyl}-biphenyl-4-yl)-2-oxo-oxazolidin-5-(S)-ylmethyl]-acetamide | 1 |
| 1021 | N-(3-{2-Fluoro-4'-[2-(3-methoxy-benzylamino)-thiazol-4-ylmethyl]-biphenyl-4-yl}-2-oxo-oxazolidin-5-(S)-ylmethyl)-acetamide | 1 |
| 1022 | N-{3-[4'-(3-Cyano-azetidin-1-ylmethyl)-2-fluoro-biphenyl-4-yl]-2-oxo-oxazolidin-5-(S)-ylmethyl}-acetamide | 0.25 |

TABLE 2-continued

| Compound Number | Structure | MICs |
|---|---|---|
| 1023 | N-[3-(2-Fluoro-4'-[1,2,3]triazol-2-ylmethyl-biphenyl-4-yl)-2-oxo-oxazolidin-5-(S)-ylmethyl]-acetamide | 0.25 |
| 1024 | N-{3-[4'-(5-Amino-tetrazol-2-ylmethyl)-2-fluoro-biphenyl-4-yl]-2-oxo-oxazolidin-5-(S)-ylmethyl}-acetamide | 0.25 |
| 1025 | N-{3-[4'-(5-Amino-tetrazol-1-ylmethyl)-2-fluoro-biphenyl-4-yl]-2-oxo-oxazolidin-5-(S)-ylmethyl}-acetamide | 0.5 |
| 1026 | 1-{4'-[5-(S)-(Acetylamino-methyl)-2-oxo-oxazolidin-3-yl]-2'-fluoro-biphenyl-4-ylmethyl}-5-amino-1H-[1,2,3]triazole-4-carboxylic acid amide | 2 |

TABLE 2-continued

| Compound Number | Structure | MICs |
|---|---|---|
| 1027 | N-{3-[2-Fluoro-4'-(7-oxo-6,7-dihydro-[1,2,3]triazolo[4,5-d]pyrimidin-3-ylmethyl)-biphenyl-4-yl]-2-oxo-oxazolidin-5-(S)-ylmethyl}-acetamide | 1 |
| 1028 | N-{3-[2-Fluoro-4'-(4-hydroxymethyl-[1,2,3]triazol-1-ylmethyl)-biphenyl-4-yl]-2-oxo-oxazolidin-5-(S)-ylmethyl}-acetamide | 1 |
| 1029 | N-(3-{2-Fluoro-4'-[4-(2-hydroxy-ethyl)-piperazin-1-ylmethyl]-biphenyl-4-yl}-2-oxo-oxazolidin-5-(S)-ylmethyl)-acetamide | 2 |

TABLE 2-continued

| Compound Number | Structure | MICs |
|---|---|---|
| 1030 | N-(3-{2-Fluoro-4'-[4-(2-hydroxy-ethyl)-piperidin-1-ylmethyl]-biphenyl-4-yl}-2-oxo-oxazolidin-5-(S)-ylmethyl)-acetamide | 2 |
| 1031 | N-{3-[4'-(R)-(1-Amino-2-imidazol-1-yl-ethyl)-2-fluoro-biphenyl-4-yl]-2-oxo-oxazolidin-5-(S)-ylmethyl}-acetamide | 8 |
| 1032 | 5-(S)-Aminomethyl-3-(2-fluoro-4'-tetrazol-1-ylmethyl-biphenyl-4-yl)-oxazolidin-2-one | 32 |
| 1033 | 2-Chloro-N-[3-(2-fluoro-4'-tetrazol-1-ylmethyl-biphenyl-4-yl)-2-oxo-oxazolidin-5-(S)-ylmethyl]-acetamide | 0.25 |

TABLE 2-continued

| Compound Number | Structure | MICs |
|---|---|---|
| 1034 | 2,2-Dichloro-N-[3-(2-fluoro-4'-tetrazol-1-ylmethyl-biphenyl-4-yl)-2-oxo-oxazolidin-5-(S)-ylmethyl]-acetamide | 0.5 |
| 1035 | N-{3-[3-Fluoro-4-(6-tetrazol-1-ylmethyl-pyridin-3-yl)-phenyl]-2-oxo-oxazolidin-5-(S)-ylmethyl}-acetamide | 0.5 |
| 1036 | N-{3-[3-Fluoro-4-(6-[1,2,3]triazol-1-ylmethyl-pyridin-3-yl)-phenyl]-2-oxo-oxazolidin-5-(S)-ylmethyl}-acetamide | 1 |
| 1037 | N-[3-(2-Fluoro-4'-[1,2,4]triazol-1-ylmethyl-biphenyl-4-yl)-2-oxo-oxazolidin-5-(S)-ylmethyl]-acetamide | 0.5 |

TABLE 2-continued

| Compound Number | Structure | MICs |
|---|---|---|
| 1038 | N-(3-{4'-[4-(3-Chloro-5-trifluoromethyl-pyridin-2-yl)-piperazin-1-ylmethyl]-2-fluoro-biphenyl-4-yl}-2-oxo-oxazolidin-5-(S)-ylmethyl)-acetamide | 128 |
| 1039 | [{4'-[5-(S)-(Acetylamino-methyl)-2-oxo-oxazolidin-3-yl]-2'-fluoro-biphenyl-4-yl}-(2H-tetrazol-5-(R/S)-yl)-methyl]-carbamic acid benzyl ester | 128 |
| 1040 | N-(3-{4'-[Amino-(2H-tetrazol-5-(R/S)-yl)-methyl]-2-fluoro-biphenyl-4-yl}-2-oxo-oxazolidin-5-(S)-ylmethyl)-acetamide | 128 |

TABLE 2-continued

| Compound Number | Structure | MICs |
|---|---|---|
| 1041 | [{4'-[5-(S)-(Acetylamino-methyl)-2-oxo-oxazolidin-3-yl]-2'-fluoro-biphenyl-4-yl}-(2-methyl-2H-tetrazol-5-(R/S)-yl)-methyl]-carbamic acid benzyl ester | 1 |
| 1042 | N-(3-{4'-[Amino-(2-methyl-2H-tetrazol-5-(R/S)-yl)-methyl]-2-fluoro-biphenyl-4-yl}-2-oxo-oxazolidin-5-(S)-ylmethyl)-acetamide | 64 |
| 1043 | N-[3-(2-Fluoro-4'-pyrazol-1-ylmethyl-biphenyl-4-yl)-2-oxo-oxazolidin-5-(S)-ylmethyl]-acetamide | 0.25 |
| 1044 | N-(3-{2-Fluoro-4'-[2-(4-formyl-piperazin-1-yl)-1-(S)-hydroxy-ethyl]-biphenyl-4-yl}-2-oxo-oxazolidin-5-(S)-ylmethyl)-acetamide | 0.5 |

TABLE 2-continued

| Compound Number | Structure | MICs |
|---|---|---|
| 1045 | N-(3-{2-Fluoro-4'-[1-(R)-(4-formyl-piperazin-1-yl)-2-hydroxy-ethyl]-biphenyl-4-yl}-2-oxo-oxazolidin-5-(S)-ylmethyl)-acetamide | 0.5 |
| 1046 | N-{3-[2-Fluoro-4'-(1-(S)-hydroxy-2-imidazol-1-yl-ethyl)-biphenyl-4-yl]-2-oxo-oxazolidin-5-(S)-ylmethyl}-acetamide | 1 |
| 1047 | N-[3-(2-Fluoro-4'-tetrazol-1-ylmethyl-biphenyl-4-yl)-2-oxo-oxazolidin-5-(S)-ylmethyl]-acetamide | 0.25 |
| 1048 | N-[3-(2,6-Difluoro-4'-tetrazol-1-ylmethyl-biphenyl-4-yl)-2-oxo-oxazolidin-5-(S)-ylmethyl]-acetamide | 1 |

TABLE 2-continued

| Compound Number | Structure | MICs |
|---|---|---|
| 1049 | 1-{4'-[5-(S)-(Acetylamino-methyl)-2-oxo-oxazolidin-3-yl]-2'-fluoro-biphenyl-4-ylmethyl}-1H-pyrazole-4-carboxylic acid ethyl ester | 0.5 |
| 1050 | N-{3-[2-Fluoro-4'-(4-hydroxymethyl-imidazol-1-ylmethyl)-biphenyl-4-yl]-2-oxo-oxazolidin-5-(S)-ylmethyl}-acetamide | 2 |
| 1051 | 1-{4'-[5-(S)-(Acetylamino-methyl)-2-oxo-oxazolidin-3-yl]-2'-fluoro-biphenyl-4-ylmethyl}-1H-pyrazole-4-carboxylic acid | 1 |
| 1052 | N-{3-[2-Fluoro-4'-(4-methyl-pyrazol-1-ylmethyl)-biphenyl-4-yl]-2-oxo-oxazolidin-5-(S)-ylmethyl}-acetamide | 1 |

TABLE 2-continued

| Compound Number | Structure | MICs |
|---|---|---|
| 1053 | N-{3-[4'-(3-Amino-pyrazol-1-ylmethyl)-2-fluoro-biphenyl-4-yl]-2-oxo-oxazolidin-5-(S)-ylmethyl}-acetamide | 1 |
| 1054 | N-[3-(2-Fluoro-4'-pyrrol-1-ylmethyl-biphenyl-4-yl)-2-oxo-oxazolidin-5-(S)-ylmethyl]-acetamide | 0.5 |
| 1055 | N-{3-[2-Fluoro-4'-(3-formyl-pyrrol-1-ylmethyl)-biphenyl-4-yl]-2-oxo-oxazolidin-5-(S)-ylmethyl}-acetamide | 0.25 |
| 1056 | N-[3-(2-Fluoro-4'-tetrazol-2-ylmethyl-biphenyl-4-yl)-2-oxo-oxazolidin-5-(S)-ylmethyl]-acetamide | 0.25 |
| 1057 | 3-{4'-[5-(S)-(Acetylamino-methyl)-2-oxo-oxazolidin-3-yl]-2'-fluoro-biphenyl-4-ylmethyl}-5-amino-3H-imidazole-4-carboxylic acid amide | 1 |

TABLE 2-continued

| Compound Number | Structure | MICs |
|---|---|---|
| 1058 | N-{3-[2-Fluoro-4'-(5-methyl-tetrazol-1-ylmethyl)-biphenyl-4-yl]-2-oxo-oxazolidin-5-(S)-ylmethyl}-acetamide | 0.5 |
| 1059 | N-{3-[2-Fluoro-4'-(5-methyl-tetrazol-2-ylmethyl)-biphenyl-4-yl]-2-oxo-oxazolidin-5-(S)-ylmethyl}-acetamide | 0.5 |
| 1060 | N-(3-{2-Fluoro-4'-[1-(R)-hydroxy-2-(1H-tetrazol-5-yl)-ethyl]-biphenyl-4-yl}-2-oxo-oxazolidin-5-(S)-ylmethyl)-acetamide | 64 |
| 1061 | N-{3-[2-Fluoro-4'-(1-(S)-hydroxy-2-[1,2,3]triazol-1-yl-ethyl)-biphenyl-4-yl]-2-oxo-oxazolidin-5-(S)-ylmethyl}-acetamide | 1 |
| 1062 | N-{3-[4'-(2-Azetidin-1-yl-1-(S)-hydroxy-ethyl)-2-fluoro-biphenyl-4-yl]-2-oxo-oxazolidin-5-(S)-ylmethyl}-acetamide | 8 |

TABLE 2-continued

| Compound Number | Structure | MICs |
|---|---|---|
| 1063 | N-{3-[4'-(1-(R)-Azetidin-1-yl-2-hydroxy-ethyl)-2-fluoro-biphenyl-4-yl]-2-oxo-oxazolidin-5-(S)-ylmethyl}-acetamide | 8 |
| 1064 | N-[3-(2-Fluoro-4'-thiomorpholin-4-ylmethyl-biphenyl-4-yl)-2-oxo-oxazolidin-5-(S)-ylmethyl]-acetamide | 2 |
| 1065 | N-{3-[2-Fluoro-4'-(1-oxo-1 lambda*4*-thiomorpholin-4-ylmethyl)-biphenyl-4-yl]-2-oxo-oxazolidin-5-(S)-ylmethyl}-acetamide | 2 |
| 1066 | N-{3-[2-Fluoro-4'-(2-methyl-imidazol-1-ylmethyl)-biphenyl-4-yl]-2-oxo-oxazolidin-5-(S)-ylmethyl}-acetamide | 1 |
| 1067 | N-{3-[2-Fluoro-4'-(5-methyl-imidazol-1-ylmethyl)-biphenyl-4-yl]-2-oxo-oxazolidin-5-(S)-ylmethyl}-acetamide | 1 |

TABLE 2-continued

| Compound Number | Structure | MICs |
|---|---|---|
| 1068 | N-{3-[4'-(2,4-Dimethyl-imidazol-1-ylmethyl)-2-fluoro-biphenyl-4-yl]-2-oxo-oxazolidin-5-(S)-ylmethyl}-acetamide | 1 |
| 1069 | N-{3-[4'-(3-Amino-[1,2,4]triazol-1-ylmethyl)-2-fluoro-biphenyl-4-yl]-2-oxo-oxazolidin-5-(S)-ylmethyl}-acetamide | 1 |
| 1070 | N-[3-(2-Fluoro-4'-thiazolidin-3-ylmethyl-biphenyl-4-yl)-2-oxo-oxazolidin-5-(S)-ylmethyl]-acetamide | |
| 1071 | N-{3-[3-Fluoro-4-(6-pyrrol-1-ylmethyl-pyridin-3-yl)-phenyl]-2-oxo-oxazolidin-5-(S)-ylmethyl}-acetamide | 0.25 |
| 1072 | N-{3-[3-Fluoro-4-(6-[1,2,4]triazol-1-ylmethyl-pyridin-3-yl)-phenyl]-2-oxo-oxazolidin-5-(S)-ylmethyl}-acetamide | 1 |

TABLE 2-continued

| Compound Number | Structure | MICs |
|---|---|---|
| 1073 | N-{3-[2-Fluoro-4'-(2-hydroxy-1-(R)-[1,2,3]triazol-1-yl-ethyl)-biphenyl-4-yl]-2-oxo-oxazolidin-5-(S)-ylmethyl}-acetamide | 1 |
| 1074 | N-(3-{4'-[1-(R)-(3,3-Difluoro-piperidin-1-yl)-2-hydroxy-ethyl]-2-fluoro-biphenyl-4-yl}-2-oxo-oxazolidin-5-(S)-ylmethyl)-acetamide | 4 |
| 1075 | N-(3-{4'-[2-(3,3-Difluoro-piperidin-1-yl)-1-(S)-hydroxy-ethyl]-2-fluoro-biphenyl-4-yl}-2-oxo-oxazolidin-5-(S)-ylmethyl)-acetamide | 2 |
| 1076 | N-{3-[3-Fluoro-4-(6-pyrazol-1-ylmethyl-pyridin-3-yl)-phenyl]-2-oxo-oxazolidin-5-(S)-ylmethyl}-acetamide | 1 |

TABLE 2-continued

| Compound Number | Structure | MICs |
|---|---|---|
| 1077 | N-{3-[3-Fluoro-4-(6-imidazol-1-ylmethyl-pyridin-3-yl)-phenyl]-2-oxo-oxazolidin-5-(S)-ylmethyl}-acetamide | 4 |
| 1078 | N-{3-[2-Fluoro-4'-(2-methylsulfanyl-4,5-dihydro-imidazol-1-ylmethyl)-biphenyl-4-yl]-2-oxo-oxazolidin-5-(S)-ylmethyl}-acetamide | 2 |
| 1079 | N-{3-[2-Fluoro-4'-(5-methylsulfanyl-tetrazol-1-ylmethyl)-biphenyl-4-yl]-2-oxo-oxazolidin-5-(S)-ylmethyl}-acetamide | 2 |
| 1080 | N-{3-[2-Fluoro-4'-(5-methylsulfanyl-tetrazol-2-ylmethyl)-biphenyl-4-yl]-2-oxo-oxazolidin-5-(S)-ylmethyl}-acetamide | 0.25 |

TABLE 2-continued

| Compound Number | Structure | MICs |
|---|---|---|
| 1081 | N-{3-[4'-(5-Ethylsulfanyl-tetrazol-1-ylmethyl)-2-fluoro-biphenyl-4-yl]-2-oxo-oxazolidin-5-(S)-ylmethyl}-acetamide | 2 |
| 1082 | N-{3-[4'-(5-Ethylsulfanyl-tetrazol-2-ylmethyl)-2-fluoro-biphenyl-4-yl]-2-oxo-oxazolidin-5-(S)-ylmethyl}-acetamide | 0.5 |
| 1083 | N-{3-[4'-(5-Chloro-tetrazol-1-ylmethyl)-2-fluoro-biphenyl-4-yl]-2-oxo-oxazolidin-5-(S)-ylmethyl}-acetamide | 0.5 |
| 1084 | 3-(2-Fluoro-4'-imidazol-1-ylmethyl-biphenyl-4-yl)-5-(R)-[1,2,3]triazol-1-ylmethyl-oxazolidin-2-one | 0.25 |
| 1085 | 3-(2-Fluoro-4'-pyrazol-1-ylmethyl-biphenyl-4-yl)-5-(R)-[1,2,3]triazol-1-ylmethyl-oxazolidin-2-one | 0.5 |

TABLE 2-continued

| Compound Number | Structure | MICs |
|---|---|---|
| 1086 | N-{3-[2-Fluoro-4'-(1H-imidazol-4-ylmethyl)-biphenyl-4-yl]-2-oxo-oxazolidin-5-(S)-ylmethyl}-acetamide | 0.5 |
| 1087 | N-{3-[2-Fluoro-4'-(3-(S)-hydroxy-pyrrolidin-1-ylmethyl)-biphenyl-4-yl]-2-oxo-oxazolidin-5-(S)-ylmethyl}-acetamide | 4 |
| 1088 | N-{3-[2-Fluoro-4'-(3-(R)-hydroxy-pyrrolidin-1-ylmethyl)-biphenyl-4-yl]-2-oxo-oxazolidin-5-(S)-ylmethyl}-acetamide | 4 |
| 1089 | N-{3-[2,6-Difluoro-4'-(4-hydroxymethyl-[1,2,3]triazol-1-ylmethyl)-biphenyl-4-yl]-2-oxo-oxazolidin-5-(S)-ylmethyl}-acetamide | 1 |
| 1090 | N-[3-(4'-Azetidin-1-ylmethyl-2-fluoro-biphenyl-4-yl)-2-oxo-oxazolidin-5-(S)-ylmethyl]-acetamide | 2 |

TABLE 2-continued

| Compound Number | Structure | MICs |
|---|---|---|
| 1091 | N-{3-[4'-(3-(R)-Amino-pyrrolidin-1-ylmethyl)-2-fluoro-biphenyl-4-yl]-2-oxo-oxazolidin-5-(S)-ylmethyl}-acetamide | 2 |
| 1092 | N-{3-[4'-(3-(S)-Amino-pyrrolidin-1-ylmethyl)-2-fluoro-biphenyl-4-yl]-2-oxo-oxazolidin-5-(S)-ylmethyl}-acetamide | 4 |
| 1093 | 1-{4'-[5-(S)-(Acetylamino-methyl)-2-oxo-oxazolidin-3-yl]-2'-fluoro-biphenyl-4-ylmethyl}-pyrrolidine-3-(R/S)-carboxylic acid amide | 2 |
| 1094 | N-{3-[2-Fluoro-4'-(4-fluoro-piperidin-1-ylmethyl)-biphenyl-4-yl]-2-oxo-oxazolidin-5-(S)-ylmethyl}-acetamide | 1 |
| 1095 | N-{3-[2-Fluoro-4'-(5-fluoromethyl-2-oxo-oxazolidin-3-(R/S)ylmethyl)-biphenyl-4-yl]-2-oxo-oxazolidin-5-(S)-ylmethyl}-acetamide | 0.5 |

TABLE 2-continued
| Compound Number | Structure | MICs |
|---|---|---|
| 1096 | 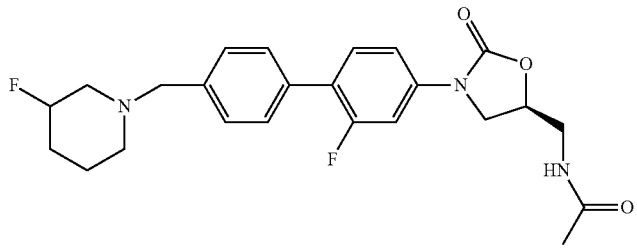 [SMILES: CC(=O)NC[C@H]1CN(c2ccc(-c3ccc(CN4CCCC(F)C4)cc3)c(F)c2)C(=O)O1] N-{3-[2-Fluoro-4'-(3-(R/S)-fluoro-piperidin-1-ylmethyl)-biphenyl-4-yl]-2-oxo-oxazolidin-5-(S)-ylmethyl}-acetamide | 1 |
| 1097 | 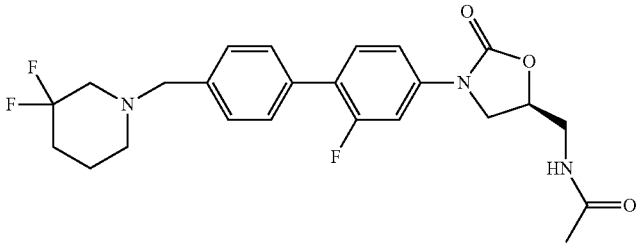 [SMILES: CC(=O)NC[C@H]1CN(c2ccc(-c3ccc(CN4CCCC(F)(F)C4)cc3)c(F)c2)C(=O)O1] N-{3-[4'-(3,3-Difluoro-piperidin-1-ylmethyl)-2-fluoro-biphenyl-4-yl]-2-oxo-oxazolidin-5-(S)-ylmethyl}-acetamide | 2 |
| 1098 | 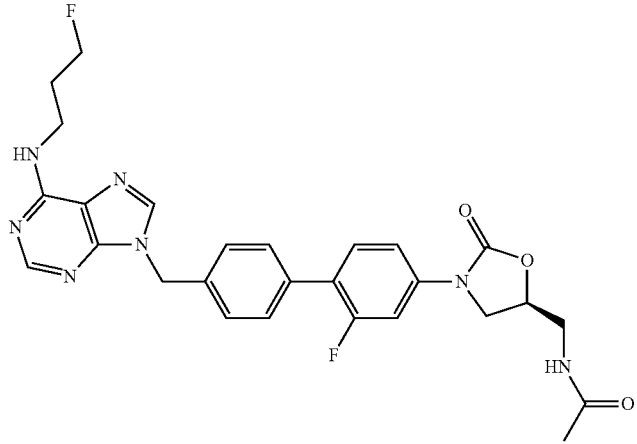 [SMILES: CC(=O)NC[C@H]1CN(c2ccc(-c3ccc(Cn4cnc5c(NCCCF)ncnc54)cc3)c(F)c2)C(=O)O1] N-(3-{2-Fluoro-4'-[6-(3-fluoro-propylamino)-purin-9-ylmethyl]-biphenyl-4-yl}-2-oxo-oxazolidin-5-(S)-ylmethyl)-acetamide | 2 |

TABLE 2-continued
| Compound Number | Structure | MICs |
|---|---|---|
| 1099 | 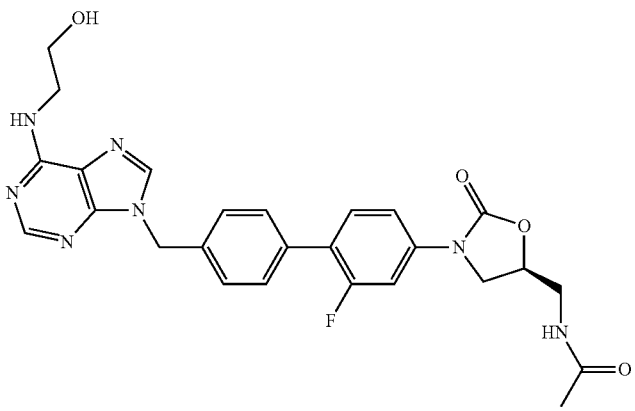 [SMILES: CC(=O)NC[C@H]1CN(c2ccc(-c3ccc(Cn4cnc5c(NCCO)ncnc54)cc3)c(F)c2)C(=O)O1]<br>N-(3-{2-Fluoro-4'-[6-(2-hydroxy-ethylamino)-purin-9-ylmethyl]-biphenyl-4-yl}-2-oxo-oxazolidin-5-(S)-ylmethyl)-acetamide | 2 |
| 1100 | 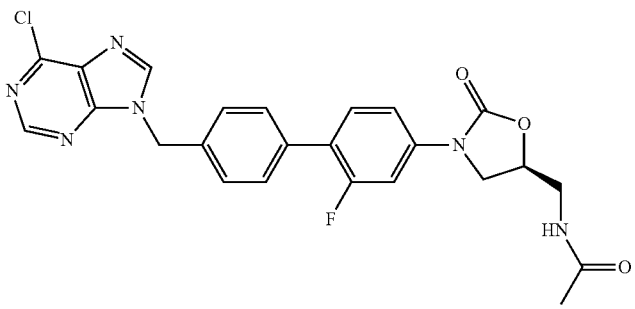 [SMILES: CC(=O)NC[C@H]1CN(c2ccc(-c3ccc(Cn4cnc5c(Cl)ncnc54)cc3)c(F)c2)C(=O)O1]<br>N-{3-[4'-(6-Chloro-purin-9-ylmethyl)-2-fluoro-biphenyl-4-yl]-2-oxo-oxazolidin-5-(S)-ylmethyl}-acetamide | 1 |
| 1101 | 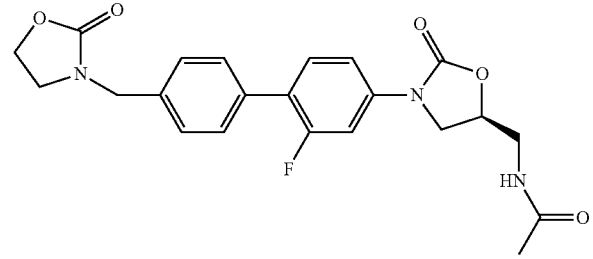 [SMILES: CC(=O)NC[C@H]1CN(c2ccc(-c3ccc(CN4CCOC4=O)cc3)c(F)c2)C(=O)O1]<br>N-{3-[2-Fluoro-4'-(2-oxo-oxazolidin-3-ylmethyl)-biphenyl-4-yl]-2-oxo-oxazolidin-5-(S)-ylmethyl}-acetamide | 0.25 |

TABLE 2-continued

| Compound Number | Structure | MICs |
|---|---|---|
| 1102 | N-(3-{2-Fluoro-4'-[6-(2-fluoro-ethylamino)-purin-9-ylmethyl]-biphenyl-4-yl}-2-oxo-oxazolidin-5-(S)-ylmethyl)-acetamide | 1 |
| 1103 | N-(3-{4'-[6-(2,2-Difluoro-ethylamino)-purin-9-ylmethyl]-2-fluoro-biphenyl-4-yl}-2-oxo-oxazolidin-5-(S)-ylmethyl)-acetamide | 1 |
| 1104 | N-(3-{2-Fluoro-4'-[6-(2,2,2-trifluoro-ethylamino)-purin-9-ylmethyl]-biphenyl-4-yl}-2-oxo-oxazolidin-5-(S)-ylmethyl)-acetamide | 1 |

TABLE 2-continued

| Compound Number | Structure | MICs |
|---|---|---|
| 1105 | N-{3-[4'-(6-Dimethylamino-purin-9-ylmethyl)-2-fluoro-biphenyl-4-yl]-2-oxo-oxazolidin-5-(S)-ylmethyl}-acetamide | 1 |
| 1106 | N-{3-[2-Fluoro-4'-(6-methylamino-purin-9-ylmethyl)-biphenyl-4-yl]-2-oxo-oxazolidin-5-(S)-ylmethyl}-acetamide | 1 |
| 1107 | N-(3-{2-Fluoro-4'-[6-(3-hydroxy-propylamino)-purin-9-ylmethyl]-biphenyl-4-yl}-2-oxo-oxazolidin-5-(S)-ylmethyl)-acetamide | 2 |
| 1108 | N-(3-{2-Fluoro-4'-[6-(2-methylsulfanyl-ethylamino)-purin-9-ylmethyl]-biphenyl-4-yl}-2-oxo-oxazolidin-5-(S)-ylmethyl)-acetamide | 2 |

TABLE 2-continued

| Compound Number | Structure | MICs |
|---|---|---|
| 1109 | 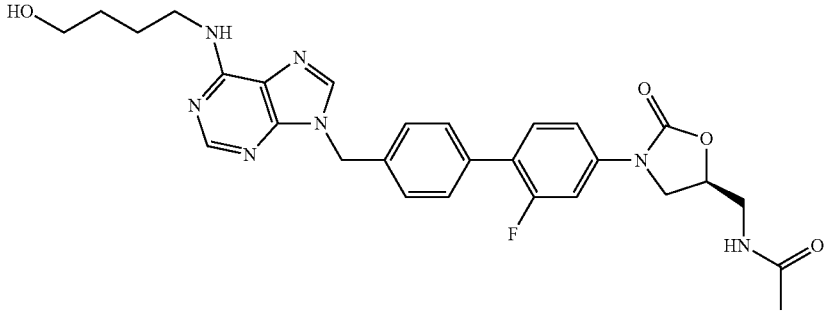 [SMILES: CC(=O)NC[C@H]1CN(c2ccc(-c3ccc(Cn4cnc5c(NCCCCO)ncnc54)cc3)c(F)c2)C(=O)O1] N-(3-{2-Fluoro-4'-[6-(4-hydroxy-butylamino)-purin-9-ylmethyl]-biphenyl-4-yl}-2-oxo-oxazolidin-5-(S)-ylmethyl)-acetamide | 2 |
| 1110 | 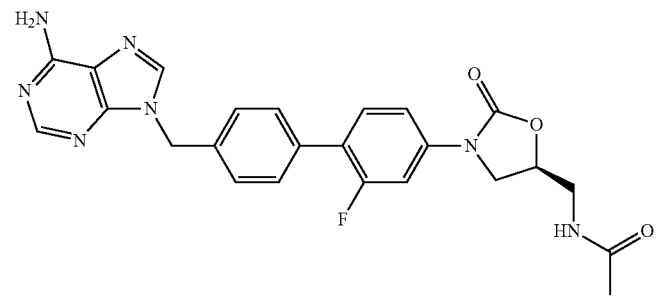 [SMILES: CC(=O)NC[C@H]1CN(c2ccc(-c3ccc(Cn4cnc5c(N)ncnc54)cc3)c(F)c2)C(=O)O1] N-{3-[4'-(6-Amino-purin-9-ylmethyl)-2-fluoro-biphenyl-4-yl]-2-oxo-oxazolidin-5-(S)-ylmethyl}-acetamide | 1 |
| 1111 | 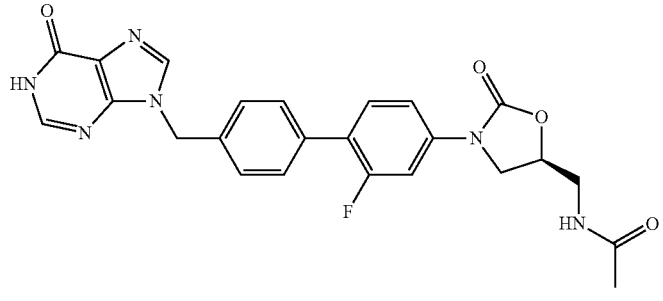 [SMILES: CC(=O)NC[C@H]1CN(c2ccc(-c3ccc(Cn4cnc5c(=O)[nH]cnc54)cc3)c(F)c2)C(=O)O1] N-{3-[2-Fluoro-4'-(6-oxo-1,6-dihydro-purin-9-ylmethyl)-biphenyl-4-yl]-2-oxo-oxazolidin-5-(S)-ylmethyl}-acetamide | 2 |
| 1112 | 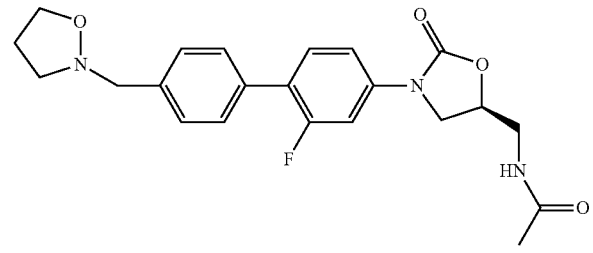 [SMILES: CC(=O)NC[C@H]1CN(c2ccc(-c3ccc(CN4CCCO4)cc3)c(F)c2)C(=O)O1] N-[3-(2-Fluoro-4'-isoxazolidin-2-ylmethyl-biphenyl-4-yl)-2-oxo-oxazolidin-5-(S)-ylmethyl]-acetamide | 1 |

TABLE 2-continued

| Compound Number | Structure | MICs |
|---|---|---|
| 1113 | N-{3-[4'-(2-Amino-imidazol-1-ylmethyl)-2-fluoro-biphenyl-4-yl]-2-oxo-oxazolidin-5-(S)-ylmethyl}-acetamide | 2 |
| 1114 | N-{3-[2-Fluoro-4'-(7-oxo-4,5-dihydro-[1,2,3]triazolo[1,5-c]pyrimidin-6-ylmethyl)-biphenyl-4-yl]-2-oxo-oxazolidin-5-(S)-ylmethyl}-acetamide | |
| 1115 | N-[3-(2-Fluoro-4'-pyrrolidin-1-ylmethyl-biphenyl-4-yl)-2-oxo-oxazolidin-5-(S)-ylmethyl]-acetamide | |
| 1116 | N-[3-(2-Fluoro-4'-piperidin-1-ylmethyl-biphenyl-4-yl)-2-oxo-oxazolidin-5-(S)-ylmethyl]-acetamide | |

TABLE 2-continued

| Compound Number | Structure | MICs |
|---|---|---|
| 1117 | N-{3-[2-Fluoro-4'-(1-(S)-hydroxy-2-morpholin-4-yl-ethyl)-biphenyl-4-yl]-2-oxo-oxazolidin-5-(S)-ylmethyl}-acetamide | |
| 1118 | N-{3-[2-Fluoro-4'-(2-hydroxy-1-(R)-morpholin-4-yl-ethyl)-biphenyl-4-yl]-2-oxo-oxazolidin-5-(S)-ylmethyl}-acetamide | |
| 1119 | (1-{4'-[5-(S)-(Acetylamino-methyl)-2-oxo-oxazolidin-3-yl]-2'-fluoro-biphenyl-4-ylmethyl}-pyrrolidin-3-(R)-yl)-carbamic acid tert-butyl ester | |
| 1120 | (1-{4'-[5-(S)-(Acetylamino-methyl)-2-oxo-oxazolidin-3-yl]-2'-fluoro-biphenyl-4-ylmethyl}-pyrrolidin-3-(S)-yl)-carbamic acid tert-butyl ester | |

TABLE 2-continued

| Compound Number | Structure | MICs |
|---|---|---|
| 1121 | 1-{4'-[5-(S)-(Acetylamino-methyl)-2-oxo-oxazolidin-3-yl]-2'-fluoro-biphenyl-4-ylmethyl}-piperidine-3-(R/S)-carboxylic acid amide | |
| 1122 | 1-{4'-[5-(S)-(Acetylamino-methyl)-2-oxo-oxazolidin-3-yl]-2'-fluoro-biphenyl-4-ylmethyl}-pyrrolidine-2-(S)-carboxylic acid amide | |
| 1123 | N-{3-[2-Fluoro-4'-(3-oxo-piperazin-1-ylmethyl)-biphenyl-4-yl]-2-oxo-oxazolidin-5-(S)-ylmethyl}-acetamide | |
| 1124 | N-{3 [4'-(2,2-Dimethyl-4-oxo-imidazolidin-1-ylmethyl)-2-fluoro-biphenyl-4-yl]-2-oxo-oxazolidin-5-(S)-ylmethyl}-acetamide | |

TABLE 2-continued

| Compound Number | Structure | MICs |
|---|---|---|
| 1125 | 1-{4'[5-(S)-(Acetylamino-methyl)-2-oxo-oxazolidin-3-yl]-2'-fluoro-biphenyl-4-ylmethyl}-azetidine-3-(R/S)-carboxylic acid amide | |
| 1126 | 1-{4'-[5-(Acetylamino-methyl)-2-oxo-oxazolidin-3-yl]-2'-fluoro-biphenyl-4-ylmethyl}-azetidine-2-carboxylic acid amide | |
| 1127 | N-{3-[2-Fluoro-4'-(2-oxo-piperazin-1-ylmethyl)-biphenyl-4-yl]-2-oxo-oxazolidin-5-(S)-ylmethyl}-acetamide | |
| 1128 | 2-(4-{4'-[5-(S)-(Acetylamino-methyl)-2-oxo-oxazolidin-3-yl]-2'-fluoro-biphenyl-4-ylmethyl}-3-oxo-piperazin-1-yl)-acetamide | |

TABLE 2-continued

| Compound Number | Structure | MICs |
|---|---|---|
| 1129 | N-{3-[4'-(4-Cyanomethyl-2-oxo-piperazin-1-ylmethyl)-2-fluoro-biphenyl-4-yl]-2-oxo-oxazolidin-5-(S)-ylmethyl}-acetamide | |
| 1130 | N-{3-[2-Fluoro-4'-(2-oxo-4-[1,2,3]thiadiazol-4-ylmethyl-piperazin-1-ylmethyl)-biphenyl-4-yl]-2-oxo-oxazolidin-5-(S)-ylmethyl}-acetamide | |
| 2001 | N-{3-[2-Fluoro-4'-(5-methyl-isoxazol-3-yloxymethyl)-biphenyl-4-yl]-2-oxo-oxazolidin-5-(S)-ylmethyl}-acetamide | |
| 2002 | N-{3-[2-Fluoro-4'-([1,2,4]triazol-4-ylaminomethyl)-biphenyl-4-yl]-2-oxo-oxazolidin-5-(S)-ylmethyl}-acetamide | |

TABLE 2-continued

| Compound Number | Structure | MICs |
|---|---|---|
| 2003 | N-(3-{2-Fluoro-4'-[(3-methyl-isoxazol-5-ylamino)-methyl]-biphenyl-4-yl}-2-oxo-oxazolidin-5-(S)-ylmethyl)-acetamide | |
| 2004 | N-(3-{2-Fluoro-4'-[(5-methyl-isoxazol-3-ylamino)-methyl]-biphenyl-4-yl}-2-oxo-oxazolidin-5-(S)-ylmethyl)-acetamide | |
| 2005 | 4-({4'-[5-(S)-(Acetylamino-methyl)-2-oxo-oxazolidin-3-yl]-2'-fluoro-biphenyl-4-ylmethyl}-amino)-piperidine-1-carboxylic acid ethyl ester | |
| 2006 | N-(3-{4'-[(1-Aza-bicyclo[2.2.2]oct-3-ylamino)-methyl]-2-fluoro-biphenyl-4-yl}-2-oxo-oxazolidin-5-(S)-ylmethyl)-acetamide | |

TABLE 2-continued

| Compound Number | Structure | MICs |
|---|---|---|
| 2007 | 2-({4'-[5-(S)-(Acetylamino-methyl)-2-oxo-oxazolidin-3-yl]-2'-fluoro-biphenyl-4-ylmethyl}-amino)-benzamide | |
| 2008 | 2-({4'-[5-(S)-(Acetylamino-methyl)-2-oxo-oxazolidin-3-yl]-2'-fluoro-biphenyl-4-ylmethyl}-amino)-thiophene-3-carboxylic acid amide | |
| 2009 | N-(3-{2-Fluoro-4'-[(3-oxo-isoxazolidin-4-(R)-ylamino)-methyl]-biphenyl-4-yl}-2-oxo-oxazolidin-5-(S)-ylmethyl)-acetamide | |
| 2010 | N-(3-{2-Fluoro-4'-[(3-oxo-isoxazolidin-4-(S)-ylamino)-methyl]-biphenyl-4-yl}-2-oxo-oxazolidin-5-(S)-ylmethyl)-acetamide | |

TABLE 2-continued

| Compound Number | Structure | MICs |
|---|---|---|
| 2011 | N-{3-[4'-(Azetidin-3-(R/S)-ylaminomethyl)-2-fluoro-biphenyl-4-yl]-2-oxo-oxazolidin-5-(S)-ylmethyl}-acetamide | 8 |
| 2012 | N-(3-{4'-[(3-Aminomethyl-[1,2,4]thiadiazol-5-ylamino)-methyl]-2-fluoro-biphenyl-4-yl}-2-oxo-oxazolidin-5-(S)-ylmethyl)-acetamide | 1 |
| 2013 | N-[5-({4'[5-(S)-(Acetylamino-methyl)-2-oxo-oxazolidin-3-yl]-2'-fluoro-biphenyl-4-ylmethyl}-amino)-[1,2,4]thiadiazol-3-ylmethyl]-2-(S)-amino-propionamide | 1 |
| 2014 | 2,6-Diamino-hexanoic acid [5-({4'-[5-(acetylamino-methyl)-2-oxo-oxazolidin-3-yl]-2'-fluoro-biphenyl-4-ylmethyl}-amino)-[1,2,4]thiadiazol-3-ylmethyl]-amide | 2 |

TABLE 2-continued

| Compound Number | Structure | MICs |
|---|---|---|
| 2015 | N-{3-[2-Fluoro-4'-(1-methyl-1H-tetrazol-5-ylsulfanylmethyl)-biphenyl-4-yl]-2-oxo-oxazolidin-5-(S)-ylmethyl}-acetamide | 0.25 |
| 2016 | N-{3-[2-Fluoro-4'-(3H-[1,2,3]triazol-4-ylsulfanylmethyl)-biphenyl-4-yl]-2-oxo-oxazolidin-5-(S)-ylmethyl}-acetamide | 0.25 |
| 2017 | N-{3-[4'-(4,6-Dioxo-1,4,5,6-tetrahydro-pyrimidin-2-ylsulfanylmethyl)-2-fluoro-biphenyl-4-yl]-2-oxo-oxazolidin-5-(S)-ylmethyl}-acetamide | 16 |
| 2018 | N-{3-[2-Fluoro-4'-(pyridin-2-ylsulfanylmethyl)-biphenyl-4-yl]-2-oxo-oxazolidin-5-(S)-ylmethyl}-acetamide | 0.25 |

TABLE 2-continued

| Compound Number | Structure | MICs |
|---|---|---|
| 2019 | N-{3-[2-Fluoro-4'-(pyridin-4-ylsulfanylmethyl)-biphenyl-4-yl]-2-oxo-oxazolidin-5-(S)-ylmethyl}-acetamide | 1 |
| 2020 | N-{3-[2-Fluoro-4'-(1-methyl-1H-tetrazole-5-sulfinylmethyl)-biphenyl-4-yl]-2-oxo-oxazolidin-5-(S)-ylmethyl}-acetamide | 0.25 |
| 2021 | N-{3-[2-Fluoro-4'-(3H-[1,2,3]triazole-4-sulfinylmethyl)-biphenyl-4-yl]-2-oxo-oxazolidin-5-(S)-ylmethyl}-acetamide | 2 |
| 2022 | N-{3-[2-Fluoro-4'-(pyridine-4-sulfinylmethyl)-biphenyl-4-yl]-2-oxo-oxazolidin-5-(S)-ylmethyl}-acetamide | 2 |
| 2023 | N-{3-[2-Fluoro-4'-(pyridine-2-sulfinylmethyl)-biphenyl-4-yl]-2-oxo-oxazolidin-5-(S)-ylmethyl}-acetamide | 1 |

TABLE 2-continued

| Compound Number | Structure | MICs |
|---|---|---|
| 2024 | N-{3-[2-Fluoro-4'-(1-methyl-1H-tetrazole-5-sulfonylmethyl)-biphenyl-4-yl]-2-oxo-oxazolidin-5-(S)-ylmethyl}-acetamide | 0.25 |
| 2025 | N-{3-[2-Fluoro-4'-(3H-[1,2,3]triazole-4-sulfonylmethyl)-biphenyl-4-yl]-2-oxo-oxazolidin-5-(S)-ylmethyl}-acetamide | 8 |
| 2026 | N-(3-{2-Fluoro-4'-[2-(3H-[1,2,3]triazol-4-ylsulfanyl)-ethyl]-biphenyl-4-yl}-2-oxo-oxazolidin-5-(S)-ylmethyl)-acetamide | 0.25 |
| 2027 | N-(3-{4'-[1-(2-Dimethylamino-ethyl)-1H-tetrazol-5-ylsulfanylmethyl]-2-fluoro-biphenyl-4-yl}-2-oxo-oxazolidin-5-(S)-ylmethyl)-acetamide | 1 |

TABLE 2-continued

| Compound Number | Structure | MICs |
|---|---|---|
| 2028 | N-{3-[4'-(5-Amino-4H-[1,2,4]triazol-3-ylsulfanylmethyl)-2-fluoro-biphenyl-4-yl]-2-oxo-oxazolidin-5-(S)-ylmethyl}-acetamide | 0.25 |
| 2029 | N-{3-[2-Fluoro-4'-([1,3,4]thiadiazol-2-ylsulfanylmethyl)-biphenyl-4-yl]-2-oxo-oxazolidin-5-(S)-ylmethyl}-acetamide | 0.25 |
| 2030 | N-{3-[2-Fluoro-4'-(thiazol-2-ylsulfanylmethyl)-biphenyl-4-yl]-2-oxo-oxazolidin-5-(S)-ylmethyl}-acetamide | 1 |
| 2031 | N-{3-[2-Fluoro-4'-(4-methyl-thiazol-2-ylsulfanylmethyl)-biphenyl-4-yl]-2-oxo-oxazolidin-5-(S)-ylmethyl}-acetamide | 1 |
| 2032 | N-{3-[2-Fluoro-4'-(1H-imidazol-2-ylsulfanylmethyl)-biphenyl-4-yl]-2-oxo-oxazolidin-5-(S)-ylmethyl}-acetamide | 1 |

TABLE 2-continued

| Compound Number | Structure | MICs |
|---|---|---|
| 2033 | N-{3-[2-Fluoro-4'-(2-methyl-2H-[1,2,4]triazol-3-ylsulfanylmethyl)-biphenyl-4-yl]-2-oxo-oxazolidin-5-(S)-ylmethyl}-acetamide | 1 |
| 2034 | N-{3-[2-Fluoro-4'-(2-methyl-2H-[1,2,4]triazol-3-ylsulfanylmethyl)-biphenyl-4-yl]-2-oxo-oxazolidin-5-(S)-ylmethyl}-acetamide | 2 |
| 2035 | N-{3-[2-Fluoro-4'-([1,3,4]thiadiazole-2-sulfinylmethyl)-biphenyl-4-yl]-2-oxo-oxazolidin-5-(S)-ylmethyl}-acetamide | 1 |
| 2036 | N-{3-[2-Fluoro-4'-(thiazole-2-sulfinylmethyl)-biphenyl-4-yl]-2-oxo-oxazolidin-5-(S)-ylmethyl}-acetamide | 1 |

TABLE 2-continued

| Compound Number | Structure | MICs |
|---|---|---|
| 2037 | N-{3-[2-Fluoro-4'-(4-methyl-thiazole-2-sulfinylmethyl)-biphenyl-4-yl]-2-oxo-oxazolidin-5-(S)-ylmethyl}-acetamide | 1 |
| 2038 | N-{3-[2-Fluoro-4'-(1H-imidazole-2-sulfinylmethyl)-biphenyl-4-yl]-2-oxo-oxazolidin-5-(S)-ylmethyl}-acetamide | 2 |
| 2039 | N-{3-[2-Fluoro-4'-(2-methyl-2H-[1,2,4]triazole-3-sulfinylmethyl)-biphenyl-4-yl]-2-oxo-oxazolidin-5-(S)-ylmethyl}-acetamide | 2 |
| 2040 | N-(3-{3-Fluoro-4-[6-(3H-[1,2,3]triazol-4-ylsulfanylmethyl)-pyridin-3-yl]-phenyl}-2-oxo-oxazolidin-5-(S)-ylmethyl)-acetamide | 0.25 |

TABLE 2-continued

| Compound Number | Structure | MICs |
|---|---|---|
| 2041 | N-{3-[2-Fluoro-4'-(pyridin-2-yl-hydrazonomethyl)-biphenyl-4-yl]-2-oxo-oxazolidin-5-(S)-ylmethyl}-acetamide | 1 |
| 2042 | N-(3-{2-Fluoro-4'-[(4-trifluoromethyl-pyrimidin-2-yl)-hydrazonomethyl]-biphenyl-4-yl}-2-oxo-oxazolidin-5-(S)-ylmethyl)-acetamide | 128 |
| 2043 | N-(3-{2-Fluoro-4'-[(1-methyl-1H-imidazole-4-sulfonylamino)-methyl]-biphenyl-4-yl}-2-oxo-oxazolidin-5-(S)-ylmethyl)-acetamide | 2 |
| 2044 | N-(3-{2-Fluoro-4'-[(6-morpholin-4-yl-pyridine-3-sulfonylamino)-methyl]-biphenyl-4-yl}-2-oxo-oxazolidin-5-(S)-ylmethyl)-acetamide | 128 |

TABLE 2-continued

| Compound Number | Structure | MICs |
|---|---|---|
| 2045 | N-{3-[2-Fluoro-4'-(pyridin-3-ylsulfamoylmethyl)-biphenyl-4-yl]-2-oxo-oxazolidin-5-(S)-ylmethyl}-acetamide | 2 |
| 2046 | N-{3-[2-Fluoro-4'-([1,2,4]triazol-4-ylaminomethyl)-biphenyl-4-yl]-2-oxo-oxazolidin-5-(S)-ylmethyl}-acetamide | 1 |
| 2047 | N-{3-[2-Fluoro-4'-(2H-[1,2,4]triazol-3-ylsulfanylmethyl)-biphenyl-4-yl]-2-oxo-oxazolidin-5-(S)-ylmethyl}-acetamide | 0.25 |
| 2048 | N-{3-[2-Fluoro-4'-(N'-pyridin-2-yl-hydrazinomethyl)-biphenyl-4-yl]-2-oxo-oxazolidin-5-(S)-ylmethyl}-acetamide | 0.5 |

TABLE 2-continued

| Compound Number | Structure | MICs |
|---|---|---|
| 2049 | N-(3-{4'-[N'-(4,5-Dihydro-1H-imidazol-2-yl)-hydrazinomethyl]-2-fluoro-biphenyl-4-yl}-2-oxo-oxazolidin-5-(S)-ylmethyl)-acetamide | 2 |
| 2050 | N-{3-[2-Fluoro-4'-(isoxazol-3-ylaminomethyl)-biphenyl-4-yl]-2-oxo-oxazolidin-5-(S)-ylmethyl}-acetamide | 0.25 |
| 2051 | N-(3-{2-Fluoro-4'-[(quinoline-8-sulfonylamino)-methyl]-biphenyl-4-yl}-2-oxo-oxazolidin-5-(S)-ylmethyl)-acetamide | 4 |
| 2052 | N-(3-{2-Fluoro-4'-[(1-methyl-1H-imidazole-4-sulfonylamino)-methyl]-biphenyl-4-yl}-2-oxo-oxazolidin-5-(S)-ylmethyl)-acetamide | 2 |

TABLE 2-continued

| Compound Number | Structure | MICs |
|---|---|---|
| 2053 | N-(3-{2-Fluoro-4'-[(6-morpholin-4-yl-pyridine-3-sulfonylamino)-methyl]-biphenyl-4-yl}-2-oxo-oxazolidin-5-(S)-ylmethyl)-acetamide | 128 |
| 2054 | N-{3-[2-Fluoro-4'-pyridin-3-ylsulfamoylmethyl)-biphenyl-4-yl]2-oxo-oxazolidin-5-(S)-ylmethyl}acetamide | 2 |
| 2055 | 5-({4'-[5-(S)-(Acetylamino-methyl)-2-oxo-oxazolidin-3-yl]-2'-fluoro-biphenyl-4-ylmethyl}-amino)-3H-imidazole-4-carboxylic acid amide | 4 |
| 2056 | N-{3-[2-Fluoro-4'-(morpholin-4-yliminomethyl)-biphenyl-4-yl]-2-oxo-oxazolidin-5-(S)-ylmethyl}-acetamide | 0.25 |

TABLE 2-continued

| Compound Number | Structure | MICs |
|---|---|---|
| 2057 | N-(3-{2-Fluoro-4'-[(4-methyl-piperazin-1-ylamino)-methyl]-biphenyl-4-yl}-2-oxo-oxazolidin-5-(S)-ylmethyl)-acetamide | 1 |
| 2058 | N-(3-{2-Fluoro-4'-[(4-trifluoromethyl-benzenesulfonylamino)-methyl]-biphenyl-4-yl}-2-oxo-oxazolidin-5-(S)-ylmethyl)-acetamide | 32 |
| 2059 | N-(3-{2-Fluoro-4'-[(2-oxo-piperidin-3-(S)-ylamino)-methyl]-biphenyl-4-yl}-2-oxo-oxazolidin-5-(S)-ylmethyl)-acetamide | 2 |
| 3001 | N-{3-[2-Fluoro-4'-(pyridin-4-ylmethylsulfanyl)-biphenyl-4-yl]-2-oxo-oxazolidin-5-(S)-ylmethyl}-acetamide | 1 |

TABLE 2-continued

| Compound Number | Structure | MICs |
|---|---|---|
| 3002 | N-{3-[2-Fluoro-4'-(pyridin-4-ylmethanesulfinyl)-biphenyl-4-yl]-2-oxo-oxazolidin-5-(S)-ylmethyl}-acetamide | 1 |
| 3003 | N-{3-[2-Fluoro-4'-(pyridin-4-ylmethanesulfonyl)-biphenyl-4-yl]-2-oxo-oxazolidin-5-(S)-ylmethyl}-acetamide | 2 |
| 3004 | N-{3-[2-Fluoro-4'-(1-oxy-pyridin-4-ylmethanesulfonyl)-biphenyl-4-yl]-2-oxo-oxazolidin-5-(S)-ylmethyl}-acetamide | 4 |
| 3005 | N-(3-{2-Fluoro-4'-[(pyridin-4-ylmethyl)-sulfamoyl]-biphenyl-4-yl}-2-oxo-oxazolidin-5-(S)-ylmethyl)-acetamide | 2 |
| 3006 | N-(3-{2-Fluoro-4'-[(pyridin-2-ylmethyl)-sulfamoyl]-biphenyl-4-yl}-2-oxo-oxazolidin-5-(S)-ylmethyl)-acetamide | 16 |

TABLE 2-continued

| Compound Number | Structure | MICs |
|---|---|---|
| 3007 | N-{3-[2-Fluoro-4'-(2-pyridin-2-yl-ethylsulfamoyl)-biphenyl-4-yl]-2-oxo-oxazolidin-5-(S)-ylmethyl}-acetamide | 1 |
| 4001 | N-{4'-[5-(S)-(Acetylamino-methyl)-2-oxo-oxazolidin-3-yl]-2'-fluoro-biphenyl-4-ylmethyl}-3-(6-methyl-2,4-dioxo-1,2,3,4-tetrahydro-pyrimidin-5-yl)-acrylamide | 0.25 |
| 4002 | N-{4'-[5-(S)-(Acetylamino-methyl)-2-oxo-oxazolidin-3-yl]-2'-fluoro-biphenyl-4-ylmethyl}-3-pyridin-3-yl-acrylamide | 4 |
| 4003 | N-{4'-[5-(S)-(Acetylamino-methyl)-2-oxo-oxazolidin-3-yl]-2'-fluoro-biphenyl-4-ylmethyl}-3-(2,4-dimethoxy-6-methyl-pyrimidin-5-yl)-acrylamide | 128 |

TABLE 2-continued

| Compound Number | Structure | MICs |
|---|---|---|
| 4004 | N-{4'-[5-(S)-(Acetylamino-methyl)-2-oxo-oxazolidin-3-yl]-2'-fluoro-biphenyl-4-ylmethyl}-3-(4-hydroxy-2-methoxy-6-methyl-pyrimidin-5-yl)-acrylamide | 2 |
| 4005 | N-{4'-[5-(S)-(Acetylamino-methyl)-2-oxo-oxazolidin-3-yl]-2'-fluoro-biphenyl-4-ylmethyl}-3-(1,3-dimethyl-2,4-dioxo-1,2,3,4-tetrahydro-pyrimidin-5-yl)-acrylamide | 2 |
| 4006 | N-{4'-[5-(S)-(Acetylamino-methyl)-2-oxo-oxazolidin-3-yl]-2'-fluoro-biphenyl-4-ylmethyl}-3-pyrimidin-5-yl-acrylamide | 8 |

TABLE 2-continued

| Compound Number | Structure | MICs |
|---|---|---|
| 4007 | N-{4'-[5-(S)-(Acetylamino-methyl)-2-oxo-oxazolidin-3-yl]-2'-fluoro-biphenyl-4-ylmethyl}-3-(1-methyl-6-oxo-1,6-dihydro-pyrimidin-5-yl)-acrylamide | 1 |
| 4008 | Quinoline-4-carboxylic acid {4'-[5-(S)-(acetylamino-methyl)-2-oxo-oxazolidin-3-yl]-2'-fluoro-biphenyl-4-ylmethyl}-amide | 1 |
| 4009 | Quinoline-3-carboxylic acid {4'-[5-(S)-(acetylamino-methyl)-2-oxo-oxazolidin-3-yl]-2'-fluoro-biphenyl-4-ylmethyl}-amide | 32 |

TABLE 2-continued

| Compound Number | Structure | MICs |
|---|---|---|
| 4010 | 1-Methyl-1H-pyrrole-2-carboxylic acid {4'-[5-(S)-(acetylamino-methyl)-2-oxo-oxazolidin-3-yl]-2'-fluoro-biphenyl-4-ylmethyl}-amide | 1 |
| 4011 | 1H-Indole-6-carboxylic acid {4'-[5-(S)-(acetylamino-methyl)-2-oxo-oxazolidin-3-yl]-2'-fluoro-biphenyl-4-ylmethyl}-amide | 1 |
| 4012 | N-{4'-[5-(S)-(Acetylamino-methyl)-2-oxo-oxazolidin-3-yl]-2'-fluoro-biphenyl-4-ylmethyl}-3-methanesulfonyl-benzamide | 4 |

TABLE 2-continued

| Compound Number | Structure | MICs |
|---|---|---|
| 4013 | N-{4'-[5-(S)-(Acetylamino-methyl)-2-oxo-oxazolidin-3-yl]-2'-fluoro-biphenyl-4-ylmethyl}-4-fluoro-benzamide | 8 |
| 4014 | Benzo[1,3]dioxole-5-carboxylic acid {4'-[5-(S)-(acetylamino-methyl)-2-oxo-oxazolidin-3-yl]-2'-fluoro-biphenyl-4-ylmethyl}-amide | 4 |
| 4015 | 5-Methoxy-1H-indole-2-carboxylic acid {4'-[5-(S)-(acetylamino-methyl)-2-oxo-oxazolidin-3-yl]-2'-fluoro-biphenyl-4-ylmethyl}-amide | 4 |

TABLE 2-continued

| Compound Number | Structure | MICs |
|---|---|---|
| 4016 | 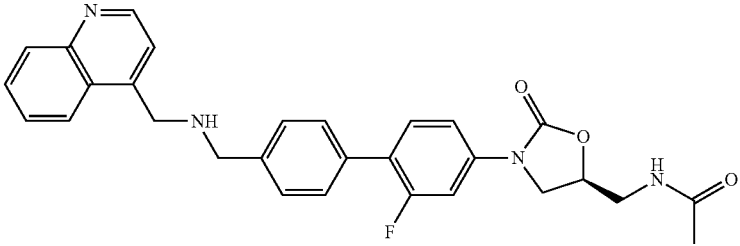 [SMILES: CC(=O)NC[C@H]1CN(c2ccc(-c3ccc(CNCc4ccnc5ccccc45)cc3)c(F)c2)C(=O)O1]<br>N-[3-(2-Fluoro-4'-{[(quinolin-4-ylmethyl)-amino]-methyl}-biphenyl-4-yl)-2-oxo-oxazolidin-5-(S)-ylmethyl]-acetamide | 1 |
| 4017 | 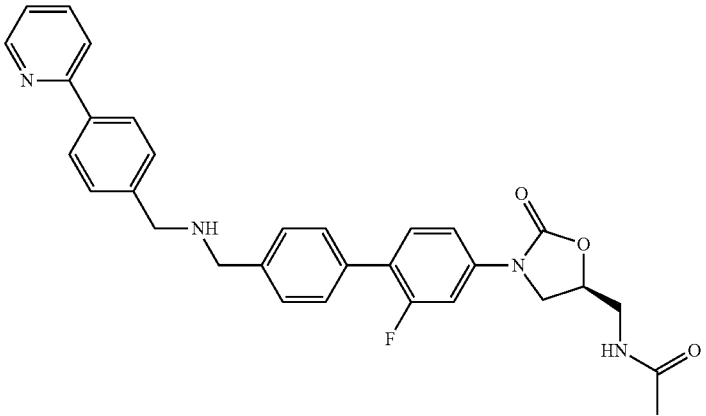 [SMILES: CC(=O)NC[C@H]1CN(c2ccc(-c3ccc(CNCc4ccc(-c5ccccn5)cc4)cc3)c(F)c2)C(=O)O1]<br>N-(3-{2-Fluoro-4'-[(4-pyridin-2-yl-benzylamino)-methyl]-biphenyl-4-yl}-2-oxo-oxazolidin-5-(S)-ylmethyl)-acetamide | 2 |
| 4018 | 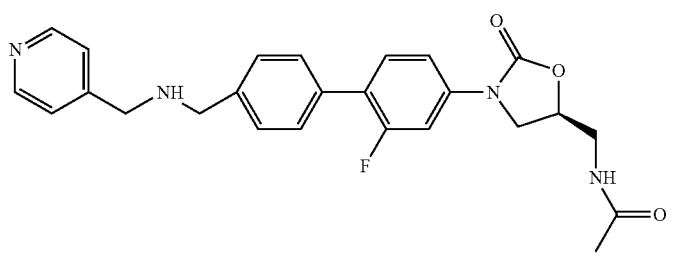 [SMILES: CC(=O)NC[C@H]1CN(c2ccc(-c3ccc(CNCc4ccncc4)cc3)c(F)c2)C(=O)O1]<br>N-[3-(2-Fluoro-4'-{[(pyridin-4-ylmethyl)-amino]-methyl}-biphenyl-4-yl)-2-oxo-oxazolidin-5-(S)-ylmethyl]-acetamide | 1 |
| 4019 | 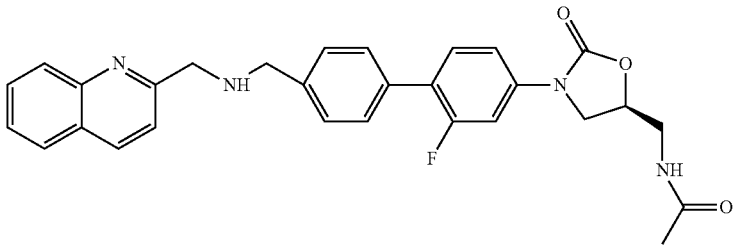 [SMILES: CC(=O)NC[C@H]1CN(c2ccc(-c3ccc(CNCc4ccc5ccccc5n4)cc3)c(F)c2)C(=O)O1]<br>N-[3-(2-Fluoro-4'-{[(quinolin-2-ylmethyl)-amino]-methyl}-biphenyl-4-yl)-2-oxo-oxazolidin-5-(S)-ylmethyl]-acetamide | 0.5 |

TABLE 2-continued

| Compound Number | Structure | MICs |
|---|---|---|
| 4020 | N-[3-(4'-{[[Benzofuran-2-ylmethyl)-amino]-methyl}-2-fluoro-biphenyl-4-yl)-2-oxo-oxazolidin-5-(S)-ylmethyl]-acetamide | 2 |
| 4021 | N-[3-(2-Fluoro-4'-{[(quinolin-3-ylmethyl)-amino]-methyl}-biphenyl-4-yl)-2-oxo-oxazolidin-5-(S)-ylmethyl]-acetamide | 0.25 |
| 4022 | N-[3-(2-Fluoro-4'-{[(naphthalen-1-ylmethyl)-amino]-methyl}-biphenyl-4-yl)-2-oxo-oxazolidin-5-(S)-ylmethyl]-acetamide | 4 |
| 4023 | N-[3-(2-Fluoro-4'-{[(furan-3-ylmethyl)-amino]-methyl}-biphenyl-4-yl)-2-oxo-oxazolidin-5-(S)-ylmethyl]-acetamide | 1 |

TABLE 2-continued

| Compound Number | Structure | MICs |
|---|---|---|
| 4024 | N-[3-(2-Fluoro-4'-{[(pyridin-2-ylmethyl)-amino]-methyl}-biphenyl-4-yl)-2-oxo-oxazolidin-5-(S)-ylmethyl]-acetamide | 1 |
| 4025 | N-[3-(2-Fluoro-4'-{[(pyridin-3-ylmethyl)-amino]-methyl}-biphenyl-4-yl)-2-oxo-oxazolidin-5-(S)-ylmethyl]-acetamide | 1 |
| 4026 | N-[3-(2-Fluoro-4'-{[(furan-2-ylmethyl)-amino]-methyl}-biphenyl-4-yl)-2-oxo-oxazolidin-5-(S)-ylmethyl]-acetamide | 1 |
| 4027 | N-[3-(2-Fluoro-2'-methoxy-4'-{[(pyridin-4-ylmethyl)-amino]-methyl}-biphenyl-4-yl)-2-oxo-oxazolidin-5-(S)-ylmethyl]-acetamide | 8 |

TABLE 2-continued

| Compound Number | Structure | MICs |
|---|---|---|
| 4028 | N-[3-(2-Fluoro-4'-{[(furan-3-ylmethyl)-amino]-methyl}-2'-methoxy-biphenyl-4-yl)-2-oxo-oxazolidin-5-(S)-ylmethyl]-acetamide | 8 |
| 4029 | N-[3-(2-Fluoro-4'-{2-hydroxy-1-(R)-[(pyridin-4-ylmethyl)-amino]-ethyl}-biphenyl-4-yl)-2-oxo-oxazolidin-5-(S)-ylmethyl]-acetamide | 4 |
| 4030 | N-[3-(4'-{1-(R)-[(2,4-Dihydroxy-6-methyl-pyrimidin-5-ylmethyl)-amino]-2-hydroxy-ethyl}-2-fluoro-biphenyl-4-yl)-2-oxo-oxazolidin-5-(S)-ylmethyl]-acetamide | 64 |

TABLE 2-continued

| Compound Number | Structure | MICs |
|---|---|---|
| 4031 | 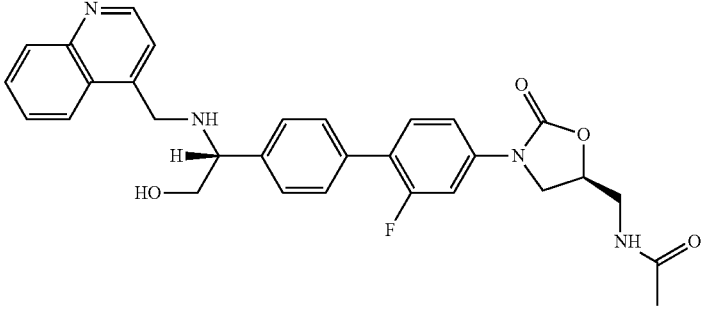 [SMILES: CC(=O)NC[C@H]1CN(c2ccc(-c3ccc([C@H](CO)NCc4ccnc5ccccc45)cc3)c(F)c2)C(=O)O1]<br>N-[3-(2-Fluoro-4'-{2-hydroxy-1-(R)-[(quinolin-4-ylmethyl)-amino]-ethyl}-biphenyl-4-yl)-2-oxo-oxazolidin-5-(S)-ylmethyl]-acetamide | 2 |
| 4032 | 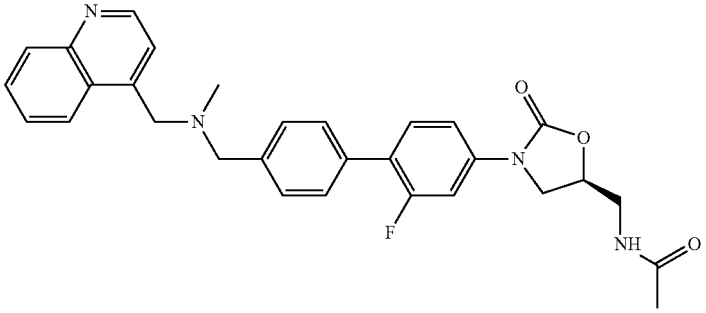 [SMILES: CC(=O)NC[C@H]1CN(c2ccc(-c3ccc(CN(C)Cc4ccnc5ccccc45)cc3)c(F)c2)C(=O)O1]<br>N-(3-{2-Fluoro-4'-[(methyl-quinolin-4-ylmethyl-amino)-methyl]-biphenyl-4-yl}-2-oxo-oxazolidin-5-(S)-ylmethyl)-acetamide | 1 |
| 4033 | 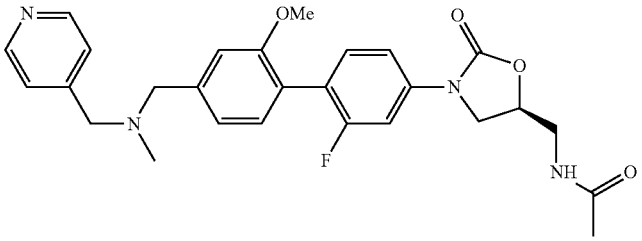 [SMILES: COc1cc(CN(C)Cc2ccncc2)ccc1-c1ccc(N2C[C@H](CNC(C)=O)OC2=O)cc1F]<br>N-(3-{2-Fluoro-2'-methoxy-4'-[(methyl-pyridn-4-ylmethyl-amino)-methyl]-biphenyl-4-yl}-2-oxo-oxazolidin-5-(S)-ylmethyl)-acetamide | 8 |
| 4034 | 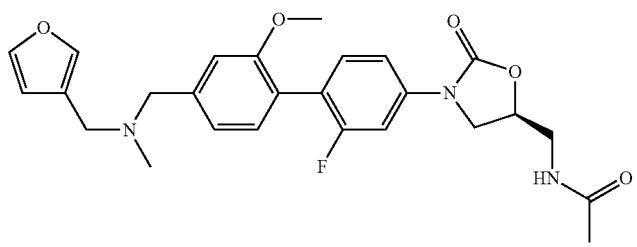 [SMILES: COc1cc(CN(C)Cc2ccoc2)ccc1-c1ccc(N2C[C@H](CNC(C)=O)OC2=O)cc1F]<br>N-(3-{2-Fluoro-4'-[(furan-3-ylmethyl-methyl-amino)-methyl]-2'-methoxy-biphenyl-4-yl}-2-oxo-oxazolidin-5-(S)-ylmethyl)-acetamide | 32 |

TABLE 2-continued

| Compound Number | Structure | MICs |
|---|---|---|
| 4035 | N-(3-{4'-[(Ethyl-pyridin-4-ylmethyl-amino)-methyl]-2-fluoro-biphenyl-4-yl}-2-oxo-oxazolidin-5-(S)-ylmethyl)-acetamide | 2 |
| 4036 | N-[3-(4'-{[(2,4-Dihydroxy-6-methyl-pyrimidin-5-ylmethyl)-methyl-amino]-methyl}-2-fluoro-biphenyl-4-yl)-2-oxo-oxazolidin-5-(S)-ylmethyl]-acetamide | 4 |
| 4037 | N-[3-(4'-{[Bis-(4-hydroxy-3-methoxy-benzyl)-amino]-methyl}-2-fluoro-biphenyl-4-yl)-2-oxo-oxazolidin-5-(S)-ylmethyl]-acetamide | 2 |
| 4038 | N-[3-(2-Fluoro-4'-{[(isoxazol-4-ylmethyl)-amino]-methyl}-biphenyl-4-yl)-2-oxo-oxazolidin-5-(S)-ylmethyl]-acetamide | 0.25 |

| Compound Number | Structure | MICs |
|---|---|---|
| 4039 | N-(3-{2-Fluoro-2'-methoxy-4'-[(methyl-pyridin-4-ylmethyl-amino)-methyl]-biphenyl-4-yl}-2-oxo-oxazolidin-5-(S)-ylmethyl)-acetamide | 8 |
| 4040 | N-[3-(2-Fluoro-2'-methoxy-4'-{[(pyridin-4-ylmethyl)-amino]-methyl}-biphenyl-4-yl)-2-oxo-oxazolidin-5-(S)-ylmethyl]-acetamide | 8 |
| 4041 | N-(3-{2-Fluoro-2'-methoxy-4'-[(methyl-pyridin-4-ylmethyl-amino)-methyl]-biphenyl-4-yl}-2-oxo-oxazolidin-5-(S)-ylmethyl)-acetamide | 8 |
| 4042 | N-[3-(2-Fluoro-4'-{[(furan-3-ylmethyl)-amino]-methyl}-2'-methoxy-biphenyl-4-yl)-2-oxo-oxazolidin-5-(S)-ylmethyl]-acetamide | 8 |

TABLE 2-continued

| Compound Number | Structure | MICs |
|---|---|---|
| 4043 | N-(3-{2-Fluoro-4'-[(furan-3-ylmethyl-methyl-amino)-methyl]-2'-methoxy-biphenyl-4-yl}-2-oxo-oxazolidin-5-(S)-ylmethyl)-acetamide | 32 |
| 4044 | N-(3-{2-Fluoro-4'-[(methyl-pyridin-4-ylmethyl-amino)-methyl]-biphenyl-4-yl}-2-oxo-oxazolidin-5-(S)-ylmethyl)-acetamide | 1 |
| 4045 | N-(3-{2-Fluoro-4'-[(methyl-pyridin-2-ylmethyl-amino)-methyl]-biphenyl-4-yl}-2-oxo-oxazolidin-5-(S)-ylmethyl)-acetamide | 2 |

TABLE 2-continued

| Compound Number | Structure | MICs |
|---|---|---|
| 4046 | N-[3-(4'-{[(3,5-Dichloro-benzyl)-methyl-amino]-methyl}-2-fluoro-biphenyl-4-yl)-2-oxo-oxazolidin-5-(S)-ylmethyl]-acetamide | 4 |
| 4047 | N-(3-{2-Fluoro-4'-[(methyl-pyridin-3-ylmethyl-amino)-methyl]-biphenyl-4-yl}-2-oxo-oxazolidin-5-(S)-ylmethyl)-acetamide | 2 |
| 4048 | N-[3-(2-Fluoro-4'-{[(1H-pyrrol-2-ylmethyl)-amino]-methyl}-biphenyl-4-yl)-2-oxo-oxazolidin-5-(S)-ylmethyl]-acetamide | 2 |
| 4049 | N-[3-(2-Fluoro-4'-{[(1-methyl-1H-indol-2-ylmethyl)-amino]-methyl}-biphenyl-4-yl)-2-oxo-oxazolidin-5-(S)-ylmethyl]-acetamide | 1 |

TABLE 2-continued

| Compound Number | Structure | MICs |
|---|---|---|
| 4050 | 1H-Indole-6-carboxylic acid {4'-[5-(S)-(acetylamino-methyl)-2-oxo-oxazolidin-3-yl]-2'-fluoro-biphenyl-4-ylmethyl}-methyl-amide | 1 |
| 4051 | 1-Methyl-1H-pyrrole-2-carboxylic acid {4'-[5-(S)-(acetylamino-methyl)-2-oxo-oxazolidin-3-yl]-2'-fluoro-biphenyl-4-ylmethyl}-methyl-amide | 4 |
| 4052 | N-{3-[3-Fluoro-4-(5-{[(pyridin-4-ylmethyl)-amino]-methyl}-pyridin-2-yl)-phenyl]-2-oxo-oxazolidin-5-(S)-ylmethyl}-acetamide | 64 |
| 4053 | N-{3-[3-Fluoro-4-(5-{[(furan-3-ylmethyl)-amino]-methyl}-pyridin-2-yl)-phenyl]-2-oxo-oxazolidin-5-(S)-ylmethyl}-acetamide | 4 |

TABLE 2-continued

| Compound Number | Structure | MICs |
|---|---|---|
| 4054 | N-[3-(2-Fluoro-4'-{[(6-methoxy-pyridin-3-ylmethyl)-amino]-methyl}-biphenyl-4-yl)-2-oxo-oxazolidin-5-(S)-ylmethyl]-acetamide | 1 |
| 4055 | N-[3-(2-Fluoro-4'-{[(6-methoxy-pyridin-3-ylmethyl)-methyl-amino]-methyl}-biphenyl-4-yl)-2-oxo-oxazolidin-5-(S)-ylmethyl]-acetamide | 2 |
| 4056 | N-(3-{4'-[(2,5-Bis-trifluoromethyl-benzylamino)-methyl]-2-fluoro-biphenyl-4-yl}-2-oxo-oxazolidin-5-(S)-ylmethyl)-acetamide | 2 |
| 4057 | N-[3-(2-Fluoro-4'-{[(6-methyl-2,4-dioxo-1,2,3,4-tetrahydro-pyrimidin-5-ylmethyl)-amino]-methyl}-biphenyl-4-yl)-2-oxo-oxazolidin-5-(S)-ylmethyl]-acetamide | 16 |

TABLE 2-continued

| Compound Number | Structure | MICs |
|---|---|---|
| 4058 | N-[3-(2-Fluoro-4'-{[(furan-3-ylmethyl)-amino]-methyl}-2'-methoxy-biphenyl-4-yl)-2-oxo-oxazolidin-5-(S)-ylmethyl]-acetamide | 8 |
| 4059 | N-[3-(2-Fluoro-4'-{[(1-methyl-1H-pyrrol-2-ylmethyl)-amino]-methyl}-biphenyl-4-yl)-2-oxo-oxazolidin-5-(S)-ylmethyl]-acetamide | 2 |
| 4060 | N-[3-(2-Fluoro-4'-{[(isoquinolin-4-ylmethyl)-amino]-methyl}-biphenyl-4-yl)-2-oxo-oxazolidin-5-(S)-ylmethyl]-acetamide | 2 |
| 4061 | N-(3-{2-Fluoro-4'-[(furan-3-ylmethyl-methyl-amino)-methyl]-biphenyl-4-yl}-2-oxo-oxazolidin-5-(S)-ylmethyl)-acetamide | 4 |

TABLE 2-continued

| Compound Number | Structure | MICs |
|---|---|---|
| 4062 | N-(3-{4'-[(4-Dimethylamino-benzylamino)-methyl]-2-fluoro-biphenyl-4-yl}-2-oxo-oxazolidin-5-(S)-ylmethyl)-acetamide | 2 |
| 4063 | N-(3-{4'-[(4-Chloro-benzylamino)-methyl]-2-fluoro-biphenyl-4-yl}-2-oxo-oxazolidin-5-(S)-ylmethyl)-acetamide | 2 |
| 4064 | N-(3-{4'-[(2,4-Dichloro-benzylamino)-methyl]-2-fluoro-biphenyl-4-yl}-2-oxo-oxazolidin-5-(S)-ylmethyl)-acetamide | 2 |
| 4065 | N-[3-(2-Fluoro-4'-{[(isoquinolin-5-ylmethyl)-amino]-methyl}-biphenyl-4-yl)-2-oxo-oxazolidin-5-(S)-ylmethyl]-acetamide | 2 |

TABLE 2-continued

| Compound Number | Structure | MICs |
|---|---|---|
| 4066 | N-[3-(2-Fluoro-4'-{[(3H-imidazol-4-ylmethyl)-amino]-methyl}-biphenyl-4-yl)-2-oxo-oxazolidin-5-(S)-ylmethyl]-acetamide | 8 |
| 4067 | N-[3-(2-Fluoro-4'-{[(3H-imidazol-4-ylmethyl)-methyl-amino]-methyl}-biphenyl-4-yl)-2-oxo-oxazolidin-5-(S)-ylmethyl]-acetamide | 4 |
| 4068 | N-[3-(2-Fluoro-4'-{[(1H-imidazol-4-ylmethyl)-(3H-imidazol-4-ylmethyl)-amino]-methyl}-biphenyl-4-yl)-2-oxo-oxazolidin-5-(S)-ylmethyl]-acetamide | 128 |
| 4069 | N-[3-(2-Fluoro-4'-{[(5-nitro-furan-2-ylmethyl)-amino]-methyl}-biphenyl-4-yl)-2-oxo-oxazolidin-5-(S)-ylmethyl]-acetamide | 1 |

TABLE 2-continued

| Compound Number | Structure | MICs |
|---|---|---|
| 4070 | N-(3-{4'-[(3-Cyano-benzylamino)-methyl]-2-fluoro-biphenyl-4-yl}-2-oxo-oxazolidin-5-(S)-ylmethyl)-acetamide | 1 |
| 4071 | N-[3-(2-Fluoro-4'-{[(quinolin-6-ylmethyl)-amino]-methyl}-biphenyl-4-yl)-2-oxo-oxazolidin-5-(S)-ylmethyl]-acetamide | 2 |
| 4072 | N-[3-(2-Fluoro-4'-{[(6-methyl-pyridin-2-ylmethyl)-amino]-methyl}-biphenyl-4-yl)-2-oxo-oxazolidin-5-(S)-ylmethyl]-acetamide | 2 |
| 4073 | N-{3-[3-Fluoro-4-(6-{[(pyridin-4-ylmethyl)-amino]-methyl}-pyridin-3-yl)-phenyl]-2-oxo-oxazolidin-5-(S)-ylmethyl}-acetamide | 2 |

TABLE 2-continued

| Compound Number | Structure | MICs |
|---|---|---|
| 4074 | N-[3-(2-Fluoro-4'-{[(thiazol-2-ylmethyl)-amino]-methyl}-biphenyl-4-yl)-2-oxo-oxazolidin-5-(S)-ylmethyl]-acetamide | 1 |
| 4075 | N-[3-(2-Fluoro-4'-{[(5-hydroxymethyl-furan-2-ylmethyl)-amino]-methyl}-biphenyl-4-yl)-2-oxo-oxazolidin-5-(S)-ylmethyl]-acetamide | 2 |
| 4076 | N-[3-(2-Fluoro-4'-{[(1-methyl-1H-imidazol-2-ylmethyl)-amino]-methyl}-biphenyl-4-yl)-2-oxo-oxazolidin-5-(S)-ylmethyl]-acetamide | 4 |
| 4077 | N-[3-(4'-{[(Benzo[b]thiophen-3-ylmethyl)-amino]-methyl}-2-fluoro-biphenyl-4-yl)-2-oxo-oxazolidin-5-(S)-ylmethyl]-acetamide | 16 |

TABLE 2-continued

| Compound Number | Structure | MICs |
|---|---|---|
| 4078 | N-[3-(4'-{[(5-Bromo-furan-2-ylmethyl)-amino]-methyl}-2-fluoro-biphenyl-4-yl)-2-oxo-oxazolidin-5-(S)-ylmethyl]-acetamide | 2 |
| 4079 | N-(3-{2-Fluoro-4'-[(3-imidazol-1-yl-propylamino)-methyl]-biphenyl-4-yl}-2-oxo-oxazolidin-5-(S)-ylmethyl)-acetamide | 32 |
| 4080 | N-{3-[2-Fluoro-4'-(N-pyridin-4-ylmethyl-carbamimidoyl)-biphenyl-4-yl]-2-oxo-oxamlidin-5-(S)-ylmethyl}-acetamide | 128 |
| 4081 | N-[3-(2-Fluoro-4'-{[(5-methyl-furan-2-ylmethyl)-amino]-methyl}-biphenyl-4-yl)-2-oxo-oxazolidin-5-(S)-ylmethyl]-acetamide | 2 |

TABLE 2-continued

| Compound Number | Structure | MICs |
|---|---|---|
| 4082 | N-[3-(2-Fluoro-4'-{[(5-methyl-3H-imidazol-4-ylmethyl)-amino]-methyl}-biphenyl-4-yl)-2-oxo-oxazolidin-5-(S)-ylmethyl]-acetamide | 32 |
| 4083 | N-[3-(2-Fluoro-4'-{[(1H-indol-3-ylmethyl)-amino]-methyl}-biphenyl-4-yl)-2-oxo-oxazolidin-5-(S)-ylmethyl]-acetamide | 2 |
| 4084 | N-[3-(2-Fluoro-4'-{[(5-phenyl-thiophen-2-ylmethyl)-amino]-methyl}-biphenyl-4-yl)-2-oxo-oxazolidin-5-(S)-ylmethyl]-acetamide | 128 |
| 4085 | N-[3-(4'-{[(4,5-Dimethyl-furan-2-ylmethyl)-amino]-methyl}-2-fluoro-biphenyl-4-yl)-2-oxo-oxazolidin-5-(S)-ylmethyl]-acetamide | 4 |

TABLE 2-continued

| Compound Number | Structure | MICs |
|---|---|---|
| 4086 | N-[3-(2-Fluoro-4'-{[(thiophen-3-ylmethyl)-amino]-methyl}-biphenyl-4-yl)-2-oxo-oxazolidin-5-(S)-ylmethyl]-acetamide | 4 |
| 4087 | N-(3-{2-Fluoro-4'-[(2-pyridin-2-yl-ethylamino)-methyl]-biphenyl-4-yl}-2-oxo-oxazolidin-5-(S)-ylmethyl)-acetamide | 4 |
| 4088 | N-[2-Oxo-3-(2,2',3'-trifluoro-4'-{[(furan-2-ylmethyl)-amino]-methyl}-biphenyl-4-yl)-oxazolidin-5-(S)-ylmethyl]-acetamide | 2 |
| 4089 | N-[2-Oxo-3-(2,2',3'-trifluoro-4'-{[(pyridin-4-ylmethyl)-amino]-methyl}-biphenyl-4-yl)-oxazolidin-5-(S)-ylmethyl]-acetamide | 2 |

TABLE 2-continued

| Compound Number | Structure | MICs |
|---|---|---|
| 4090 | N-[2-Oxo-3-(2,2',3'-trifluoro-4'-{[(pyridin-2-ylmethyl)-amino]-methyl}-biphenyl-4-yl)-oxazolidin-5-(S)-ylmethyl]-acetamide | 4 |
| 4091 | N-[3-(2-Fluoro-4'-{[(1H-imidazol-2-ylmethyl)-amino]-methyl}-biphenyl-4-yl)-2-oxo-oxazolidin-5-(S)-ylmethyl]-acetamide | 8 |
| 4092 | N-[3-(4'-{[(1H-Benzoimidazol-2-ylmethyl)-amino]-methyl}-2-fluoro-biphenyl-4-yl)-2-oxo-oxazolidin-5-(S)-ylmethyl]-acetamide | 4 |
| 4093 | N-(3-{2-Fluoro-4'-[(4-sulfamoyl-benzylamino)-methyl]-biphenyl-4-yl}-2-oxo-oxazolidin-5-(S)-ylmethyl)-acetamide | 8 |

TABLE 2-continued

| Compound Number | Structure | MICs |
|---|---|---|
| 4094 | N-[3-(2-Fluoro-4'-{[2-(4-sulfamoyl-phenyl)-ethylamino]-methyl}-biphenyl-4-yl)-2-oxo-oxazolidin-5-(S)-ylmethyl]-acetamide | 2 |
| 4095 | N-[3-(2-Fluoro-4'-{[[(3-hydroxy-5-hydroxymethyl-2-methyl-pyridin-4-ylmethyl)-amino]-methyl}-biphenyl-4-yl)-2-oxo-oxazolidin-5-(S)-ylmethyl]-acetamide | 4 |
| 4096 | N-[3-(2-Fluoro-4'-{[2-(4-methyl-thiazol-5-yl)-ethylamino]-methyl}-biphenyl-4-yl)-2-oxo-oxazolidin-5-(S)-ylmethyl]-acetamide | 4 |
| 4097 | N-{3-[2-Fluoro-4'-(N-pyridin-2-ylmethyl-carbamimidoyl)-biphenyl-4-yl]-2-oxo-oxazolidin-5-(S)-ylmethyl}-acetamide | 16 |

TABLE 2-continued

| Compound Number | Structure | MICs |
|---|---|---|
| 4098 | N-[3-(2-Fluoro-4'-{[(5-methoxy-1H-indol-3-ylmethyl)-amino]-methyl}-biphenyl-4-yl)-2-oxo-oxazolidin-5-(S)-ylmethyl]-acetamide | 2 |
| 4099 | N-[3-(2-Fluoro-4'-{[(3-methyl-thiophen-2-ylmethyl)-amino]-methyl}-biphenyl-4-yl)-2-oxo-oxazolidin-5-(S)-ylmethyl]-acetamide | 4 |
| 4100 | N-[3-(4'-{[(1-Benzenesulfonyl-1H-pyrrol-2-ylmethyl)-amino]-methyl}-2-fluoro-biphenyl-4-yl)-2-oxo-oxazolidin-5-(S)-ylmethyl]-acetamide | 4 |
| 4101 | N-[3-(4'-{[(2,4-Dioxo-1,2,3,4-tetrahydro-pyrimidin-5-ylmethyl)-amino]-methyl}-2-fluoro-biphenyl-4-yl)-2-oxo-oxazolidin-5-(S)-ylmethyl]-acetamide | 1 |

TABLE 2-continued

| Compound Number | Structure | MICs |
|---|---|---|
| 4102 | 4'-[5-(S)-(Acetylamino-methyl)-2-oxo-oxazolidin-3-yl]-2'-fluoro-biphenyl-4-carboxylic acid (pyridin-4-ylmethyl)-amide | 2 |
| 4103 | N-[3-(4'-{[(2,5-Dimethyl-furan-3-ylmethyl)-amino]-methyl}-2-fluoro-biphenyl-4-yl)-2-oxo-oxazolidin-5-(S)-ylmethyl]-acetamide | 8 |
| 4104 | N-[3-(2-Fluoro-4'-{[(5-methyl-3-phenyl-isoxazol-4-ylmethyl)-amino]-methyl}-biphenyl-4-yl)-2-oxo-oxazolidin-5-(S)-ylmethyl]-acetamide | 0.25 |
| 4105 | N-[3-(2-Fluoro-4'-{[(5-methyl-2-trifluoromethyl-furan-3-ylmethyl)-amino]-methyl}-biphenyl-4-yl)-2-oxo-oxazolidin-5-(S)-ylmethyl]-acetamide | 0.5 |

TABLE 2-continued

| Compound Number | Structure | MICs |
|---|---|---|
| 4106 | 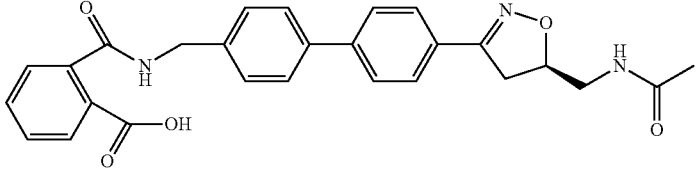<br>N-{4'-[5-(R)-(Acetylamino-methyl)-4,5-dihydro-isoxazol-3-yl]-biphenyl-4-ylmethyl}-phthalamic acid | 128 |
| 4107 | 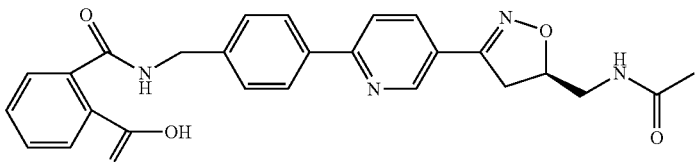<br>N-(4-{5-[5-(R)-(Acetylamino-methyl)-4,5-(S)-dihydro-isoxazol-3-yl]-pyridin-2-yl}-benzyl)-phthalamic acid | 128 |
| 4108 | 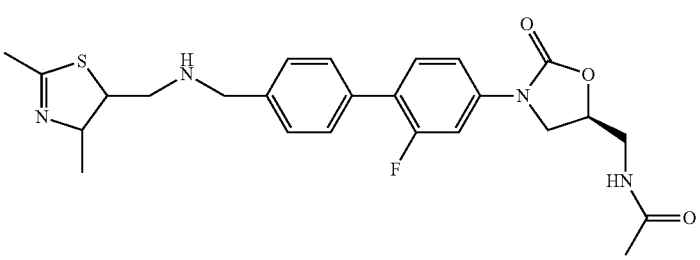 [SMILES: CC(=O)NC[C@H]1CN(c2ccc(-c3ccc(CNCc4cc(C)c(C)o4)cc3)c(F)c2)C(=O)O1]<br>N-[3-(4'-{[(2,4-Dimethyl-thiazol-5-ylmethyl)-amino]-methyl}-2-fluoro-biphenyl-4-yl)-2-oxo-oxazolidin-5-(S)-ylmethyl]-acetamide | 4 |
| 4109 | 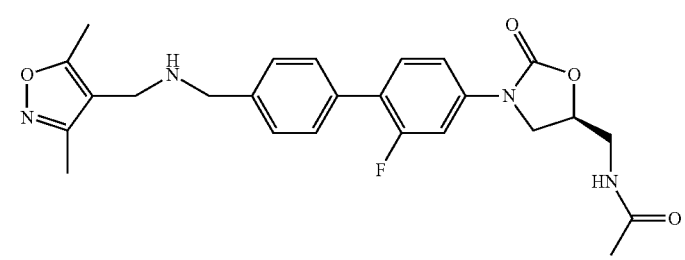 [SMILES: CC(=O)NC[C@H]1CN(c2ccc(-c3ccc(CNCc4c(C)noc4C)cc3)c(F)c2)C(=O)O1]<br>N-[3-(4'-{[(3,5-Dimethyl-isoxazol-4-ylmethyl)-amino]-methyl}-2-fluoro-biphenyl-4-yl)-2-oxo-oxazolidin-5-(S)-ylmethyl]-acetamide | 1 |
| 4110 | 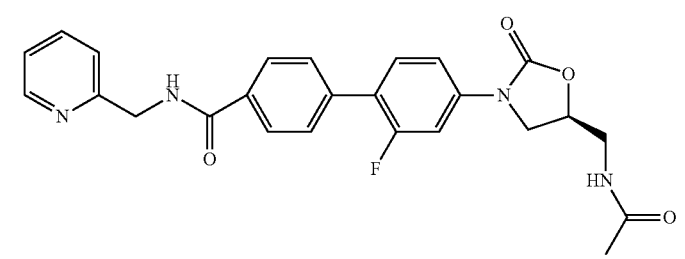 [SMILES: CC(=O)NC[C@H]1CN(c2ccc(-c3ccc(C(=O)NCc4ccccn4)cc3)c(F)c2)C(=O)O1]<br>4'-[5-(S)-(Acetylamino-methyl)-2-oxo-oxazolidin-3-yl]-2'-fluoro-biphenyl-4-carboxylic acid (pyridin-2-ylmethyl)-amide | 0.25 |

TABLE 2-continued

| Compound Number | Structure | MICs |
|---|---|---|
| 4111 | 4'-[5-(S)-(Acetylamino-methyl)-2-oxo-oxazolidin-3-yl]-2'-fluoro-biphenyl-4-carboxylic acid (furan-2-ylmethyl)-amide | 2 |
| 4112 | 4'-[5-(S)-(Acetylamino-methyl)-2-oxo-oxazolidin-3-yl]-2'-fluoro-biphenyl-4-carboxylic acid [2-(4-methyl-thiazol-5-yl)-ethyl]-amide | 0.25 |
| 4113 | N-[3-(2-Fluoro-4'-{[(2-thiophen-2-yl-thiazol-4-ylmethyl)-amino]-methyl}-biphenyl-4-yl)-2-oxo-oxazolidin-5-(S)-ylmethyl]-acetamide | 0.25 |
| 4114 | N-[3-(2-Fluoro-4'-{[2-(2-oxo-imidazolidin-1-yl)-ethylamino]-methyl}-biphenyl-4-yl)-2-oxo-oxazolidin-5-(S)-ylmethyl]-acetamide | 16 |

TABLE 2-continued

| Compound Number | Structure | MICs |
|---|---|---|
| 4115 | 4'-[5-(S)-(Acetylamino-methyl)-2-oxo-oxazolidin-3-yl]-2'-fluoro-biphenyl-4-carboxylic acid (2-pyridin-2-yl-ethyl)-amide | 0.5 |
| 4116 | 4'-[5-(S)-(Acetylamino-methyl)-2-oxo-oxazolidin-3-yl]-2'-fluoro-biphenyl-4-carboxylic acid [2-(3H-imidazol-4-yl)-ethyl]-amide | 1 |
| 4117 | N-[3-(2-Fluoro-4'-{[(2-morpholin-4-yl-pyridin-3-ylmethyl)-amino]-methyl}-biphenyl-4-yl)-2-oxo-oxazolidin-5-(S)-ylmethyl]-acetamide | 8 |
| 4118 | N-[3-(2-Fluoro-4'-{[(6-morpholin-4-yl-pyridin-3-ylmethyl)-amino]-methyl}-biphenyl-4-yl)-2-oxo-oxazolidin-5-(S)-ylmethyl]-acetamide | 8 |

TABLE 2-continued

| Compound Number | Structure | MICs |
|---|---|---|
| 4119 | N-[3-(2-Fluoro-4'-{[(5-pyridin-2-yl-thiophen-2-ylmethyl)-amino]-methyl}-biphenyl-4-yl)-2-oxo-oxazolidin-5-(S)-ylmethyl]-acetamide | 1 |
| 4120 | 5-[({4'-[5-(S)-(Acetylamino-methyl)-2-oxo-oxazolidin-3-yl]-2'-fluoro-biphenyl-4-ylmethyl}-amino)-methyl]-2-methyl-furan-3-carboxylic acid methyl ester | 1 |
| 4121 | N-[3-(4'-{[(Benzothiazol-2-ylmethyl)-amino]-methyl}-2-fluoro-biphenyl-4-yl)-2-oxo-oxazolidin-5-(S)-ylmethyl]-acetamide | 0.5 |
| 4122 | N-[3-(2-Fluoro-4'-{[(2-phenyl-thiazol-4-ylmethyl)-amino]-methyl}-biphenyl-4-yl)-2-oxo-oxazolidin-5-(S)-ylmethyl]-acetamide | 1 |

TABLE 2-continued

| Compound Number | Structure | MICs |
|---|---|---|
| 4123 | N-[3-(2-Fluoro-4'-{[(2-phenyl-1H-imidazol-4-ylmethyl)-amino]-methyl}-biphenyl-4-yl)-2-oxo-oxazolidin-5-(S)-ylmethyl]-acetamide | 16 |
| 4124 | N-[3-(4'-{[(2-Ethyl-3H-imidazol-4-ylmethyl)-amino]-methyl}-2-fluoro-biphenyl-4-yl)-2-oxo-oxazolidin-5-(S)-ylmethyl]-acetamide | 16 |
| 4125 | N-[3-(4'-{[(5-Chloro-1-methyl-3-trifluoromethyl-1H-pyrazol-4-ylmethyl)-amino]-methyl}-2-fluoro-biphenyl-4-yl)-2-oxo-oxazolidin-5-(S)-ylmethyl]-acetamide | 0.5 |

TABLE 2-continued

| Compound Number | Structure | MICs |
|---|---|---|
| 4126 | N-[3-(4'-{[(5-Chloro-1,3-dimethyl-1H-pyrazol-4-ylmethyl)-amino]-methyl}-2-fluoro-biphenyl-4-yl)-2-oxo-oxazolidin-5-(S)-ylmethyl]-acetamide | 0.5 |
| 4127 | N-[3-(2-Fluoro-4'-{[(3-thiophen-2-yl-1H-pyrazol-4-ylmethyl)-amino]-methyl}-biphenyl-4-yl)-2-oxo-oxazolidin-5-(S)-ylmethyl]-acetamide | 0.5 |
| 4128 | N-[3-(4'-{[(5-Cyano-6-methylsulfanyl-pyridin-2-ylmethyl)-amino]-methyl}-2-fluoro-biphenyl-4-yl)-2-oxo-oxazolidin-5-(S)-ylmethyl]-acetamide | 0.5 |

TABLE 2-continued

| Compound Number | Structure | MICs |
|---|---|---|
| 4129 | N-[3-(4'-{[(2-Amino-4-oxo-4H-chromen-3-ylmethyl)-amino]-methyl}-2-fluoro-biphenyl-4-yl)-2-oxo-oxazolidin-5-(S)-ylmethyl]-acetamide | 4 |
| 4130 | N-[3-(2-Fluoro-4'-{[(2-methyl-5-phenyl-furan-3-ylmethyl)-amino]-methyl}-biphenyl-4-yl)-2-oxo-oxazolidin-5-(S)-ylmethyl]-acetamide | 2 |
| 4131 | N-[3-(4'-{[(3,4-Dihydro-2H-pyran-2-ylmethyl)-amino]-methyl}-2-fluoro-biphenyl-4-yl)-2-oxo-oxazolidin-5-(S)-ylmethyl]-acetamide | 1 |
| 4132 | N-[3-(4'-{[(Pyridin-4-ylmethyl)-amino]-methyl}-biphenyl-4-yl)-4,5-dihydro-isoxazol-5-(R)-ylmethyl]-acetamide | 4 |
| 4133 | N-{3-[6-(4-{[(Pyridin-4-ylmethyl)-amino]-methyl}-phenyl)-pyridin-3-yl]-4,5-dihydro-isoxazol-5-(R)-ylmethyl}-acetamide | 128 |

TABLE 2-continued

| Compound Number | Structure | MICs |
|---|---|---|
| 4134 | N-{2-Oxo-3-[6-(4-{[(pyridin-4-ylmethyl)-amino]-methyl}-phenyl)-pyridin-3-yl]-oxazolidin-5-(S)-ylmethyl}-acetamide | 16 |
| 4135 | N-[3-(4'-{[(4-Amino-pyridin-3-ylmethyl)-amino]-methyl}-2-fluoro-biphenyl-4-yl)-2-oxo-oxazolidin-5-(S)-ylmethyl]-acetamide | 4 |
| 4136 | N-[3-(4'-{[2-(1,3-Dioxo-1,3-dihydro-isoindol-2-yl)-ethanesulfonylamino]-methyl}-2-fluoro-biphenyl-4-yl)-2-oxo-oxazolidin-5-(S)-ylmethyl]-acetamide | 8 |
| 4137 | N-[3-(2-Fluoro-4'-{[(thiophen-2-ylmethyl)-amino]-methyl}-biphenyl-4-yl)-2-oxo-oxazolidin-5-(S)-ylmethyl]-acetamide | 0.5 |

TABLE 2-continued

| Compound Number | Structure | MICs |
|---|---|---|
| 4138 | N-[3-(2-Fluoro-4'-{[(quinolin-7-ylmethyl)-amino]-methyl}-biphenyl-4-yl)-2-oxo-oxazolidin-5-(S)-ylmethyl]-acetamide | 1 |
| 4139 | N-[3-(4'-{[(4-Chloro-1-methyl-1H-pyrazol-3-ylmethyl)-amino]-methyl}-2-fluoro-biphenyl-4-yl)-2-oxo-oxazolidin-5-(S)-ylmethyl]-acetamide | 2 |
| 4140 | N-[3-(2-Fluoro-4'-{[(3-methyl-[1,2,4]oxadiazol-5-ylmethyl)-amino]-methyl}-biphenyl-4-yl)-2-oxo-oxazolidin-5-(S)-ylmethyl]-acetamide | 2 |
| 4141 | N-[3-(2-Fluoro-4'-{[(5-methyl-[1,2,4]oxadiazol-3-ylmethyl)-amino]-methyl}-biphenyl-4-yl)-2-oxo-oxazolidin-5-(S)-ylmethyl]-acetamide | 2 |

TABLE 2-continued

| Compound Number | Structure | MICs |
|---|---|---|
| 4142 | N-{4'-[5-(S)-(Acetylamino-methyl)-2-oxo-oxazolidin-3-yl]-2'-fluoro-biphenyl-4-ylmethyl}-isonicotinamide | 2 |
| 4143 | 4'-[5-(S)-(Acetylamino-methyl)-2-oxo-oxazolidin-3-yl]-2'-fluoro-biphenyl-4-carboxylic acid (thiazol-2-ylmethyl)-amide | 1 |
| 4144 | N-[3-(2-Fluoro-4'-{1-(R/S)-[(furan-3-ylmethyl)-amino]-ethyl}-biphenyl-4-yl)-2-oxo-oxazolidin-5-(S)-ylmethyl]-acetamide | 4 |
| 4145 | N-[3-(2-Fluoro-4'-{1-(R/S)-[(thiazol-2-ylmethyl)-amino]-ethyl}-biphenyl-4-yl)-2-oxo-oxazolidin-5-(S)-ylmethyl]-acetamide | 2 |

TABLE 2-continued

| Compound Number | Structure | MICs |
|---|---|---|
| 4146 | N-[3-(2-Fluoro-4'-{[(5-methyl-2-phenyl-2H-[1,2,3]triazol-4-ylmethyl)-amino]-methyl}-biphenyl-4-yl)-2-oxo-oxazolidin-5-(S)-ylmethyl]-acetamide | 4 |
| 4147 | N-(3-{2-Fluoro-4'-[(4-pyrrol-1-yl-benzylamino)-methyl]-biphenyl-4-yl}-2-oxo-oxazolidin-5-(S)-ylmethyl)-acetamide | 4 |
| 4148 | N-[3-(2-Fluoro-4'-{[3-(5-methyl-1H-pyrazol-4-yl)-propylamino]-methyl}-biphenyl-4-yl)-2-oxo-oxazolidin-5-(S)-ylmethyl]-acetamide | 2 |
| 4149 | N-[3-(2-Fluoro-4'-{2-[(pyridin-4-ylmethyl)-amino]-ethyl}-biphenyl-4-yl)-2-oxo-oxazolidin-5-(S)-ylmethyl]-acetamide | 1 |

TABLE 2-continued

| Compound Number | Structure | MICs |
|---|---|---|
| 4150 | N-[3-(2-Fluoro-4'-{[2-(R/S)-(1-methyl-pyrrolidin-2-yl)-ethylamino]-methyl}-biphenyl-4-yl)-2-oxo-oxazolidin-5-(S)-ylmethyl]-acetamide | 16 |
| 4151 | N-[3-(2-Fluoro-4'-{[(2-methoxy-pyridin-3-ylmethyl)-amino]-methyl}-biphenyl-4-yl)-2-oxo-oxazolidin-5-(S)-ylmethyl]-acetamide | 2 |
| 4152 | N-[3-(4'-{[(2-Amino-pyridin-3-ylmethyl)-amino]-methyl}-2-fluoro-biphenyl-4-yl)-2-oxo-oxazolidin-5-(S)-ylmethyl]-acetamide | 2 |
| 4153 | N-[3-(2-Fluoro-4'-{[(pyrrolidin-3-(R/S)-ylmethyl)-amino]-methyl}-biphenyl-4-yl)-2-oxo-oxazolidin-5-(S)-ylmethyl]-acetamide | 4 |

TABLE 2-continued

| Compound Number | Structure | MICs |
|---|---|---|
| 4154 | N-[3-(2,3'-Difluoro-4'-{[(thiazol-2-ylmethyl)-amino]-methyl}-biphenyl-4-yl)-2-oxo-oxazolidin-5-(S)-ylmethyl]-acetamide | 1 |
| 4155 | N-[3-(2,3'-Difluoro-4'-{[(pyridin-4-ylmethyl)-amino]-methyl}-biphenyl-4-yl)-2-oxo-oxazolidin-5-(S)-ylmethyl]-acetamide | 2 |
| 4156 | N-[3-(2-Fluoro-4'-{[3-(2-oxo-pyrrolidin-1-yl)-propylamino]-methyl}-biphenyl-4-yl)-2-oxo-oxazolidin-5-(S)-ylmethyl]-acetamide | 16 |
| 4157 | 4-[({4'-[5-(S)-(Acetylamino-methyl)-2-oxo-oxazolidin-3-yl]-2'-fluoro-biphenyl-4-ylmethyl}-amino)-methyl]-1-cyclopropyl-2,5-dimethyl-1H-pyrrole-3-carboxylic acid ethyl ester | 8 |

TABLE 2-continued

| Compound Number | Structure | MICs |
|---|---|---|
| 4158 | N-{3-[2-Fluoro-4'-({[5-(3-sulfamoyl-phenyl)-furan-2-ylmethyl]-amino}-methyl)-biphenyl-4-yl]-2-oxo-oxazolidin-5-(S)-ylmethyl}-acetamide | 2 |
| 4159 | N-(3-{2-Fluoro-4'-[(1-pyridin-4-(R/S)-yl-ethylamino)-methyl]-biphenyl-4-yl}-2-oxo-oxazolidin-5-(S)-ylmethyl)-acetamide | 2 |
| 4160 | N-(3-{2-Fluoro-4'-[1-(R/S)-(1-pyridin-4-(R/S)-yl-ethylamino)-ethyl]-biphenyl-4-yl}-2-oxo-oxazolidin-5-(S)-ylmethyl)-acetamide | 8 |
| 4161 | N-[3-(4'-{[(5-Ethyl-furan-2-ylmethyl)-amino]-methyl}-2-fluoro-biphenyl-4-yl)-2-oxo-oxazolidin-5-(S)-ylmethyl]-acetamide | 2 |

TABLE 2-continued

| Compound Number | Structure | MICs |
|---|---|---|
| 4162 | N-[3-(4'-{[(5-Ethyl-thiophen-2-ylmethyl)-amino]-methyl}-2-fluoro-biphenyl-4-yl)-2-oxo-oxazolidin-5-(S)-ylmethyl]-acetamide | 2 |
| 4163 | N-[3-(2-Fluoro-4'-{[(1,3,5-trimethyl-1H-pyrazol-4-ylmethyl)-amino]-methyl}-biphenyl-4-yl)-2-oxo-oxazolidin-5-(S)-ylmethyl]-acetamide | 8 |
| 4164 | N-[3-(2,3'-Difluoro-4'-{[([1,2,3]thiadiazol-4-ylmethyl)-amino]-methyl}-biphenyl-4-yl)-2-oxo-oxazolidin-5-(S)-ylmethyl]-acetamide | 1 |
| 4165 | N-[3-(2-Fluoro-4'-{[(2-methyl-1H-imidazol-4-ylmethyl)-amino]-methyl}-biphenyl-4-yl)-2-oxo-oxazolidin-5-(S)-ylmethyl]-acetamide | 4 |

TABLE 2-continued

| Compound Number | Structure | MICs |
|---|---|---|
| 4166 | N-[3-(2-Fluoro-3'-{[([1,2,3]thiadiazol-4-ylmethyl)-amino]-methyl}-biphenyl-4-yl)-2-oxo-oxazolidin-5-(S)-ylmethyl]-acetamide | 8 |
| 4167 | N-[3-(2-Fluoro-4'-{[(5-methylsulfanyl-thiophen-2-ylmethyl)-amino]-methyl}-biphenyl-4-yl)-2-oxo-oxazolidin-5-(S)-ylmethyl]-acetamide | 2 |
| 4168 | N-[3-(4'-{[(4-Bromo-1-methyl-1H-pyrazol-3-ylmethyl)-amino]-methyl}-2-fluoro-biphenyl-4-yl)-2-oxo-oxazolidin-5-(S)-ylmethyl]-acetamide | 2 |
| 4169 | N-[3-(4'-{[(4-Bromo-2H-pyrazol-3-ylmethyl)-amino]-methyl}-2-fluoro-biphenyl-4-yl)-2-oxo-oxazolidin-5-(S)-ylmethyl]-acetamide | 2 |

TABLE 2-continued

| Compound Number | Structure | MICs |
|---|---|---|
| 4170 | N-{3-[4'-(Benzylsulfamoyl-methyl)-2-fluoro-biphenyl-4-yl]-2-oxo-oxazolidin-5-(S)-ylmethyl}-acetamide | 128 |
| 4171 | N-[3-(2-Fluoro-4'-{2-hydroxy-1-[([1,2,3]thiadiazol-4-(R/S)-ylmethyl)-amino]-ethyl}-biphenyl-4-yl)-2-oxo-oxazolidin-5-(S)-ylmethyl]-acetamide | 4 |
| 4172 | N-[3-(2-Fluoro-4'-{2-hydroxy-1-[([1,2,3]thiadiazol-4-(R/S)-ylmethyl)-amino]-ethyl}-biphenyl-4-yl)-2-oxo-oxazolidin-5-(S)-ylmethyl]-acetamide | 8 |
| 4173 | 4'-[5-(S)-(Acetylamino-methyl)-2-oxo-oxazolidin-3-yl]-2'-fluoro-biphenyl-4-carboxylic acid [1-carbamoyl-2-(S)-(3H-imidazol-4-yl)-ethyl]-amide | 32 |

TABLE 2-continued

| Compound Number | Structure | MICs |
|---|---|---|
| 4174 | 2-({4'-[5-(S)-(Acetylamino-methyl)-2-oxo-oxazolidin-3-yl]-2'-fluoro-biphenyl-4-ylmethyl}-amino)-3-(S)-(1H-imidazol-4-yl)-propionamide | |
| 4175 | 2-({4'-[5-(S)-(Acetylamino-methyl)-2-oxo-oxazolidin-3-yl]-2'-fluoro-biphenyl-4-ylmethyl}-amino)-3-(S)-(1H-indol-3-yl)-propionamide | 2 |
| 4176 | N-[3-(2-Fluoro-2',5'-dimethyl-4'-{[(pyridin-4-ylmethyl)-amino]-methyl}-biphenyl-4-yl)-2-oxo-oxazolidin-5-(S)-ylmethyl]-acetamide | 128 |
| 4177 | N-(3-{4'-[(2,2-Difluoro-2-pyridin-2-yl-ethylamino)-methyl]-2-fluoro-biphenyl-4-yl}-2-oxo-oxazolidin-5-(S)-ylmethyl)-acetamide | 4 |

TABLE 2-continued

| Compound Number | Structure | MICs |
|---|---|---|
| 4178 | N-[3-(2-Fluoro-4'-{[(5-(S)-oxo-4,5-dihydro-1H-[1,2,4]triazol-3-ylmethyl)-amino]-methyl}-biphenyl-4-yl)-2-oxo-oxazolidin-5-(S)-ylmethyl]-acetamide | 8 |
| 4179 | N-[3-(2-Fluoro-4'-{[(3-fluoro-pyridin-4-ylmethyl)-amino]-methyl}-biphenyl-4-yl)-2-oxo-oxazolidin-5-(S)-ylmethyl]-acetamide | 2 |
| 4180 | N-[3-(2-Fluoro-4'-{[(5-methylamino-[1,2,4]thiadiazol-3-ylmethyl)-amino]-methyl}-biphenyl-4-yl)-2-oxo-oxazolidin-5-(S)-ylmethyl]-acetamide | 1 |
| 4181 | N-[3-(4'-{[(6-Bromo-pyridin-3-ylmethyl)-amino]-methyl}-2-fluoro-biphenyl-4-yl)-2-oxo-oxazolidin-5-(S)-ylmethyl]-acetamide | 1 |

| Compound Number | Structure | MICs |
|---|---|---|
| 4182 | N-[3-(4'-{[(5-Bromo-pyridin-2-ylmethyl)-amino]-methyl}-2-fluoro-biphenyl-4-yl)-2-oxo-oxazolidin-5-(S)-ylmethyl]-acetamide | 2 |
| 4183 | N-[3-(2-Fluoro-4'-{[(isoxazol-3-ylmethyl)-amino]-methyl}-biphenyl-4-yl)-2-oxo-oxazolidin-5-(S)-ylmethyl]-acetamide | 1 |
| 4184 | 2-{4'-[5-(S)-(Acetylamino-methyl)-2-oxo-oxazolidin-3-yl]-2'-fluoro-biphenyl-4-yl}-2-(R)-[(pyridin-4-ylmethyl)-amino]-acetamide | 16 |
| 4185 | 2-{4'-[5-(S)-(Acetylamino-methyl)-2-oxo-oxazolidin-3-yl]-2'-fluoro-biphenyl-4-yl{-2-(R)-[(pyridin-2-ylmethyl)-amino]-acetamide | 16 |

TABLE 2-continued

| Compound Number | Structure | MICs |
|---|---|---|
| 4186 | 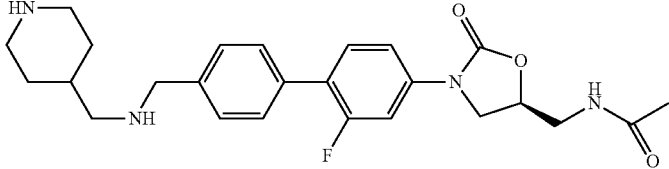 [SMILES: CC(=O)NC[C@H]1CN(c2ccc(-c3ccc(CNCC4CCNCC4)cc3)c(F)c2)C(=O)O1]<br>N-[3-(2-Fluoro-4'-{[(piperidin-4-ylmethyl)-amino]-methyl}-biphenyl-4-yl)-2-oxo-oxazolidin-5-(S)-ylmethyl]-acetamide | 64 |
| 4187 | 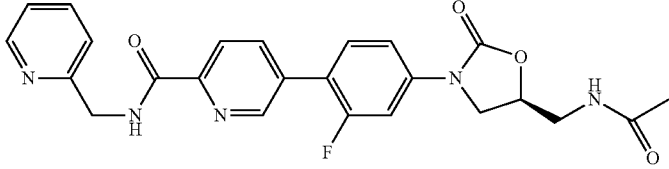 [SMILES: CC(=O)NC[C@H]1CN(c2ccc(-c3ccc(C(=O)NCc4ccccn4)nc3)c(F)c2)C(=O)O1]<br>5-{4-[5-(S)-(Acetylamino-methyl)-2-oxo-oxazolidin-3-yl]-2-fluoro-phenyl}-pyridine-2-carboxylic acid (pyridin-2-ylmethyl)-amide | 1 |
| 4188 | 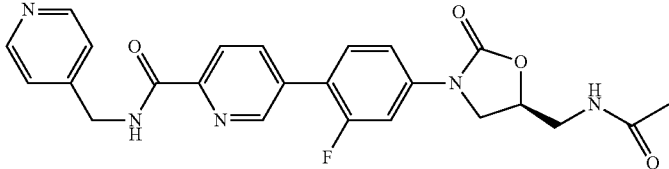 [SMILES: CC(=O)NC[C@H]1CN(c2ccc(-c3ccc(C(=O)NCc4ccncc4)nc3)c(F)c2)C(=O)O1]<br>5-{4-[5-(S)-(Acetylamino-methyl)-2-oxo-oxazolidin-3-yl]-2-fluoro-phenyl}-pyridine-2-carboxylic acid (pyridin-4-ylmethyl)-amide | 1 |
| 4189 | 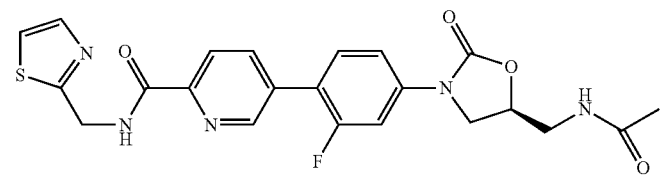 [SMILES: CC(=O)NC[C@H]1CN(c2ccc(-c3ccc(C(=O)NCc4nccs4)nc3)c(F)c2)C(=O)O1]<br>5-{4-[5-(S)-(Acetylamino-methyl)-2-oxo-oxazolidin-3-yl]-2-fluoro-phenyl}-pyridine-2-carboxylic acid (thiazol-2-ylmethyl)-amide | 1 |
| 4190 | 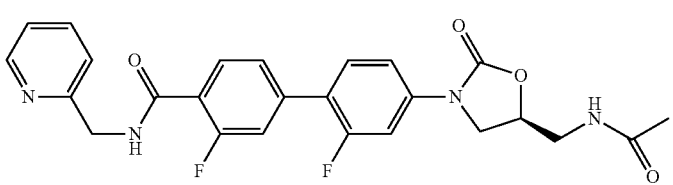 [SMILES: CC(=O)NC[C@H]1CN(c2ccc(-c3ccc(C(=O)NCc4ccccn4)c(F)c3)c(F)c2)C(=O)O1]<br>4'-[5-(S)-(Acetylamino-methyl)-2-oxo-oxazolidin-3-yl]-3,2'-difluoro-biphenyl-4-carboxylic acid (pyridin-2-ylmethyl)-amide | 1 |

TABLE 2-continued

| Compound Number | Structure | MICs |
|---|---|---|
| 4191 | 4'-[5-(S)-(Acetylamino-methyl)-2-oxo-oxazolidin-3-yl]-3,2'-difluoro-biphenyl-4-carboxylic acid [2-(3H-imidazol-4-yl)-ethyl]-amide | 1 |
| 4192 | N-{3-[2-Fluoro-4'-(pyridin-2-ylmethoxymethyl)-biphenyl-4-yl]-2-oxo-oxazolidin-5-(S)-ylmethyl}-acetamide | 1 |
| 4193 | N-{4'-[5-(S)-(Acetylamino-methyl)-2-oxo-oxazolidin-3-yl]-2'-fluoro-biphenyl-4-ylmethyl}-3-(1-methyl-6-oxo-1,6-dihydro-pyridin-3-yl)-acrylamide | 8 |
| 4194 | N-{4'-[5-(S)-(Acetylamino-methyl)-2-oxo-oxazolidin-3-yl]-2'-fluoro-biphenyl-4-ylmethyl}-3-(1-methyl-2-oxo-1,2-dihydro-pyridin-3-yl)-acrylamide | 2 |

| Compound Number | Structure | MICs |
|---|---|---|
| 4195 | N-(3-{3-Fluoro-4-[6-(pyridin-2-ylmethoxymethyl)-pyridin-3-yl]-phenyl}-2-oxo-oxazolidin-5-(S)-ylmethyl)-acetamide | 1 |
| 4196 | N-{3-[2-Fluoro-4'-(pyridin-4-ylmethoxymethyl)-biphenyl-4-yl]-2-oxo-oxazolidin-5-(S)-ylmethyl}-acetamide | 1 |
| 4197 | N-(3-{3-Fluoro-4-[5-(pyridin-2-ylmethoxymethyl)-pyridin-2-yl]-phenyl}-2-oxo-oxazolidin-5-(S)-ylmethyl)-acetamide | 4 |
| 4198 | N-{3-[2-Fluoro-4'-(1-oxy-pyridin-4-ylmethoxymethyl)-biphenyl-4-yl]-2-oxo-oxazolidin-5-(S)-ylmethyl}-acetamide | 2 |

TABLE 2-continued

| Compound Number | Structure | MICs |
|---|---|---|
| 4199 | N-[3-(2-Fluoro-4'-{1-(R)-hydroxy-2-[(oxazol-4-ylmethyl)-amino]-ethyl}-biphenyl-4-yl)-2-oxo-oxazolidin-5-(S)-ylmethyl]-acetamide | 4 |
| 4200 | N-[3-(2-Fluoro-4'-{2-hydroxy-1-(S)-[(oxazol-4-ylmethyl)-amino]-ethyl}-biphenyl-4-yl)-2-oxo-oxazolidin-5-(S)-ylmethyl]-acetamide | 4 |
| 4201 | N-[3-(2-Fluoro-4'-{1-(R)-hydroxy-2-[(pyridin-4-ylmethyl)-amino]-ethyl}-biphenyl-4-yl)-2-oxo-oxazolidin-5-(S)-ylmethyl]-acetamide | 2 |
| 4202 | N-[3-(2-Fluoro-4'-{2-hydroxy-1-(R)-[(pyridin-4-ylmethyl)-amino]-ethyl}-biphenyl-4-yl)-2-oxo-oxazolidin-5-(S)-ylmethyl]-acetamide | 4 |

TABLE 2-continued

| Compound Number | Structure | MICs |
|---|---|---|
| 4203 | N-[3-(2-Fluoro-4'-{[(pyrimidin-5-ylmethyl)-amino]-methyl}-biphenyl-4-yl)-2-oxo-oxazolidin-5-(S)-ylmethyl]-acetamide | 1 |
| 4204 | N-(3-{4'-[(Acetyl-[1,2,3]thiadiazol-4-ylmethyl-amino)-methyl]-2-fluoro-biphenyl-4-yl}-2-oxo-oxazolidin-5-(S)-ylmethyl)-acetamide | 2 |
| 4205 | 4'-[5-(S)-(Acetylamino-methyl)-2-oxo-oxazolidin-3-yl]-2'-fluoro-biphenyl-4-carboxylic acid (oxazol-4-ylmethyl)-amide | 1 |
| 4206 | N-[3-(2-Fluoro-4'-{[([1,2,4]thiadiazol-3-ylmethyl)-amino]-methyl}-biphenyl-4-yl)-2-oxo-oxazolidin-5-(S)-ylmethyl]-acetamide | 1 |

TABLE 2-continued

| Compound Number | Structure | MICs |
|---|---|---|
| 4207 | 2-(4-Chloro-benzylamino)-thiazole-4-carboxylic acid {4'-[5-(S)-(acetylamino-methyl)-2-oxo-oxazolidin-3-yl]-2'-fluoro-biphenyl-4-ylmethyl}-amide | 2 |
| 4208 | N-[3-(2-Fluoro-4'-{[(oxazol-5-ylmethyl)-amino]-methyl}-biphenyl-4-yl)-2-oxo-oxazolidin-5-(S)-ylmethyl]-acetamide | 1 |
| 4209 | N-[3-(4'-{[([1,3]Dioxolan-2-ylmethyl)-amino]-methyl}-2-fluoro-biphenyl-4-yl)-2-oxo-oxazolidin-5-(S)-ylmethyl]-acetamide | 0.5 |
| 4210 | N-(3-{2-Fluoro-4'-[(oxiranylmethyl-amino)-methyl]-biphenyl-4-yl}-2-oxo-oxazolidin-5-(S)-ylmethyl)-acetamide | 4 |

TABLE 2-continued

| Compound Number | Structure | MICs |
|---|---|---|
| 4211 | N-{3-[2-Fluoro-4'-(pyridin-4-ylmethylsulfanylmethyl)-biphenyl-4-yl]-2-oxo-oxazolidin-5-(S)-ylmethyl}-acetamide | 0.25 |
| 4212 | N-{3-[2-Fluoro-4'-(pyridin-4-ylmethanesulfinylmethyl)-biphenyl-4-yl]-2-oxo-oxazolidin-5-(S)-ylmethyl}-acetamide | 0.25 |
| 4213 | 3-(2-Fluoro-4'-{[(pyridin-4-ylmethyl)-amino]-methyl}-biphenyl-4-yl)-5-(R)-hydroxymethyl-oxazolidin-2-one | 4 |
| 4214 | N-{3-[2-Fluoro-4'-(pyridin-4-ylmethanesulfonylmethyl)-biphenyl-4-yl]-2-oxo-oxazolidin-5-(S)-ylmethyl}-acetamide | 1 |

TABLE 2-continued

| Compound Number | Structure | MICs |
|---|---|---|
| 4215 | N-(3-{2-Fluoro-4'-[(methyl-quinolin-3-ylmethyl-amino)-methyl]-biphenyl-4-yl}-2-oxo-oxazolidin-5-(S)-ylmethyl)-acetamide | 0.25 |
| 4216 | N-{3-[2-Fluoro-4'-(pyridin-2-ylmethylsulfanylmethyl)-biphenyl-4-yl]-2-oxo-oxazolidin-5-(S)-ylmethyl}-acetamide | 0.5 |
| 4217 | N-{3-[2-Fluoro-4'-(pyridin-2-ylmethanesulfinylmethyl)-biphenyl-4-yl]-2-oxo-oxazolidin-5-(S)-ylmethyl}-acetamide | 1 |
| 4218 | N-[3-(2-Fluoro-4'-{[(1-methyl-1H-indol-3-ylmethyl)-amino]-methyl}-biphenyl-4-yl)-2-oxo-oxazolidin-5-(S)-ylmethyl]-acetamide | 2 |

TABLE 2-continued

| Compound Number | Structure | MICs |
|---|---|---|
| 4219 | N-[3-(2-Fluoro-4'-{[(tetrahydro-furan-3-ylmethyl)-amino]-methyl}-biphenyl-4-yl)-2-oxo-oxazolidin-5-(S)-ylmethyl]-acetamide | 8 |
| 4220 | N-[3-(2-Fluoro-4'-{[(tetrahydro-furan-3-ylmethyl)-amino]-methyl}-biphenyl-4-yl)-2-oxo-oxazolidin-5-(S)-ylmethyl]-acetamide | 0.25 |
| 4221 | N-[3-(2-Fluoro-4'-{[(thiophen-2-ylmethyl)-amino]-methyl}-biphenyl-4-yl)-2-oxo-oxazolidin-5-(S)-ylmethyl]-acetamide | 2 |
| 4222 | N-{3-[2-Fluoro-4'-(N-furan-2-ylmethyl-carbamimidoyl)-biphenyl-4-yl]-2-oxo-oxazolidin-5-(S)-ylmethyl}-acetamide | 16 |

TABLE 2-continued

| Compound Number | Structure | MICs |
|---|---|---|
| 4223 | 5-{4-[5-(S)-(Acetylamino-methyl)-2-oxo-oxazolidin-3-yl]-2-fluoro-phenyl}-pyridine-2-carboxylic acid [2-(3H-imidazol-4-yl)-ethyl]-amide | 2 |
| 4224 | 4'-[5-(S)-(Acetylamino-methyl)-2-oxo-oxazolidin-3-yl]-2'-fluoro-biphenyl-4-carboxylic acid ([1,2,4]oxadiazol-3-ylmethyl)-amide | 0.5 |
| 4225 | 4'-[5-(S)-(Acetylamino-methyl)-2-oxo-oxazolidin-3-yl]-2'-fluoro-biphenyl-4-carboxylic acid ([1,2,4]thiadiazol-3-ylmethyl)-amide | 1 |
| 4226 | N-[3-(2-Fluoro-4'-oxiranylmethylsulfanylmethyl-biphenyl-4-yl)-2-oxo-oxazolidin-5-(S)-ylmethyl]-acetamide | 1 |
| 4227 | N-[3-(2-Fluoro-4'-{[2-(1H-imidazol-4-yl)-ethylamino]-methyl}-biphenyl-4-yl)-2-oxo-oxazolidin-5-(S)-ylmethyl]-acetamide | 4 |

TABLE 2-continued

| Compound Number | Structure | MICs |
|---|---|---|
| 4228 | N-[3-(2-Fluoro-4'-{[2-(5-methyl-3H-indol-3-yl)-ethylamino]-methyl}-biphenyl-4-yl)-2-oxo-oxazolidin-5-(S)-ylmethyl]-acetamide | 2 |
| 4229 | N-[3-(2-Fluoro-4'-{[(5-methyl-isoxazol-3-ylmethyl)-amino]-methyl}-biphenyl-4-yl)-2-oxo-oxazolidin-5-(S)-ylmethyl]-acetamide | 0.25 |
| 4230 | 3-(2-Fluoro-4'-{[(pyridin-4-ylmethyl)-amino]-methyl}-biphenyl-4-yl)-5-(R)-[1,2,4]triazol-1-ylmethyl-oxazolidin-2-one | 32 |
| 4231 | 3-(2-Fluoro-4'-{[(pyridin-4-ylmethyl)-amino]-methyl}-biphenyl-4-yl)-5-(R)-(1-methyl-1H-tetrazol-5-ylsulfanylmethyl)-oxazolidin-2-one | 32 |
| 4232 | N-[3-(2-Fluoro-4'-{1-(R/S)-[(pyridin-4-ylmethyl)-amino]-ethyl}-biphenyl-4-yl)-2-oxo-oxazolidin-5-(S)-ylmethyl]-acetamide | 8 |

TABLE 2-continued

| Compound Number | Structure | MICs |
|---|---|---|
| 4233 | N-[3-(2-Fluoro-4'-{[([1,2,4]oxadiazol-3-ylmethyl)-amino]-methyl}-biphenyl-4-yl)-2-oxo-oxazolidin-5-(S)-ylmethyl]-acetamide | 0.5 |
| 4234 | N-[3-(2-Fluoro-4'-{[(oxazol-4-ylmethyl)-amino]-methyl}-biphenyl-4-yl)-2-oxo-oxazolidin-5-(S)-ylmethyl]-acetamide | 2 |
| 4235 | N-{3-[3-Fluoro-4-(6-{[(oxazol-4-ylmethyl)-amino]-methyl}-pyridin-3-yl)-phenyl]-2-oxo-oxazolidin-5-(S)-ylmethyl}-acetamide | 2 |
| 4236 | N-(3-{2-Fluoro-4'-[N'-(pyridine-4-carbonyl)-hydrazinomethyl]-biphenyl-4-yl}-2-oxo-oxazolidin-5-(S)-ylmethyl)-acetamide | 0.25 |
| 4237 | N-(3-{2-Fluoro-4'-[N'-(pyridine-3-carbonyl)-hydrazinomethyl]-biphenyl-4-yl}-2-oxo-oxazolidin-5-(S)-ylmethyl)-acetamide | 0.25 |

TABLE 2-continued

| Compound Number | Structure | MICs |
|---|---|---|
| 4238 | N-[3-(2-Fluoro-4'-{[(oxazol-5-ylmethyl)-amino]-methyl}-biphenyl-4-yl)-2-oxo-oxazolidin-5-(S)-ylmethyl]-acetamide | 1 |
| 4239 | N-{4'-[5-(S)-(Acetylamino-methyl)-2-oxo-oxazolidin-3-yl]-2'-fluoro-biphenyl-4-ylmethyl}-2-[1,2,3]triazol-1-yl-acetamide | 2 |
| 4240 | N-{4'-[5-(S)-(Acetylamino-methyl)-2-oxo-oxazolidin-3-yl]-2'-fluoro-biphenyl-4-ylmethyl}-2-(4-hydroxymethyl-[1,2,3]triazol-1-yl)-acetamide | 16 |
| 4241 | N-{4'-[5-(S)-(Acetylamino-methyl)-2-oxo-oxazolidin-3-yl]-2'-fluoro-biphenyl-4-ylmethyl}-2-[4-(2-hydroxy-butyl)-[1,2,3]triazol-1-yl]-acetamide | 4 |

TABLE 2-continued

| Compound Number | Structure | MICs |
|---|---|---|
| 4242 | 2-Methyl-thiazole-4-carboxylic acid {4'-[5-(S)-(acetylaminomethyl)-2-oxo-oxazolidin-3-yl]-2'-fluoro-biphenyl-4-ylmethyl}-amide | 2 |
| 4243 | 2-Methyl-thiazole-4-carboxylic acid {4'45-(S)-(acetylaminomethyl)-2-oxo-oxazolidin-3-yl]-2'-fluoro-biphenyl-4-ylmethyl}-amide | 4 |
| 4244 | N-{3-[2-Fluoro-4'-([1,2,4]oxadiazol-3-ylmethylsulfanylmethyl)-biphenyl-4-yl]-2-oxo-oxazolidin-5-(S)-ylmethyl}-acetamide | 0.5 |
| 4245 | N-[3-(2-Fluoro-4'-{[(1-oxy-pyridin-4-ylmethyl)-amino]-methyl}-biphenyl-4-yl)-2-oxo-oxazolidin-5-(S)-ylmethyl]-acetamide | 2 |

TABLE 2-continued

| Compound Number | Structure | MICs |
|---|---|---|
| 4246 | N-{3-[4'-(2-Benzylamino-1-(S)-hydroxy-ethyl)-2-fluoro-biphenyl-4-yl]-2-oxo-oxazolidin-5-(S)-ylmethyl}-acetamide | 4 |
| 4247 | N-[3-(4'-{2-[Benzyl-(3-fluoro-propyl)-amino]-1-(S)-hydroxy-ethyl}-2-fluoro-biphenyl-4-yl)-2-oxo-oxazolidin-5-(S)-ylmethyl]-acetamide | 8 |
| 4248 | N-[3-(4'-{2-[Benzyl-(2-methylsulfanyl-ethyl)-amino]-1-(S)-hydroxy-ethyl}-2-fluoro-biphenyl-4-yl)-2-oxo-oxazolidin-5-(S)-ylmethyl]-acetamide | 4 |
| 4249 | N-[3-(4'-{2-[Benzyl-(3-chloro-3,3-difluoro-propyl)-amino]-1-(S)-hydroxy-ethyl}-2-fluoro-biphenyl-4-yl)-2-oxo-oxazolidin-5-(S)-ylmethyl]-acetamide | 8 |

TABLE 2-continued

| Compound Number | Structure | MICs |
|---|---|---|
| 4250 | N-(2-{4'-[5-(S)-(Acetylamino-methyl)-2-oxo-oxazolidin-3-yl]-2'-fluoro-biphenyl-4-yl}-2-(S)-hydroxy-ethyl)-N-benzyl-acetamide | 2 |
| 4251 | N-(3-{4'-[2-(Benzyl-methyl-amino)-1-(S)-hydroxy-ethyl]-2-fluoro-biphenyl-4-yl}-2-oxo-oxazolidin-5-(S)-ylmethyl)-acetamide | 2 |
| 4252 | N-{3-[3-Fluoro-4-(6-{[(isoxazol-4-ylmethyl)-amino]-methyl}-pyridin-3-yl)-phenyl]-2-oxo-oxazolidin-5-(S)-ylmethyl}-acetamide | 2 |
| 4253 | N-[3-(4'-{[(3-Bromo-isoxazol-5-ylmethyl)-amino]-methyl}-2-fluoro-biphenyl-4-yl)-2-oxo-oxazolidin-5-(S)-ylmethyl]-acetamide | 0.5 |

TABLE 2-continued

| Compound Number | Structure | MICs |
|---|---|---|
| 4254 | N-[3-(2-Fluoro-4'-{2-[(isoxazol-4-ylmethyl)-amino]-1-methoxyimino-ethyl}-biphenyl-4-yl)-2-oxo-oxazolidin-5-(S)-ylmethyl]-acetamide | 2 |
| 4255 | N-[3-(2-Fluoro-4'-{1-methoxyimino-2-[(oxazol-4-ylmethyl)-amino]-ethyl}-biphenyl-4-yl)-2-oxo-oxazolidin-5-(S)-ylmethyl]-acetamide | 2 |
| 4256 | N-[3-(4'-{[3-(1-Benzyl-1H-[1,2,3]triazol-4-yl)-propylamino]-methyl}-2-fluoro-biphenyl-4-yl)-2-oxo-oxazolidin-5-(S)-ylmethyl]-acetamide | 4 |
| 4257 | N-[3-(2-Fluoro-4'-{[(2-fluoro-pyridin-3-ylmethyl)-amino]-methyl}-biphenyl-4-yl)-2-oxo-oxazolidin-5-(S)-ylmethyl]-acetamide | 0.5 |

TABLE 2-continued

| Compound Number | Structure | MICs |
|---|---|---|
| 4258 | N-[3-(2-Fluoro-4'-{[3-(3H-[1,2,3]triazol-4-yl)-propylamino]-methyl}-biphenyl-4-yl)-2-oxo-oxazolidin-5-(S)-ylmethyl]-acetamide | 4 |
| 4259 | N-(3-{2-Fluoro-4'-[(2-pyrrolidin-1-yl-ethylamino)-methyl]-biphenyl-4-yl}-2-oxo-oxazolidin-5-(S)-ylmethyl)-acetamide | 4 |
| 4260 | N-[3-(3-Fluoro-4-morpholin-4-yl-phenyl)-2-oxo-oxazolidin-5-(S)-ylmethyl]-3-(5-pyrimidin-2-yl-pyridin-2-yl)-propionamide | 4 |
| 4261 | N-[3-(2-Fluoro-2'-methoxy-4'-{[(pyridin-4-ylmethyl)-amino]-methyl}-biphenyl-4-yl)-2-oxo-oxazolidin-5-(S)-ylmethyl]-acetamide | 8 |

TABLE 2-continued

| Compound Number | Structure | MICs |
|---|---|---|
| 4262 | N-(3-{2-Fluoro-4'-[(2-[1,2,3]triazol-1-yl-ethylamino)-methyl]-biphenyl-4-yl}-2-oxo-oxazolidin-5-(S)-ylmethyl)-acetamide | 2 |
| 4263 | N-{3-[4'-(Benzyloxyamino-methyl)-2-fluoro-biphenyl-4-yl]-2-oxo-oxazolidin-5-(S)-ylmethyl}-acetamide | 2 |
| 4264 | N-(3-{2-Fluoro-4'-[(3-[1,2,3]triazol-1-yl-propylamino)-methyl]-biphenyl-4-yl}-2-oxo-oxazolidin-5-(S)-ylmethyl)-acetamide | 4 |
| 4265 | N-[3-(4'-{[Benzyloxy-(3-fluoro-propyl)-amino]-methyl}-2-fluoro-biphenyl-4-yl)-2-oxo-oxazolidin-5-(S)-ylmethyl]-acetamide | 4 |

TABLE 2-continued

| Compound Number | Structure | MICs |
|---|---|---|
| 4266 | N-[3-(2-Fluoro-4'-{[2-(3H-[1,2,3]triazol-4-yl)-ethylamino]-methyl}-biphenyl-4-yl)-2-oxo-oxazolidin-5-(S)-ylmethyl]-acetamide | 4 |
| 4267 | N-[3-(2-Fluoro-4'-{[(3H-[1,2,3]triazol-4-ylmethyl)-amino]-methyl}-biphenyl-4-yl)-2-oxo-oxazolidin-5-(S)-ylmethyl]-acetamide | 0.25 |
| 4268 | 3-(2-Fluoro-4'-{[(3H-[1,2,3]triazol-4-ylmethyl)-amino]-methyl}-biphenyl-4-yl)-5-(R)-[1,2,3]triazol-1-ylmethyl-oxazolidin-2-one | 0.25 |
| 4269 | N-[3-(2-Fluoro-4'-{[(5-methyl-3H-[1,2,3]triazol-4-ylmethyl)-amino]-methyl}-biphenyl-4-yl)-2-oxo-oxazolidin-5-(S)-ylmethyl]-acetamide | 2 |

TABLE 2-continued

| Compound Number | Structure | MICs |
|---|---|---|
| 4270 | N-[3-(4'-{[Bis-(5-methyl-3H-[1,2,3]triazol-4-ylmethyl)-amino]-methyl}-2-fluoro-biphenyl-4-yl)-2-oxo-oxazolidin-5-(S)-ylmethyl]-acetamide | 4 |
| 4271 | N-(3-{2-Fluoro-4'-[N'-(4-methyl-[1,2,3]thiadiazole-carbonyl)-hydrazinomethyl]-biphenyl-4-yl}-2-oxo-oxazolidin-5-(S)-ylmethyl)-acetamide | 0.25 |
| 4272 | N-[3-(2-Fluoro-4'-{[(3-methyl-3H-[1,2,3]triazol-4-ylmethyl)-amino]-methyl}-biphenyl-4-yl)-2-oxo-oxazolidin-5-(S)-ylmethyl]-acetamide | 0.25 |
| 4273 | N-[3-(2-Fluoro-4'-{[(2-methyl-2H-[1,2,3]triazol-4-ylmethyl)-amino]-methyl}-biphenyl-4-yl)-2-oxo-oxazolidin-5-(S)-ylmethyl]-acetamide | 0.25 |

TABLE 2-continued

| Compound Number | Structure | MICs |
|---|---|---|
| 4274 | N-(3-{2-Fluoro-4'-[(3-fluoro-2-[1,2,3]triazol-1-yl-propylamino)-methyl]-biphenyl-4-yl}-2-oxo-oxazolidin-5-(S)-ylmethyl)-acetamide | 2 |
| 4275 | N-[3-(2-Fluoro-4'-{[2-(4-fluoro-phenyl)-2-(R/S)-hydroxy-ethylamino]-methyl}-biphenyl-4-yl)-2-oxo-oxazolidin-5-(S)-ylmethyl]-acetamide | 0.5 |
| 4276 | N-[3-(2-Fluoro-4'-{[methyl-(3H-[1,2,3]triazol-4-ylmethyl)-amino]-methyl}-biphenyl-4-yl)-2-oxo-oxazolidin-5-(S)-ylmethyl]-acetamide | 0.25 |
| 4277 | N-{3-[3-Fluoro-4-(6-{[(3H-[1,2,3]triazol-4-ylmethyl)-amino]-methyl}-pyridin-3-yl)-phenyl]-2-oxo-oxazolidin-5-(S)-ylmethyl}-acetamide | 4 |

TABLE 2-continued

| Compound Number | Structure | MICs |
|---|---|---|
| 4278 | N-[3-(2-Fluoro-4'-{[1-(R/S)-(3H-[1,2,3]triazol-4-yl)-ethylamino]-methyl}-biphenyl-4-yl)-2-oxo-oxazolidin-5-(S)-ylmethyl]-acetamide | 2 |
| 4279 | N-[3-(2-Fluoro-4'-{[(pyrrolidin-2-(R/S)-ylmethyl)-amino]-methyl}-biphenyl-4-yl)-2-oxo-oxazolidin-5-(S)-ylmethyl]-acetamide | 4 |
| 4280 | {4'-[5-(S)-(Acetylamino-methyl)-2-oxo-oxazolidin-3-yl]-2'-fluoro biphenyl-4-ylmethyl}-(1-methyl-1H-tetrazol-5-ylmethyl)-carbamic acid tert-butyl ester | 1 |
| 4281 | {4'-[5-(S)-(Acetylamino-methyl)-2-oxo-oxazolidin-3-yl]-2'-fluoro-biphenyl-4-ylmethyl}-(2-methyl-2H-tetrazol-5-ylmethyl)-carbamic acid tert-butyl ester | 2 |

TABLE 2-continued

| Compound Number | Structure | MICs |
|---|---|---|
| 4282 | N-[3-(2-Fluoro-4'-{[(1H-tetrazol-5-ylmethyl)-amino]-methyl}-biphenyl-4-yl)-2-oxo-oxazolidin-5-(S)-ylmethyl]-acetamide | 16 |
| 4283 | N-[3-(2-Fluoro-4'-{[(1-methyl-1H-tetrazol-5-ylmethyl)-amino]-methyl}-biphenyl-4-yl)-2-oxo-oxazolidin-5-(S)-ylmethyl]-acetamide | 0.25 |
| 4284 | N-[3-(2-Fluoro-4'-{[(2-methyl-2H-tetrazol-5-ylmethyl)-amino]-methyl}-biphenyl-4-yl)-2-oxo-oxazolidin-5-(S)-ylmethyl]-acetamide | 0.25 |
| 4285 | N-[3-(2-Fluoro-4'-{[(N-hydroxy-pyridine-4-carboximidoyl)-amino]-methyl}-biphenyl-4-yl)-2-oxo-oxazolidin-5-(S)-ylmethyl]-acetamide | 8 |

TABLE 2-continued

| Compound Number | Structure | MICs |
|---|---|---|
| 4286 | N-[3-(4'-{2-[Benzyl-(2-methanesulfonyl-ethyl)-amino]-1-(S)-hydroxy-ethyl}-2-fluoro-biphenyl-4-yl)-2-oxo-oxazolidin-5-(S)-ylmethyl]-acetamide | 2 |
| 4287 | N-[3-(4'-{[2-(1,3-Dioxo-1,3-dihydro-isoindol-2-yl)-ethanesulfonylamino]-methyl}-2-fluoro-biphenyl-4-yl)-2-oxo-oxazolidin-5-(S)-ylmethyl]-acetamide | 8 |
| 4288 | N-{3-[4'-(Benzylsulfamoyl-methyl)-2-fluoro-biphenyl-4-yl]-2-oxo-oxazolidin-5-(S)-ylmethyl}-acetamide | 128 |

TABLE 2-continued

| Compound Number | Structure | MICs |
|---|---|---|
| 4289 | 5-Oxo-pyrrolidine-2-carboxylic acid {4'-[5-(S)-(acetylamino-methyl)-2-oxo-oxazolidin-3-yl]-2'-fluoro-biphenyl-4-ylmethyl}-amide | 8 |
| 4290 | 3-({4'-[5-(S)-(Acetylamino-methyl)-2-oxo-oxazolidin-3-yl]-2'-fluoro-biphenyl-4-ylmethyl}-carbamoyl)-azetidine-1-carboxylic acid tert-butyl ester | 16 |
| 4291 | Azetidine-3-carboxylic acid {4'-[5-(S)-(acetylamino-methyl)-2-oxo-oxazolidin-3-yl]-2'-fluoro-biphenyl-4-ylmethyl}-amide | 8 |
| 4292 | N-{4'-[5-(S)-(Acetylamino-methyl)-2-oxo-oxazolidin-3-yl]-2'-fluoro-biphenyl-4-ylmethyl}-2-(R)-amino-3-(3H-imidazol-4-yl)-propionamide | 16 |

TABLE 2-continued

| Compound Number | Structure | MICs |
|---|---|---|
| 4293 | 2-({4'-[5-(S)-(Acetylamino-methyl)-2-oxo-oxazolidin-3-yl]-2'-fluoro-biphenyl-4-ylmethyl}-amino)-2-pyridin-3-yl-acetamide | 4 |
| 4294 | N-{4'-[5-(S)-(Acetylamino-methyl)-2-oxo-oxazolidin-3-yl]-2'-fluoro-biphenyl-4-ylmethyl}-2-amino-2-pyridin-3-yl-acetamide | 4 |
| 4295 | 2-({4'-[5-(S)-(Acetylamino-methyl)-2-oxo-oxazolidin-3-yl]-2'-fluoro-biphenyl-4-ylmethyl}-carbamoyl)-azetidine-1-carboxylic acid tert-butyl ester | 8 |
| 4296 | Azetidine-2-carboxylic acid {4'-[5-(S)-(acetylamino-methyl)-2-oxo-oxazolidin-3-yl]-2'-fluoro-biphenyl-4-ylmethyl}-amide | 2 |

TABLE 2-continued

| Compound Number | Structure | MICs |
|---|---|---|
| 4297 | 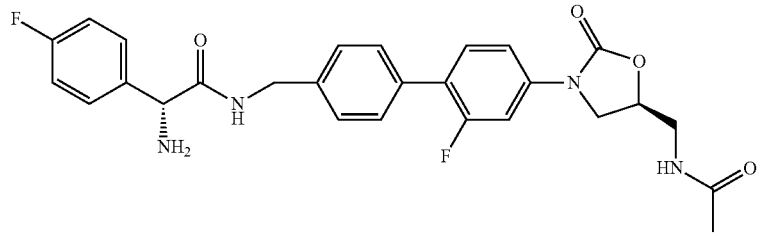 [SMILES: CC(=O)NC[C@H]1CN(c2ccc(-c3ccc(CNC(=O)[C@H](N)c4ccc(F)cc4)cc3)c(F)c2)C(=O)O1]<br>N-{4'-[5-(S)-(Acetylamino-methyl)-2-oxo-oxazolidin-3-yl]-2'-fluoro-biphenyl-4-ylmethyl}-2-(R)-amino-2-(4-fluoro-phenyl)-acetamide | 2 |
| 4298 | 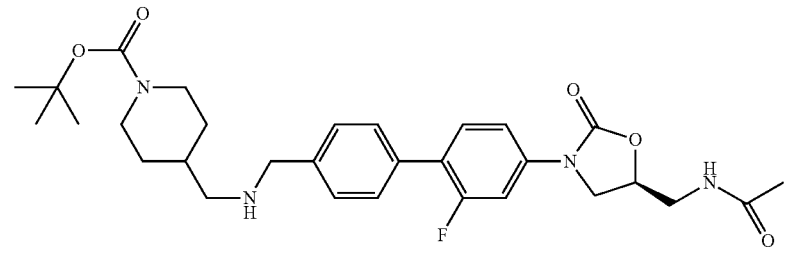 [SMILES: CC(=O)NC[C@H]1CN(c2ccc(-c3ccc(CNCC4CCN(C(=O)OC(C)(C)C)CC4)cc3)c(F)c2)C(=O)O1]<br>4-[({4'-[5-(S)-(Acetylamino-methyl)-2-oxo-oxazolidin-3-yl]-2'-fluoro-biphenyl-4-ylmethyl}-amino)-methyl]-piperidine-1-carboxylic acid tert-butylester | 8 |
| 4299 | 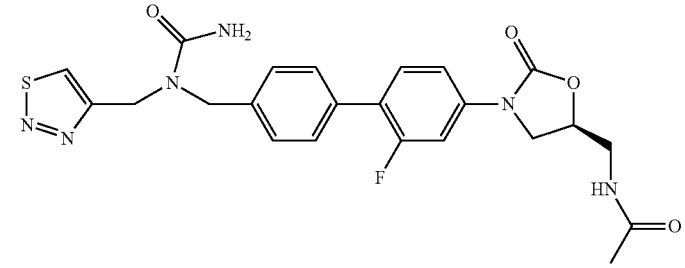 [SMILES: CC(=O)NC[C@H]1CN(c2ccc(-c3ccc(CN(Cc4csnn4)C(N)=O)cc3)c(F)c2)C(=O)O1]<br>N-{3-[2-Fluoro-4'-(1-[1,2,3]thiadiazol-4-ylmethyl-ureidomethyl)-biphenyl-4-yl]-2-oxo-oxazolidin-5-(S)-ylmethyl}-acetamide | 2 |
| 4300 | 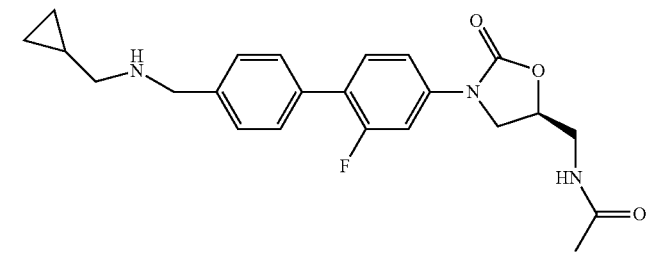 [SMILES: CC(=O)NC[C@H]1CN(c2ccc(-c3ccc(CNCC4CC4)cc3)c(F)c2)C(=O)O1]<br>N-(3-{4'-[(Cyclopropylmethyl-amino)-methyl]-2-fluoro-biphenyl-4-yl}-2-oxo-oxazolidin-5-(S)-ylmethyl)-acetamide | 4 |

TABLE 2-continued

| Compound Number | Structure | MICs |
|---|---|---|
| 4301 | 4-(R)-Hydroxy-pyrrolidine-2-(S)-carboxylicacid {4'-[5-(S)-(acetylamino-methyl)-2-oxo-oxazolidin-3-yl]-2'-fluoro-biphenyl-4-ylmethyl}-amide | 8 |
| 4302 | N-{4'-[5-(S)-(Acetylamino-methyl)-2-oxo-oxazolidin-3-yl]-2'-fluoro-biphenyl-4-ylmethyl}-2-(S)-amino-3-pyridin-2-yl-propionamide | 8 |
| 4303 | [1-(S)-({4'-[5-(S)-(Acetylamino-methyl)-2-oxo-oxazolidin-3-yl]-2'-fluoro-biphenyl-4-ylmethyl}-carbamoyl)-2-pyridin-2-yl-ethyl]-carbamic acid tert-butyl ester | 8 |
| 4304 | [1-({4'-[5-(S)-(Acetylamino-methyl)-2-oxo-oxazolidin-3-yl]-2'-fluoro-biphenyl-4-ylmethyl}-carbamoyl)-cyclopropyl]-carbamic acid tert-butyl ester | 16 |

TABLE 2-continued

| Compound Number | Structure | MICs |
|---|---|---|
| 4305 | 2-({4'-[5-(S)-(Acetylamino-methyl)-2-oxo-oxazolidin-3-yl]-2'-fluoro-biphenyl-4-ylmethyl}-carbamoyl)-2,5-dihydro-pyrrole-1-(S)-carboxylic acid tert-butylester | 16 |
| 4306 | 2,5-Dihydro-1H-pyrrole-2-(S)-carboxylic acid {4'-[5-(S)-(acetylamino-methyl)-2-oxo-oxazolidin-3-yl]-2'-fluoro-biphenyl-4-ylmethyl}-amide | 2 |
| 4307 | N-{4'-[5-(S)-(Acetylamino-methyl)-2-oxo-oxazolidin-3-yl]-2'-fluoro-biphenyl-4-ylmethyl}-2-(R)-amino-3-(1H-indol-3-yl)-propionamide | 2 |
| 4308 | [1-(R)-({4'-[5-(S)-(Acetylamino-methyl)-2-oxo-oxazolidin-3-yl]-2'-fluoro-biphenyl-4-ylmethyl}-carbamoyl)-2-(1H-indol-3-yl)-ethyl]-carbamic acid tert-butyl ester | 128 |

TABLE 2-continued

| Compound Number | Structure | MICs |
|---|---|---|
| 4309 | Pyrrolidine-2-(S)-carboxylic acid {4'-[5-(S)-(acetylamino-methyl)-2-oxo-oxazolidin-3-yl]-2'-fluoro-biphenyl-4-ylmethyl}-amide | 8 |
| 4310 | N-{4'-[5-(S)-(Acetylamino-methyl)-2-oxo-oxazolidin-3-yl]-2'-fluoro-biphenyl-4-ylmethyl}-2-(R)-amino-3-pyridin-3-yl-propionamide | 4 |
| 4311 | 2-({4'-[5-(S)-(Acetylamino-methyl)-2-oxo-oxazolidin-3-yl]-2'-fluoro-biphenyl-4-ylmethyl}-carbamoyl)-4-(R)-hydroxy-pyrrolidine-1-(S)-carboxylic acid tert-butyl ester | 16 |
| 4312 | 2-({4'-[5-(S)-(Acetylamino-methyl)-2-oxo-oxazolidin-3-yl]-2'-fluoro-biphenyl-4-ylmethyl}-amino)-3-(S)-(1H-indol-3-yl)-propionamide<br>2-({4'-[5-(S)-(Acetylamino-methyl)-2-oxo-oxazolidin-3-yl]-2'-fluoro-biphenyl-4-ylmethyl}-amino)-3-(1H-imidazol-4-yl)-propionamide | 2 |

TABLE 2-continued

| Compound Number | Structure | MICs |
|---|---|---|
| 4314 | N-(3-{2-Fluoro-4'-[(2-oxo-2-piperazin-1-yl-ethylamino)-methyl]-biphenyl-4-yl}-2-oxo-oxazolidin-5-(S)-ylmethyl)-acetamide | 4 |
| 4315 | 4-[2-({4'-[5-(S)-(Acetylamino-methyl)-2-oxo-oxazolidin-3-yl]-2'-fluoro-biphenyl-4-ylmethyl}-amino)-acetyl]-piperazine-1-carboxylic acid tert-butyl ester | 4 |
| 4316 | N-(3-{2-Fluoro-4'-[(2-morpholin-4-yl-2-oxo-ethylamino)-methyl]-biphenyl-4-yl}-2-oxo-oxazolidin-5-(S)-ylmethyl)-acetamide | 4 |
| 4317 | 3-[({4'-[5-(S)-(Acetylamino-methyl)-2-oxo-oxazolidin-3-yl]-2'-fluoro-biphenyl-4-ylmethyl}-amino)-methyl]-pyrrolidine-1-carboxylic acid tert-butyl ester | 16 |

TABLE 2-continued

| Compound Number | Structure | MICs |
|---|---|---|
| 4318 | N-(3-{2-Fluoro-4'-[(2-morpholin-4-yl-ethylamino)-methyl]-biphenyl-4-yl}-2-oxo-oxazolidin-5-(S)-ylmethyl)-acetamide | 16 |
| 4319 | Cyclopropanecarboxylic acid {4'-[5-(S)-(acetylamino-methyl)-2-oxo-oxazolidin-3-yl]-2'-fluoro-biphenyl-4-ylmethyl}-amide | 16 |
| 4320 | N-(3-{2-Fluoro-4'-[(furan-3-ylmethyl-methyl-amino)-methyl]-2'-methoxy-biphenyl-4-yl}-2-oxo-oxazolidin-5-(S)-ylmethyl)-acetamide | 32 |
| 4321 | 1-Amino-cyclopropanecarboxylic acid {4'-[5-(S)-(acetylamino-methyl)-2-oxo-oxazolidin-3-yl]-2'-fluoro-biphenyl-4-ylmethyl}-amide | 2 |

| Compound Number | Structure | MICs |
|---|---|---|
| 4322 | Piperazine-2-(R/S)-carboxylic acid {4'-[5-(S)-(acetylamino-methyl)-2-oxo-oxazolidin-3-yl]-2'-fluoro-biphenyl-4-ylmethyl}-amide | 2 |
| 5001 | N-[3-(2-Fluoro-4'-{[2-(3H-[1,2,3]triazol-4-ylsulfanyl)-ethylamino]-methyl}-biphenyl-4-yl)-2-oxo-oxazolidin-5-(S)-ylmethyl]-acetamide | 1 |
| 5002 | N-[3-(2-Fluoro-4'-{[3-(3H-[1,2,3]triazol-4-ylsulfanyl)-propylamino]-methyl}-biphenyl-4-yl)-2-oxo-oxazolidin-5-(S)-ylmethyl]-acetamide | 0.25 |
| 5003 | N-[3-(2-Fluoro-4'-{[2-([1,3,4]thiadiazol-2-ylsulfanyl)-ethylamino]-methyl}-biphenyl-4-yl)-2-oxo-oxazolidin-5-(S)-ylmethyl]-acetamide | 1 |

TABLE 2-continued

| Compound Number | Structure | MICs |
|---|---|---|
| 5004 | 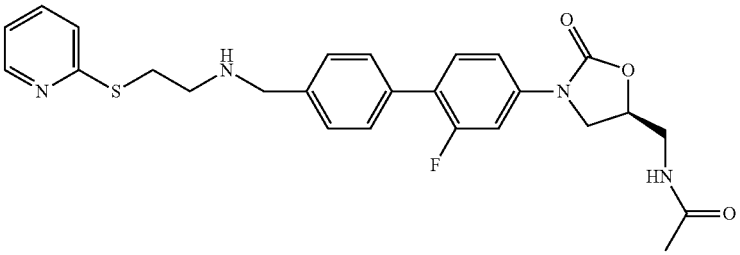 [SMILES: CC(=O)NC[C@H]1CN(c2ccc(-c3ccc(CNCCSc4ccccn4)cc3)c(F)c2)C(=O)O1]<br>N-[3-(2-Fluoro-4'-{[2-(pyridin-2-ylsulfanyl)-ethylamino]-methyl}-biphenyl-4-yl)-2-oxo-oxazolidin-5-(S)-ylmethyl]-acetamide | 1 |
| 5005 | 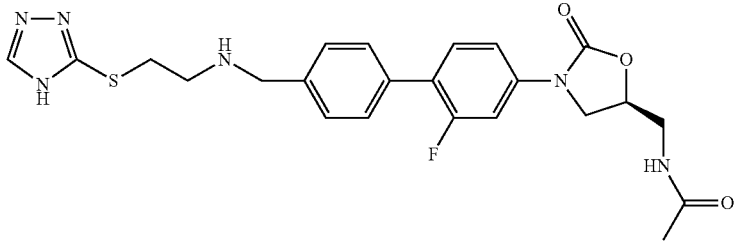 [SMILES: CC(=O)NC[C@H]1CN(c2ccc(-c3ccc(CNCCSc4nnc[nH]4)cc3)c(F)c2)C(=O)O1]<br>N-[3-(2-Fluoro-4'-{[2-(4H-[1,2,4]triazol-3-ylsulfanyl)-ethylamino]-methyl}-biphenyl-4-yl)-2-oxo-oxazolidin-5-(S)-ylmethyl]-acetamide | 0.5 |
| 5006 | 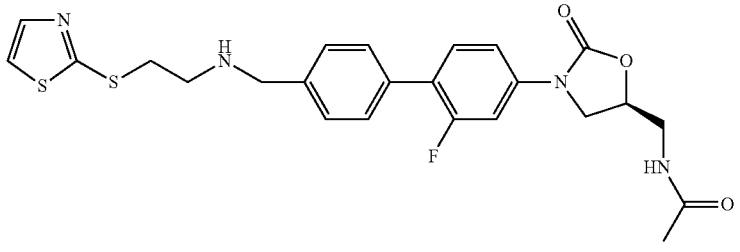 [SMILES: CC(=O)NC[C@H]1CN(c2ccc(-c3ccc(CNCCSc4nccs4)cc3)c(F)c2)C(=O)O1]<br>N-[3-(2-Fluoro-4'-{[2-(thiazol-2-ylsulfanyl)-ethylamino]-methyl}-biphenyl-4-yl)-2-oxo-oxazolidin-5-(S)-ylmethyl]-acetamide | 1 |
| 5007 | 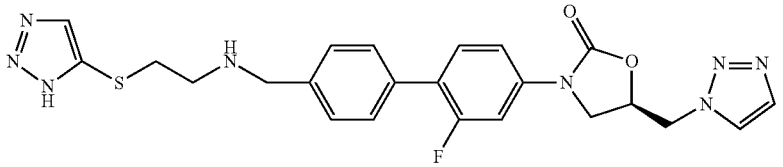 [SMILES: O=C1O[C@@H](Cn2ccnn2)CN1c1ccc(-c2ccc(CNCCSc3cnn[nH]3)cc2)c(F)c1]<br>3-(2-Fluoro-4'-{[2-(3H-[1,2,3]triazol-4-ylsulfanyl)-ethylamino]-methyl}-biphenyl-4-yl)-5-(R)-[1,2,3]triazol-1-ylmethyl-oxazolidin-2-one | 0.25 |

TABLE 2-continued

| Compound Number | Structure | MICs |
|---|---|---|
| 5008 | N-[3-(2-Fluoro-4'-{[2-(1H-imidazol-2-ylsulfanyl)-ethylamino]-methyl}-biphenyl-4-yl)-2-oxo-oxazolidin-5-(S)-ylmethyl]-acetamide | 2 |
| 5009 | N-[3-(2-Fluoro-4'-{[2-(pyrimidin-2-ylsulfanyl)-ethylamino]-methyl}-biphenyl-4-yl)-2-oxo-oxazolidin-5-(S)-ylmethyl]-acetamide | 1 |
| 5010 | 2-[2-({4'-[5-(S)-(Acetylamino-methyl)-2-oxo-oxazolidin-3-yl]-2'-fluoro-biphenyl-4-ylmethyl}-amino)-ethylsulfanyl]-1H-imidazole-4-carboxylic acid ethyl ester | 4 |
| 5011 | N-[3-(2-Fluoro-4'-{[2-(S)-(hydroxy-3-(4H-[1,2,4]triazol-3-ylsulfanyl)-propylamino]-methyl}-biphenyl-4-yl)-2-oxo-oxazolidin-5-(S)-ylmethyl]-acetamide | 4 |

TABLE 2-continued

| Compound Number | Structure | MICs |
|---|---|---|
| 5012 | N-(3-{2-Fluoro-4'-[(3-pyridin-4-yl-ureido)-methyl]-biphenyl-4-yl}-2-oxo-oxazolidin-5-(S)-ylmethyl)-acetamide | 2 |
| 5013 | N-(3-{2-Fluoro-4'-[3-(3-fluoro-phenyl)-ureidomethyl]-biphenyl-4-yl}-2-oxo-oxazolidin-5-(S)-ylmethyl)-acetamide | 32 |
| 5014 | N-{4'-[5-(S)-(Acetylamino-methyl)-2-oxo-oxazolidin-3-yl]-2'-fluoro-biphenyl-4-ylmethyl}-2-(2,4-dichloro-phenoxy)-acetamide | 16 |
| 5015 | N-[3-(4'-{[3-(3-Chloro-5-trifluoromethyl-pyridin-2-ylamino)-propylamino]-methyl}-2-fluoro-biphenyl-4-yl)-2-oxo-oxazolidin-5-(S)-ylmethyl]-acetamide | 4 |

TABLE 2-continued

| Compound Number | Structure | MICs |
|---|---|---|
| 6001 | N-(3-{2-Fluoro-4'-[3-(3-imidazol-1-yl-propyl)-ureido]-biphenyl-4-yl}-2-oxo-oxazolidin-5-(S)-ylmethyl)-acetamide | 16 |
| 6002 | N-{3-[2-Fluoro-4'-(3-thiazol-2-ylmethyl-ureido)-biphenyl-4-yl]-2-oxo-oxazolidin-5-(S)-ylmethyl}-acetamide | 2 |
| 6003 | N-(3-{2-Fluoro-4'-[3-(2-pyridin-2-yl-ethyl)-ureido]-biphenyl-4-yl}-2-oxo-oxazolidin-5-(S)-ylmethyl)-acetamide | 2 |
| 6004 | N-{3-[2-Fluoro-4'-(3-pyridin-4-ylmethyl-ureido)-biphenyl-4-yl]-2-oxo-oxazolidin-5-(S)-ylmethyl}-acetamide | 1 |

TABLE 2-continued

| Compound Number | Structure | MICs |
|---|---|---|
| 6005 | N-{3-[2-Fluoro-4'-(3-pyridin-2-ylmethyl-ureido)-biphenyl-4-yl]-2-oxo-oxazolidin-5-(S)-ylmethyl}-acetamide | 1 |
| 6006 | N-{3-[2-Fluoro-4'-(3-pyridin-4-yl-ureido)-biphenyl-4-yl]-2-oxo-oxazolidin-5-(S)-ylmethyl}-acetamide | 128 | or a pharmaceutically, acceptable salt, ester, or prodrug thereof.

An antibiotic compound particularly useful in the invention is radezolid (compound 4267, structure shown below), or a pharmaceutically acceptable salt, ester, tautomer, or prodrug thereof:

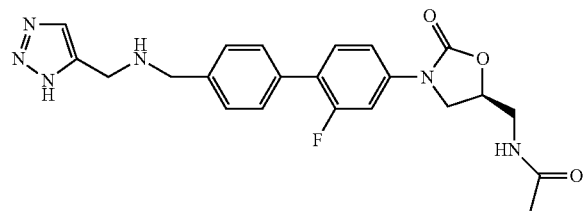 [SMILES: CC(=O)NC[C@H]1CN(c2ccc(-c3ccc(CNCc4cnn[nH]4)cc3)c(F)c2)C(=O)O1]

Other names for the compound radezolid include:
RX-1741;
N-[3-(2-Fluoro-4'-{[(3H-[1,2,3]triazol-4-ylmethyl)-amino]-methyl}-biphenyl-4-yl)-2-oxo-oxazolidin-5-(S)-ylmethyl]-acetamide;
N-[3-(2-Fluoro-4'-{[(1H-[1,2,3]triazol-4-ylmethyl)-amino]-methyl}-biphenyl-4-yl)-2-oxo-oxazolidin-5-(S)-ylmethyl]-acetamide;
N-{[(5S)-3-(2-fluoro-4'-{[(1H-1,2,3-triazol-5-ylmethyl)amino]methyl}biphenyl-4-yl)-2-oxo-1,3-oxazolidin-5-yl]methyl}acetamide;
869884-78-6;
UNII-53PC6LO35W; and
(S)—N-((3-(4'-((((1H-1,2,3-triazol-5-yl)methyl)amino)methyl)-2-fluoro-[1,1'-biphenyl]-4-yl)-2-oxooxazolidin-5-yl)methyl)acetamide.

As used herein, the term radezolid can also be used to refer to tautomers of radezolid, for example, the compound (S)—N-((3-(4'-((((1H-1,2,3-triazol-4-yl)methyl)amino)methyl)-2-fluoro-[1,1'-biphenyl]-4-yl)-2-oxooxazolidin-5-yl)methyl)acetamide Other Aspects of the Compounds of the Present Invention Antibiotic compounds designed, selected and/or optimized for use in the present invention, after being produced, can be characterized using a variety of assays known to those skilled in the art to determine whether the compounds have biological activity. For example, the antibiotic compounds can be characterized by conventional assays, including but not limited to those assays described below, to determine whether the compounds have a predicted activity, binding activity and/or binding specificity.

Furthermore, high-throughput screening can be used to speed up analysis using such assays. As a result, it can be possible to screen rapidly the molecules described herein for activity, for example as anti-bacterial. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin, *High Throughput Screening*, (Marcel Dekker, 1998); and U.S. Pat. No. 5,763,263. High-throughput assays can use one or more different assay techniques including, but not limited to, those described below.

(1) Surface Binding Studies. A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor RTM from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (FP) is a measurement technique that can readily be applied to protein-protein, protein-ligand, or RNA-ligand interactions in order to derive $IC_{50}$s and $K_d$s of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or $^{35}S$ methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is an inhibitor of protein synthesis.

Furthermore, the antibiotic compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule could be acting as a protein synthesis inhibitor. More specifically, the activity of the compounds of interest against bacterial pathogens can be demonstrated by the ability of the compound to inhibit growth of defined strains of human pathogens, particularly *Propionibacterium acnes* and *Propionibacterium granulosum* and resistant strains thereof. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays can be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition. NCCLS Document M100-S12/M7 (ISBN 1-56238-394-9)).

4. Formulation and Administration

The methods of the present invention can be practiced by delivering the antibiotic compounds of the present invention using any suitable carrier. The dose of antibiotic compound, mode of administration and use of suitable carrier will depend upon the intended patient or subject and the targeted microorganism, e.g., the target bacterial organism. The formulations, both for human medical use and veterinary use, of the antibiotic compounds according to the present invention typically include such antibiotic compounds in association with a pharmaceutically acceptable carrier.

The carrier(s) should be "acceptable" in the sense of being compatible with compounds of the present invention and not deleterious to the recipient. Pharmaceutically acceptable carriers, in this regard, are intended to include any and all solvents, dispersion media, coatings, absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

In some embodiments, the methods, uses and compositions for use disclosed herein can further include an additional active agent. In some embodiments, the additional active agent is selected from the group consisting of salicylic acid, benzoyl peroxide, glycolic acid, lactic acid, citric acid, lactobionic acid, triclosan, triclocarban and combinations thereof. Other exemplary agents which can be used in accordance with the present disclosure include those discussed in Decker, A.; Graber, E. M. *J. Clin. Aesthet. Dermatol.* 2012, 5(5), 32-40, the contents of which are hereby incorporated by reference in their entirety.

A pharmaceutical composition of the invention can be formulated to be compatible with its intended route of administration. These can include solids and semisolids. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

A wide variety of formulations and administration methods can be found in S. K. Niazi, ed., Handbook of Pharmaceutical Formulations, Vols. 1-6 [Vol. 1 Compressed Solid Products, Vol. 2 Uncompressed Drug Products, Vol. 3 Liquid Products, Vol. 4 Semi-Solid Products, Vol. 5 Over the Counter Products, and Vol. 6 Sterile Products], CRC Press, Apr. 27, 2004.

Useful solutions for oral or parenteral administration can be prepared by any of the methods well known in the pharmaceutical art, described, for example, in *Remington's Pharmaceutical Sciences*, 18th ed. (Mack Publishing Company, 1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Formulations suitable for topical administration, including eye treatment, include liquid or semi-liquid preparations such as liniments, lotions, gels, applicants, oil-in-water or water-in-oil emulsions such as creams, ointments or pastes; foams; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

Additionally, the carrier for a topical formulation can be in the form of a hydroalcoholic system (e.g. liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems. Nonlimiting examples of the topical carrier systems useful in the present invention are described in the following four references, all of which are incorporated herein by reference in their entirety: "Sun Products Formulary", Cosmetics & Toiletries, vol. 105, pp. 122-139 (December 1990); "Sun Products Formulary", Cosmetics & Toiletries, vol. 102, pp. 117-136 (March 1987); U.S. Pat. No. 4,960,764 to Figueroa et al., issued Oct. 2, 1990; and U.S. Pat. No. 4,254,105 to Fukuda et al., issued Mar. 3, 1981.

The pharmaceutically-acceptable topical carriers, in total, typically comprise from about 0.1% to about 99.8% by weight of the compositions useful in the present invention, alternatively from about 0.1% to about 99.9%, alternatively from about 0.1% to about 99%, alternatively from about 5% to about 99%, alternatively from about 10% to about 99%, alternatively from about 20% to about 99%, alternatively about 50% to about 99%, alternatively from about 80% to about 99%, and alternatively from about 85% to about 95%.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the therapeutic effect to be achieved, and the limitations inherent in the art of compounding such an active compound for the treatment of individuals.

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

In conjunction with the methods of the present invention, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

Generally, an effective amount of dosage of active compound will be in the range of from about 0.01 to about 1500, depending on the mode of administration. The amount administered will also likely depend on such variables as the condition to be treated, the severity of the condition, the age and overall health status of the patient, the relative biological efficacy of the compound delivered, the formulation of the compound, the presence and types of excipients in the formulation, and the route of administration. Also, it is to be understood that the initial dosage administered can be increased beyond the above upper level in order to rapidly achieve the desired tissue level or blood level, or the initial dosage can be smaller than the optimum.

Nonlimiting doses of active compound comprise from about 0.1 to about 1500 mg per dose. Nonlimiting examples of doses, which can be formulated as a unit dose for convenient administration to a patient include: about 0.10 mg, about 0.15 mg, about 0.20 mg, about 0.25 mg, about 0.30 mg, about 0.35 mg, about 0.40 mg, about 0.45 mg, about 0.50 mg, about 0.75 mg, about 1 mg, about 2 mg, about 2.5 mg, about 3 mg, about 4 mg, about 5 mg, about 7.5 mg, about 10 mg, about 12.5 mg, about 15, mg, about 20 mg, about 25 mg, about 30 mg, about 35 mg, about 40 mg, about 45 mg, about 50 mg, about 60 mg, about 70 mg, about 75 mg, about 80 mg, about 90 mg, about 100 mg, about 110 mg, about 120 mg, about 125 mg, about 130 mg, about 140 mg, about 150 mg, about 160 mg, about 170 mg, about 175 mg, about 180 mg, about 190 mg, about 200 mg, about 210 mg, about 220 mg, about 225 mg, about 230 mg, about 240 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050, mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, and about 1500 mg. The foregoing doses are useful for administering the compounds of the present invention according to the methods of the present invention.

Alternatively, the amount of active ingredient in the compositions useful in the methods of the present invention can be described on a weight percentage basis. Nonlimiting amounts of active ingredients include about 0.01%, about 0.015%, about 0.02%, about 0.025% about 0.03%, about 0.035% about 0.04%, about 0.045%, about 0.05%, about 0.055%, about 0.06%, about 0.065%, about 0.07%, about 0.075%, about 0.080%, about 0.085%, about 0.090%, about 0.095%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.25%, about 1.5%, about 1.75%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, and about 99.9%.

See, e.g., PCT Application No. WO 2005/019211 A2, published, Mar. 3, 2005, which describes various aspects useful in the present invention.

Optional Components

In addition to the required components of the compositions useful in the present invention, a variety of optional components can also be incorporated.

Anti-Acne Agents

The compositions useful in the present invention can also contain anti-acne agents in addition to the antibiotics. These other anti-acne agents can comprise from about 0.01% to about 20% by weight of the compositions useful herein, or alternatively from about 0.01% to about 10%, and yet alternatively from about 0.1% to about 5%. Mixtures of these additional anti-acne actives may also be used. Examples of these other anti-acne agents, particularly for oral compositions include conventional antibiotic agents such as erythromycin, agents such as tretinoin, etc. Examples of these other anti-acne agents, particularly for topical compositions include keratolytics such as sulfur, lactic acid, glycolic, pyruvic acid, urea, resorcinol, and N-acetylcysteine; retinoids such as retinoic acid and its derivatives (e.g., cis and trans); antibiotics, antimicrobials, antibacterials, antifungals, antiprotozoals, and antivirals (e.g., benzoyl peroxide, octopirox, erythromycin, tetracycline, triclosan, azelaic acid and its derivatives, phenoxy ethanol and phenoxy propanol, ethyl acetate, clindamycin and meclocycline, triclosan, chlorhexidine, tetracycline, neomycin, miconazole hydrochloride, octopirox, parachlorometaxylenol, nystatin, tolnaftate, clotrimazole, and the like); sebostats such as flavonoids; hydroxy acids; antipruritic drugs including, for example, pharmaceutically-acceptable salts of methdilizine and trimeprazine; and bile salts such as scymnol sulfate and its derivatives, deoxycholate, and cholate. Other exemplary agents which can be used in accordance with the present disclosure include those discussed in Decker, A.; Graber, E. M. *J. Clin. Aesthet. Dermatol.* 2012, 5(5), 32-40, the contents of which are hereby incorporated by reference in their entirety.

Also useful, particularly for oral and topical compositions are non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Other Components for Topical Compositions

The following components are especially useful for topical compositions.

Humectants, Moisturizers, and Skin Conditioners

Particularly for topical compositions, optional component of the compositions useful in the instant invention is at least one humectant/moisturizer/skin conditioner. A variety of these materials can be employed and each can be present at a level of from about 0.1% to about 20%, alternatively from about 1% to about 10% and yet alternatively from about 2% to about 5%. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, hexylene glycol and the like; polyethylene glycol; sugars and starches; sugar and starch derivatives (e.g., alkoxylated glucose); hyaluronic acid; lactamide monoethanolamine; acetamide monoethanolamine; and mixtures thereof.

In certain embodiments for topical compositions, humectants/moisturizers/skin conditioners useful herein are the $C_3$-$C_6$ diols and triols, and also aloe vera gel. Especially preferred is the triol, glycerol, and also aloe vera gel.

Surfactants

The compositions useful in the methods of the present invention, particularly the topical compositions, can optionally comprise one or more surfactants. The surfactants can be present at a level from about 0.1% to about 10%, alternatively from about 0.2% to about 5%, and yet alternatively from about 0.2% to about 2.5%. Suitable surfactants include, but are not limited to, nonionic surfactants such as polyalkylene glycol ethers of fatty alcohols, and anionic surfactants such as taurates and alkyl sulfates. Non-limiting examples of these surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, Detergents and Emulsifiers, North American Edition (1986), published by Allured Publishing Corporation, which is incorporated herein by reference in its entirety.

Emollients

The compositions useful in the methods of the present invention, particularly topical compositions, can also optionally comprise at least one emollient. Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24, 1990, which is incorporated herein by reference in its entirety.

The emollients can typically comprise in total from about 1% to about 50%, preferably from about 1% to about 25%, and more preferably from about 1% to about 10% by weight of the compositions useful in the present invention.

Sunscreens

The compositions useful in the methods of the present invention for topical administration can also optionally comprise at least one sun screening agent. A wide variety of one or more sun screening agents are suitable for use in the present invention and are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety.

Preferred among those sunscreens which are useful in the compositions of the instant invention are those selected from the group consisting of ethylHexyl p-methoxycinnamate, octocrylene, octyl salicylate, oxybenzone, and mixtures thereof.

Other useful sunscreens include the solid physical sunblocks such as titanium dioxide (micronized titanium dioxide, 0.03 microns), zinc oxide, silica, iron oxide and the like. Without being limited by theory, it is believed that these inorganic materials provide a sun screening benefit through reflecting, scattering, and absorbing harmful UV, visible, and infrared radiation.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sun screening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sun screening agents provide higher efficacy, broader UV absorption, lower skin penetration and longer lasting efficacy relative to conventional sunscreens.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206-38269, Aug. 25, 1978, which is incorporated herein by reference in its entirety.

Delivery Methods for Topical Compositions

The topical compositions useful for the methods of the instant invention can also be delivered from a variety of delivery devices. The following are two nonlimiting examples.

Medicated Cleansing Pads

The compositions useful herein can be incorporated into a medicated cleansing pad. Preferably, these pads comprise from about 50% to about 75% by weight of one or more layers of nonwoven fabric material and from about 20% to about 75% by weight (on dry solids basis) of a water soluble polymeric resin. These pads are described in detail in U.S. Pat. No. 4,891,228, to Thaman et al., issued Jan. 2, 1990 and U.S. Pat. No. 4,891,227, to Thaman et al., issued Jan. 2, 1990; both of which are incorporated by reference herein in their entirety.

Dispensing Devices

The compositions useful herein can also be incorporated into and delivered from a soft-tipped or flexible dispensing device. These devices are useful for the controlled delivery of the compositions to the skin surface and have the advantage that the treatment composition itself never need be directly handled by the user. Nonlimiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve. The valve can include a diaphragm formed from an elastically fluid impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620,648, to Schwartzman, issued Sep. 15, 1987; U.S. Pat. No. 3,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference in their entirety. Examples of applicators useful herein are commercially available from Dab-O-Matic, Mount Vernon, N.Y.

4. Embodiments

In one aspect, disclosed herein is a method of treating, preventing, or reducing the risk of a skin infection caused or mediated by *Propionibacterium acnes, Gardnerella vaginalis,* or *Staphylococcus aureus* in a patient, the method comprising administering a pharmaceutically effective amount of a compound having the formula:

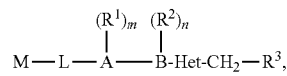

or a pharmaceutically acceptable tautomer, salt, ester, or prodrug thereof, wherein:

A is selected from the group consisting of:

phenyl, pyridyl, pyrazinyl, pyrimidinyl, and pyridazinyl;

B is selected from the group consisting of:

phenyl, pyridyl, pyrazinyl, pyrimidinyl, and pyridazinyl;

Het-CH$_2$—R$^3$ is selected from the group consisting of:

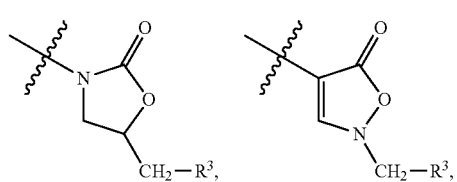

-continued

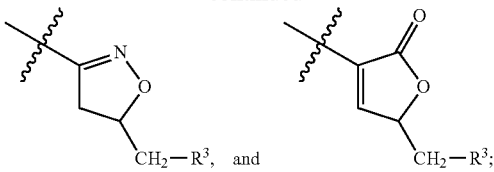

M is selected from the group consisting of:
a) saturated, unsaturated, or aromatic $C_{3-14}$ carbocycle, and b) saturated, unsaturated, or aromatic 3-14 membered heterocycle containing one or more heteroatoms selected from the group consisting of nitrogen, oxygen, and sulfur,
wherein a) or b) optionally is substituted with one or more $R^5$ groups;

M-L is selected from the group consisting of:
a) M-X, b) M-$L^1$, c) M-$L^1$-X, d) M-X-$L^2$, e) M-$L^1$-X-$L^2$, f) M-X-$L^1$-X-$L^2$, g) M-$L^1$-X-$L^2$-X, h) M-X-X—, i) M-$L^1$-X-X—, j) M-X-X-$L^2$, and k) M-$L^1$-X-X-$L^2$, wherein X, at each occurrence, independently is selected from the group consisting of:
a) —O—, b) —$NR^4$—, c) —N(O)—, d) —N($OR^4$)—, e) —S(O)$_p$—, f) —$SO_2NR^4$—, g) —$NR^4SO_2$—, h) —$NR^4$—N=, i) =N—$NR^4$—, j) —O—N=, k) =N—O—, l) —N=, m) =N—, n) —$NR^4$—$NR^4$—, o) —$NR^4$C(O)O—, p) —OC(O)$NR^4$—, q) —$NR^4$C(O)$NR^4$— r) —$NR^4$C($NR^4$)$NR^4$—, and s)

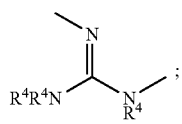

$L^1$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups; and $L^2$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups;

$R^1$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —C(O)$R^4$, k) —C(O)$OR^4$, l) —OC(O)$R^4$, m) —C(O)$NR^4R^4$, n) —$NR^4$C(O)$R^4$, o) —OC(O)$NR^4R^4$, p) —$NR^4$C(O)$OR^4$, q) —$NR^4$C(O)$NR^4R^4$, r) —C(S)$R^4$, s) —C(S)$OR^4$, t) —OC(S)$R^4$, u) —C(S)$NR^4R^4$, v) —$NR^4$C(S)$R^4$, w) —OC(S)$NR^4R^4$, x) —$NR^4$C(S)$OR^4$, y) —$NR^4$C(S)$NR^4R^4$, z) —$NR^4$C($NR^4$)$NR^4R^4$, aa) —S(O)$_p$$R^4$, bb) —$SO_2NR^4R^4$, and cc) $R^4$;

$R^2$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —C(O)$R^4$, k) —C(O)$OR^4$, l) —OC(O)$R^4$, m) —C(O)$NR^4R^4$, n) —$NR^4$C(O)$R^4$, o) —OC(O)$NR^4R^4$, p) —$NR^4$C(O)$OR^4$, q) —$NR^4$C(O)$NR^4R^4$, r) —C(S)$R^4$, s) —C(S)$OR^4$, t) —OC(S)$R^4$, u) —C(S)$NR^4R^4$, v) —$NR^4$C(S)$R^4$, w) —OC(S)$NR^4R^4$, x) —$NR^4$C(S)$OR^4$, y) —$NR^4$C(S)$NR^4R^4$, z) —$NR^4$C($NR^4$)$NR^4R^4$, aa) —S(O)$_p$$R^4$, bb) —$SO_2NR^4R^4$, and cc) $R^4$;

$R^3$ is selected from the group consisting of:
a) —$OR^4$, b) —$NR^4R^4$, c) —C(O)$R^4$, d) —C(O)$OR^4$, e) —OC(O)$R^4$, f) —C(O)$NR^4R^4$, g) —$NR^4$C(O)$R^4$, h) —OC(O)$NR^4R^4$, i) —$NR^4$C(O)$OR^4$, j) —$NR^4$C(O)$NR^4R^4$, k) —C(S)$R^4$, l) —C(S)$OR^4$, m) —OC(S)$R^4$, n) —C(S)$NR^4R^4$, o) —$NR^4$C(S)$R^4$, p) —OC(S)$NR^4R^4$, q) —$NR^4$C(S)$OR^4$, r) —$NR^4$C(S)$NR^4R^4$, s) —$NR^4$C($NR^4$)$NR^4R^4$, t) —S(O)$_p$$R^4$, u) —$SO_2NR^4R^4$, and v) $R^4$;

$R^4$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
wherein any of b)-p) optionally is substituted with one or more $R^5$ groups;

$R^5$, at each occurrence, is independently selected from the group consisting of:
a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —C(O)$R^6$, p) —C(O)$OR^6$, q) —OC(O)$R^6$, r) —C(O)$NR^6R^6$, s) —$NR^6$C(O)$R^6$, t) —OC(O)$NR^6R^6$, u) —$NR^6$C(O)$OR^6$, v) —$NR^6$C(O)$NR^6R^6$, w) —C(S)$R^6$, x) —C(S)$OR^6$, y) —OC(S)$R^6$, z) —C(S)$NR^6R^6$, aa) —$NR^6$C(S)$R^6$, bb) —OC(S)$NR^6R^6$, cc) —$NR^6$C(S)$OR^6$, dd) —$NR^6$C(S)$NR^6R^6$, ee) —$NR^6$C($NR^6$)$NR^6R^6$, ff) —S(O)$_p$$R^6$, gg) —$SO_2NR^6R^6$, and hh) $R^6$;

$R^6$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R⁷ groups;

R⁷, at each occurrence, independently is selected from the group consisting of:

a) F, b) Cl, c) Br, d) I, e) =O, f) =S, g) =NR⁸, h) =NOR⁸, i) =N—NR⁸R⁸, j) —CF₃, k) —OR⁸, l) —CN, m) —NO₂, n) —NR⁸R⁸, o) —C(O)R⁸, p) —C(O)OR⁸, q) —OC(O)R⁸, r) —C(O)NR⁸R⁸, s) —NR⁸C(O)R⁸, t) —OC(O)NR⁸R⁸, u) —NR⁸C(O)OR⁸, v) —NR⁸C(O)NR⁸R⁸, w) —C(S)R⁸, x) —C(S)OR⁸, y) —OC(S)R⁸, z) —C(S)NR⁸R⁸, aa) —NR⁸C(S)R⁸, bb) —OC(S)NR⁸R⁸, cc) —NR⁸C(S)OR⁸, dd) —NR⁸C(S)NR⁸R⁸, ee) —NR⁸C(NR⁸)NR⁸R⁸, ff) —S(O)ₚR⁸, gg) —SO₂NR⁸R⁸, hh) $C_{1-6}$ alkyl, ii) $C_{2-6}$ alkenyl, jj) $C_{2-6}$ alkynyl, kk) $C_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur, wherein any of hh)-ll) optionally is substituted with one or more moieties selected from the group consisting of R⁸, F, Cl, Br, I, —CF₃, —OR⁸, —SR⁸, —CN, —NO₂, —NR⁸R⁸, —C(O)R⁸, —C(O)OR⁸, —OC(O)R⁸, —C(O)NR⁸R⁸, —NR⁸C(O)R⁸, —OC(O)NR⁸R⁸, —NR⁸C(O)OR⁸, —NR⁸C(O)NR⁸R⁸, —C(S)R⁸, —C(S)OR⁸, —OC(S)R⁸, —C(S)NR⁸R⁸, —NR⁸C(S)R⁸, —OC(S)NR⁸R⁸, —NR⁸C(S)OR⁸, —NR⁸C(S) NR⁸R⁸, —NR⁸C(NR⁸)NR⁸R⁸, —SO₂NR⁸R⁸, and —S(O)ₚ R⁸;

R⁸, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —CF₃, —OH, —OCH₃, —SH, —SCH₃, —CN, —NO₂, —NH₂, —NHCH₃, —N(CH₃)₂, —C(O)CH₃, —C(O)OCH₃, —C(O)NH₂, —NHC(O)CH₃, —SO₂NH₂, —SO₂NHCH₃, —SO₂N(CH₃)₂, and —S(O)ₚCH₃;

m, at each occurrence, independently is 0, 1, 2, 3, or 4;

n, at each occurrence, independently is 0, 1, 2, 3, or 4; and p, at each occurrence, independently is 0, 1, or 2.

In some embodiments, the compound has the formula:

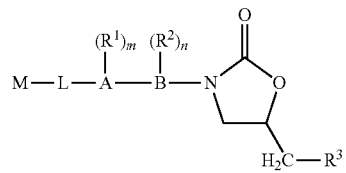

or a pharmaceutically acceptable salt, ester or prodrug thereof.

In some embodiments, the compound has the formula:

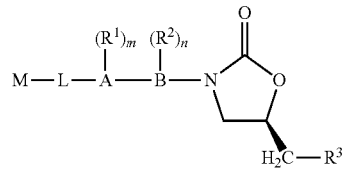

or a pharmaceutically acceptable salt, ester or prodrug thereof.

In some embodiments, A is selected from the group consisting of phenyl and pyridyl. In some embodiments, B is selected from the group consisting of phenyl and pyridyl. In some embodiments, m is 0, 1, or 2. In some embodiments, n is 0, 1, or 2. In some embodiments, A is selected from the group consisting of phenyl and pyridyl, B is selected from the group consisting of phenyl and pyridyl, m is 0, 1, or 2 and n is 0, 1, or 2.

In some embodiments, A-B is:

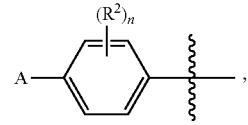

In some embodiments, A-B is:

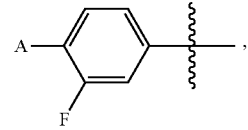

In some embodiments, A-B is:

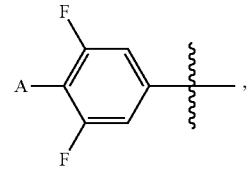

In some embodiments, A-B is:

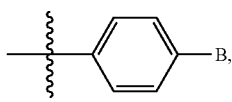

In some embodiments, A-B is:

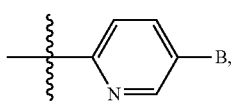

In some embodiments, $R^3$ is —NHC(O)$R^4$. In some embodiments, $R^3$ is:

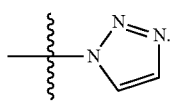

In some embodiments, $R^4$ is —CH$_3$.
In some embodiments, the compound has the formula:

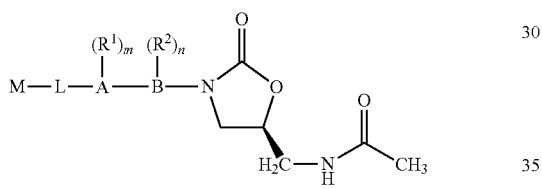

or a pharmaceutically acceptable salt, ester or prodrug thereof.

In some embodiments, the compound has the formula:

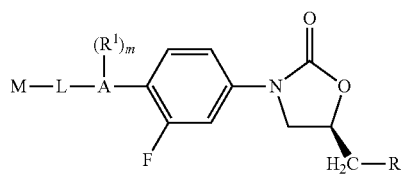

or a pharmaceutically acceptable salt, ester or prodrug thereof.
In some embodiments:
A is a phenyl;
B is a phenyl;
Het-CH$_2$—$R^3$ is:

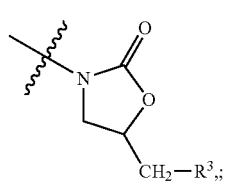

M is a 5-membered unsaturated heterocycle containing one or more nitrogen heteroatoms optionally substituted with one or more $R^5$ groups, wherein the heterocycle contains only nitrogen atoms;
M-L is M-$L^1$-X-$L^2$, wherein
X, at each occurrence, independently is selected from the group consisting of:
a) —$NR^4$—, b) —$SO_2NR^4$—
$L^1$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups; and
$L^2$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups;
$R^1$, at each occurrence, independently is selected from the group consisting of:
a) F, b) Cl, c) Br, d);
$R^2$, at each occurrence, independently is selected from the group consisting of:
a) F, b) Cl, c) Br, d);
$R^3$ is —$NR^4C(O)R^4$;
$R^4$, at each occurrence, independently is selected from the group consisting of:
a) H, b) $C_{1-6}$ alkyl;
$R^5$, at each occurrence, is independently selected from the group consisting of:
a) F, b) Cl, c) Br, d) I, e) =O, f) =S, g) —CF$_3$, h) —CN, i) —NO$_2$, j) —$NR^6R^6$, k) —C(O)$R^6$, l) —C(O)$NR^6R^6$, m) —S(O)$_pR^6$, and n) $R^6$;
$R^6$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more $R^7$ groups;
$R^7$, at each occurrence, independently is selected from the group consisting of:
a) F, b) Cl, c) Br, d) I, e) =$NR^8$, f) —CF$_3$, g) —$OR^8$, h) —CN, i) —NO$_2$, j) —$NR^8R^8$, k) —C(O)$R^8$, and l) —C(O)$OR^8$;
$R^8$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more moieties selected from the group consisting of F, Cl, Br, I, —CF$_3$, and —OH;
m is 0, 1, 2, 3, or 4;
n is 0, 1, 2, 3, or 4; and
p, at each occurrence, independently is 0, 1, or 2.
In some embodiments, the compound has the formula:

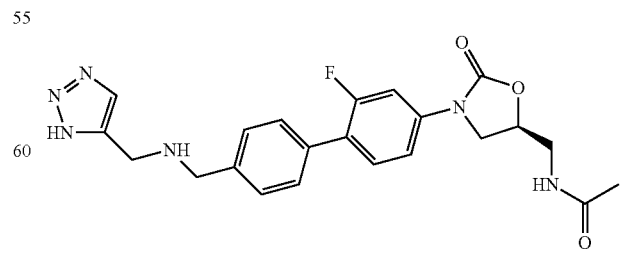

or a pharmaceutically acceptable tautomer, salt, ester, or prodrug thereof.

In some embodiments, the compound has the formula:

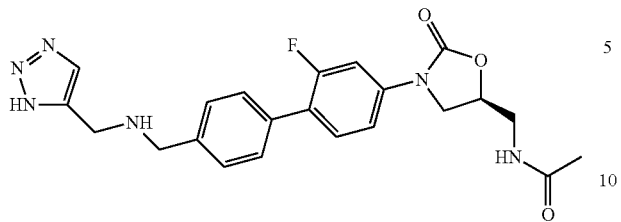

wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a method of treating, preventing, or reducing the risk of a skin infection caused or mediated by *Propionibacterium acnes, Gardnerella vaginalis,* or *Staphylococcus aureus* in a patient, the method comprising administering a pharmaceutically effective amount of a compound having the formula:

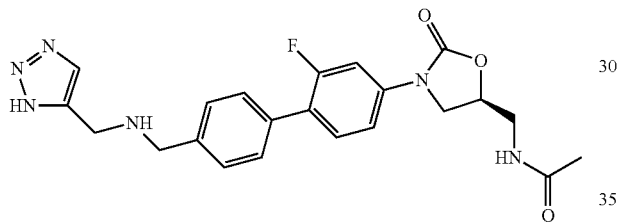

or a pharmaceutically acceptable tautomer, salt, ester, or prodrug thereof.

In some embodiments, the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In some embodiments, the skin infection is treated in the patient. In some embodiments, the skin infection is prevented in the patient. In some embodiments, the method reduces the risk of the skin infection in the patient.

In some embodiments, the skin infection is caused or mediated by *Propionibacterium acnes*. In some embodiments, the skin infection is caused or mediated by *Staphylococcus aureus*. In some embodiments, the skin infection is caused or mediated by *Gardnerella vaginalis*.

In some embodiments, the skin infection is selected from acne vulgaris, rosacea, impetigo, otitis externa, bacterial conjunctivitis, and bacterial vaginosis. In some embodiments, the skin infection is acne vulgaris. In some embodiments, the skin infection is bacterial vaginosis.

In some embodiments, the compound, composition or medicament is administered orally, parentally, or topically. In some embodiments, the compound, composition or medicament is administered topically.

In some embodiments, the compound is administered in a topical formulation comprising one or more dermatologically acceptable carriers and one or more compounds having the formula:

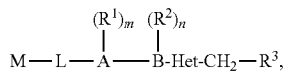

or a pharmaceutically acceptable tautomer, salt, ester, or prodrug thereof, wherein:

A is selected from the group consisting of:
phenyl, pyridyl, pyrazinyl, pyrimidinyl, and pyridazinyl;

B is selected from the group consisting of:
phenyl, pyridyl, pyrazinyl, pyrimidinyl, and pyridazinyl;

Het-CH$_2$—R$^3$ is selected from the group consisting of:

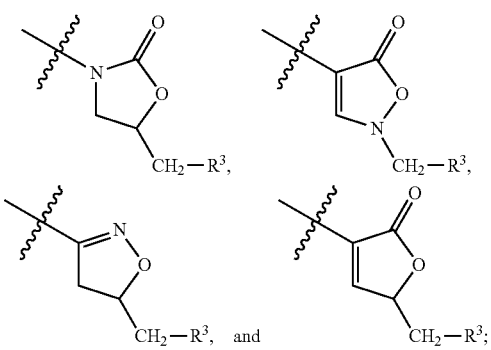

M is selected from the group consisting of:
a) saturated, unsaturated, or aromatic C$_{3-14}$ carbocycle, and b) saturated, unsaturated, or aromatic 3-14 membered heterocycle containing one or more heteroatoms selected from the group consisting of nitrogen, oxygen, and sulfur,
wherein a) or b) optionally is substituted with one or more R$^5$ groups;

M-L is selected from the group consisting of:
a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X-X—, i) M-L$^1$-X-X—, j) M-X-X-L$^2$, and k) M-L$^1$-X-X-L$^2$, wherein X, at each occurrence, independently is selected from the group consisting of:
a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N═, i) ═N—NR$^4$—, j) —O—N═, k) ═N—O—, l) —N═, m) ═N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and s)

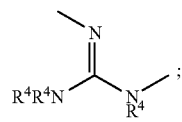

L$^1$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups; and L$^2$ is selected from the group consisting of:
a) C$_{1-6}$ alkyl, b) C$_{2-6}$ alkenyl, and c) C$_{2-6}$ alkynyl, wherein any of a)-c) optionally is substituted with one or more $R^5$ groups;

$R^1$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)R^4$, bb) —$SO_2NR^4R^4$, and cc) $R^4$;

$R^2$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)R^4$, bb) —$SO_2NR^4R^4$, and cc) $R^4$;

$R^3$ is selected from the group consisting of:
a) —$OR^4$, b) —$NR^4R^4$, c) —$C(O)R^4$, d) —$C(O)OR^4$, e) —$OC(O)R^4$, f) —$C(O)NR^4R^4$, g) —$NR^4C(O)R^4$, h) —$OC(O)NR^4R^4$, i) —$NR^4C(O)OR^4$, j) —$NR^4C(O)NR^4R^4$, k) —$C(S)R^4$, l) —$C(S)OR^4$, m) —$OC(S)R^4$, n) —$C(S)NR^4R^4$, o) —$NR^4C(S)R^4$, p) —$OC(S)NR^4R^4$, q) —$NR^4C(S)OR^4$, r) —$NR^4C(S)NR^4R^4$, s) —$NR^4C(NR^4)NR^4R^4$, t) —$S(O)_pR^4$, u) —$SO_2NR^4R^4$, and v) $R^4$;

$R^4$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated,
unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl,
m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more $R^5$ groups;

$R^5$, at each occurrence, is independently selected from the group consisting of:
a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —$C(O)R^6$, p) —$C(O)OR^6$, q) —$OC(O)R^6$, r) —$C(O)NR^6R^6$, s) —$NR^6C(O)R^6$, t) —$OC(O)NR^6R^6$, u) —$NR^6C(O)OR^6$, v) —$NR^6C(O)NR^6R^6$, w) —$C(S)R^6$, x) —$C(S)OR^6$, y) —$OC(S)R^6$, z) —$C(S)NR^6R^6$, aa) —$NR^6C(S)R^6$, bb) —$OC(S)NR^6R^6$, cc) —$NR^6C(S)OR^6$, dd) —$NR^6C(S)NR^6R^6$, ee) —$NR^6C(NR^6)NR^6R^6$, ff) —$S(O)_pR^6$, gg) —$SO_2NR^6R^6$, and hh) $R^6$;

$R^6$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated,
unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl,
m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more $R^7$ groups;

$R^7$, at each occurrence, independently is selected from the group consisting of:
a) F, b) Cl, c) Br, d) I, e) =O, f) =S, g) =$NR^8$, h) =$NOR^8$, i) =N—$NR^8R^8$, j) —$CF_3$, k) —$OR^8$, l) —CN, m) —$NO_2$, n) —$NR^8R^8$, o) —$C(O)R^8$, p) —$C(O)OR^8$, q) —$OC(O)R^8$, r) —$C(O)NR^8R^8$, s) —$NR^8C(O)R^8$, t) —$OC(O)NR^8R^8$, u) —$NR^8C(O)OR^8$, v) —$NR^8C(O)NR^8R^8$, w) —$C(S)R^8$, x) —$C(S)OR^8$, y) —$OC(S)R^8$, z) —$C(S)NR^8R^8$, aa) —$NR^8C(S)R^8$, bb) —$OC(S)NR^8R^8$, cc) —$NR^8C(S)OR^8$, dd) —$NR^8C(S)NR^8R^8$, ee) —$NR^8C(NR^8)NR^8R^8$, ff) —$S(O)_pR^8$, gg) —$SO_2NR^8R^8$, hh) $C_{1-6}$ alkyl, ii) $C_{2-6}$ alkenyl, jj) $C_{2-6}$ alkynyl, kk) $C_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur,
wherein any of hh)-ll) optionally is substituted with one or more moieties selected from the group consisting of $R^8$, F, Cl, Br, I, —$CF_3$, —$OR^8$, —$SR^8$, —CN, —$NO_2$, —$NR^8R^8$, —$C(O)R^8$, —$C(O)OR^8$, —$OC(O)R^8$, —$C(O)NR^8R^8$, —$NR^8C(O)R^8$, —$OC(O)NR^8R^8$, —$NR^8C(O)OR^8$, —$NR^8C(O)NR^8R^8$, —$C(S)R^8$, —$C(S)OR^8$, —$OC(S)R^8$, —$C(S)NR^8R^8$, —$NR^8C(S)R^8$, —$OC(S)NR^8R^8$, —$NR^8C(S)OR^8$, —$NR^8C(S)NR^8R^8$, —$NR^8C(NR^8)NR^8R^8$, —$SO_2NR^8R^8$, and —$S(O)_p R^8$;

$R^8$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated,
unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl,
m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —CF$_3$, —OH, —OCH$_3$, —SH, —SCH$_3$, —CN, —NO$_2$, —NH$_2$, —NHCH$_3$, —N(CH$_3$)$_2$, —C(O)CH$_3$, —C(O)OCH$_3$, —C(O)NH$_2$, —NHC(O)CH$_3$, —SO$_2$NH$_2$, —SO$_2$NHCH$_3$, —SO$_2$N(CH$_3$)$_2$, and —S(O)$_p$CH$_3$;

m, at each occurrence, independently is 0, 1, 2, 3, or 4;
n, at each occurrence, independently is 0, 1, 2, 3, or 4; and
p, at each occurrence, independently is 0, 1, or 2.

In another aspect, disclosed herein is a topical formulation for use in treating, preventing, or reducing the risk of a skin infection caused or mediated by *Propionibacterium acnes*, *Gardnerella vaginalis*, or *Staphylococcus aureus* in a patient, the formulation comprising one or more dermatologically acceptable carriers and one or more compounds having the formula:

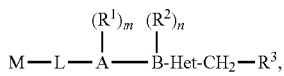

or a pharmaceutically acceptable tautomer, salt, ester, or prodrug thereof, wherein:

A is selected from the group consisting of:
phenyl, pyridyl, pyrazinyl, pyrimidinyl, and pyridazinyl;
B is selected from the group consisting of:
phenyl, pyridyl, pyrazinyl, pyrimidinyl, and pyridazinyl;
Het-CH$_2$—R$^3$ is selected from the group consisting of:

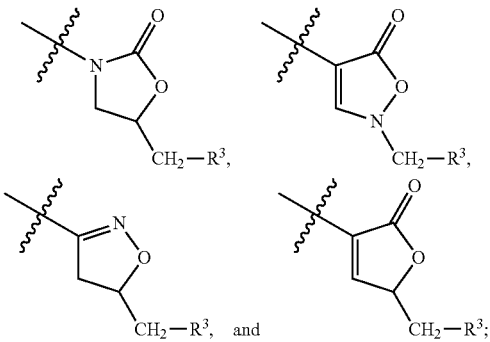

M is selected from the group consisting of:
a) saturated, unsaturated, or aromatic C$_{3-14}$ carbocycle, and b) saturated, unsaturated, or aromatic 3-14 membered heterocycle containing one or more heteroatoms selected from the group consisting of nitrogen, oxygen, and sulfur,
wherein a) or b) optionally is substituted with one or more R$^5$ groups;

M-L is selected from the group consisting of:
a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X-X—, i) M-L$^1$-X-X—, j) M-X-X-L$^2$, and k) M-L$^1$-X-X-L$^2$, wherein X, at each occurrence, independently is selected from the group consisting of:
a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N=, i) =N—NR$^4$—, j) —O—N=, k) =N—O—, l) —N=, m) =N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and s)

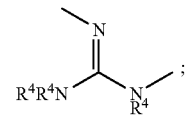

L$^1$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups; and
L$^2$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups;

R$^1$, at each occurrence, independently is selected from the group consisting of:
a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;

R$^2$, at each occurrence, independently is selected from the group consisting of:
a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;

R$^3$ is selected from the group consisting of:
a) —OR$^4$, b) —NR$^4$R$^4$, c) —C(O)R$^4$, d) —C(O)OR$^4$, e) —OC(O)R$^4$, f) —C(O)NR$^4$R$^4$, g) —NR$^4$C(O)R$^4$, h) —OC(O)NR$^4$R$^4$, i) —NR$^4$C(O)OR$^4$, j) —NR$^4$C(O)NR$^4$R$^4$, k) —C(S)R$^4$, l) —C(S)OR$^4$, m) —OC(S)R$^4$, n) —C(S)NR$^4$R$^4$, o) —NR$^4$C(S)R$^4$, p) —OC(S)NR$^4$R$^4$, q —NR$^4$C(S)OR$^4$, r) —NR$^4$C(S)NR$^4$R$^4$, s) —NR$^4$C(NR$^4$)NR$^4$R$^4$, t) —S(O)$_p$R$^4$, u) —SO$_2$NR$^4$R$^4$, and v) R$^4$;

R$^4$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R$^5$ groups;

R$^5$, at each occurrence, is independently selected from the group consisting of:
a) F, b) Cl, c) Br, d) I, e) =O, f) =S, g) =NR$^6$, h) =NOR$^6$, i) =N—NR$^6$R$^6$, j) —CF$_3$, k) —OR$^6$, l) —CN, m) —NO$_2$, n) —NR$^6$R$^6$, o) —C(O)R$^6$, p) —C(O)OR$^6$, q) —OC(O)R$^6$, r) —C(O)NR$^6$R$^6$, s) —NR$^6$C(O)R$^6$, t) —OC(O)NR$^6$R$^6$, u) —NR$^6$C(O)OR$^6$, v) —NR$^6$C(O)NR$^6$R$^6$, w) —C(S)R$^6$, x) —C(S)OR$^6$, y) —OC(S)R$^6$, z) —C(S)NR$^6$R$^6$, aa) —NR$^6$C(S)R$^6$, bb) —OC(S)NR$^6$R$^6$, cc) —NR$^6$C(S)OR$^6$, dd) —NR$^6$C(S)NR$^6$R$^6$, ee) —NR$^6$C(NR$^6$)NR$^6$R$^6$, ff) —S(O)$_p$R$^6$, gg) —SO$_2$NR$^6$R$^6$, and hh) R$^6$;

R$^6$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R$^7$ groups;

R$^7$, at each occurrence, independently is selected from the group consisting of:
a) F, b) Cl, c) Br, d) I, e) =O, f) =S, g) =NR$^8$, h) =NOR$^8$, i) =N—NR$^8$R$^8$, j) —CF$_3$, k) —OR$^8$, l) —CN, m) —NO$_2$, n) —NR$^8$R$^8$, o) —C(O)R$^8$, p) —C(O)OR$^8$, q) —OC(O)R$^8$, r) —C(O)NR$^8$R$^8$, s) —NR$^8$C(O)R$^8$, t) —OC(O)NR$^8$R$^8$, u) —NR$^8$C(O)OR$^8$, v) —NR$^8$C(O)NR$^8$R$^8$, w) —C(S)R$^8$, x) —C(S)OR$^8$, y) —OC(S)R$^8$, z) —C(S)NR$^8$R$^8$, aa) —NR$^8$C(S)R$^8$, bb) —OC(S)NR$^8$R$^8$, cc) —NR$^8$C(S)OR$^8$, dd) —NR$^8$C(S)NR$^8$R$^8$, ee) —NR$^8$C(NR$^8$)NR$^8$R$^8$, ff) —S(O)$_p$R$^8$, gg) —SO$_2$NR$^8$R$^8$, hh) C$_{1-6}$ alkyl, ii) C$_{2-6}$ alkenyl, jj) C$_{2-6}$ alkynyl, kk) C$_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur, wherein any of hh)-ll) optionally is substituted with one or more moieties selected from the group consisting of R$^8$, F, Cl, Br, I, —CF$_3$, —OR$^8$, —SR$^8$, —CN, —NO$_2$, —NR$^8$R$^8$, —C(O)R$^8$, —C(O)OR$^8$, —OC(O)R$^8$, —C(O)NR$^8$R$^8$, —NR$^8$C(O)R$^8$, —OC(O)NR$^8$R$^8$, —NR$^8$C(O)OR$^8$, —NR$^8$C(O)NR$^8$R$^8$, —C(S)R$^8$, —C(S)OR$^8$, —OC(S)R$^8$, —C(S)NR$^8$R$^8$, —NR$^8$C(S)R$^8$, —OC(S)NR$^8$R$^8$, —NR$^8$C(S)OR$^8$, —NR$^8$C(S) NR$^8$R$^8$, —NR$^8$C(NR$^8$)NR$^8$R$^8$, —SO$_2$NR$^8$R$^8$, and —S(O)$_p$ R$^8$;

R$^8$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —CF$_3$, —OH, —OCH$_3$, —SH, —SCH$_3$, —CN, —NO$_2$, —NH$_2$, —NHCH$_3$, —N(CH$_3$)$_2$, —C(O)CH$_3$, —C(O)OCH$_3$, —C(O)NH$_2$, —NHC(O)CH$_3$, —SO$_2$NH$_2$, —SO$_2$NHCH$_3$, —SO$_2$N(CH$_3$)$_2$, and —S(O)$_p$CH$_3$;

m, at each occurrence, independently is 0, 1, 2, 3, or 4;

n, at each occurrence, independently is 0, 1, 2, 3, or 4; and p, at each occurrence, independently is 0, 1, or 2.

In some embodiments, the compound has the formula:

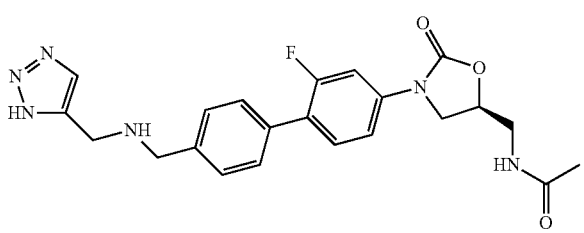 [SMILES: CC(=O)NC[C@H]1CN(c2ccc(-c3ccc(CNCc4cnn[nH]4)cc3)c(F)c2)C(=O)O1]

or a pharmaceutically acceptable tautomer, salt, ester, or prodrug thereof.

In some embodiments, the compound has the formula:

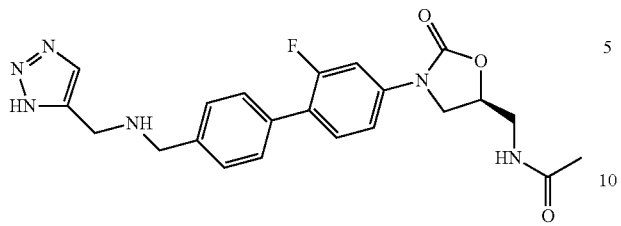

wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a topical formulation for use in treating, preventing, or reducing the risk of a skin infection caused or mediated by *Propionibacterium acnes*, *Gardnerella vaginalis*, or *Staphylococcus aureus* in a patient, the formulation comprising one or more dermatologically acceptable carriers and one or more compounds having the formula:

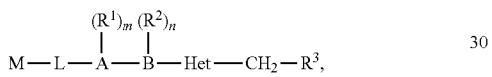

or a pharmaceutically acceptable tautomer, salt, ester, or prodrug thereof, wherein:

A is a phenyl;
B is a phenyl;
Het—CH$_2$—R$^3$ is:

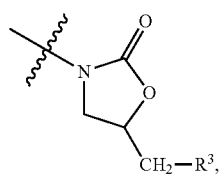

M is a 5-membered unsaturated heterocycle containing one or more nitrogen heteroatoms optionally substituted with one or more R$^5$ groups, wherein the heterocycle contains only nitrogen atoms;
M-L is M-L$^1$-X-L$^2$, wherein
X, at each occurrence, independently is selected from the group consisting of:
  a) —NR$^4$—, b) —SO$_2$NR$^4$—
L$^1$ is selected from the group consisting of:
  a) C$_{1-6}$ alkyl, b) C$_{2-6}$ alkenyl, and c) C$_{2-6}$ alkynyl,
  wherein any of a)-c) optionally is substituted with one or more R$^5$ groups; and
L$^2$ is selected from the group consisting of:
  a) C$_{1-6}$ alkyl, b) C$_{2-6}$ alkenyl, and c) C$_{2-6}$ alkynyl,
  wherein any of a)-c) optionally is substituted with one or more R$^5$ groups;

R$^1$, at each occurrence, independently is selected from the group consisting of:
  a) F, b) Cl, c) Br, d) I;
R$^2$, at each occurrence, independently is selected from the group consisting of:
  a) F, b) Cl, c) Br, d) I;
R$^3$ is —NR$^4$C(O)R$^4$;
R$^4$, at each occurrence, independently is selected from the group consisting of:
  a) H, b) C$_{1-6}$ alkyl;
R$^5$, at each occurrence, is independently selected from the group consisting of:
  a) F, b) Cl, c) Br, d) I, e) =O, f) =S, g) —CF$_3$, h) —CN, i) —NO$_2$, j) —NR$^6$R$^6$, k) —C(O)R$^6$, l) —C(O)NR$^6$R$^6$, m) —S(O)$_p$R$^6$, and n) R$^6$;
R$^6$, at each occurrence, independently is selected from the group consisting of:
  a) H, b) C$_{1-6}$ alkyl, c) C$_{2-6}$ alkenyl, d) C$_{2-6}$ alkynyl, wherein any of b)-d) optionally is substituted with one or more R$^7$ groups;
R$^7$, at each occurrence, independently is selected from the group consisting of:
  a) F, b) Cl, c) Br, d) I, e) =NR$^8$, f) —CF$_3$, g) —OR$^8$, h) —CN, i) —NO$_2$, j) —NR$^8$R$^8$, k) —C(O)R$^8$, and l) —C(O)OR$^8$;
R$^8$, at each occurrence, independently is selected from the group consisting of:
  a) H, b) C$_{1-6}$ alkyl, c) C$_{2-6}$ alkenyl, d) C$_{2-6}$ alkynyl, wherein any of b)-d) optionally is substituted with one or more moieties selected from the group consisting of F, Cl, Br, I, —CF$_3$, and —OH;
m is 0, 1, 2, 3, or 4;
n is 0, 1, 2, 3, or 4; and
p, at each occurrence, independently is 0, 1, or 2.

In some embodiments, the compound has the formula:

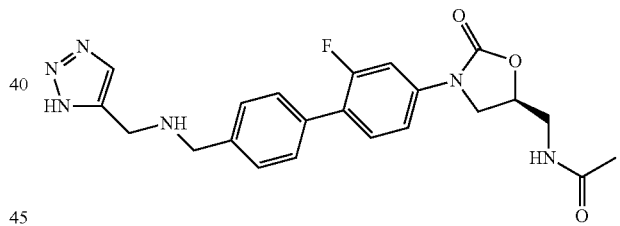

or a pharmaceutically acceptable tautomer, salt, ester, or prodrug thereof.

In some embodiments, the compound has the formula:

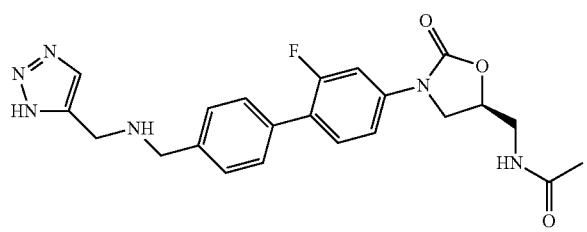 [SMILES: CC(=O)NC[C@H]1CN(c2ccc(-c3ccc(CNCc4cnn[nH]4)cc3)c(F)c2)C(=O)O1]

wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a topical formulation for use in treating, preventing, or reducing the risk of a skin infection caused or mediated by *Propionibacterium acnes, Gardnerella vaginalis,* or *Staphylococcus aureus* in a patient, the formulation comprising one or more dermatologically acceptable carriers and a compound having the formula:

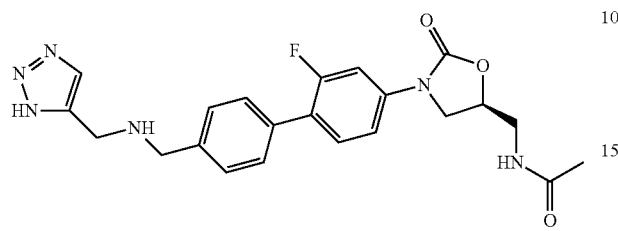

or a pharmaceutically acceptable tautomer, salt, ester, or prodrug thereof.

In some embodiments, the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In some embodiments, disclosed herein is a method of treating, preventing, or reducing the risk of a skin infection caused or mediated by *Propionibacterium acnes, Gardnerella vaginalis,* or *Staphylococcus aureus* in a patient, the method comprising administering a pharmaceutically effective amount of the topical formulation disclosed herein.

In some embodiments, the method is a method of treating a skin infection caused or mediated by *Propionibacterium acnes, Gardnerella vaginalis,* or *Staphylococcus aureus* in a patient. In some embodiments, the method is a method of preventing a skin infection caused or mediated by *Propionibacterium acnes, Gardnerella vaginalis,* or *Staphylococcus aureus* in a patient. In some embodiments, the method is a method of reducing the risk of a skin infection caused or mediated by *Propionibacterium acnes, Gardnerella vaginalis,* or *Staphylococcus aureus* in a patient.

In some embodiments, the skin infection is caused or mediated by *Propionibacterium acnes*. In some embodiments, the skin infection is caused or mediated by *Staphylococcus aureus*. In some embodiments, the skin infection is caused or mediated by *Gardnerella vaginalis*.

In some embodiments, the skin infection is selected from acne vulgaris, rosacea, impetigo, otitis externa, bacterial conjunctivitis, and bacterial vaginosis. In some embodiments, the skin infection is acne vulgaris. In some embodiments, the skin infection is bacterial vaginosis.

In some embodiments, the compound has the formula:

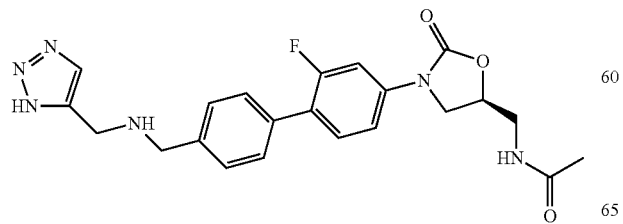

or a pharmaceutically acceptable tautomer, salt, ester, or prodrug thereof.

In some embodiments, the compound has the formula:

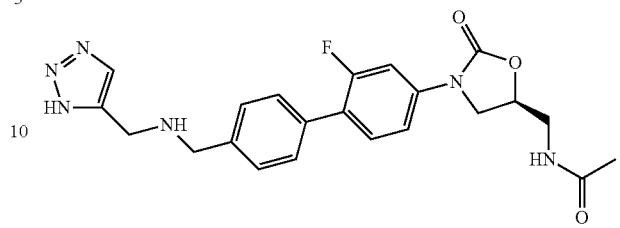

wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a use of a compound having the formula:

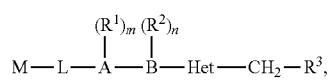

or a pharmaceutically acceptable tautomer, salt, ester, or prodrug thereof, wherein:
A is selected from the group consisting of:
phenyl, pyridyl, pyrazinyl, pyrimidinyl, and pyridazinyl;
B is selected from the group consisting of:
phenyl, pyridyl, pyrazinyl, pyrimidinyl, and pyridazinyl;
Het-CH$_2$—R$^3$ is selected from the group consisting of:

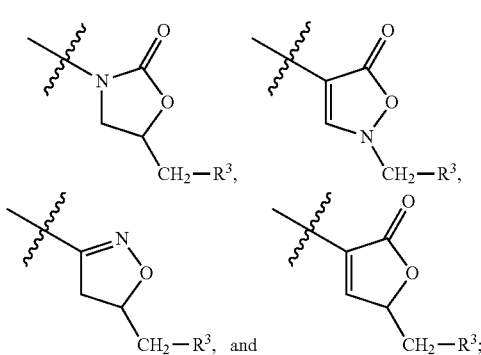

M is selected from the group consisting of:
a) saturated, unsaturated, or aromatic C$_{3-14}$ carbocycle, and b) saturated, unsaturated, or aromatic 3-14 membered heterocycle containing one or more heteroatoms selected from the group consisting of nitrogen, oxygen, and sulfur,
wherein a) or b) optionally is substituted with one or more R$^5$ groups;
M-L is selected from the group consisting of:
a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X-X—, i) M-L$^1$-X-X—, j) M-X-X-L$^2$, and k) M-L$^1$-X-X-L$^2$, wherein X, at each occurrence, independently is selected from the group consisting of:
a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N=, i) =N—NR$^4$—, j) —O—N=, k) =N—O—, l) —N=, m) =N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and s)

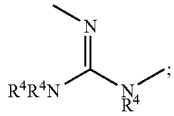

L$^1$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups; and
L$^2$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups;
R$^1$, at each occurrence, independently is selected from the group consisting of:
a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;
R$^2$, at each occurrence, independently is selected from the group consisting of:
a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;
R$^3$ is selected from the group consisting of:
a) —OR$^4$, b) —NR$^4$R$^4$, c) —C(O)R$^4$, d) —C(O)OR$^4$, e) —OC(O)R$^4$, f) —C(O)NR$^4$R$^4$, g) —NR$^4$C(O)R$^4$, h) —OC(O)NR$^4$R$^4$, i) —NR$^4$C(O)OR$^4$, j) —NR$^4$C(O)NR$^4$R$^4$, k) —C(S)R$^4$, l) —C(S)OR$^4$, m) —OC(S)R$^4$, n) —C(S)NR$^4$R$^4$, o) —NR$^4$C(S)R$^4$, p) —OC(S)NR$^4$R$^4$, q) —NR$^4$C(S)OR$^4$, r) —NR$^4$C(S)NR$^4$R$^4$, s) —NR$^4$C(NR$^4$)NR$^4$R$^4$, t) —S(O)$_p$R$^4$, u) —SO$_2$NR$^4$R$^4$, and v) R$^4$;
R$^4$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R$^5$ groups;
R$^5$, at each occurrence, is independently selected from the group consisting of:
a) F, b) Cl, c) Br, d) I, e) =O, f) =S, g) =NR$^6$, h) =NOR$^6$, i) =N—NR$^6$R$^6$, j) —CF$_3$, k) —OR$^6$, l) —CN, m) —NO$_2$, n) —NR$^6$R$^6$, o) —C(O)R$^6$, p) —C(O)OR$^6$, q) —OC(O)R$^6$, r) —C(O)NR$^6$R$^6$, s) —NR$^6$C(O)R$^6$, t) —OC(O)NR$^6$R$^6$, u) —NR$^6$C(O)OR$^6$, v) —NR$^6$C(O)NR$^6$R$^6$, w) —C(S)R$^6$, x) —C(S)OR$^6$, y) —OC(S)R$^6$, z) —C(S)NR$^6$R$^6$, aa) —NR$^6$C(S)R$^6$, bb) —OC(S)NR$^6$R$^6$, cc) —NR$^6$C(S)OR$^6$, dd) —NR$^6$C(S)NR$^6$R$^6$, ee) —NR$^6$C(NR$^6$)NR$^6$R$^6$, ff) —S(O)$_p$R$^6$, gg) —SO$_2$NR$^6$R$^6$, and hh) R$^6$;
R$^6$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more R$^7$ groups;
R$^7$, at each occurrence, independently is selected from the group consisting of:
a) F, b) Cl, c) Br, d) I, e) =O, f) =S, g) =NR$^8$, h) =NOR$^8$, i) =N—NR$^8$R$^8$, j) —CF$_3$, k) —OR$^8$, l) —CN, m) —NO$_2$, n) —NR$^8$R$^8$, o) —C(O)R$^8$, p) —C(O)OR$^8$, q) —OC(O)R$^8$, r) —C(O)NR$^8$R$^8$, s) —NR$^8$C(O)R$^8$, t) —OC(O)NR$^8$R$^8$, u) —NR$^8$C(O)OR$^8$, v) —NR$^8$C(O)NR$^8$R$^8$, w) —C(S)R$^8$, x) —C(S)OR$^8$, y) —OC(S)R$^8$, z) —C(S)NR$^8$R$^8$, aa) —NR$^8$C(S)R$^8$, bb) —OC(S)NR$^8$R$^8$, cc) —NR$^8$C(S)OR$^8$, dd) —NR$^8$C(S)NR$^8$R$^8$, ee) —NR$^8$C(NR$^8$)NR$^8$R$^8$, ff) —S(O)$_p$R$^8$, gg) —SO$_2$NR$^8$R$^8$, hh) C$_{1-6}$ alkyl, ii) C$_{2-6}$ alkenyl, jj) C$_{2-6}$ alkynyl, kk) C$_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur, wherein any of hh)-ll) optionally is substituted with one or more moieties selected from the group consisting of R⁸, F, Cl, Br, I, —CF₃, —OR⁸, —SR⁸, —CN, —NO₂, —NR⁸R⁸, —C(O)R⁸, —C(O)OR⁸, —OC(O)R⁸, —C(O)NR⁸R⁸, —NR⁸C(O)R⁸, —OC(O)NR⁸R⁸, —NR⁸C(O) OR⁸, —NR⁸C(O)NR⁸R⁸, —C(S)R⁸, —C(S)OR⁸, —OC(S)R⁸, —C(S)NR⁸R⁸, —NR⁸C(S)R⁸, —OC (S)NR⁸R⁸, —NR⁸C(S)OR⁸, —NR⁸C(S) NR⁸R⁸, —NR⁸C(NR⁸)NR⁸R⁸, —SO₂NR⁸R⁸, and —S(O)$_p$ R⁸;

R⁸, at each occurrence, independently is selected from the group consisting of:
  a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —CF₃, —OH, —OCH₃, —SH, —SCH₃, —CN, —NO₂, —NH₂, —NHCH₃, —N(CH₃)₂, —C(O)CH₃, —C(O) OCH₃, —C(O)NH₂, —NHC(O)CH₃, —SO₂NH₂, —SO₂NHCH₃, —SO₂N(CH₃)₂, and —S(O)$_p$ CH₃;

m, at each occurrence, independently is 0, 1, 2, 3, or 4;
n, at each occurrence, independently is 0, 1, 2, 3, or 4; and
p, at each occurrence, independently is 0, 1, or 2, in the manufacture of a medicament for treating, preventing, or reducing the risk of a skin infection caused or mediated by *Propionibacterium acnes, Gardnerella vaginalis*, or *Staphylococcus aureus* in a patient.

In some embodiments, the compound has the formula:

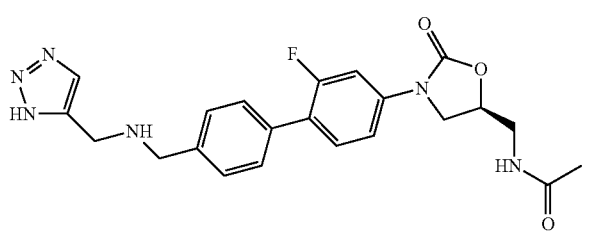 [SMILES: CC(=O)NC[C@H]1CN(c2ccc(-c3ccc(CNCc4cnn[nH]4)cc3)c(F)c2)C(=O)O1]

or a pharmaceutically acceptable tautomer, salt, ester, or prodrug thereof.

In some embodiments, the compound has the formula:

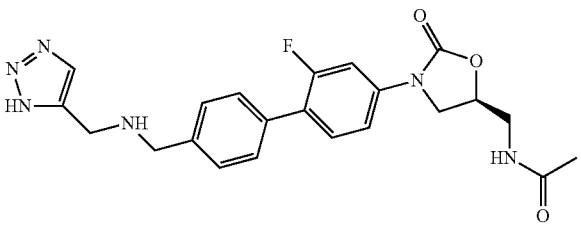 [SMILES: CC(=O)NC[C@H]1CN(c2ccc(-c3ccc(CNCc4cnn[nH]4)cc3)c(F)c2)C(=O)O1]

wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a use of a compound having the formula:

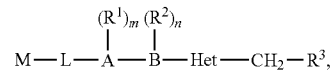

or a pharmaceutically acceptable tautomer, salt, ester, or prodrug thereof, wherein:
  A is a phenyl;
  B is a phenyl;
  Het-CH₂—R³ is:

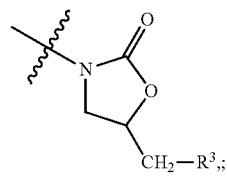

M is a 5-membered unsaturated heterocycle containing one or more nitrogen heteroatoms optionally substituted with one or more R⁵ groups, wherein the heterocycle contains only nitrogen atoms;
M-L is M-L¹-X-L², wherein
  X, at each occurrence, independently is selected from the group consisting of:
    a) —NR⁴—, b) —SO₂NR⁴—
  L¹ is selected from the group consisting of:
    a) C$_{1-6}$ alkyl, b) C$_{2-6}$ alkenyl, and c) C$_{2-6}$ alkynyl, wherein any of a)-c) optionally is substituted with one or more R⁵ groups; and
  L² is selected from the group consisting of:
    a) C$_{1-6}$ alkyl, b) C$_{2-6}$ alkenyl, and c) C$_{2-6}$ alkynyl, wherein any of a)-c) optionally is substituted with one or more R⁵ groups;
R¹, at each occurrence, independently is selected from the group consisting of:
  a) F, b) Cl, c) Br, d);
R², at each occurrence, independently is selected from the group consisting of:
  a) F, b) Cl, c) Br, d);
R³ is —NR⁴C(O)R⁴;

$R^4$, at each occurrence, independently is selected from the group consisting of:
a) H, b) $C_{1-6}$ alkyl;

$R^5$, at each occurrence, is independently selected from the group consisting of:
a) F, b) Cl, c) Br, d) I, e) =O, f) =S, g) —$CF_3$, h) —CN, i) —$NO_2$, j) —$NR^6R^6$, k) —$C(O)_pR^6$, l) —$C(O)NR^6R^6$, m) —$S(O)_pR^6$, and n) $R^6$;

$R^6$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more $R^7$ groups;

$R^7$, at each occurrence, independently is selected from the group consisting of:
a) F, b) Cl, c) Br, d) I, e) =$NR^8$, f) —$CF_3$, g) —$OR^8$, h) —CN, i) —$NO_2$, j) —$NR^8R^8$, k) —$C(O)R^8$, and l) —$C(O)OR^8$;

$R^8$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more moieties selected from the group consisting of F, Cl, Br, I, —$CF_3$, and —OH;

m is 0, 1, 2, 3, or 4;

n is 0, 1, 2, 3, or 4; and p, at each occurrence, independently is 0, 1, or 2, in the manufacture of a medicament for treating, preventing, or reducing the risk of a skin infection caused or mediated by *Propionibacterium acnes, Gardnerella vaginalis*, or *Staphylococcus aureus* in a patient comprising.

In some embodiments, the compound has the formula:

or a pharmaceutically acceptable tautomer, salt, ester, or prodrug thereof.

In some embodiments, the compound has the formula:

wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a use of a compound having the formula:

or a pharmaceutically acceptable tautomer, salt, ester, or prodrug thereof, in the manufacture of a medicament for treating, preventing, or reducing the risk of a skin infection caused or mediated by *Propionibacterium acnes, Gardnerella vaginalis*, or *Staphylococcus aureus* in a patient.

In some embodiments, the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a use of a compound having the formula:

$$M-L-A\overset{(R^1)_m}{|}-B\overset{(R^2)_n}{|}-Het-CH_2-R^3,$$

or a pharmaceutically acceptable tautomer, salt, ester, or prodrug thereof, wherein:

A is selected from the group consisting of:
phenyl, pyridyl, pyrazinyl, pyrimidinyl, and pyridazinyl;

B is selected from the group consisting of:
phenyl, pyridyl, pyrazinyl, pyrimidinyl, and pyridazinyl;

Het-$CH_2$—$R^3$ is selected from the group consisting of:

M is selected from the group consisting of:
a) saturated, unsaturated, or aromatic $C_{3-14}$ carbocycle, and b) saturated, unsaturated, or aromatic 3-14 membered heterocycle containing one or more heteroatoms selected from the group consisting of nitrogen, oxygen, and sulfur,
wherein a) or b) optionally is substituted with one or more $R^5$ groups;

M-L is selected from the group consisting of:
a) M-X, b) M-$L^1$-X, c) M-$L^1$-X, d) M-X-$L^2$, e) M-$L^1$-X-$L^2$, f) M-X-$L^1$-X-$L^2$, g) M-$L^1$-X-$L^2$-X, h) M-X-X—, i) M-$L^1$-X-X—, j) M-X-X-$L^2$, and k) M-$L^1$-X-X-$L^2$, wherein X, at each occurrence, independently is selected from the group consisting of:
a) —O—, b) —$NR^4$—, c) —N(O)—, d) —N($OR^4$)—, e) —S(O)$_p$—, f) —$SO_2NR^4$—, g) —$NR^4SO_2$—, h) —$NR^4$—N=, i) =N—$NR^4$—, j) —O—N=, k) =N—O—, l) —N=, m) =N—, n) —$NR^4$—$NR^4$—, o) —$NR^4$C(O)O—, p) —OC(O)$NR^4$—, q) —$NR^4$C(O)$NR^4$— r) —$NR^4$C($NR^4$)$NR^4$—, and s)

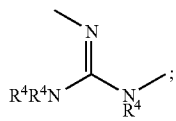

$L^1$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups; and $L^2$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups;

$R^1$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —C(O)$R^4$, k) —C(O)$OR^4$, l) —OC(O)$R^4$, m) —C(O)$NR^4R^4$, n) —$NR^4$C(O)$R^4$, o) —OC(O)$NR^4R^4$, p) —$NR^4$C(O)$OR^4$, q) —$NR^4$C(O)$NR^4R^4$, r) —C(S)$R^4$, s) —C(S)$OR^4$, t) —OC(S)$R^4$, u) —C(S)$NR^4R^4$, v) —$NR^4$C(S)$R^4$, w) —OC(S)$NR^4R^4$, x) —$NR^4$C(S)$OR^4$, y) —$NR^4$C(S)$NR^4R^4$, z) —$NR^4$C($NR^4$)$NR^4R^4$, aa) —S(O)$_pR^4$, bb) —$SO_2NR^4R^4$, and cc) $R^4$;

$R^2$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —C(O)$R^4$, k) —C(O)$OR^4$, l) —OC(O)$R^4$, m) —C(O)$NR^4R^4$, n) —$NR^4$C(O)$R^4$, o) —OC(O)$NR^4R^4$, p) —$NR^4$C(O)$OR^4$, q) —$NR^4$C(O)$NR^4R^4$, r) —C(S)$R^4$, s) —C(S)$OR^4$, t) —OC(S)$R^4$, u) —C(S)$NR^4R^4$, v) —$NR^4$C(S)$R^4$, w) —OC(S)$NR^4R^4$, x) —$NR^4$C(S)$OR^4$, y) —$NR^4$C(S)$NR^4R^4$, z) —$NR^4$C($NR^4$)$NR^4R^4$, aa) —S(O)$_pR^4$, bb) —$SO_2NR^4R^4$, and cc) $R^4$;

$R^3$ is selected from the group consisting of:
a) —$OR^4$, b) —$NR^4R^4$, c) —C(O)$R^4$, d) —C(O)$OR^4$, e) —OC(O)$R^4$, f) —C(O)$NR^4R^4$, g) —$NR^4$C(O)$R^4$, h) —OC(O)$NR^4R^4$, i) —$NR^4$C(O)$OR^4$, j) —$NR^4$C(O)$NR^4R^4$, k) —C(S)$R^4$, l) —C(S)$OR^4$, m) —OC(S)$R^4$, n) —C(S)$NR^4R^4$, o) —$NR^4$C(S)$R^4$, p) —OC(S)$NR^4R^4$, q) —$NR^4$C(S)$OR^4$, r) —$NR^4$C(S)$NR^4R^4$, s) —$NR^4$C($NR^4$)$NR^4R^4$, t) —S(O)$_pR^4$, u) —$SO_2NR^4R^4$, and v) $R^4$;

$R^4$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
wherein any of b)-p) optionally is substituted with one or more $R^5$ groups;

$R^5$, at each occurrence, is independently selected from the group consisting of:
a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —C(O)$R^6$, p) —C(O)$OR^6$, q) —OC(O)$R^6$, r) —C(O)$NR^6R^6$, s) —$NR^6$C(O)$R^6$, t) —OC(O)$NR^6R^6$, u) —$NR^6$C(O)$OR^6$, v) —$NR^6$C(O)$NR^6R^6$, w) —C(S)$R^6$, x) —C(S)$OR^6$, y) —OC(S)$R^6$, z) —C(S)$NR^6R^6$, aa) —$NR^6$C(S)$R^6$, bb) —OC(S)$NR^6R^6$, cc) —$NR^6$C(S)$OR^6$, dd) —$NR^6$C(S)$NR^6R^6$, ee) —$NR^6$C($NR^6$)$NR^6R^6$, ff) —S(O)$_pR^6$, gg) —$SO_2NR^6R^6$, and hh) $R^6$;

$R^6$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
wherein any of b)-p) optionally is substituted with one or more $R^7$ groups;

$R^7$, at each occurrence, independently is selected from the group consisting of:
a) F, b) Cl, c) Br, d) I, e) =O, f) =S, g) =$NR^8$, h) =$NOR^8$, i) =N—$NR^8R^8$, j) —$CF_3$, k) —$OR^8$, l) —CN, m) —$NO_2$, n) —$NR^8R^8$, o) —C(O)$R^8$, p) —C(O)$OR^8$, q) —OC(O)$R^8$, r) —C(O)$NR^8R^8$, s)

—NR⁸C(O)R⁸, t) —OC(O)NR⁸R⁸, u) —NR⁸C(O)OR⁸, v) —NR⁸C(O)NR⁸R⁸, w) —C(S)R⁸, x) —C(S)OR⁸, y) —OC(S)R⁸, z) —C(S)NR⁸R⁸, aa) —NR⁸C(S)R⁸, bb) —OC(S)NR⁸R⁸, cc) —NR⁸C(S)OR⁸, dd) —NR⁸C(S)NR⁸R⁸, ee) —NR⁸C(NR⁸)NR⁸R⁸, ff) —S(O)$_p$R⁸, gg) —SO₂NR⁸R⁸, hh) C$_{1-6}$ alkyl, ii) C$_{2-6}$ alkenyl, jj) C$_{2-6}$ alkynyl, kk) C$_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur, wherein any of hh)-ll) optionally is substituted with one or more moieties selected from the group consisting of R⁸, F, Cl, Br, I, —CF₃, —OR⁸, —SR⁸, —CN, —NO₂, —NR⁸R⁸, —C(O)R⁸, —C(O)OR⁸, —OC(O)R⁸, —C(O)NR⁸R⁸, —NR⁸C(O)R⁸, —OC(O)NR⁸R⁸, —NR⁸C(O)OR⁸, —NR⁸C(O)NR⁸R⁸, —C(S)R⁸, —C(S)OR⁸, —OC(S)R⁸, —C(S)NR⁸R⁸, —NR⁸C(S)R⁸, —OC(S)NR⁸R⁸, —NR⁸C(S)OR⁸, —NR⁸C(S) NR⁸R⁸, —NR⁸C(NR⁸)NR⁸R⁸, —SO₂NR⁸R⁸, and —S(O)$_p$ R⁸;

R⁸, at each occurrence, independently is selected from the group consisting of:

a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —CF₃, —OH, —OCH₃, —SH, —SCH₃, —CN, —NO₂, —NH₂, —NHCH₃, —N(CH₃)₂, —C(O)CH₃, —C(O)OCH₃, —C(O)NH₂, —NHC(O)CH₃, —SO₂NH₂, —SO₂NHCH₃, —SO₂N(CH₃)₂, and —S(O)$_p$CH₃;

m, at each occurrence, independently is 0, 1, 2, 3, or 4;

n, at each occurrence, independently is 0, 1, 2, 3, or 4; and p, at each occurrence, independently is 0, 1, or 2, for treating, preventing, or reducing the risk of a skin infection caused or mediated by *Propionibacterium acnes*, *Gardnerella vaginalis*, or *Staphylococcus aureus* in a patient.

In some embodiments, the compound has the formula:

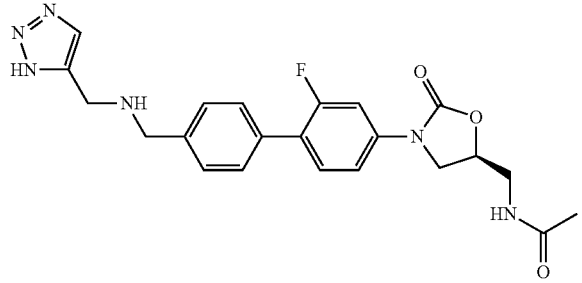 [SMILES: CC(=O)NC[C@H]1CN(c2ccc(-c3ccc(CNCc4cnn[nH]4)cc3)c(F)c2)C(=O)O1]

or a pharmaceutically acceptable tautomer, salt, ester, or prodrug thereof.

In some embodiments, the compound has the formula:

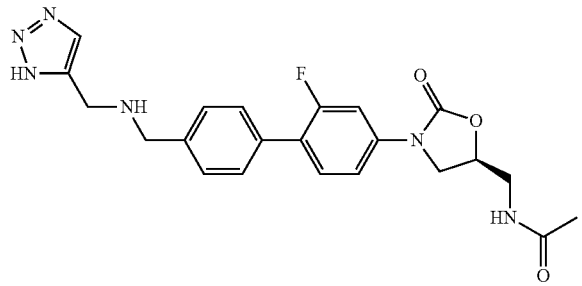 [SMILES: CC(=O)NC[C@H]1CN(c2ccc(-c3ccc(CNCc4cnn[nH]4)cc3)c(F)c2)C(=O)O1]

wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a use of a compound having the formula:

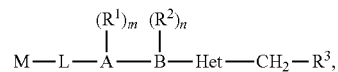

or a pharmaceutically acceptable tautomer, salt, ester, or prodrug thereof, wherein:

A is a phenyl;
B is a phenyl;
Het-CH₂—R³ is:

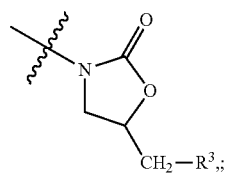

M is a 5-membered unsaturated heterocycle containing one or more nitrogen heteroatoms optionally substituted with one or more R⁵ groups, wherein the heterocycle contains only nitrogen atoms;

M-L is M-L¹-X-L², wherein

X, at each occurrence, independently is selected from the group consisting of:
a) —NR$^4$—, b) —SO$_2$NR$^4$—
L$^1$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups; and
L$^2$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups;
R$^1$, at each occurrence, independently is selected from the group consisting of:
a) F, b) Cl, c) Br, d) I;
R$^2$, at each occurrence, independently is selected from the group consisting of:
a) F, b) Cl, c) Br, d) I;
R$^3$ is —NR$^4$C(O)R$^4$;
R$^4$, at each occurrence, independently is selected from the group consisting of:
a) H, b) C$_{1-6}$ alkyl;
R$^5$, at each occurrence, is independently selected from the group consisting of:
a) F, b) Cl, c) Br, d) I, e) =O, f) =S, g) —CF$_3$, h) —CN, i) —NO$_2$, j) —NR$^6$R$^6$, k) —C(O)R$^6$, l) —C(O)NR$^6$R$^6$, m) —S(O)$_p$R$^6$, and n) R$^6$;
R$^6$, at each occurrence, independently is selected from the group consisting of:
a) H, b) C$_{1-6}$ alkyl, c) C$_{2-6}$ alkenyl, d) C$_{2-6}$ alkynyl, wherein any of b)-d) optionally is substituted with one or more R$^7$ groups;
R$^7$, at each occurrence, independently is selected from the group consisting of:
a) F, b) Cl, c) Br, d) I, e) =NR$^8$, f) —CF$_3$, g) —OR$^8$, h) —CN, i) —NO$_2$, j) —NR$^8$R$^8$, k) —C(O)R$^8$, and l) —C(O)OR$^8$;
R$^8$, at each occurrence, independently is selected from the group consisting of:
a) H, b) C$_{1-6}$ alkyl, c) C$_{2-6}$ alkenyl, d) C$_{2-6}$ alkynyl, wherein any of b)-d) optionally is substituted with one or more moieties selected from the group consisting of F, Cl, Br, I, —CF$_3$, and —OH;
m is 0, 1, 2, 3, or 4;
n is 0, 1, 2, 3, or 4; and
p, at each occurrence, independently is 0, 1, or 2,
for treating, preventing, or reducing the risk of a skin infection caused or mediated by *Propionibacterium acnes, Gardnerella vaginalis*, or *Staphylococcus aureus* in a patient.

In some embodiments, the compound has the formula:

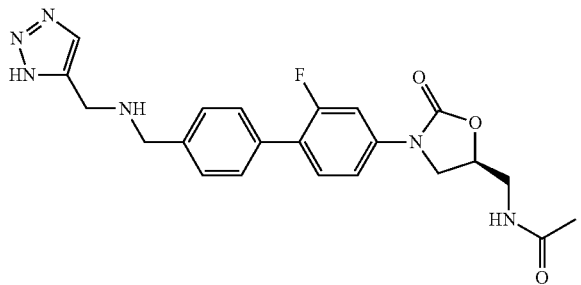 [SMILES: CC(=O)NC[C@H]1CN(c2ccc(-c3ccc(CNCc4cnn[nH]4)cc3)c(F)c2)C(=O)O1]

or a pharmaceutically acceptable tautomer, salt, ester, or prodrug thereof.

In some embodiments, the compound has the formula:

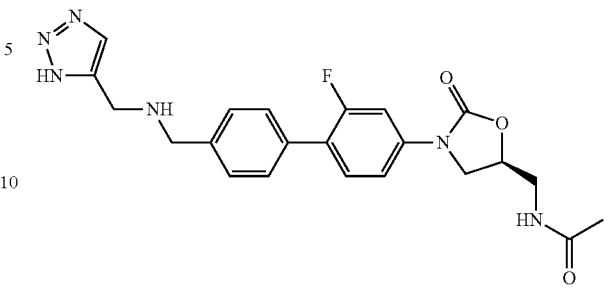

wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In another aspect, disclosed herein is a use of a compound having the formula:

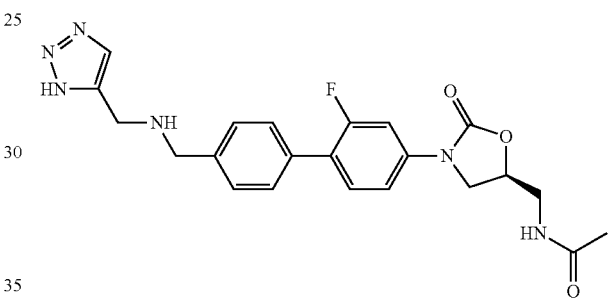

or a pharmaceutically acceptable tautomer, salt, ester, or prodrug thereof, for treating, preventing, or reducing the risk of a skin infection caused or mediated by *Propionibacterium acnes, Gardnerella vaginalis*, or *Staphylococcus aureus* in a patient.

In some embodiments, the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

In some embodiments, the use is a use in the manufacture of a medicament for treating a skin infection caused or mediated by *Propionibacterium acnes, Gardnerella vaginalis*, or *Staphylococcus aureus* in a patient. In some embodiments, the use is a use in the manufacture of a medicament for preventing a skin infection caused or mediated by *Propionibacterium acnes, Gardnerella vaginalis*, or *Staphylococcus aureus* in a patient. In some embodiments, the use is a use in the manufacture of a medicament for reducing the risk of a skin infection caused or mediated by *Propionibacterium acnes, Gardnerella vaginalis* or *Staphylococcus aureus* in a patient.

In some embodiments, the skin infection is caused or mediated by *Propionibacterium acnes*. In some embodiments, the skin infection is caused or mediated by *Staphylococcus aureus*. In some embodiments, the skin infection is caused or mediated by *Gardnerella vaginalis*.

In some embodiments, the skin infection is selected from acne vulgaris, rosacea, impetigo, otitis externa, bacterial conjunctivitis, and bacterial vaginosis. In some embodiments, the skin infection is acne vulgaris. In some embodiments, the skin infection is bacterial vaginosis.

In some embodiments, the medicament is administered orally, parentally, or topically. In some embodiments, the medicament is administered topically.

In some embodiments, the patient is a mammal or domestic animal. In some embodiments, the patient is a human.

In some embodiments, the compound is administered once daily or twice daily. In some embodiments, the compound is administered once daily. In some embodiments, the compound is administered twice daily.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

Example 1

Anti-Microbial Activity of Radezolid and Comparator Agents

The in vitro antimicrobial activity of radezolid (compound 4267) and comparator antimicrobial agents were evaluated against several different types of bacteria. Bacterial isolates were obtained from the American Type Culture Collection (ATCC), Manassas, Va.

Susceptibility testing was performed by the agar dilution reference method (radezolid, linezolid, and clindamycin) and broth microdilution method (all agents) as described by the Clinical and Laboratory Standards Institute (CLSI).

For the agar dilution method, Brucella agar (BBL, 211086) was prepared according to the manufacturer's instructions and cooled to 48-50° C. in a water bath. Once the agar was cooled, it was supplemented with 10 mL of hemin+vitamin K1 Solution (Remel, R450951), 1 mL of 1 mg/mL vitamin K1 working solution (Sigma, V3501), and 50 mL laked sheep blood (Remel, R54004). The media was dispensed into 50 mL centrifuge tubes and held at 48-50° C. The antimicrobial agents were reconstituted and prepared at 200× the desired concentrations for ranges of 0.03-8 μg/mL (radezolid and linezolid) and 0.06-16 μg/mL (clindamycin). The diluted antimicrobial agents were added to the dispensed media, gently mixed, and poured into sterile petri dishes. Once hardened, the plates were held in anaerobic jars at room temperature and used the following day.

For broth microdilution testing a master 96-well tray at 100× the highest desired concentration was prepared by adding compound to an appropriate well in the first column and serially diluting through the 10th column. DMSO or water was added to the 11th and 12th columns for growth and sterility controls. A 1:10 dilution was made into a 96-well tray containing Brucella Broth (BBL, 211088) supplemented with hemin+vitamin K1, and 5% lysed horse blood (1HB) (Remel, R54092). Daughter plates containing 10 μL of each well of the 10× tray were dispensed.

The anaerobic bacterial isolates were removed from frozen stocks and placed into thioglycollate broth with hemin and vitamin K1 and without indicator (THIO) (Anaerobe Systems, AS-805). The G. vaginalis isolates were reconstituted from the ATCC vials using Brucella Broth (BRU-Broth) (Anaerobe Systems, AS-105) and plated onto Brucella Blood Agar plates (BRU) (Anaerobe Systems, AS-141) and chocolate agar plates (CA) (BD BBL, 221169). THIO and BRU were incubated for 48 hours in an anaerobic jar at 35° C.; CA plates were incubated at 35° C. for 48 hours in 5% $CO_2$. The S. aureus isolate was removed from a frozen stock, streaked onto TSA with 5% sheep blood (BA) (BD BBL, 221261), and incubated overnight at 35° C. in ambient air. The day before testing the anaerobes and G. vaginalis were subcultured to fresh BRU and THIO and S. aureus was subcultured to BA; all were incubated as required.

On the day of testing, a 0.5 McFarland equivalent of each isolate was prepared in Brucella broth with hemin+vitamin K1. For the agar dilution method, 2 μL spots were inoculated onto each agar plate containing antibiotic in ascending concentration order, as well as BRU and CA plates before and after each set of compound as growth control (beginning) and to assess any drug carryover (end). BRU plates and those containing compound were incubated at 35° C. in an anaerobic environment for 24 hours, read, and re-incubated for an additional 24 hours followed by a final reading. CA plates were incubated at 35° C. in 5% $CO_2$ for 48 hours as a negative control (note that some anaerobes are aerotolerant and may grow in $CO_2$). Following incubation, MICs were determined as the lowest concentration showing a marked reduction in growth or no growth compared to the growth control plate.

For the broth microdilution method, 0.5 mL of the 0.5 McFarland equivalent was placed into 4.5 mL of Brucella Broth with hemin, vitamin K1, and 5% 1HB. This intermediate suspension was diluted further (1.1 mL into 8.9 mL) in Brucella Broth with hemin, vitamin K1, and 5% 1HB for a final concentration of ~$10^5$ CFU/well. Trays were incubated at 35° C. in an anaerobic environment for 24 hours, read, and re-incubated for an additional 24 hours followed by a final reading. To confirm the inoculum, a sample from a growth control well was diluted and spread onto BRU and CA. The plates were incubated for 48 hours at 35° C. in an anaerobic (BRU) or 5% $CO_2$ (CA) environment; colonies were counted and the inoculum was determined. Following incubation, the MIC endpoint was determined as the lowest concentration showing no growth or significantly reduced growth. If growth was poor, the MIC endpoint was not determined.

Agar and broth microdilution MICs for radezolid, linezolid, and clindamycin against the ten isolates are shown below in Table 3, and broth microdilution MICs for the remaining comparators are shown in Table 4. The "reference" agar dilution method is recommended by CLSI for anaerobic susceptibility testing. Due to limited space, only three compounds were tested by this method: radezolid, linezolid, and clindamycin, and all isolates grew well.

The broth microdilution method is recommended by CLSI for B. fragilis group isolates only, but all isolates were tested by this method. Of the three P. acnes isolates, two did not grow in broth, and a third isolate grew poorly. The remaining isolates grew well in broth.

Comparing broth and agar dilution MICs when values were obtained for both methods, MICs were mostly identical or within 2-fold for each antimicrobial agent. Only F. magna had MICs that differed by 4-fold, for radezolid.

TABLE 3

Agar Dilution and Broth Microdilution MICs for Radezolid, Linezolid, and Clindamycin

| Organism | ATCC No. | Radezolid | | Linezolid | | Clindamycin | |
|---|---|---|---|---|---|---|---|
| | | Agar | Broth | Agar | Broth | Agar | Broth |
| B. fragilis | 25285 | 4 | 2 | 4 | 2 | 2 | 1 |
| B. thetaiotaomicron | 29741 | >8 | 8 | 4 | 4 | 8 | 8 |
| F. magna | 15794 | 0.5 | 0.125 | 2 | 1 | 1 | 0.5 |
| P. acnes | 11828 | 0.125 | No growth | 0.5 | No growth | 0.125 | No growth |
| P. acnes | 29399 | 0.125 | Poor growth | 0.5 | Poor growth | ≤0.06 | Poor growth |
| P. acnes | 11827 | 0.125 | No growth | 0.5 | No growth | ≤0.06 | No growth |
| P. granulosum | 25746 | 0.25 | 0.125 | 2 | 1 | 1 | 1 |
| G. vaginalis | 14018 | 0.06 | 0.125 | 0.5 | 0.5 | 0.25 | 0.125 |
| G. vaginalis | 49145 | 0.06 | 0.06 | 0.5 | 0.5 | 0.125 | ≤0.06 |
| S. aureus | 29213 | 1 | 2 | 2 | 4 | 0.25 | 0.25 |

Agar dilution MICs for radezolid were more potent than those of linezolid by 4-fold for P. acnes and F. magna, and by 8-fold for P. granulosum and G. vaginalis. Radezolid and linezolid demonstrated similar activity against S. aureus. Clindamycin and radezolid MICs were within 2-4-fold of each other for most of the isolates.

TABLE 4

Broth Microdilution MICs for Radezolid and Comparator Agents

| Organism | ATCC No. | RDZ | ERY | MET | TET | DOX |
|---|---|---|---|---|---|---|
| B. fragilis | 25285 | 2 | 16 | 0.5 | 0.25 | ≤0.06 |
| B. thetaiotaomicron | 29741 | 8 | 16 | 4 | 8 | 2 |
| F. magna | 15794 | 0.125 | 4 | 0.125 | 0.25 | 0.125 |
| P. acnes | 11828 | No growth | No growth | No growth | No growth | No growth |
| P. acnes | 29399 | Poor growth | Poor growth | Poor growth | Poor growth | Poor growth |
| P. acnes | 11827 | No growth | No growth | No growth | No growth | No growth |
| P. granulosum | 25746 | 0.125 | 16 | 1 | 0.25 | 0.25 |
| G. vaginalis | 14018 | 0.125 | ≤0.06 | 8 | 0.5 | 0.5 |
| G. vaginalis | 49145 | 0.06 | ≤0.06 | 4 | >32 | 32 |
| S. aureus | 29213 | 2 | 1 | >32 | 1 | 0.5 |

Abbreviations:
RDZ, radezolid;
ERY, erythromycin;
MET, metronidazole;
TET, tetracycline;
DOX, doxycycline In broth microdilution testing, radezolid was 8-fold more active than linezolid against P. granulosum and G. vaginalis 49145. Radezolid was also more active than clindamycin, erythromycin, and metronidazole against P. granulosum, and more active than metronidazole, tetracycline, and doxycycline against G. vaginalis.

The oxazolidinones and clindamycin demonstrated similar potency against B. fragilis. MICs for most agents were within 2-fold of radezolid MICs against B. thetaiotaomicron; doxycycline was 4-fold more potent.

Against F. magna, radezolid was more active than linezolid, clindamycin, and erythromycin; the other agents were similar in activity to radezolid. Metronidazole MICs were significantly higher than radezolid against S. aureus; doxycycline and clindamycin MICs were 4-fold and 8-fold lower, respectively. The MICs for the remaining comparator compounds were within 2-fold of radezolid for S. aureus.

In this study, radezolid demonstrated robust antimicrobial activity against most of the isolates tested, with agar dilution MICs of 0.06-1 µg/mL for all organisms. Radezolid demonstrated enhanced activity compared to the other oxazolidinones against several of the isolates.

Table 5 shows MICs for radezolid and comparator agents against ribosome-based resistance phenotypes. As shown in Table 5, radezolid exhibited similar or superior results to linezolid and azithromycin across all phenotypes tested.

TABLE 5

Minimum Inhibitory Concentrations (MICS) (µg/mL) for Radezolid and Comparator Agents Against Ribosome-Based Resistance Phenotypes

| Bacterial Strain | Resistance Phenotype | Linezolid | Azithromycin | Radezolid |
|---|---|---|---|---|
| Enterococcus faecalis ATCC29212 | QC | 4 | 8 | 0.25 |
| Enterococcus faecalis ATCC29212-P5 | Lin-R (G2576U) | 32 | 8 | 1 |
| Enterococcus faecalis 1069 | VanB | 4 | 128 | 0.25 |
| Enterococcus faecium A6349 | VanA + Lin-R (G2576U) | 16 | 128 | 0.5 |
| Staphylococcus aureus ATCC29213 | QC | 4 | 1 | 1 |
| Staphylococcus aureus A7820 | Lin-R (G2576U) + Mac-R (ErmC) | 64 | 128 | 16 |

TABLE 5-continued

Minimum Inhibitory Concentrations (MICS) (μg/mL) for Radezolid and Comparator Agents Against Ribosome-Based Resistance Phenotypes

| Bacterial Strain | Resistance Phenotype | Linezolid | Azithromycin | Radezolid |
|---|---|---|---|---|
| *Staphylococcus aureus* 01A1095 | Mac-R | 4 | 128 | 1 |

Example 2

Safety of Radezolid Versus Comparator Agent

Figure 2:
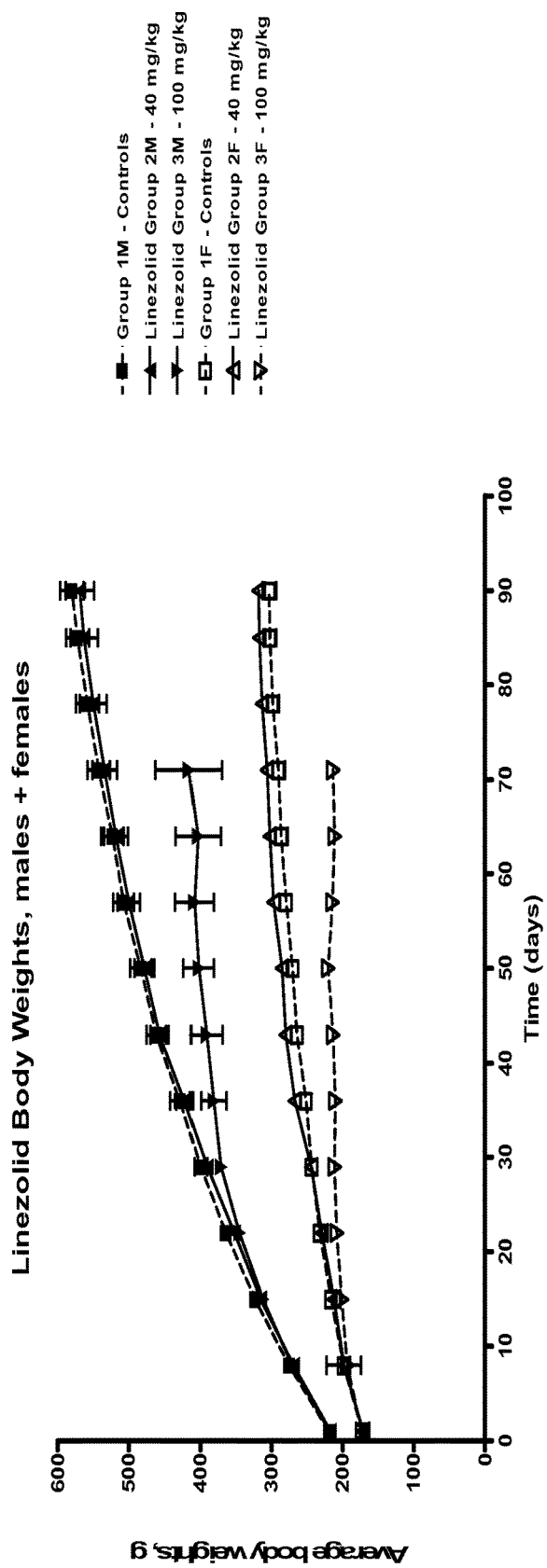
FIG. 2. shows linezolid safety in a long-term rat study, as indicated by average body weight over time.

Safety of radezolid versus comparator linezolid were tested in long-term rat studies (see FIGS. 1-2). Radezolid showed good safety. As shown in FIG. 1, the male rats generally had higher body weights than the females, with similar body weights within each of the dose groups. There was 100% survival in all dose groups. No test article-related changes were observed in hematology, coagulation, clinical chemistry, or urinalysis. An unscheduled euthanization on day 75 for high-dose linezolid groups showed decreased red cell mass, absolute reticulocyte and neutrophil counts in rats dosed with 100 mg/kg/day linezolid. This is correlated with decreased cellularity of sternal and femoral bone marrow. Table 6 shows the calculated safety margin of radezolid based on these data.

TABLE 6

Calculated Safety Margin of Radezolid

| | |
|---|---|
| Exposure (AUC 0-24): male rats at 200 mg/kg on Day 29 | 101.9 μg * hr/mL |
| Exposure (AUC 0-24): human @ 300 mg dose | 3.33 μg * hr/mL |
| Safety margin (Rat NOAEL AUC/Human efficacious AUC) | 30.8x |

Example 3

Uptake of Radezolid Versus Comparator Agent

Approximately 60% of the radezolid accumulates in the cytosol of cells while approximately 40% accumulates in the lysosome. Radezolid accumulates in mammalian cells (e.g., defense cells, macrophages, lung cells, and non-phagocytic cells) to a 17-fold greater extent than linezolid. Radezolid kills intracellular *S. aureus* (including linezolid-resistant), *Listeria monocytogenes* and *Legionella pneumophila*, organisms that reside in different cellular compartments. Accumulation affords once-daily dosing at doses lower than those predicted by plasma levels. Accumulation offers a wider safety window for radezolid as compared to linezolid. See Lemaire et al. AAC 2010, 54(6): 6549-59.

Figure 3:
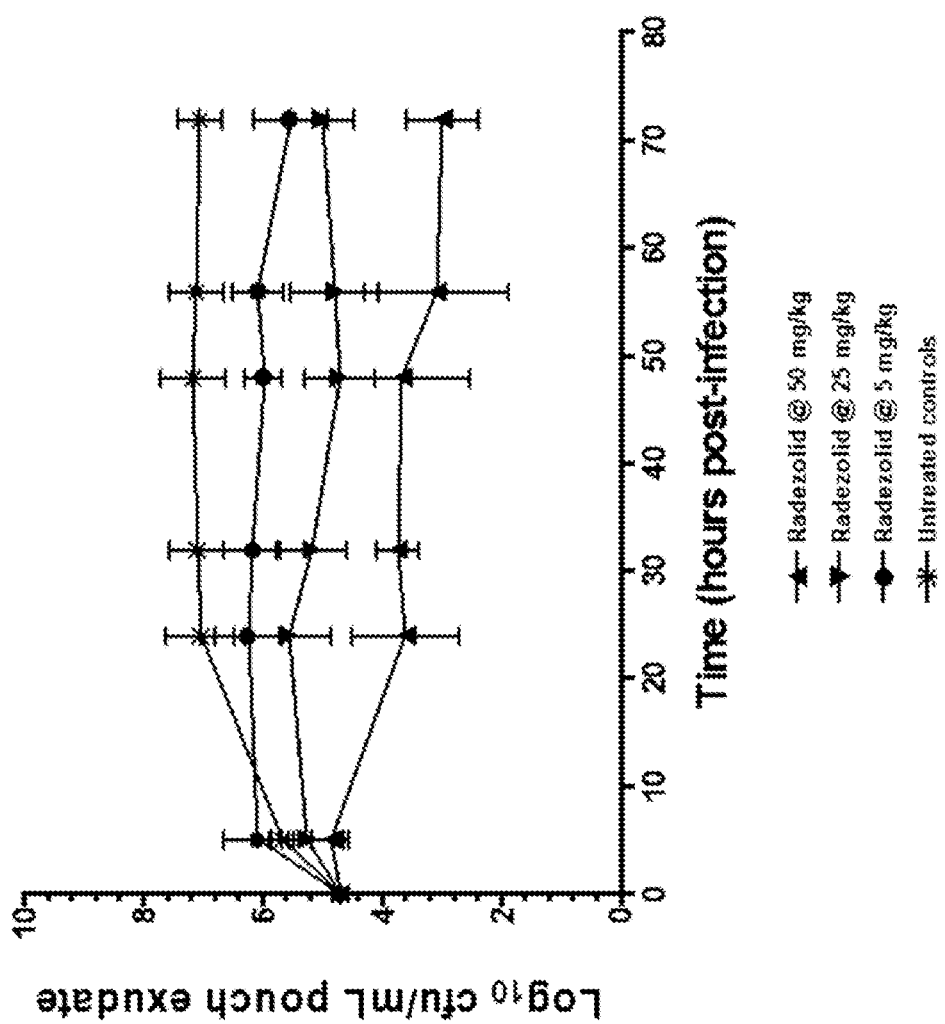
FIG. 3. shows bacterial burden in pouch over time when treated with radezolid.
Figure 4:
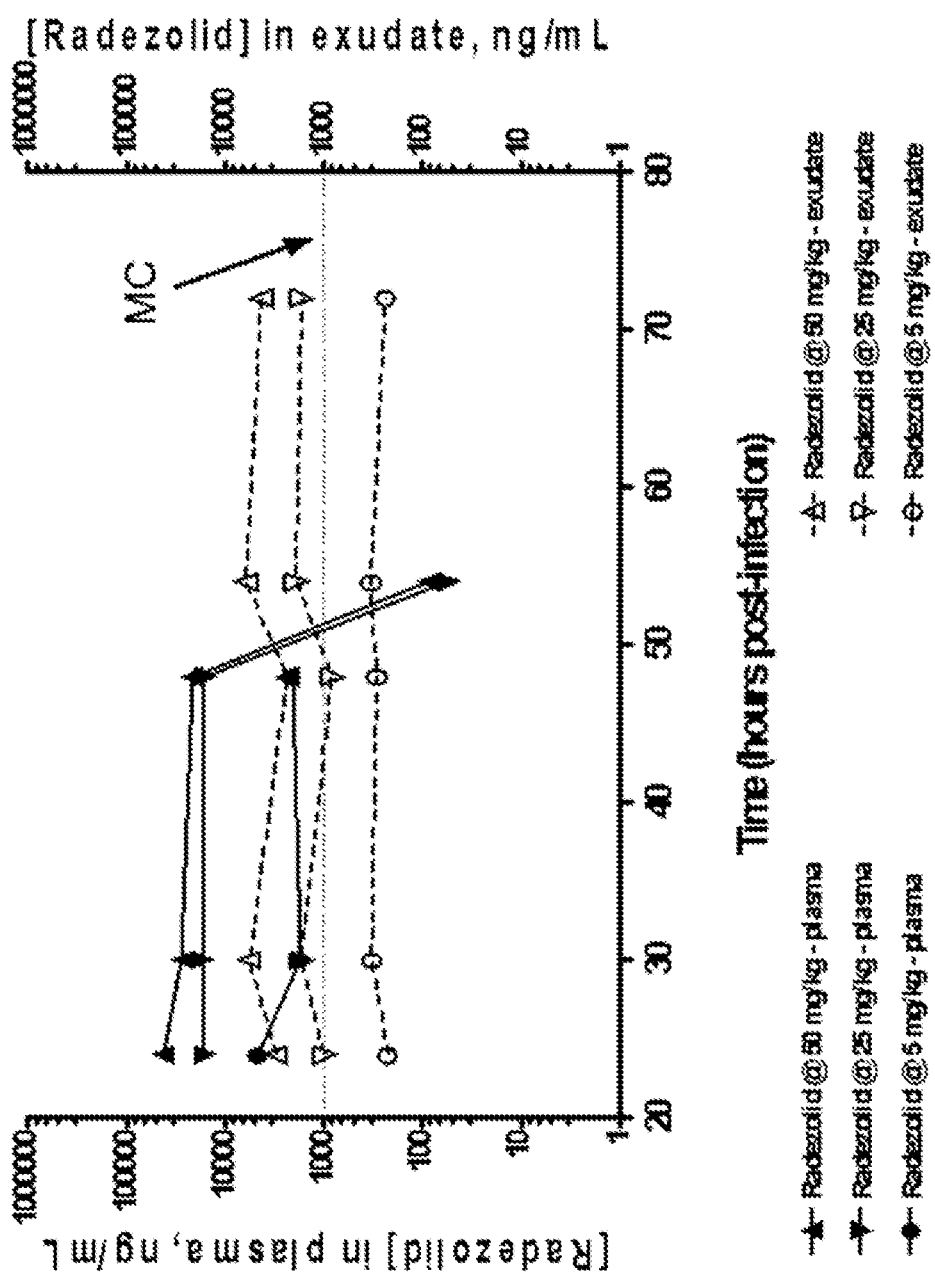
FIG. 4. shows radezolid levels in pouch and plasma over time when treated with radezolid.

Levels of radezolid remain high in granuloma pouch even as they decline in the plasma, contributing to efficacy at the site of infection (see FIGS. 3-4).

Example 4

Synthesis of (5S)—N-(3-{2-fluoro-4'-[(3-fluoro-propylamino)-methyl]-biphenyl-4-yl}-2-oxo-oxazolidin-5-ylmethyl)-acetamide mono hydrochloride salt (Compound 11)

Scheme 1 below depicts synthesis of aryl boronic acid 120, which is coupled to aryl iodide 108 to yield compound 11.

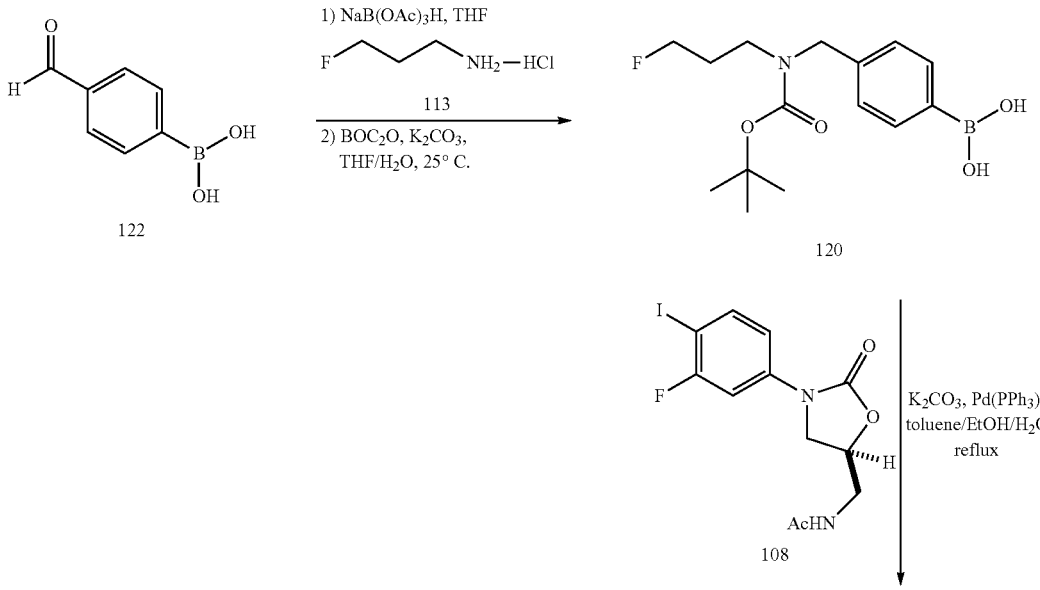

Scheme 1. Synthesis of Compound 11

347 348

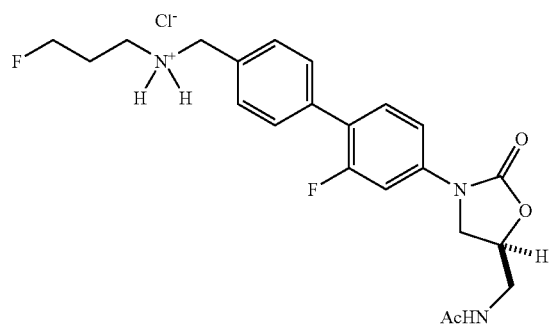

11 → HCl ← 121

-continued

A solution of 4-formylphenyl boronic acid 122 (10.0 g, 66.69 mmol) in anhydrous DMF (150 mL) was treated with 3-fluoropropylamine hydrochloride salt 113 (8.70 g, 76.70 mmol, 1.15 equiv) at room temperature. The resulting mixture was treated with NaB(OAc)$_3$H (28.30 g, 133.39 mmol, 2.0 equiv) at room temperature and stirred for 3 h. When TLC and HPLC/MS showed the reaction was complete, the reaction mixture was treated with water (150 mL), solid Na$_2$CO$_3$ (14.14 g, 133.39 mmol, 2.0 equiv), and BOC$_2$O (22.05 g, 100.04 mmol, 1.5 equiv). The resulting reaction mixture was stirred at room temperature for 3 h. When TLC and HPLC/MS showed the reaction was complete, the reaction mixture was poured into water (500 mL) and EtOAc (500 mL). The two layers were separated and the aqueous layer was treated with a 2 N aqueous HCl (130 mL) to pH 4. The aqueous layer was then extracted with EtOAc (160 mL), and the combined organic layers were washed with water (2×100 mL) and saturated aqueous NaCl (2×100 mL), dried over Na$_2$SO$_4$, and concentrated in vacuo. The residue was further dried in vacuo to afford the desired 4-(N-tert-butylcarbonyl-3-fluoropropylaminomethyl)phenyl boronic acid 120 (25.0 g) as a pale yellow oil. This product was directly used in the subsequent reaction without further purification.

A suspension of aryl boronic acid 120 (25.0 g, 64.30 mmol, 1.45 equiv) in a mixture of toluene (120 mL), EtOH (40 mL), and water (40 mL) was treated with (5S)—N-[3-(3-fluoro-4-iodo-phenyl)-2-oxo-oxazolidin-5-ylmethyl]-acetamide 108 (16.80 g, 44.44 mmol) and solid K$_2$CO$_3$ (18.40 g, 133.4 mmol, 3.0 equiv) at room temperature. The resulting reaction mixture was degassed three times under a steady stream of argon before being treated with Pd(PPh$_3$)$_4$ (2.57 g, 2.23 mmol, 0.05 equiv). The resulting reaction mixture was degassed three times under a steady stream of argon before being warmed to reflux for 8 h. When TLC and HPLC/MS showed the reaction was complete, the reaction mixture was cooled to room temperature before being poured into water (300 mL) and ethyl acetate (EtOAc, 300 mL). The two layers were separated, and the organic phase was washed with water (60 mL) and saturated aqueous NaCl (2×50 mL), dried over anhydrous Na$_2$SO$_4$, and concentrated in vacuo. The product was recrystallized from EtOAc/hexanes and dried in vacuo to afford the desired (5S)-{4'-[5-(acetylamino-methyl)-2-oxo-oxazolidin-3-yl]-2'-fluoro-biphenyl-4-ylmethyl}-(3-fluoro-propyl)-carbamic acid tert-butyl ester 121 (21.2 g, 61.5% yield for three steps) as an off-white powder.

BOC-protected amine 121 was subsequently treated with 4 N hydrogen chloride in 1,4-dioxane to afford compound 11. $^1$H NMR (300 MHz, DMSO-d$_6$) δ 1.90 (s, 3H, COCH$_3$), 2.11-2.20 (m, 2H), 3.10 (m, 2H), 3.50 (t, 2H, J=5.4 Hz), 3.87 (dd, 1H, J=6.4, 9.2 Hz), 4.24 (t, 1H, J=9.1 Hz), 4.27 (s, 2H, ARCH$_2$), 4.54 (t, 1H, J=5.8 Hz), 4.70 (t, 1H, J=5.8 Hz), 4.83 (m, 1H), 7.50 (dd, 1H, J=2.2, 8.6 Hz), 7.65-7.74 (m, 6H, aromatic-H), 8.37 (t, 1H, J=5.8 Hz, NHCOCH$_3$), 9.43 (br. s, 2H, RArN$^+$H$_2$). C$_{22}$H$_{25}$F$_2$N$_3$O$_3$HCl, LCMS (EI) m/e 418 (M$^+$+H).

Example 5

Synthesis of Radezolid

Radezolid (shown as Compound 1) and its hydrochloride salt are synthesized according to Scheme 2 below.

Scheme 2. Synthesis of Radezolid (Compound 1) and its Hydrochloride Salt

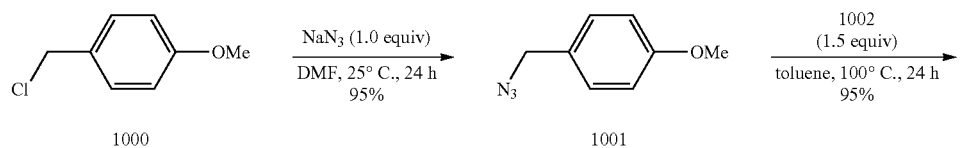

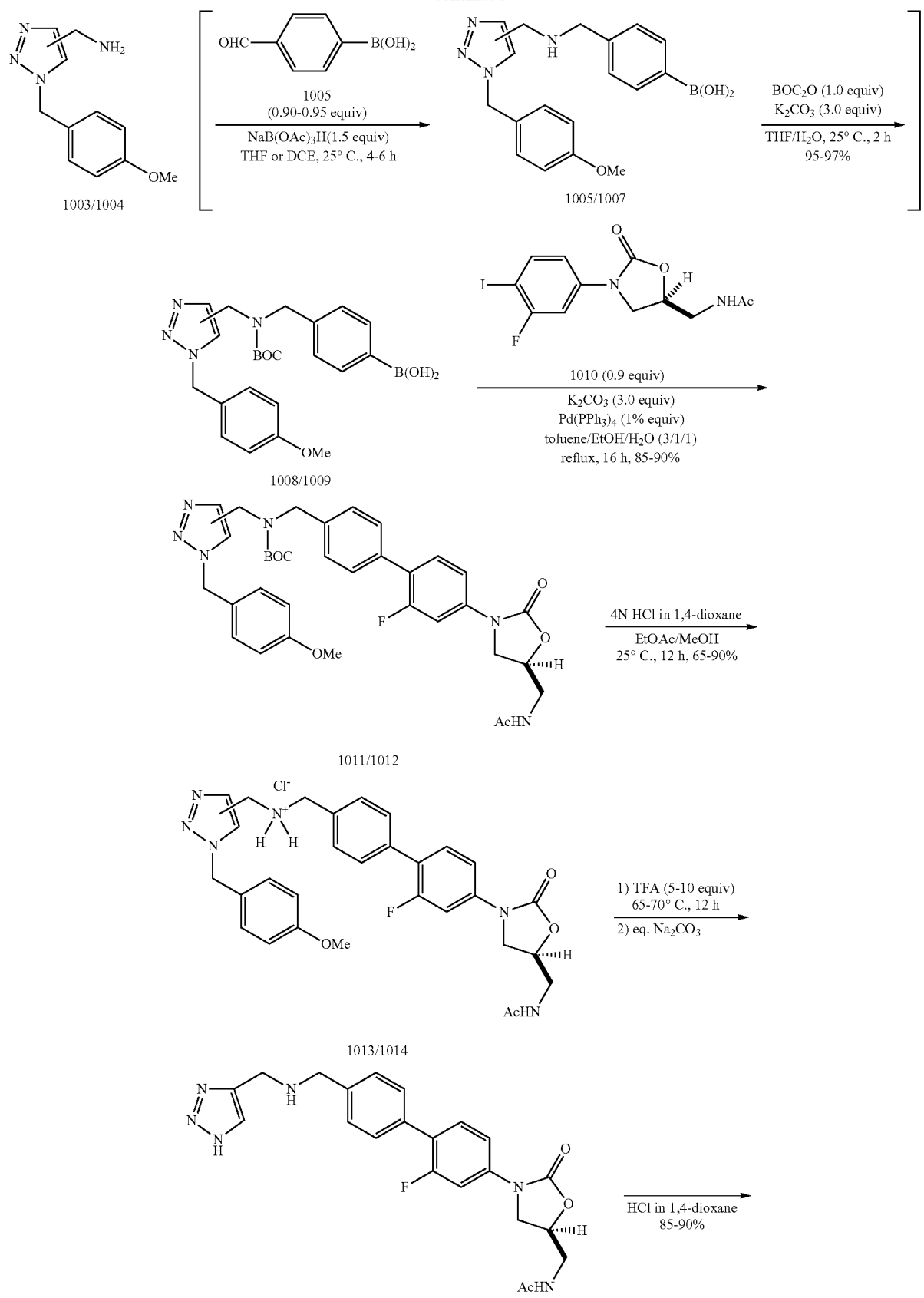

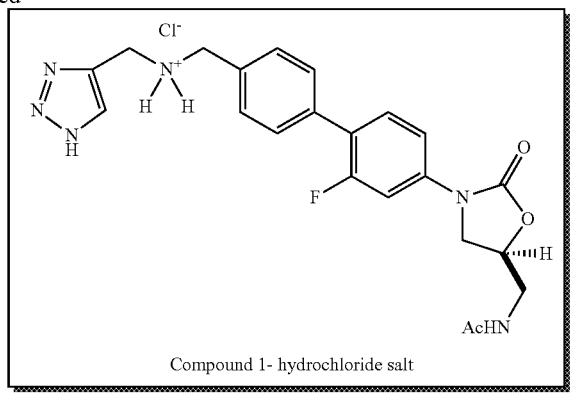
Compound 1- hydrochloride salt
Synthesis of Oxazolidinone Compound 1010
Oxazolidinone compound 1010 is prepared according to Scheme 3 below.
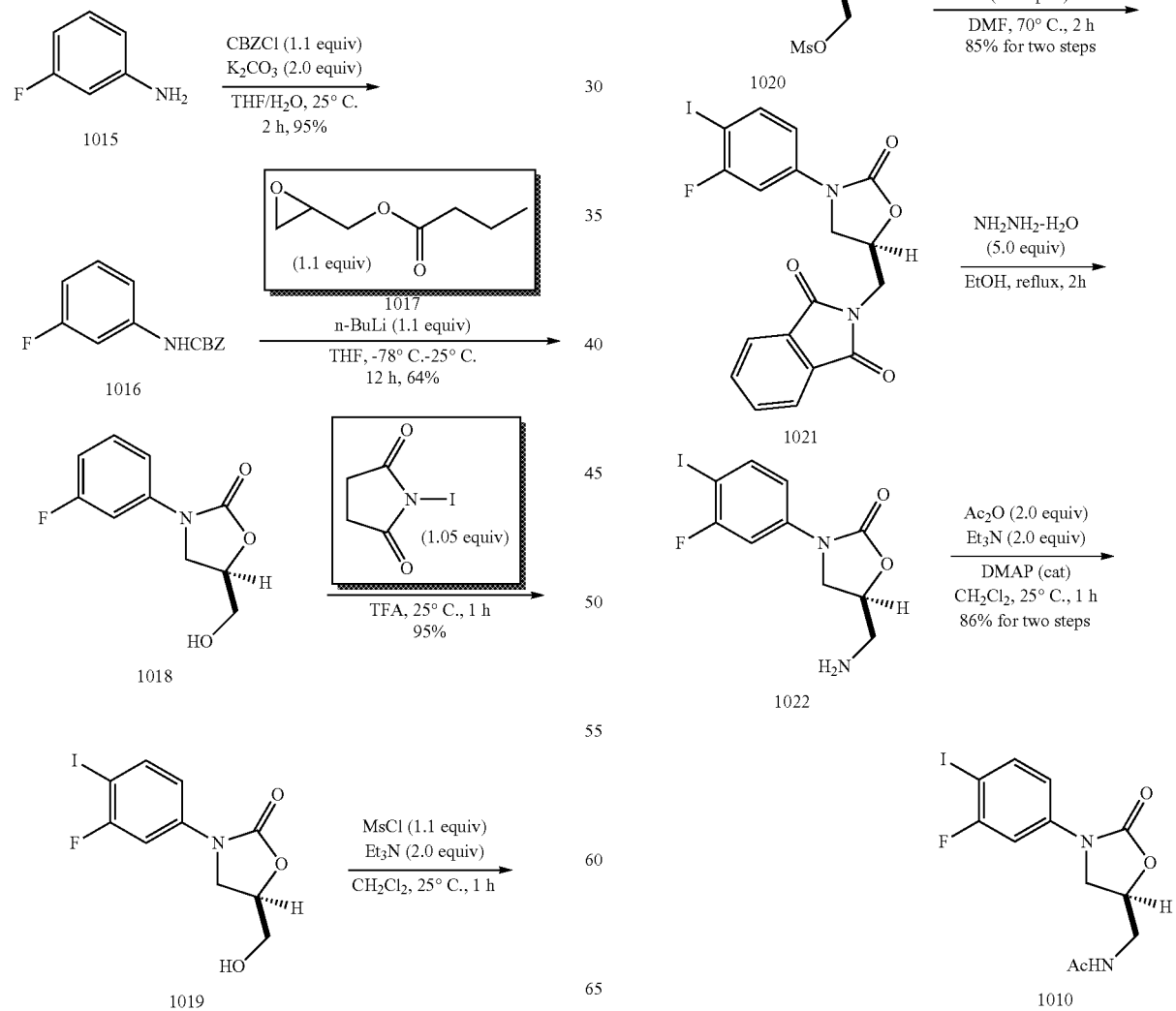

(3-Fluoro-phenyl)-carbamic acid benzyl ester (1016)

A solution of the 3-fluoro-phenylamine (1015, which is commercially available under the names 3-fluoroaniline or 1-amino-3-fluorobenzene, 18.7 g, 168.3 mmol) in tetrahydrofuran (THF, 150 mL) was treated with potassium carbonate ($K_2CO_3$, 46.45 g, 336.6 mmol, 2.0 equiv) and water (150 mL) before a solution of benzyl chloroformate (CBZCl, 31.58 g, 185.1 mmol, 26.1 mL, 1.1 equiv) in THF (50 mL) was dropwise added into the reaction mixture at room temperature under nitrogen. The resulting reaction mixture was stirred at room temperature for 2 h. When TLC showed that the reaction was complete, the reaction mixture was treated with water (100 mL) and ethyl acetate (EtOAc, 100 mL). The two layers were separated, and the aqueous layer was extracted with EtOAc (2×100 mL). The combined organic extracts were washed with water (2×100 mL) and saturated NaCl aqueous solution (100 mL), dried over $MgSO_4$, and concentrated in vacuo. The residue was further dried in vacuo to afford the crude, (3-fluoro-phenyl)-carbamic acid benzyl ester (2, 39.2 g, 41.23 g theoretical, 95%) as pale-yellow oil, which was found to be essentially pure and was directly used in the subsequent reactions without further purifications. For 1016: $^1$H NMR (300 MHz, $CDCl_3$) δ 5.23 (s, 2H, $OCH_2Ph$), 6.75-6.82 (m, 2H), 7.05 (dd, 1H, J=1.4, 8.2 Hz), 7.22-7.45 (m, 6H); $C_{14}H_{12}FNO_2$, LCMS (EI) m/e 246 ($M^++H$).

(5R)-3-(3-Fluoro-phenyl)-5-hydroxymethyl-oxazolidin-2-one (1018)

A solution of (3-fluorophenyl)-carbamic acid benzyl ester (1016, 39.2 g, 160.0 mmol) in anhydrous tetrahydrofuran (THF, 300 mL) was cooled dowel to −78° C. in a dry-ice-acetone bath before a solution of n-butyllithium (n-BuLi, 2.5 M solution in hexane, 70.4 mL, 176 mmol, 1.1 equiv) in hexane was dropwise added at −78° C. under nitrogen. The resulting reaction mixture was subsequently stirred at −78° C. for 1 h before a solution of (R)-(−)-glycidyl butyrate 1017 (25.37 g, 24.6 mL, 176 mmol, 1.1 equiv) in anhydrous THF (100 mL) was dropwise added into the reaction mixture at −78° C. under nitrogen. The resulting reaction mixture was stirred at −78° C. for 30 min before being gradually warmed up to room temperature for 12 h under nitrogen. When TLC and HPLC/MS showed that the reaction was complete, the reaction mixture was quenched with water (200 mL), and the resulting mixture was stirred at room temperature for 1 h before ethyl acetate (EtOAc, 200 mL) was added. The two layers were separated, and the aqueous layer was extracted with EtOAc (2×100 mL). The combined organic extracts were washed with water (2×100 mL) and saturated NaCl aqueous solution (100 mL), dried over $MgSO_4$, and concentrated in vacuo. The white crystals were precipitated out from the concentrated solution when most of the solvents were evaporated. The residue was then treated with 20% EtOAc-hexane (100 mL) and the resulting slurry was further stirred at room temperature for 30 min. The solids were then collected by filtration and washed with 20% EtOAc-hexane (2×50 mL) to afford the crude, (5R)-3-(3-fluoro-phenyl)-5-hydroxymethyl-oxazolidin-2-one (1018, 24.4 g, 33.76 g theoretical, 72.3%) as white crystals, which were found to be essentially pure and directly used in the subsequent reactions without further purifications. For 1018: $^1$H NMR (300 MHz, DMSO-$d_6$) δ 3.34-3.72 (m, 2H), 3.83 (dd, 1H, J=6.2, 9.0 Hz), 4.09 (t, 1H, J=12.0 Hz), 4.68-4.75 (m, 1H), 5.23 (t, 1H, J=5.6 Hz, OH), 6.96 (m, 1H), 7.32-7.56 (m, 3H); $C_{10}H_{10}FNO_3$, LCMS (EI) m/e 212 ($M^++H$).

(5R)-3-(3-Fluoro-4-iodo-phenyl)-5-hydroxymethyl-oxazolidin-2-one (1019)

A solution of (5R)-3-(3-fluoro-phenyl)-5-hydroxymethyl-oxazolidin-2-one (1018, 10.74 g, 50.9 mmol) in trifluoroacetic acid (TFA, 50 mL) was treated with N-iodosuccinimide (NIS, 12.03 g, 53.45 mmol, 1.05 equiv) at 25° C., and the resulting reaction mixture was stirred at 25° C. for 2 h. When TLC and HPLC/MS showed that the reaction was complete, the reaction mixture was concentrated in vacuo. The residue was then treated with water (100 mL) and 20% EtOAc-hexane (100 mL) at 25° C., and the resulting mixture was stirred at 25° C. for 30 min before being cooled down to 0-5° C. for 2 h. The white solids were collected by filtration, washed with water (2×25 mL) and 20% EtOAc-hexane (2×25 mL), and dried in vacuo to afford the crude, (5R)-3-(3-fluoro-4-iodo-phenyl)-5-hydroxymethyl-oxazolidin-2-one (1019, 15.1 g, 17.15 g theoretical, 88%) as off-white powders, which were found to be essentially pure and were directly used in the subsequent reactions without further purifications. For 1019: $^1$H NMR (300 MHz, DMSO-$d_6$) δ 3.58 (dd, 1H, J=4.2, 12.6 Hz), 3.67 (dd, 1H, J=3.0, 12.6 Hz), 3.67 (dd, 1H, J=6.3, 9.0 Hz), 4.07 (t, 1H, J=9.0 Hz), 4.72 (m, 1H), 5.21 (br. s, 1H, OH), 7.22 (dd, 1H, J=2.4, 8.4 Hz), 7.58 (dd, 1H, J=2.4, 11.1 Hz), 7.81 (dd, 1H, J=7.8, 8.7 Hz); $C_{10}H_9FINO_3$, LCMS (EI) m/e 338 ($M^++H$).

(5R)-Methanesulfonic acid 3-(3-fluoro-4-iodo-phenyl)-2-oxo-oxazolidin-5-ylmethyl ester (1020)

A solution of (5R)-3-(3-fluoro-4-iodo-phenyl)-5-hydroxymethyl-oxazolidin-2-one (1019, 25.2 g, 74.8 mmol) in methylene chloride ($CH_2Cl_2$, 150 mL) was treated with trimethylamine (TEA, 15.15 g, 20.9 mL, 150 mmol, 2.0 equiv) at 25° C., and the resulting mixture was cooled down to 0-5° C. before methanesulfonyl chloride (MsCl, 10.28 g, 6.95 mL, 89.7 mmol, 1.2 equiv) was dropwise introduced into the reaction mixture at 0-5° C. under nitrogen. The resulting reaction mixture was subsequently stirred at 0-5° C. for 1 h under nitrogen. When TLC and HPLC/MS showed that the reaction was complete, the reaction mixture was quenched with water (100 mL) and $CH_2Cl_2$ (100 mL). The two layers were separated, and the aqueous layer was extracted with $CH_2Cl_2$ (100 mL). The combined organic extracts were washed with water (2×100 mL) and saturated NaCl aqueous solution (100 mL), dried over $MgSO_4$, and concentrated in vacuo. The residue was further dried in vacuo to afford the crude, (5R)-methanesulfonic acid 3-(3-fluoro-4-iodo-phenyl)-2-oxo-oxazolidin-5-ylmethyl ester (1020, 30.71 g, 31.04 g theoretical, 98.9%) as an off-white powder, which was found to be essentially pure and was directly used in the subsequent reactions without further purifications. For 1020: $C_{11}H_{11}FINO_5S$, LCMS (EI) m/e 416 ($M^++H$).

(5R)-2-[3-(3-Fluoro-4-iodo-phenyl)-2-oxo-oxazolidin-5-ylmethyl]-isoindole-1,3-dione (1021)

A solution of (5R)-methanesulfonic acid 3-(3-fluoro-4-iodo-phenyl)-2-oxo-oxazolidin-5-ylmethyl ester (1020, 26.38 g, 63.57 mmol) in anhydrous N,N-dimethylformamide (DMF, 120 mL) was treated with solid potassium phthalimide (12.95 g, 70.0 mmol, 1.1 equiv) at 25° C., and the resulting reaction mixture was warmed up to 70° C. for 2 h. When TLC and HPLC showed that the reaction was complete, the reaction mixture was cooled down to room temperature before being quenched with water (400 mL), and the resulting mixture was stirred at room temperature for 10 min before being cooled down to 0-5° C. for 1 h. The white precipitates were then collected by filtration, washed with water (3×100 mL), and dried in vacuo to afford the crude, (5R)-2-[3-(3-fluoro-4-iodo-phenyl)-2-oxo-oxazolidin-5-ylmethyl]-isoindole-1,3-dione (1021, 27.85 g, 29.64 g theoretical, 94%) as an off-white powder, which was found to be essentially pure and was directly used in the subsequent reactions without further purifications. For 1021: $C_{18}H_{12}FIN_2O_4$, LCMS (EI) m/e 467 (M$^+$+H).

(5S)-5-Aminomethyl-3-(3-fluoro-4-iodo-phenyl)-oxazolidin-2-one (1022)

A solution of (5R)-2-[3-(3-fluoro-4-iodo-phenyl)-2-oxo-oxazolidin-5-ylmethyl]-isoindole-1,3-dione (1021, 23.3 g, 50.0 mmol) in ethanol (EtOH, 150 mL) was treated with hydrazine monohydrate (12.52 g, 12.1 mL, 250 mmol, 5.0 equiv) at 25° C., and the resulting reaction mixture was warmed up to reflux for 2 h. White precipitates were formed while the reaction mixture was refluxed. When TLC and HPLC showed that the reaction was complete, the reaction mixture was cooled down to room temperature before being quenched with water (100 mL). The white precipitates were totally dissolved when water was introduced into the reaction mixture and a homogeneous solution was generated. The aqueous solution was then extracted with $CH_2Cl_2$ (3×200 mL), and the combined organic extracts were washed with water (2×100 mL) and saturated NaCl aqueous solution (100 mL), dried over MgSO$_4$, and concentrated in vacuo. The residue was further dried in vacuo to afford the crude (5S)-5-aminomethyl-3-(3-fluoro-4-iodo-phenyl)-oxazolidin-2-one (1022, 16.0 g, 16.8 g theoretical, 95.2%) as a white powder, which was found to be essentially pure and was directly used in the subsequent reactions without further purifications. For 1022: $C_{10}H_{10}FIN_2O_2$, LCMS (EI) m/e 337 (M$^+$+H).

(5S)—N-[3-(3-Fluoro-4-iodo-phenyl)-2-oxo-oxazolidin-5-ylmethyl]-acetamide (1010)

A suspension of (5S)-5-aminomethyl-3-(3-fluoro-4-iodo-phenyl)-oxazolidin-2-one (1022, 16.0 g, 47.6 mmol) in $CH_2Cl_2$ (150 mL) was treated with triethylamine (TEA, 9.62 g, 13.2 mL, 95.2 mmol, 2.0 equiv) at 25° C., and the resulting reaction mixture was cooled down to 0-5° C. before being treated with acetic anhydride (Ac$_2$O, 7.29 g, 6.75 mL, 71.4 mmol, 1.5 equiv) and 4-N,N-dimethylaminopyridine (DMAP, 58 mg, 0.5 mmol, 0.01 equiv) at 0-5° C. under nitrogen. The resulting reaction mixture was subsequently stirred at 0-5° C. for 2 h. When TLC and HPLC showed that the reaction was complete, the reaction mixture was quenched with water (100 mL). The two layers were separated, and the aqueous layer was then extracted with $CH_2Cl_2$ (2×50 mL), and the combined organic extracts were washed with water (2×100 mL) and saturated NaCl aqueous solution (100 mL), dried over MgSO$_4$, and concentrated in vacuo. The residue was further dried in vacuo to afford the crude, (5S)—N-[3-(3-fluoro-4-iodo-phenyl)-2-oxo-oxazolidin-5-ylmethyl]-acetamide (1010, 17.36 g, 17.99 g theoretical, 96.5%) as white powders, which were found to be essentially pure and were directly used in the subsequent reactions without further purifications. For 1010: $^1$H NMR (300 MHz, DMSO-d$_6$) δ 1.63 (s, 3H, NHCOCH$_3$), 3.25 (t, 2H, J=5.4 Hz), 3.56 (dd, 1H, J=6.4, 9.2 Hz), 3.95 (t, 1H, J=9.1 Hz), 4.58 (m, 1H), 5.16 (t, 1H, J=5.7 Hz, OH), 7.02 (dd, 1H, J=2.4, 8.2 Hz), 7.38 (dd, 1H, J=2.4, 10.8 Hz), 7.66 (t, 1H, J=7.5, 8.4 Hz), 8.08 (t, 1H, J=5.8 Hz, NHCOCH$_3$); $C_{12}H_{12}FIN_2O_3$, LCMS (EI) m/e 379 (M$^+$+H).

Synthesis of Radezolid (Compound 1)

4-Methoxybenzyl Azide 1001

A solution of 4-methoxybenzyl chloride 1000 (51.8 g, 331.0 mmol) in anhydrous DMF (200 mL) was treated with solid sodium azide (21.5 g, 331.0 mmol, 1.0 equiv) at 25° C., and the resulting mixture was stirred at 25° C. for 24 h. When TLC and HPLC/MS showed that the reaction was complete, the reaction mixture was quenched with water (400 mL) and ethyl acetate (EtOAc, 400 mL) at room temperature. The two layers were separated, and the aqueous layer was extracted with EtOAc (200 mL). The combined organic extracts were washed with water (2×200 mL) and saturated NaCl aqueous solution (100 mL), dried over MgSO$_4$, and concentrated in vacuo. The crude 4-methoxybenzyl amide (51.2 g, 53.95 g theoretical, 94.9% yield) was obtained as a colorless oil, which by HPLC and $^1$H NMR was found to be essentially pure and was directly used in the subsequent reaction without further purifications. For 4-methoxybenzyl azide 1001: $^1$H NMR (300 MHz, CDCl$_3$) δ 3.84 (s, 3H, ArOCH$_3$), 4.29 (s, 2H, Ar—CH$_2$), 6.96 (d, 2H, J=8.7 Hz), 7.28 (d, 2H, J=7.8 Hz).

C-[1-(4-Methoxy-benzyl)-1H-[1,2,3]triazol-4-yl]-methylamine and C-[3-(4-Methoxybenzyl)-3H-[1,2,3]triazol-4-yl]-methylamine (1003 and 1004)

A solution of 4-methoxybenzylamide 1001 (61.2 g, 375.5 mmol) in toluene (188 mL) was treated with propargylamine 1002 (commercially available, 30.97 g, 38.6 mL, 563.0 mmol, 1.5 equiv) at 25° C., and the resulting reaction mixture was warmed up to gentle reflux at 100-110° C. for 21 h. When TLC and HPLC/MS showed that the reaction was complete, the reaction mixture was cooled down to room temperature before being concentrated in vacuo to remove the excess amount of propargylamine and solvent. The oily residue was then treated with 30% ethyl acetate-hexane (v/v, 260 mL), and the resulting mixture was warmed up to reflux and stirred at reflux for 30 min before being cooled down to room temperature for 1 h. The pale-yellow solids were then collected by filtration, washed with 30% ethyl acetate-hexane (v/v, 2×100 mL), and dried in vacuo at 40° C. for overnight to afford the crude, cycloaddition product (78.8 g, 81.75 g theoretical, 96.4%) as a mixture of two regioisomers, C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004), in a ratio of 1.2 to 1 by $^1$H NMR. The crude cycloaddition product was found to be essentially pure and the two regioisomers were not separated before being used directly in the subsequent reaction without further purification. For 1003 and 1004: $^1$H NMR (300 MHz, DMSO-d$_6$) δ 1.82 (br. s, 2H, NH$_2$), 3.72 and 3.73 (two s, 3H, Ar—OCH$_3$), 5.47 and 5.53 (two s, 2H, ArCH$_2$), 6.89 and 6.94 (two d, 2H, J=8.7 Hz, Ar—H), 7.17 and 7.29 (two d, 2H, J=8.7 Hz, Ar—H), 7.58 and 7.87 (two br. s, 1H, triazole-CH); $C_{11}H_{14}N_4O$, LCMS (EI) m/e 219 (M$^+$+H) and 241 (M$^+$+Na).

4-({tert-Butoxycarbonyl-[1-(4-methoxy-benzyl)-1H-[1,2,3]triazol-4-ylmethyl]-amino}-methyl)-phenylboronic acid and 4-({tert-Butoxycarbonyl-[3-(4-methoxy-benzyl)-3H-[1,2,3]triazol-4-ylmethyl]amino}-methyl)-phenylboronic acid (1008 and 1009)

Method A. A solution of the regioisomeric C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004, 20.0 g, 91.74 mmol) in 1,2-dichloroethane (DCE, 280 mL) was treated with 4-formylphenylboronic acid 1005 (commercially available, 12.39 g, 82.57 mmol, 0.9 equiv) at room temperature, and the resulting reaction mixture was stirred at room temperature for 10 min. Sodium triacetoxyborohydride (NaB(OAc)$_3$H, 29.2 g, 137.6 mmol, 1.5 equiv) was then added to the reaction mixture in three portions over the period of 1.5 h at room temperature, and the resulting reaction mixture was stirred at room temperature for an additional 3.5 h. When TLC and HPLC/MS showed that the reductive amination reaction was complete, the reaction mixture was concentrated in vacuo. The residue, which contained a regioisomeric mixture of 4-({[1-(4-methoxy-benzyl)-1H-[1,2,3]triazol-4-ylmethyl]-amino}-methyl)-phenylboronic acid and 4-({[3-(4-methoxy-benzyl)-3H-[1,2,3]triazol-4-ylmethyl]-amino}-methyl)-phenylboronic acid as the reductive amination products (1006 and 1007), was then treated with tetrahydrofuran (THF, 100 mL) and water (water, 100 mL). The resulting solution was subsequently treated with solid potassium carbonate (K$_2$CO$_3$, 37.98 g, 275.2 mmol, 3.0 equiv) and di-tert-butyl dicarbonate (BOC$_2$O, 20.02 g, 91.74 mmol, 1.0 equiv) at room temperature and the reaction mixture was stirred at room temperature for 2 h. When TLC and HPLC/MS showed that the N-BOC protection reaction was complete, the reaction mixture was treated with ethyl acetate (EtOAc, 150 mL) and water (water, 100 mL). The two layers were separated, and the aqueous layer was extracted with ethyl acetate (50 mL). The combined organic extracts were washed with water (50 mL), 1.5 N aqueous HCl solution (2×100 mL), water (100 mL), and saturated aqueous NaCl solution (100 mL), dried over MgSO$_4$, and concentrated in vacuo. The crude, regioisomeric 4-({tert-butoxycarbonyl-[1-(4-methoxy-benzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]-amino}-methyl)-phenylboronic acid (1008 and 1009, 35.98 g, 37.32 g, 96.4%) was obtained as a pale-yellow oil, which solidified upon standing at room temperature in vacuo. This crude material was directly used in the subsequent reaction without further purification. For 1008 and 1009: $^1$H NMR (300 MHz, DMSO-d$_6$) δ 1.32 and 1.37 (two br. s, 9H, COOC(CH$_3$)$_3$), 3.70, 3.73 and 3.74 (three s, 3H, Ar—OCH$_3$), 4.07-4.39 (m, 4H), 5.49 and 5.52 (two s, 2H), 6.70-8.04 (m, 9H, Ar—H and triazole-CH); $C_{23}H_{29}BN_4O_5$, LCMS (EI) m/e 453 (M$^+$+H) and 475 (M$^+$+Na).

Method B. A solution of the regioisomeric C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004, 20.06 g, 92.0 mmol) in tetrahydrofuran (THF, 300 mL) was treated with 4-formylphenylboronic acid (13.11 g, 87.4 mmol, 0.95 equiv) at room temperature, and the resulting reaction mixture was stirred at room temperature for 10 min. Sodium triacetoxyborohydride (NaB(OAc)$_3$H, 29.25 g, 138.0 mmol, 1.5 equiv) was then added to the reaction mixture in three portions over the period of 1.5 h at room temperature, and the resulting reaction mixture was stirred at room temperature for an additional 3.5 h. When TLC and HPLC/MS showed that the reductive amination reaction was complete, the reaction mixture, which contained a regioisomeric mixture of 4-({[1-(4-methoxy-benzyl)-1H-[1,2,3]triazol-4-ylmethyl]-amino}-methyl)-phenylboronic acid and 4-({[3-(4-methoxy-benzyl)-3H-[1,2,3]triazol-4-ylmethyl]-amino}-methyl)-phenylboronic acid as the reductive amination products (1006 and 1007), was then treated with water (water, 200 mL). The resulting aqueous solution was subsequently treated with solid potassium carbonate (K$_2$CO$_3$, 38.0 g, 276 mmol, 3.0 equiv) and di-tert-butyl dicarbonate (BOC$_2$O, 20.08 g, 92 mmol, 1.0 equiv) at room temperature and the reaction mixture was stirred at room temperature for 2 h. When TLC and HPLC/MS showed that the N-BOC protection reaction was complete, the reaction mixture was treated with ethyl acetate (EtOAc, 150 mL) and water (water, 100 mL). The two layers were separated, and the aqueous layer was extracted with ethyl acetate (50 mL). The combined organic extracts were washed with water (50 mL), 1.5 N aqueous HCl solution (2×100 mL), water (100 mL), and saturated aqueous NaCl solution (100 mL), dried over MgSO$_4$, and concentrated in vacuo. The crude, 4-({tert-butoxycarbonyl-[1-(4-methoxy-benzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]-amino}-methyl)-phenylboronic acid (1008 and 1009, 38.45 g, 39.50 g, 97.3%) was obtained as a pale-yellow oil, which solidified upon standing at room temperature in vacuo. This crude material was found to be essentially identical in every comparable aspect as the material obtained from Method A and was directly used in the subsequent reaction without further purification.

(5S)-{4'-[5-(Acertylamino-methyl)-2-oxo-oxazolidin-3-yl-2'-fluoro-biphenyl-4-ylmethyl}-[1-(4-methoxy-benzyl)-1H-[1,2,3]triazol-4-ylmethyl]-carbamic acid tert-butyl ester and (5S)-{4'-[5-(Acetylamino-methyl)-2-oxo-oxazolidin-3-yl]-2'-fluoro-biphenyl-4-ylmethyl}-[1-(4-methoxy-benzyl)-1H-[1,2,3]triazol-5-ylmethyl]-carbamic acid tert-butyl ester (1011 and 1012)

A suspension of the crude regioisomeric mixture of 4-({tert-butoxycarbonyl-[1-(4-methoxybenzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]-amino}-methyl)-phenylboronic acid (1008 and 1009, 37.62 g, 83.23 mmol) and N-[3-(3-fluoro-4-iodo-phenyl)-2-oxo-oxazolidin-5-ylmethyl]-acetamide (1010, 28.32 g, 74.9 mmol, 0.90 equiv) in toluene (150 mL) was treated with powder K$_2$CO$_3$ (34.45 g, 249.7 mol, 3.0 equiv), EtOH (50 mL), and water (50 mL) at 25° C., and the resulting mixture was degassed three times under a steady stream of Argon at 25° C. Pd(PPh$_3$)$_4$ (866 mg, 0.749 mmol, 0.01 equiv) was subsequently added to the reaction mixture, and the resulting reaction mixture was degassed three times again under a steady stream of Argon at 25° C. before being warmed up to gentle reflux for 18 h. When TLC and HPLC/MS showed the coupling reaction was complete, the reaction mixture was cooled down to room temperature before being treated with water (100 mL) and ethyl acetate (100 mL). The two layers were then separated, and the aqueous layer was extracted with EtOAc (100 mL). The combined organic extracts were washed with water (50 mL), 1.5 N aqueous HCl solution (2×150 mL), water (100 mL), and the saturated aqueous NaCl solution (100 mL), dried over MgSO$_4$, and concentrated in vacuo. The residual oil was solidified upon standing at room temperature in vacuo to afford the crude, (5S)-{4'-[5-(acetylamino-methyl)-2-oxo-oxazolidin-3-yl]-2'-fluorobiphenyl-4-ylmethyl}-[1-(4-methoxy-benzyl)-1H-[1,2,3]triazol-4-ylmethyl]-carbamic acid tert-butylester (1011) and (5S)-{4'-[5-(acetylamino-methyl)-2-oxo-oxazolidin-3-yl]-2'-fluorobiphenyl-4-ylmethyl}-[1-(4-methoxy-benzyl)-1H-[1,2,3]triazol-5-ylmethyl]-carbamic acid tert-butylester (1012) as a regioisomeric mixture. This crude product (43.36 g, 49.28 g theoretical, 88%) was used directly in the subsequent reaction without further purification. For the mixture of 1011 and 1012: $^1$H NMR (300 MHz, DMSO-d$_6$) δ 1.35 and 1.38 (two br. s, 9H, COO(CH$_3$)$_3$), 1.85 (s, 3H, COCH$_3$), 3.45 (t, 2H, J=5.4 Hz), 3.73 and 3.76 (two s, 3H, Ar—OCH$_3$), 3.79 (dd, 1H, J=6.6, 9.1 Hz), 4.18 (t, 1H, J=9.1 Hz), 4.35-4.43 (m, 4H), 4.73-4.81 (m, 1H), 5.50 (br. s, 2H), 6.90 and 6.98 (two d, 2H, J=8.7 Hz), 7.28 and 7.32 (two d, 2H, J=8.7 Hz), 7.35 (dd, 2H, J=2.2, 8.6 Hz), 7.42 (dd, 1H, J=2.2, 8.6 Hz), 7.49-7.63 (m, 4H, aromatic-H), 7.90 and 7.99 (two br. s, 1H, triazole-CH), 8.29 (t, 1H, J=5.8 Hz, NHCOCH$_3$); C$_{35}$H$_{39}$FN$_6$O$_6$, LCMS (EI)$_{m/e}$ 659 (M$^+$+H) and 681 (M$^+$+Na).

(5S)—N-{3-[2-Fluoro-4'-({[1-(4-methoxy-benzyl)-1H-[1,2,3]triazol-4-ylmethyl]-amino}-methyl)-biphenyl-4-yl]-2-oxo-oxazolidin-5-ylmethyl}-acetamide Hydrochloride (1013) and (5S)—N-{3-[2-Fluoro-4'-({[1-(4-methoxy-benzyl)-1H-[1,2,3]triazol-5-ylmethyl]-amino}-methyl)-biphenyl-4-yl]-2-oxo-oxazolidin-5-ylmethyl}-acetamide Hydrochloride (1014)

A solution of a regioisomeric mixture of (5S)-{4'-[5-(acetylamino-methyl)-2-oxo-oxazolidin-3-yl]-2'-fluoro-biphenyl-4-methyl}-[1-(4-methoxy-benzyl)-1H-[1,2,3]triazol-4-ylmethyl]-carbamic acid tert-butyl ester and (5S)-{4'-[5-(acetylamino-methyl)-2-oxo-oxazolidin-3-yl]-2'-fluorobiphenyl-4-ylmethyl}-[1-(4-methoxy-benzyl)-1H-[1,2,3]triazol-5-ylmethyl]-carbamic acid tert-butyl ester (1011 and 1012, 37.28 g, 56.65 mmol) in ethyl acetate (EtOAc, 150 mL) and methanol (MeOH, 30 mL) was treated with a solution of 4 N hydrogen chloride in 1,4-dioxane (113.3 mL, 453.2 mmol, 8.0 equiv) at room temperature, and the resulting reaction mixture was stirred at room temperature for 12 h. When TLC and HPLC/MS showed that the N-BOC deprotection reaction was complete, the solvents were removed in vacuo. The residue was then suspended in 250 mL of 5% methanol (MeOH) in acetonitrile (CH$_3$CN), and the resulting slurry was stirred at room temperature for 1 h. The solids were then collected by filtration, washed with toluene (2×100 mL) and 5% methanol in acetonitrile (2×50 mL), and dried in vacuo to afford a regioisomeric mixture of the crude, (5S)—N-{3-[2-fluoro-4'-({[1-(4-methoxy-benzyl)-1H-[1,2,3]triazol-4-ylmethyl]-amino}-methyl)-biphenyl-4-yl]-2-oxo-oxazolidin-5-ylmethyl}-acetamide hydrochloride and (5S)—N-{3-[2-fluoro-4'-({[1-(4-methoxy-benzyl)-1H-[1,2,3]triazol-5-ylmethyl]-amino}-methyl)-biphenyl-4-yl]-2-oxo-oxazolidin-5-ylmethyl}-acetamide hydrochloride (1013 and 1014, 30.0 g, 33.68 g theoretical, 89.1% yield) as off-white crystals in a ratio of 1.2 to 1. This material was found by $^1$H NMR and HPLC/MS to be essentially pure and was directly used in the subsequent reactions without further purification. For the regioisomeric mixture of 1013 and 1014: $^1$H NMR (300 MHz, DMSO-d$_6$) δ 1.84 (s, 3H, COCH$_3$), 3.44 (t, 2H, J=5.4 Hz), 3.71 and 3.74 (two s, 3H, Ar—OCH$_3$), 3.80 (dd, 1H, J=6.6, 9.1 Hz), 4.17 (t, 1H, J=9.1 Hz), 4.23-4.30 (m, 4H), 4.73-4.80 (m, 1H), 5.58 and 5.70 (two s, 2H), 6.88 and 6.93 (two d, 2H, J=8.7 Hz), 7.15 and 7.32 (two d, 2H, J=8.7 Hz), 7.43 (dd, 2H, J=2.2, 8.6 Hz), 7.52-7.62 (m, 6H, aromatic-H), 8.28 (s, 1H, triazole-CH), 8.32 (t, 1H, J=5.8 Hz, NHCOCH$_3$), 9.91 and 10.32 (two br. s, 2H, ArCH$_2$N$^+$H$_2$); C$_{30}$H$_{31}$FN$_6$O$_4$, LCMS (EI) m/e 559 (M$^+$+H) and 581 (M$^+$+Na).

(5S)—N-[3-(2-Fluoro-4'-{[(1H-[1,2,3]triazol-4-ylmethyl)-amino]-methyl}-biphenyl-4-yl)-2-oxo-oxazolidin-5-ylmethyl]-acetamide (1) (radezolid)

A solution of the crude regioisomeric mixture of (5S)—N-{3-[2-fluoro-4'-({[1-(4-methoxy-benzyl)-1H-[1,2,3]triazol-4-ylmethyl]-amino}-methyl)-biphenyl-4-yl]-2-oxo-oxazolidin-5-ylmethyl}-acetamide hydrochloride and (5S)—N-{3-[2-fluoro-4'-({[1-(4-methoxy-benzyl)-1H-[1,2,3]triazol-5-ylmethyl]-amino}-methyl)-biphenyl-4-yl]-2-oxo-oxazolidin-5-ylmethyl}-acetamide hydrochloride (1013 and 1014, 29.17 g, 49.07 mmol) in trifluoroacetic acid (TFA, 150 mL) was warmed up to 65-70° C., and the resulting reaction mixture was stirred at 65-70° C. for 12 h. When TLC and HPLC/MS showed that the deprotection reaction was complete, the solvents were removed in vacuo. The residual solids were then treated with ethyl acetate (EtOAc, 100 mL) and water (150 mL) before being treated with a saturated aqueous solution of sodium carbonate (30 mL) at room temperature. The resulting mixture was then stirred at room temperature for 1 h before the solids were collected by filtration, washed with EtOAc (2×50 mL) and water (2×50 mL), and dried in vacuo at 40-45° C. to afford the crude, (5S)—N-[3-(2-fluoro-4'-{[(1H-[1,2,3]triazol-4-ylmethyl)-amino]-methyl}-biphenyl-4-yl)-2-oxo-oxazolidin-5-ylmethyl]-acetamide (1 as the free base, 18.9 g, 21.49 g theoretical, 87.9%) as an off-white powder, which by HPLC/MS and $^1$H NMR was found to be one pure regioisomer and this regioisomer was found to be identical to the material obtained from deprotection of 1013 alone by the same method. For 1 as the free base: $^1$H NMR (300 MHz, DMSO-d$_6$) δ 1.85 (s, 3H, COCH$_3$), 3.44 (t, 2H, J=5.4 Hz), 3.74 (s, 2H), 3.77 (s, 2H), 3.79 (dd, 1H, J=6.4, 9.2 Hz), 4.17 (t, 1H, J=9.1 Hz), 4.72-4.81 (m, 1H), 7.39-7.62 (m, 7H, aromatic-H), 7.73 (s, 1H, triazole-CH), 8.29 (t, 1H, J=5.8 Hz, NHCOCH$_3$), 9.72 (br. s, 2H, ArCH$_2$N$^+$H$_2$), 15.20 (hr. s, 1H, triazole-NH); C$_{22}$H$_{23}$FN$_6$O$_3$, LCMS (EI) m/e 439 (M$^+$+H) and 461 (M$^+$+Na); DSC onset melt at 208.4° C.

(5S)—N-[3-(2-Fluoro-4'-{[(1H-[1,2,3]triazol-4-ylmethyl)-amino]-methyl}-biphenyl-4-yl)-2-oxo-oxazolidin-5-ylmethyl]-acetamide chloride (1 hydrochloride salt)

A suspension of 1 free base (18.0 g, 41.1 mmol) in ethyl acetate (EtOAc, 80 mL), and methanol (MeOH, 20 mL) was treated with a solution of 4.0 N hydrogen chloride in 1,4-dioxane (41.1 mL, 164.4 mmol, 4.0 equiv) at room temperature, and the resulting mixture was stirred at room temperature for 8 h. The solvents were then removed in vacuo, and the residue was further dried in vacuo before being treated with a mixture of 10% methanol in acetonitrile (80 mL). The solids were collected by filtration, washed with 10% MeOH/acetonitrile (2×40 mL), and dried in vacuo to afford 1 hydrochloride salt (18.13 g, 19.50 g theoretical, 93% yield) as off-white crystals; DSC endotherm at 266° C.; onset melt at 261° C.

Recrystallization of Radezolid Hydrochloride

The crude 1 hydrochloride salt was recrystallized from acetonitrile and water according to the following procedure: A suspension of the crude 1 hydrochloride salt (50.0 g) in acetonitrile (1250 mL) was warmed up to reflux before the distilled water (water, 280 mL) was gradually introduced to the mixture. The resulting clear yellow to light brown solution was then stirred at reflux for 10 min before being cooled down to 45-55° C. The solution was then filtered through a Celite bed at 45-55° C., and the filtrates were gradually cooled down to room temperature before being further cooled down to 0-5° C. in an ice bath for 1 h. The solids were then collected by filtration, washed with acetonitrile (2×50 mL), and dried in vacuo at 40° C. for 24 h to afford the recrystallized 1 hydrochloride salt (42.5 g, 50.0 g theoretical, 85% recovery) as off-white crystals. For 1: $^1$H NMR (300 MHz, DMSO-$d_6$) δ 1.86 (s, 3H, COCH$_3$), 3.45 (t, 2H, J=5.4 Hz), 3.84 (dd, 1H, J=6.4, 9.2 Hz), 4.19 (t, 1H, J=9.1 Hz), 4.24 (br. s, 2H), 4.31(br. s, 2H), 4.74-4.79 (m, 1H), 7.44 (dd, 1H, J=2.2, 8.6 Hz), 7.57-7.66 (m, 6H, aromatic-H), 8.17 (s, 1H, triazole-CH), 8.30 (t, 1H, J=5.8 Hz, NHCOCH$_3$), 9.72 (br. s, 2H, ArCH$_2$N$^+$H$_2$), 15.20 (br. s, 1H, triazole-NH); $^{13}$C NMR (75 MHz, DMSO-$d_6$) δ 22.57, 40.69, 41.50, 47.36, 49.23, 71.85, 105.70 (d, J=28.5 Hz), 114.14 (d, J=2.9 Hz), 122.29 (d, J=13.3 Hz), 128.82 (d, J=3.0 Hz), 130.70, 130.94, 131.0, 131.22, 135.30, 137.92 (br. s), 139.66 (d, J=11.2 Hz), 154.11, 159.13 (d, J=243.5 Hz), 170.19; $C_{22}H_{23}FN_6O_3$—HCl, LCMS (EI) m/e 439 (M$^+$+H) and 461 (M$^+$+Na); FTIR cm$^{-1}$ 3300, ~3400-~2300, 3003, 2933, 2810, 2779, 1730, 1654, 1552, 1502, and 807; DSC endotherm at 266° C.; onset melt at 261° C.

Radezolid Sulfate Salt

To ~1 g of radezolid free base was added 15 mL of acetonitrile/water (2/3 by volume) to generate a radezolid slurry. To the radezolid slurry was added 1 equivalent of sulfuric acid dissolved in water. The resulting clear solution was evaporated on a rotary evaporator with water bath setting at 50° C. The solution formed a white wet gel. The wet gel was dried under a nitrogen stream. 10 mL of methanol was added to dissolve the gel. The gel remained undissolved. 35 mL of DCM was added subsequently, and the gel-like solid turned into a fluffy white solid. The mixture was further mixed on a slurry wheel overnight. The solid was collected by vacuum filtration on a paper filter, and dried under reduced pressure for ~30 min. Yielded ~0.7 g of crystalline (low crystallinity) salt. (Note: There was some loss during the rotary evaporation). DSC endotherm at 72 and 166° C.; onset melt at 158° C.

Radezolid Tosylate Salt

To ~1 g of radezolid free base was added 20 mL of water to generate a radezolid slurry. To the radezolid slurry was added 1 equivalent of toluenesulfonic acid dissolved in methanol at ambient temperature. The radezolid dissolved upon mixing. Some tacky solid formed and attached to the wall of the glass vial. As another 0.5 equivalents of acid added to the mixture, more solid formed. Solid was scraped off the vial. The mixture was further mixed on a slurry wheel overnight. A white soft precipitation formed along the wall of the vial. A white chunky solid formed upon addition of 20 mL of acetone. A solid was collected by vacuum filtration. Yielded ~0.4 g of crystalline salt. DSC endotherm at 97 and 173° C.; onset melt at 168° C.

Radezolid Esylate Salt

To ~1.1 g of radezolid free base was added 15 mL of acetonitrile/water (2/3 by volume) to generate a radezolid slurry. To the radezolid slurry was added 1.2 equivalents of acid dissolved in methanol. The resulting clear solution was evaporated on a rotary evaporator with water bath setting at 50° C. Glassy gel was generated. The resulting white foamy gel was resuspended in 35 mL of acetone. The mixture was further mixed on a slurry wheel overnight. A white solid was collected by vacuum filtration on a paper filter and dried under reduced pressure for ~15 min. Yielded ~1.3 g of crystalline salt. DSC endotherm at 57 and 222° C.; onset melt at 216° C.

Radezolid Ethanedisulfonate Salt

To ~1.1 g of radezolid free base was added 15 mL of acetonitrile/water (2/3 by volume) to generate a radezolid slurry. To the radezolid slurry was added 0.74 equivalents of acid dissolved in methanol. The resulting clear solution was evaporated on a rotary evaporator with water bath setting at 50° C. The resulting clear gel was resuspended in 8 mL of methanol, and sonicated. A white gel-like solid formed after sonication. 60 mL of DCM was added subsequently. A white solid formed. The mixture was further mixed on a slurry wheel overnight. A white precipitate was collected by vacuum filtration on a paper filter and dried under reduced pressure for ~20 min. Yielded ~1.4 g of crystalline salt. DSC endotherm at 204° C.; onset melt at 198° C.

Radezolid Pyroglutamate Salt. To ~1.1 g of radezolid free base was added 15 mL of acetonitrile/water (2/3 by volume) to generate an API slurry. To the API slurry was added 1.5 equivalents of pyroglutamic acid dissolved in water. The resulting clear solution was evaporated on a rotary evaporator with water bath setting at 50° C., resulted in a clear gel. The gel was resuspended in acetone in a final volume of ~35 mL. The mixture was further mixed on a slurry wheel overnight. The solid was collected by vacuum filtration on a paper filter, dried under reduced pressure for 30 min. Yielded ~1.3 g of amorphous salt. DSC endotherm at 80 and 118° C.; exotherm at 128° C.; $T_g$ of 79° C.

Radezolid Mesylate Salt

To ~1.1 g of radezolid free base was added 15 mL of acetonitrile/water (2/3 by volume) to generate a radezolid slurry. To the radezolid slurry was added 1.4 equivalents of acid dissolved in water. The resulting clear solution was evaporated on a rotary evaporator with water bath setting at 50° C., resulted in a mixture of clear gel and white solid. To the mixture was added 30 mL of acetone. The suspension was further mixed on a slurry wheel overnight. Solid was collected by vacuum filtration on a paper filter, rinsed briefly with acetone, and dried under reduced pressure for ~5 min. Yielded ~1.3 g of crystalline salt. DSC endotherm at 82 and 203° C.; onset melt at 198° C.

Radezolid Mesylate Salt (25 g Scale)

A sample of radezolid free base (23.5 g, 53.6 mmol) was suspended in a mixture of water (200 mL) and acetonitrile (20 mL) at room temperature. Neat methanesulfonic acid (3.56 mL, 54.9 mmol) was added. As the acid was added, the slurry thinned and became clear with a few solid particles. Stirring was continued at room temperature for 1 h until all particles had dissolved. The solution was transferred to a rotovap with the water bath set at 50° C., and approximately 22 mL of solvent was stripped at 100 mBar. The warm solution was cooled in an ice bath and a white precipitate formed. After holding at 0° C. for approximately 1 h, the precipitate was collected by filtration, and the filter cake was washed with cold water (20 mL). The filter cake was then dried in a vacuum oven for 48 h (house vacuum ca. 100 mBar, 65° C.). The radezolid mesylate salt was obtained as a white powder in 90% yield (25.7 g). An estimate of 0.75 mol % water content was made by $^1$H NMR in $d_6$-DMSO, controlling for the amount of water present in the deuterated solvent. DSC endotherm at 82 and 203° C.; onset melt at 198° C.

Characterization of Radezolid Salts

The thermal properties were evaluated by differential scanning calorimetry (DSC) and thermogravimetric analysis (TGA) as shown in Tables 7-8 below.

DSC data were collected on a TA Instruments 2910 DSC. In general, samples in the mass range of 1 to 10 mg were crimped in aluminum sample pans and scanned from 25 to about 300° C. at 10° C./minute using a nitrogen purge at 50 mL/min.

TGA data were collected on a TA Instruments 2950 TGA. In general, samples in the mass range of 5 to 15 mg were placed in an open, pre-tarred platinum sample pan and scanned from 25 to about 150° C. at 10° C./minute using a nitrogen purge.

Dynamic vapor sorption/desorption (DVS) data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. Sodium chloride and polyvinylpyrrolidine (PVP) were used as calibration standards.

Thermal Characterization of Radezolid Salts

TABLE 7

Differential Scanning Calorimetry of Radezolid Salts

| Salt Form | Appearance | DSC Peak Temperature (° C.) Desolvation | DSC Onset Temperature (° C.) Melt |
|---|---|---|---|
| Free base | White solids | N/A | 208.4 |
| Acetate | White solids | N/A | 207.4 |
| Ascorbate | Yellow clear | N/A | N/A |
| Benzoate | White solids | 106.7 | 180.4 |
| Citrate | White solids | N/A | N/A |
| Fumarate | White solids | 155.7 | 217.5 |
| Hydrochloride | White solids | N/A | 245.8 |
| Lactate | White solids | 122.6 | 195.9 |
| Maleate | White solids | N/A | 147.3 |
| Mesylate | White solids | 100.6 | 189.3 |
| Phosphate | White solids | N/A | 178.4 |
| Salicylate | White solids | 82.1, 131.5 | 180.5 |
| Succinate | White solids | N/A | 166.7 |
| Sulfate | White solids | N/A | 180.5 |
| Tartrate | White solids | 88.7, 140.6 | 210.7 |

TABLE 8

Thermal Characterization of Radezolid Salts

| Salt | DSC Results | TGA Results | DVS Results |
|---|---|---|---|
| Esylate | Endo: 57 and 222° C. (onset: 216° C.) | 0.2933% weight loss up to 200° C. | Sorption: 0.22% weight loss upon equilibration at 5% RH; 2.930% weight gain from 5 to 95% RH Desorption: 2.999% weight loss from 95 to 5% RH |
| Ethane-1,2-disulfonate | Endo: 204° C. (onset: 198° C.) | 0.5052% weight loss up to 200° C. | Sorption: 0.017% weight loss upon equilibration at 5% RH; 2.355% weight gain from 5 to 95% RH Desorption: 2.388% weight loss from 95 to 5% RH |
| Hydrochloride | Endo: 266° C. (onset: 261° C.) | 0.1759% weight loss up to 220° C. | Sorption: 0.03% weight gain upon equilibration at 5% RH; 0.064% weight gain from 5 to 95% RH Desorption: 0.069% weight loss from 95 to 5% RH |
| Mesylate | Endo: 82 and 203° C. (onset 198° C.) | 2.774% weight loss up to 200° C. (corresponding to 0.8 moles of water) | Sorption: 0.114% weight loss upon equilibration at 5% RH; 1.025% weight gain from 5 to 95% RH Desorption: 0.835% weight loss from 95 to 5% RH |
| Pyroglutamate | Endo: 80 and 118° C.; Exo: 128° C.; Tg: 79° C. | 3.262% weight loss up to 150° C. | Sorption: 2.801% weight loss upon equilibration at 5% RH; 23.962% weight gain from 5 to 95% RH Desorption: 24.936% weight loss from 95 to 5% RH |
| Sulfate | Endo: 72 and 166° C. (onset: 158° C.) | 1.915% weight loss up to 140° C. (corresponding to 0.6 moles of water) | Sorption: 0.654% weight loss upon equilibration at 5% RH; 11.527% weight gain from 5 to 95% RH |

TABLE 8-continued

Thermal Characterization of Radezolid Salts

| Salt | DSC Results | TGA Results | DVS Results |
|---|---|---|---|
| Tosylate | Endo: 97 and 173° C. (onset: 168° C.) | 5.464% weight loss up to 100° C. (corresponding to 2 moles of water) | Desorption: 11.504% weight loss from 95 to 5% RH<br>Sorption: 0.070% weight loss upon equilibration at 5% RH; 0.435% weight gain from 5 to 95% RH<br>Desorption: 0.435% weight loss from 95 to 5% RH |

Solubility of Radezolid Salts

The solubilities of the various radezolid salts was determined and are shown in Table 9 below. Approximately 2-3.5 mg of each salt was weighed into a glass vessel at ambient temperature. HPLC grade water, 200 µL, was added to each and stirred with a stir bar for two hours. Samples were inspected for solubility both visually and/or microscopically using a Carl Zeiss SV8 stereomicroscope. Additional solvent was added periodically until the solute completely dissolved or the solubility became <0.04 mg/mL.

TABLE 9

Solubility of Radezolid Primary Isolated Salts

| Salt Form | Salt (mg) | Volume (mL) | Solubility (mg/mL) |
|---|---|---|---|
| Fumarate | 3.13 | 1.20 | 2.6 |
| Citrate | 2.56 | 1.00 | 2.6 |
| Maleate | 3.61 | 1.60 | 2.3 |
| Tartrate | 2.88 | 1.60 | 1.8 |
| Phosphate | 3.58 | 3.40 | 1.1 |
| Ascorbate | 2.51 | 75.80 | <0.03 |
| Benzoate | 2.47 | 82.20 | <0.03 |
| Salicylate | 3.61 | 122.20 | <0.03 |
| Succinate | 2.36 | 82.20 | <0.03 |
| Hydrochloride | 2.38 | 82.20 | <0.03 |
| Acetate | 2.21 | 118.20 | <0.02 |
| Lactate | 2.61 | 118.20 | <0.02 |
| Free base | 2.26 | 116.20 | <0.02 |

Solubilities of the radezolid free base and radezolid HCl salt in various solvents were estimated and are shown in Tables 10 and 11, respectively, below. A weighed sample was treated with aliquots of test solvent at ambient temperature. Complete dissolution of the test material was determined by visual inspection. Solubility was estimated based on the total solvent used to provide complete dissolution. The actual solubility may be greater than the approximate solubility calculated because of the use of solvent aliquots that were too large or due to a slow rate of dissolution. The solubility is expressed as "less than" if dissolution did not occur during the experiment. If complete dissolution was achieved as a result of only one aliquot addition, the solubility is expressed as "greater than." The approximate solubilities were rounded to the nearest whole number.

TABLE 10

Approximate Solubilities of Radezolid Free Base

| Solvent | Approximate Solubility (mg/mL) |
|---|---|
| Acetone | <1 |
| Acetonitrile | <1 |
| Dichloromethane | <1 |
| Ethyl acetate | <1 |

TABLE 10-continued

Approximate Solubilities of Radezolid Free Base

| Solvent | Approximate Solubility (mg/mL) |
|---|---|
| Ethyl ether | <1 |
| Hexafluoroisopropanol (HFIPA) | ≥245 |
| HFIPA/Methanol (1:3 by volume) | <1 |
| Hexamethyl-phosphoramide | <26 |
| Methanol | <1 |
| 2,2,2-trifluoroethanol (TFE) | ≥54 |
| Tetrahydrofuran (THF) | <1 |
| Water | <1 |

TABLE 11

Approximate Solubilities of Radezolid HCl Salt

| Solvent | Approximate Solubility (mg/mL) |
|---|---|
| 1-Butanol[b] | <2 |
| 2-Butanone[b] | <2 |
| Dioxane[b] | <2 |
| Ethanol[b] | <2 |
| Hexafluoroisopropanol (HFIPA) | ≥225 |
| Methanol[b] | <2 |
| Propionitrile[b] | <2 |
| 2-Propanol[b] | <2 |
| Tert-butanol[b] | <5 |
| Tetrahydrofuran (THF)[b] | <2 |
| 2,2,2-trifluoroethanol (TFE) | ≥6 |
| HFIPA/Dioxane (9:1) | ≥52 |
| HFIPA/Ethanol (5:1) | ≥80 |
| HFIPA/THF | ≥74 |

[b]Material never went into solution.

In another set of experiments, solubility of various radezolid salts was determined by HPLC. The results are provided in Table 12 below. Approximately 1 mL of saturated solution (with excess of solid in solution) of each salt was prepared in water. The mixture was further mixed overnight on a slurry wheel then centrifuged on a desktop centrifuge at maximum speed for ~5 min. The supernatant was collected, and pH was measured. Solubility was determined at the native pH. Then the pH was adjusted to ~3.5 with sodium hydroxide solution or an acid solution in which salt was generated. The supernatant was filtered through a 0.2 µm nylon syringe filter and diluted into 0.1% formic acid solution immediately after filtration for HPLC.

All HPLC analyses were performed using an Agilent 1100 series liquid chromatograph equipped with a diode array detector, degasser, quaternary pump, and an autosampler. The chromatographic column was a 4.6×150 mm SymmetryShield RP18 column with 3.5 µm packing (Waters). The column temperature was set to 30° C., and the detector wavelength was 270 nm with a bandwidth of 8 nm and a reference wavelength of 360 nm. The mobile phase A was 0.1% formic acid in water (HPLC grade), mobile phase B was 0.1% formic acid in methanol (HPLC grade). Flow rate was 1.2 mL/min and the column was equilibrated with 85% mobile phase A and 15% mobile phase B. The injection volume was 5 μl. The elution program was as follows: After sample was injected, the initial gradient was run from 85% mobile phase A, 15% mobile phase B to 100% mobile phase B in 25 min, followed by 3 min with 100% mobile phase B, then a reverse gradient was run from 100% mobile phase B to 15% mobile phase B in 2 min, then with another 10 min of equilibration run with 85% mobile phase A and 15% mobile phase B.

TABLE 12

Solubility Determination of Radezolid Salts in Water by HPLC at 23° C.

| Salt | Solubility at Native pH (mg/mL) | Native pH | Solubility at Adjusted pH (mg/mL) | Adjusted pH |
|---|---|---|---|---|
| Esylate | 53.8 | 4.0 | 61.7 | 3.5 |
| Ethane-1,2-disulfonate[C] | >133.2 | 2.0 | >116.9 | 3.6 |
| HCl Salt | 1.7 | 4.6 | 2.0 | 3.5 |
| Mesylate | 18.6 | 4.1 | 18.0 | 3.5 |
| Pyroglutamate[C] | >250 | N/A | N/A | N/A |
| Sulfate | 4.0 | 1.9 | 3.3 | 3.6 |
| Tosylate | 0.9 | 5.1 | 0.4 | 3.4 |

[C]Solution was not saturated.

Example 6

Topical Compositions of Radezolid

A topical composition is prepared by combining the following components utilizing conventional mixing techniques.

| Ingredients | % Weight |
|---|---|
| Deionized Water | qs 100 |
| Ethanol (SD 40B Alcohol) | 35.0 |
| Any Compounds in Table 2 | 0.5-10 |
| Salicylic Acid (Optional) | 2.0 |
| Dexpanthenol (Optional) | 3.0 |

In a suitable vessel the antibiotic compound is dissolved in ethanol with stirring. Next, if being added, the optional salicylic acid is dissolved in this ethanol mixture with stirring. If being used, the dexpanthenol is dissolved in a separate vessel in the water with stirring. The water, or if being used, the dexpanthenol solution is combined with the alcohol mixture with mixing.

Topical Gel

A topical composition is prepared by combining the following components utilizing conventional mixing techniques.

| Ingredients | % Weight |
|---|---|
| Deionized Water | qs 100 |
| Ethanol (SD 40B Alcohol) | 35.0 |
| Any Compounds in Table 2 | 0.5-10 |
| Hydrophilic Gelling Agent | 3.0 |

In a suitable vessel the antibiotic compound is dissolved in ethanol with stirring. Next, the hydrophilic gelling agent is dissolved in a separate vessel in the water with stirring. The hydrophilic gelling agent solution is combined with the alcohol mixture with mixing.

This composition is useful for topical application for the treatment of acne or other skin infections caused or mediated by *Propionibacterium acnes, Gardnerella vaginalis*, or *Staphylococcus aureus*.

Example 7

Oral Formulations of Radezolid

Tablets

Tablet compositions are made using standard mixing techniques as shown below in Tables 13-15. Both wet and dry granulation methods can be used. The tablets useful herein can have both intragranular as well as extragranular components, and some of the same components can be used both in the intragranular and extragranular portions of the tablet. The tablets can be further coated with waxes, gelatins, shellacs, and other suitable materials, and can be imprinted or polished. All components in the following tables are on a weight basis of mg, unless otherwise indicated.

TABLE 13

Tablet Formulations

| Ingredient | 1 | 2 | 3 | 4 | 5 | 6 | 7 |
|---|---|---|---|---|---|---|---|
| Radezolid | 541.6 | 541.6 | 541.6 | 541.6 | 541.6 | 541.6 | 541.6 |
| Emulsifier | 70.00[2] | 70.00[3] | 115.00[2] | 75.00[3] | 85.00[2] | 70.00[2] | 70.00[3] |
| Hydroxypropylmethylcellulose | 45.00 | 45.00 | N/A | 45.00 | N/A | 35.00 | 35.00 |
| Sodium starch glycolate | 45.00 | 45.00 | 45.00 | 45.00 | 45.00 | 35.00 | 35.00 |
| Mannitol | 54.40 | 54.40 | 54.40 | 54.40 | 54.40 | 54.40 | 54.40 |
| Microcrystalline cellulose | 32.00 | 32.00 | 32.00 | 32.00 | 32.00 | 32.00 | 32.00 |
| Fumed silica | 8.00 | 8.00 | 8.00 | 8.00 | 8.00 | 8.00 | 8.00 |
| Magnesium stearate | 4.00 | 4.00 | 4.00 | 4.00 | 4.00 | 4.00 | 4.00 |

[2]Gelucire 50/13

[3]Gelucire 44/14

TABLE 14

Tablet Formulations (continued)

| Ingredient | 8 | 9 | 10 | 11 | 12 | 13 | 14 |
|---|---|---|---|---|---|---|---|
| Radezolid | 541.6 | 541.6 | 541.6 | 541.6 | 541.6 | 541.1 | 541.6 |
| Emulsifier | 80.00[2] | 65.00[3] | 110.00[3] | 80.00[2] | 80.00[3] | 120.00[2] | 85.00[3] |
| Hydroxypropylmethylcellulose | N/A | 45.00 | N/A | 40.00 | 40.00 | N/A | 40.00 |
| Sodium starch glycolate | 35.00 | 45.00 | 50.00 | 40.00 | 40.00 | 40.00 | 40.00 |
| Mannitol | 54.40 | 54.40 | 54.40 | 54.40 | 54.40 | 54.40 | 54.40 |
| Microcrystalline cellulose | 32.00 | 32.00 | 32.00 | 32.00 | 32.00 | 32.00 | 32.00 |
| Fumed silica | 8.00 | 8.00 | 8.00 | 8.00 | 8.00 | 8.00 | 8.00 |
| Magnesium stearate | 4.00 | 4.00 | 4.00 | 4.00 | 4.00 | 4.00 | 4.00 |

[2]Gelucire 50/13
[3]Gelucire 44/14

TABLE 15

Tablet Formulations (continued)

| Ingredient | 15 | 16 | 17 | 18 | 19 | 20 |
|---|---|---|---|---|---|---|
| Radezolid | 541.1 | 541.6 | 541.6 | 541.1 | 541.6 | 541.1 |
| Emulsifier | 90.00[2] | 60.00[2] | 60.00[3] | 75.00[2] | 75.00[3] | 120.00[3] |
| Hydroxypropylmethylcellulose | N/A | 40.00 | 40.00 | N/A | 40.00 | N/A |
| Sodium starch glycolate | 40.00 | 40.00 | 40.00 | 40.00 | 40.00 | 40.00 |
| Mannitol | 54.40 | 54.40 | 54.40 | 54.40 | 54.40 | 54.40 |
| Microcrystalline cellulose | 32.00 | 32.00 | 32.00 | 32.00 | 32.00 | 32.00 |
| Fumed silica | 8.00 | 8.00 | 8.00 | 8.00 | 8.00 | 8.00 |
| Magnesium stearate | 4.00 | 4.00 | 4.00 | 4.00 | 4.00 | 4.00 |

[2]Gelucire 50/13
[3]Gelucire 44/14

Capsules

The capsule compositions are made using standard mixing techniques and are shown below in Tables 16-19. Both wet and dry granulation methods can be used to make the granulation component which is then loaded into a gelatin capsule, such as a soft gelatin capsule or a hard two piece gelatin or starch capsule. All components are on a weight basis of mg per capsule.

TABLE 16

Capsule Formulations

| Ingredient | 1 | 2 | 3 | 4 | 5 |
|---|---|---|---|---|---|
| Radezolid | 324.93 | 324.93 | 324.93 | 324.93 | 324.93 |
| Emulsifier | 65.00[2] | 125.00[2] | 65.00[2] | 65.00[2] | 65.00[2] |
| Povidone | N/A | N/A | 25.00 | 20.00 | 55.00 |
| Hydroxypropylmethylcellulose | 31.00 | N/A | N/A | 15.00 | N/A |
| Sodium starch glycolate | 30.00 | 25.00 | 30.00 | 30.00 | 30.00 |
| Mannitol | 78.00 | 66.00 | 78.00 | 78.00 | 63.00 |
| Microcrystalline cellulose | 58.57 | 46.57 | 64.57 | 64.57 | 49.57 |
| Fumed silica | 8.00 | 8.00 | 8.00 | 8.00 | 8.00 |
| Magnesium stearate | 4.50 | 4.50 | 4.50 | 4.50 | 4.50 |

[2]Gelucire 44/14

TABLE 17

Capsule Formulations (continued)

| Ingredient | 6 | 7 | 8 | 9 | 10 |
|---|---|---|---|---|---|
| Radezolid | 324.93 | 324.93 | 324.93 | 324.93 | 324.93 |
| Emulsifier | 55.00[2] | 55.00[3] | 115.00[3] | 55.00[3] | 55.00[3] |
| Povidone | 30.00 | N/A | N/A | 35.00 | 15.00 |
| Hydroxypropylmethylcellulose | N/A | 36.00 | N/A | N/A | 20.00 |
| Sodium starch glycolate | 35.00 | 35.00 | 35.00 | 30.00 | 30.00 |
| Mannitol | 78.00 | 78.00 | 66.00 | 78.00 | 78.00 |
| Microcrystalline cellulose | 64.57 | 58.57 | 46.57 | 64.57 | 64.57 |
| Fumed silica | 8.00 | 8.00 | 8.00 | 8.00 | 8.00 |
| Magnesium stearate | 4.50 | 4.50 | 4.50 | 4.50 | 4.50 |

[2]Gelucire 44/14
[3]Gelucire 50/13

TABLE 18

Capsule Formulations (continued)

| Ingredient | 11 | 12 | 13 | 14 | 15 |
|---|---|---|---|---|---|
| Radezolid | 324.93 | 324.93 | 324.93 | 324.93 | 324.93 |
| Emulsifier | 60.00[2] | 120.00[2] | 60.00[2] | 60.00[2] | 60.00[2] |
| Povidone | N/A | N/A | 30.00 | 15.00 | 60.00 |
| Hydroxypropylmethylcellulose | 36.00 | N/A | N/A | 15.00 | N/A |
| Sodium starch glycolate | 30.00 | 30.00 | 30.00 | 30.00 | 30.00 |
| Mannitol | 78.00 | 66.00 | 78.00 | 78.00 | 63.00 |
| Microcrystalline cellulose | 58.57 | 46.57 | 64.57 | 64.57 | 49.57 |
| Fumed silica | 8.00 | 8.00 | 8.00 | 8.00 | 8.00 |

TABLE 18-continued

Capsule Formulations (continued)

| Ingredient | 11 | 12 | 13 | 14 | 15 |
|---|---|---|---|---|---|
| Magnesium stearate | 4.50 | 4.50 | 4.50 | 4.50 | 4.50 |

[2]Gelucire 44/14

TABLE 19

Capsule Formulations (continued)

| Ingredient | 16 | 17 | 18 | 19 | 20 |
|---|---|---|---|---|---|
| Radezolid | 324.93 | 324.93 | 324.93 | 324.93 | 324.93 |
| Emulsifier | 60.00[2] | 60.00[3] | 120.00[3] | 60.00[3] | 60.00[3] |
| Povidone | 30.00 | N/A | N/A | 30.00 | 15.00 |
| Hydroxypropylmethylcellulose | N/A | 36.00 | N/A | N/A | 15.00 |
| Sodium starch glycolate | 30.00 | 30.00 | 30.00 | 30.00 | 30.00 |
| Mannitol | 78.00 | 78.00 | 66.00 | 78.00 | 78.00 |
| Microcrystalline cellulose | 64.57 | 58.57 | 46.57 | 64.57 | 64.57 |
| Fumed silica | 8.00 | 8.00 | 8.00 | 8.00 | 8.00 |
| Magnesium stearate | 4.50 | 4.50 | 4.50 | 4.50 | 4.50 |

[2]Gelucire 44/14
[3]Gelucire 50/13

Soft Gelatin Capsules

A soft gelatin mixture is first prepared from the following ingredients: gelatin (47.00 weight %), glycerin (15.00 weight %), and water (QS 100). The ingredients are combined in a suitable vessel and heated with mixing at about 65° C. to form a uniform solution. Using standard encapsulation methodology, the resulting solution is used to prepare soft gelatin capsules containing approximately 600 mg of the compositions of Capsules 1 to 20, above. The resulting soft gelatin capsules are suitable for oral administration.

Hard Gelatin Capsules

Hard gelatin capsules are purchased from any commercially available source. The capsules are filled manually or by capsule filling machine with approximately 600 mg of the compositions of Capsule 1 to 20 above. The resulting hard gelatin capsules are suitable for oral administration.

Solid Oral Formulation

The ingredients are combined using standard wet granulation procedures to form tablets, which are then optionally enteric coated. The resulting compositions as exemplified in Tables 20-21 are suitable for oral administration.

TABLE 20

Solid Oral Formulation Composition

| Ingredient | Amount (mg) |
|---|---|
| Radezolid | 162.5 |
| Fumaric acid | 75.00 |
| Tartaric acid | 75.00 |
| Sodium Starch Glycolate | 0-25.00 |
| Polydextrose | 25.00 |
| Gelucire 44/14 | 25-50.00 |
| Cyclodextrin (cavitron hydroxypropyl-β-cyclodextrin) | 0-125.00 |
| Mannitol | 50-100 |
| Colloidal silicon dioxide | 4.00 |

TABLE 20-continued

Solid Oral Formulation Composition

| Ingredient | Amount (mg) |
|---|---|
| Magnesium stearate | 3.50 |
| Purified Water[a] | |
| Enteric film coating | 0-100 |

[a]Purified water is used as a granulating agent and is removed during the drying process.

Pharmaceutical Composition for Oral Administration

TABLE 21

Pharmaceutical Composition for Oral Administration

| Ingredients | Percent by Weight | mg in Tablet |
|---|---|---|
| Intra Granular | | |
| Radezolid hydrochloride | 20.31 | 162.51 |
| HPMCAS-M Spray Dried | 13.28 | 106.24 |
| HPMCAS-H Spray Dried | 13.28 | 106.24 |
| Croscarmellose Sodium | 4.00 | 31.98 |
| Microcrystalline cellulose | 11.60 | 92.76 |
| Lactose monohydrate | 11.60 | 92.76 |
| Colloidal silicon dioxide | 0.75 | 6.00 |
| Magnesium Stearate | 0.9 | 1.50 |
| Extra Granular | | |
| Croscarmellose Sodium | 1.50 | 12.00 |
| Di-Cal Phosphate (DC Grade) | 23.38 | 187.00 |
| Colloidal silicon dioxide | 0.06 | 0.50 |
| Magnesium Stearate | 0.06 | 0.50 |
| Total | 100.00 | 800.00 |

The procedure for making the pharmaceutical composition for oral administration is as follows:

1. Pass radezolid hydrochloride and colloidal silicon dioxide through a #20 Mesh screen together, not sequentially.
2. Bag blend 5 minutes. Sample approximately 0.25 g to a glass vial.
3. Pass remaining intragranular ingredients, except the magnesium stearate, through a comill U5 at 1000 rpm with a 0.032R screen. Collect all in a single container.
4. Add to V-blender and blend for 1 minute at 24 rpm.
5. Remove approximately 100 g of blend.
6. Add radezolid hydrochloride and colloidal silicon dioxide from step 2 to V-blender.
7. Add 100 g of blend to container containing radezolid hydrochloride, hand shake, and add to blender, on the same side as the radezolid hydrochloride was added.
8. Blend for 15 min. at 24 rpm.
9. Pass Magnesium Stearate through a #20 Mesh Screen with the approximately 100 g of blend from step 8.
10. Blend in V (Twin Shell) blender for 4 min. at 24 RPM. Collect 50 g sample for bsv, tsv, etc.
11. Dry Granulate on TF Mini Roller compactor to a Solid Fraction of 0.6-0.7. Start with polished smooth rolls, switch to grooved if necessary.
12. Mill Dry Granulated ribbons on the Co-Mill U5 with 0.032"Conidur screen at 100 rpm. Stop after approximately 100-300 g and measure particle size.
13. If needed, change to different screen. Screen used: 0.032C and complete granulation.
14. Add granules from step 13 and extragranular croscarmellose sodium, colloidal silicon dioxide, and dicalciumphosphateto 4 qt. V-Blender and blend for 15 min. at 24 RPM.

15. Pass the extragranular magnesium stearate through a #20 Mesh Screen with approximately 100 g of blend from step 14 above.
16. Blend in V (Twin Shell) blender for 4 min. at 24 RPM. Save 100 g Final Blend for characterization.
17. Compress on Kilian T100 rotary tablet press with 0.3586×0.7174" Modified Oval to a hardness of approximately 16-20 Kp. Sample using BRPPD stratified sampling plan.

The foregoing formulation is useful for treating, preventing, or reducing the risk of a microbial infection in a patient in need thereof, e.g., a human patient.

Intravenous Formulations

Compositions for intravenous administration are made using standard techniques and are shown below in Tables 22-23.

TABLE 22

Intravenous Radezolid Hydrochloride Formulation with 2.778 mg/mL of free base

| Ingredient | Mg/mL | Batch size, mL % (w/w) | 1,000 gram batch Amt (g)/batch |
|---|---|---|---|
| Radezolid hydrochloride | 3.009 | 0.30% | 3.009 |
| Citric acid anhydrous | 4.00 | 0.40% | 4.000 |
| Sodium citrate tribasic (dihydrate) | 1.22 | 0.12% | 1.220 |
| 5% dextrose solution (D5W) | q.s. volume | q.s. | q.s. |
| 1 Normal Sodium hydroxide or phosphoric acid | q.s. pH | q.s. | q.s. |
| Total, mg | 1007 | 100.00% | 1007.000 |

Final pH is 3.5 (±0.1)
Density of the solution is 1.007 g/mL
25.0 mM Citric Buffer The procedure for making the intravenous formulation is as follows:
1. Weigh dextrose 5% solution for injection, approximately 80% of the total batch weight, into a suitable container.
2. Add the required amount of citric acid and sodium citrate tribasic (dihydrate) to the solution and mix until dissolved. Record pH.
3. Heat up the solution to 35-43° C.
4. With continuous heating at 35-43° C., add radezolid HCl salt corrected for purity and mix until dissolved.
5. Lower the solution temperature to 25° C. (±3).
6. Test for pH. The target pH is 3.5 (±0.1). Adjust with 1 Normal Sodium Hydroxide or Phosphoric acid as needed.
7. Q.S. to the final weight with dextrose 5% solution for injection.
8. Test for pH. Adjust if outside of 3.5 (±0.1). Record final pH and solution weight.
9. Filter solution (0.22 μm) and fill into vials.

TABLE 23

Intravenous Radezolid Hydrochloride Formulation with 2.778 mg/mL of free base in 10 mM Buffer

| Ingredient | Mg/mL | Batch size, mL % (w/w) | 1,000 gram batch Amt (g)/batch |
|---|---|---|---|
| Radezolid Hydrochloride | 3.009 | 0.30% | 3.009 |
| Anhydrous Citric Acid (MW = 192.12) | 1.50 | 0.15% | 1.500 |
| Sodium citrate tribasic (dihydrate) (MW = 294.10) | 0.65 | 0.06% | 0.650 |
| Dextrose Powder | 50 | 4.97% | q.s. |
| 1N Sodium hydroxide and/or phosphoric acid | q.s. | q.s. | q.s. |
| Total, mg | 1007 | 100.00% | 1007.000 |

Final pH = 3.5 ± 0.1
Density of the solution is 1.007 g/mL
10.0 mM Citric buffer The procedure for making the intravenous formulation is as follows:
1. Weigh Dextrose Powder for injection into a suitable container.
2. Add the required amount of citric acid and sodium citrate tribasic (dihydrate) to the solution and mix until dissolved. Record pH.
3. Heat up the solution to 35-43° C.
4. With continuous heating at 35-43° C., add radezolid HCl salt corrected for purity and mix until dissolved.
5. Lower the solution temperature to 25° C. (±3)
6. Test for pH. The target pH is 3.5 (+0.1). Adjust with 1 Normal Sodium Hydroxide or Phosphoric acid as needed.
7. Q.S. to the final weight with dextrose 5% solution for injection.
8. Test for pH. Adjust if outside of 3.5 (±0.1). Record final pH and solution weight.
9. Filter solution (0.22 μm) and fill into vials.

Example 8

Dissolution Testing in Simulated Gastrointestinal System

A. To Develop an Easy-to-Use 2-Step Dissolution Method Simulating Gastrointestinal Systems.

The common ion effect was studied using dissolution and microscopic methods. The microscopic method was conducted with drug suspended in water, pH 1.2, pH 4 and pH 6.5 buffers with and without sodium chloride. The dissolution of the drug and its granulations were studied using three different 2-step dissolution methods which entail the following: Method #1: simple 2-step buffers at pH 4 from 0-30 minutes and at pH 6.5 from 30-90 minutes; Method #2: simple 2-step buffers with the presence of chloride ion in both steps; Method #3: simple buffer at pH 4 with presence of chloride ion from 0-30 minutes, and buffer with bile salts and surfactants at pH 6.5 from 30-90 minutes. The two steps represent fed stomach and intestinal conditions, respectively.

The microscopy indicated that the drug formed aggregates in the presence of chloride ion. Unexpectedly, the alternative non-chloride salt (neat drug) flocculated into larger aggregates. Thus dissolution methods addressing both common ion effects and gastrointestinal conditions were studied. The results indicated that the simple buffer in the presence of chloride ion was the most discriminating dissolution medium. For the same formulations, the dissolution rates were in the following order: 2-step simple buffer without sodium chloride>2-step with bile-salts and surfactants>simple buffer with sodium chloride. Using the simple buffer system with sodium chloride enabled screen formulations to achieve the most super-saturation with a reduced common ion effect. The simple buffer system without chloride ion, on the other hand, did not provide enough power to discriminate the formulations of a drug with a low chloride $K_{sp}$.

2-Step dissolution using simple buffer with sodium chloride present is an easy-to-use surrogate for the conventional 2-step dissolution system with bile-salts and surfactants. The dissolution in such medium enables the study of super-saturation and common ion effects for formulations of high dose hydrochloride salt drugs with sub-microgram water solubility.

B. Formulation Approaches to Achieve Super-Saturation

Investigate formulation approaches to overcome poor water solubility, common ion effect, and obtain super-saturation for a drug with sub-microgram solubility.

Drug compound was granulated with various mixtures of excipients. The drug substances and the granulations were studied using 2-step dissolution methods at pH 4 from 0 to 30 minutes and at pH 6.5 from 30 to 90 minutes in the presence and absence of sodium chloride.

The dissolution data, conducted in gastrointestinal representative system, indicated that the pH modifier with a relative lower solubility improved dissolution to a greater extent than a pH modifier with a higher solubility. The data also indicated that certain surfactants and polymers selected for the formulation further enhanced supersaturation and reduced the common ion effect from chloride. Usage of common water soluble excipients in the formulation facilitated the dissolution in addition to manufacturability. Even though the alternative non-chloride salt has significantly increased solubility at acidic medium, the dissolution of neat non-chloride salt is similar to that of chloride salt. The microscopy showed that the non-chloride salt formed aggregates in the presence of chloride ion. However, once formulated with selected excipients, the advantage of the non-chloride salt is shown in dissolution.

Dissolution and bioavailability of a basic drug with poor solubility can be enhanced by using selected pH modifying agents, surfactants, and polymers. The alternative salts, when formulated with the optimized excipients, can also increase dissolution. Selecting a dissolution method which addresses both gastrointestinal system and the common ion effect is critical to selecting formulations for maximum exposure.

C. Studies on 2-Step Dissolution Testing of a Drug in a Simulated Gastrointestinal System To develop a simple 2-step dissolution method to screen formulations aimed to provide supersaturation.

To examine the effects of sodium chloride on dissolution of a hydrochloride salt of a water insoluble drug.

To discriminate formulations under fed GI pH conditions.

To study in-vivo in-vitro correlation of the dissolution system.

Traditional 2-step dissolution systems use bile salts and surfactant that is time consuming to use and sometimes not discriminating enough for formulation screening.

The goal is to develop a easy to use 2-step dissolution method, which simulates gastrointestinal pH values and the common ion effect without using bile salt and surfactant.

It is well known that hydrochloride salt of a water insoluble compound presents the common ion effect. Thus, sodium chloride was added in the dissolution buffer to simulate the common ion effect.

A hydrochloride salt of a water insoluble drug was selected as a model compound, which has the following biopharmaceutical properties:

pKa=6.8 and 9.4;
log P=0.7;
intrinsic solubility=0.01 mg/ml at pH 6.8;
solubility of salt in water=2.6, 0.2, and 0.06 mg/ml at pH 4, 5.4, and 6.5, respectively;
caco-2 permeability=$0.5 \times 10^{-6}$ cm/s
monkey oral bioavailability=15% at 20 mg/kg dose
positive food effect (4×).

TABLE 24

| pH of Gastrointestinal System and that of the Dissolution Medium | | |
|---|---|---|
| | Stomach pH | Intestine pH |
| Fast | pH 1.7<br>Buffer Capacity:<br>7-18 mM/pH | pH 6.2<br>Buffer Capacity:<br>5.6 mM/pH |
| Fed | pH 4 (ave): 6.4 (im.)<br>to 2.7 (3.5 hrs)<br>Buffer Capacity:<br>14-28 mM/pH | pH 5.4 for 4 hrs<br>Buffer Capacity:<br>18-30 mM/pH |

Bulk drug powders were wet granulated with and without excipients. Granules were dried and sized through a #18 mesh screen.

Microscopic test was conducted with drug suspended in water, pH 1.2, 4, and 6.5 buffers with and without sodium chloride.

Four dissolution media were tested. Results of these tests are shown in line-graph formats in FIGS. 5-9. Bulk drug powders were wet granulated with and without excipients. Granules were dried and sized through a No. 18 mesh screen. Dissolution of the drug and its granulations were studied using four different 2-step dissolution methods listed in the table below. The two steps represent fed stomach and intestinal conditions respectively. Intestine pH (literature) indicates published conditions in Dressman, *Pharmaceutical Research*, 23(1):165-176 (2006). These four methods are listed below.

TABLE 25

| The Four 2-Step Dissolution Methods Tested | | |
|---|---|---|
| # | 0-30 minutes | 30-90 minutes |
| 1 | pH 4 acetate buffer (100 mM) | pH 5.4 (add pH 6.4 phosphate buffer, 50 mM) |
| 2 | pH 4 acetate buffer (100 mM) | pH 6.5 (add pH 7.0 phosphate buffer, 50 mM) |
| 3 | pH 4 acetate buffer (100 mM) + 0.9% NaCl | pH 6.5 + 0.9% NaCl (add pH 7.0 phosphate buffer, 50 mM) |
| 4 | pH 4 acetate buffer (100 mM) + 0.9% NaCl | pH 6.5 + KCl + Taurocholate, and lecithin (add phosphate buffer, 50 mM with potassium chloride, taurocholate, and lecithin) |

The results of the study are shown in FIGS. 5-9.

Figure 5:
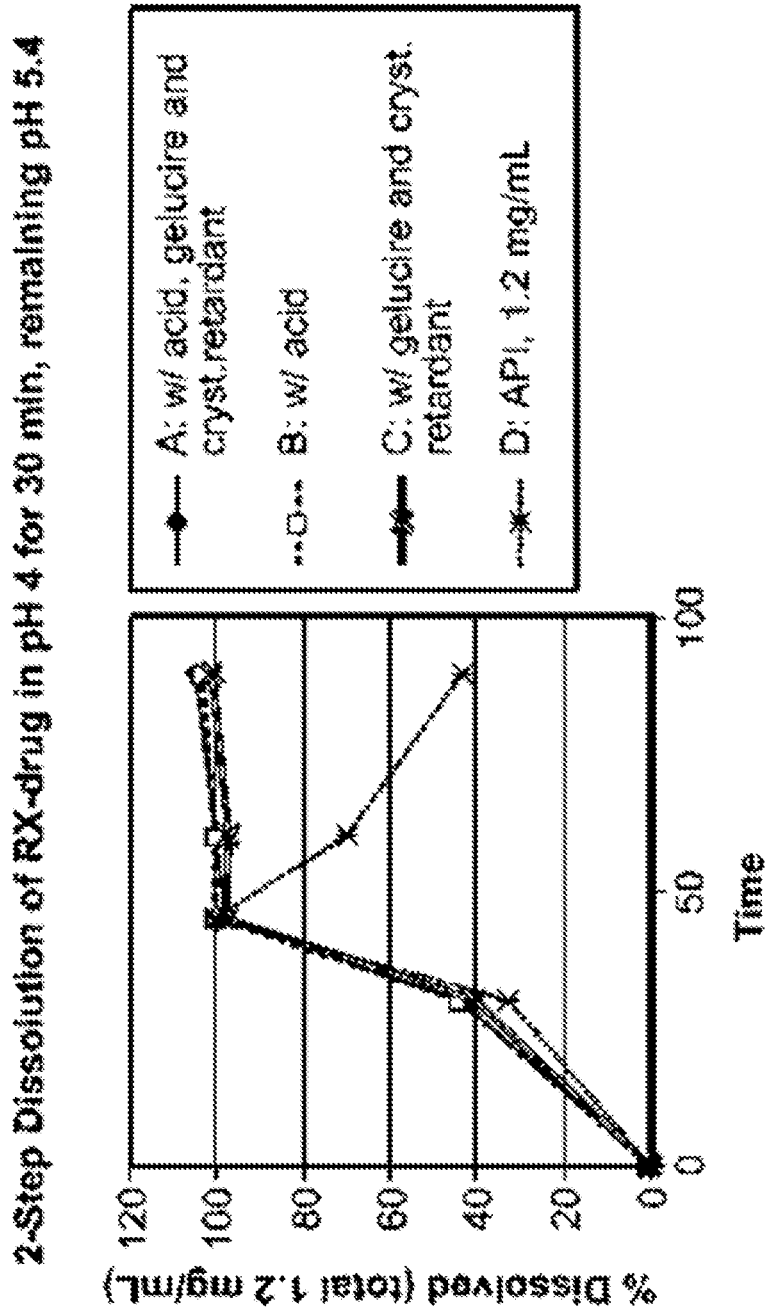
FIG. 5. shows the results of the 2-step dissolution test performed following Method 1. Dissolution of the radezolid formulation was tested in a buffer at pH 4.0 for 0-30 minutes and then after transferring to a buffer at pH 5.4 for 30-90 minutes.

FIG. 5 depicts the results of the 2-step dissolution test performed following Method 1. Dissolution of the radezolid formulation was tested in a buffer at pH 4.0 for 0-30 minutes and then after transferring to a buffer at pH 5.4 for 30-90 minutes. The two conditions did not distinguish the formulations (A-C, shown in the Table in FIG. 5) except for drug substance (not shown).

Figure 6:
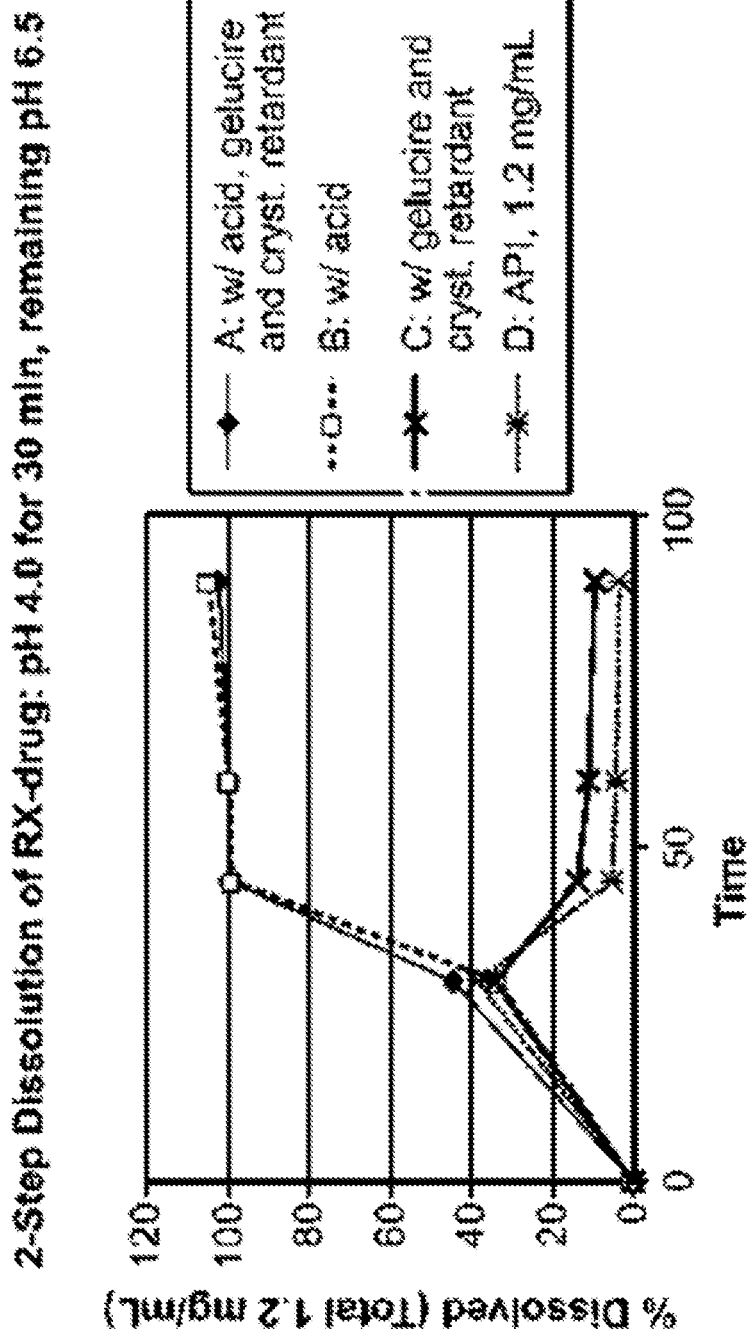
FIG. 6. shows the results of the 2-step dissolution test performed following Method 2. Dissolution of the radezolid formulation was tested in a buffer at pH 4.0 for 0-30 minutes and then after transferring to a buffer at pH 6.5 for 30-90 minutes.

FIG. 6 depicts the results of the 2-step dissolution test performed following Method 2. Dissolution of the radezolid formulation was tested in a buffer at pH 4.0 for 0-30 minutes and then after transferring to a buffer at pH 6.5 for 30-90 minutes. The percent dissolved from the formulations A and B (shown in the Table in FIG. 6) with acidifier reached 6-8 times higher than the control. But the dissolution did not address the common ion effect, and it did not distinguish acidified formulation with and without polymer dispersant.

Figure 7:
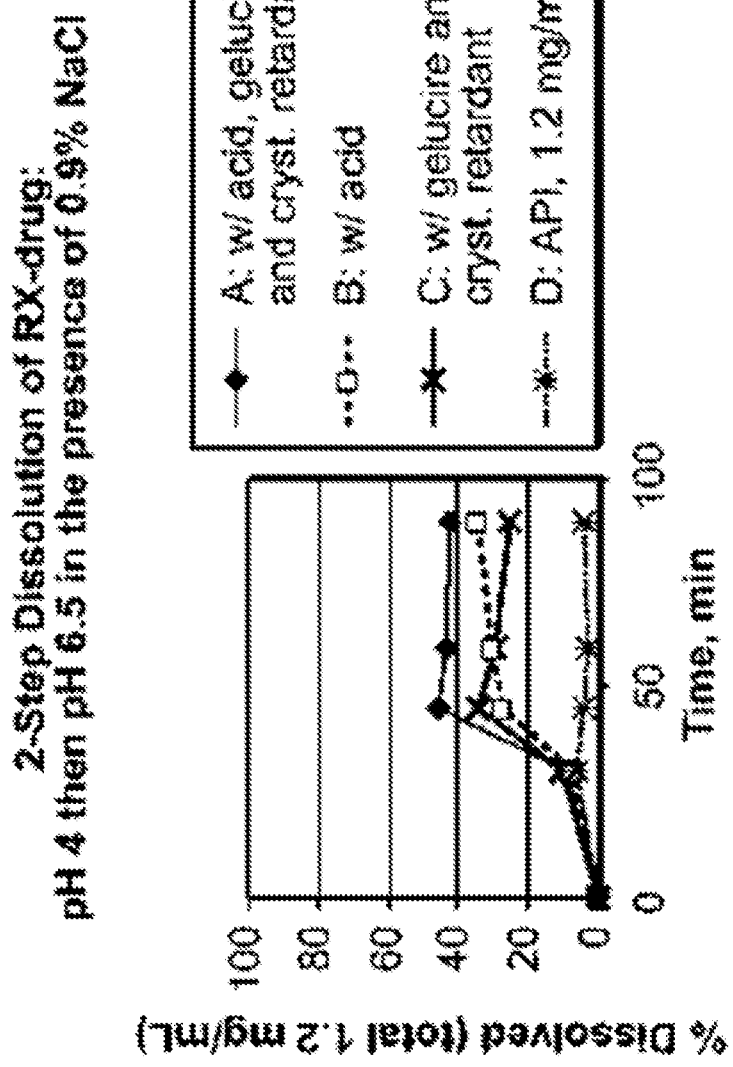
FIG. 7. shows the results of the 2-step dissolution test performed following Method 3. Dissolution of the radezolid formulation was tested in a buffer at pH 4.0 for 0-30 minutes and then after transferring to a buffer at pH 6.5 for 30-90 minutes. Both buffers had 0.9% NaCl. The two-step dissolution with 0.9% NaCl was used to simulate the common ion effect.

FIG. 7 depicts the results of the 2-step dissolution test performed following Method 3. Dissolution of the radezolid formulation was tested in a buffer at pH 4.0 for 0-30 minutes and then after transferring to a buffer at pH 6.5 for 30-90 minutes. Both buffers had 0.9% NaCl. The two-step dissolution with 0.9% NaCl was used to simulate common ion effect. Method 3 is more discriminating and slowed the release of formulation A by 50% due to common ion effect. The dissolution of formulation C (shown in the Table in FIG. 7) with Gelucire and crystallization retardant, on the other hand, increased significantly, but still less than formulation A (also shown in the Table in FIG. 7), which contains acidifier in addition to Gelucire and binder.

Figure 8:
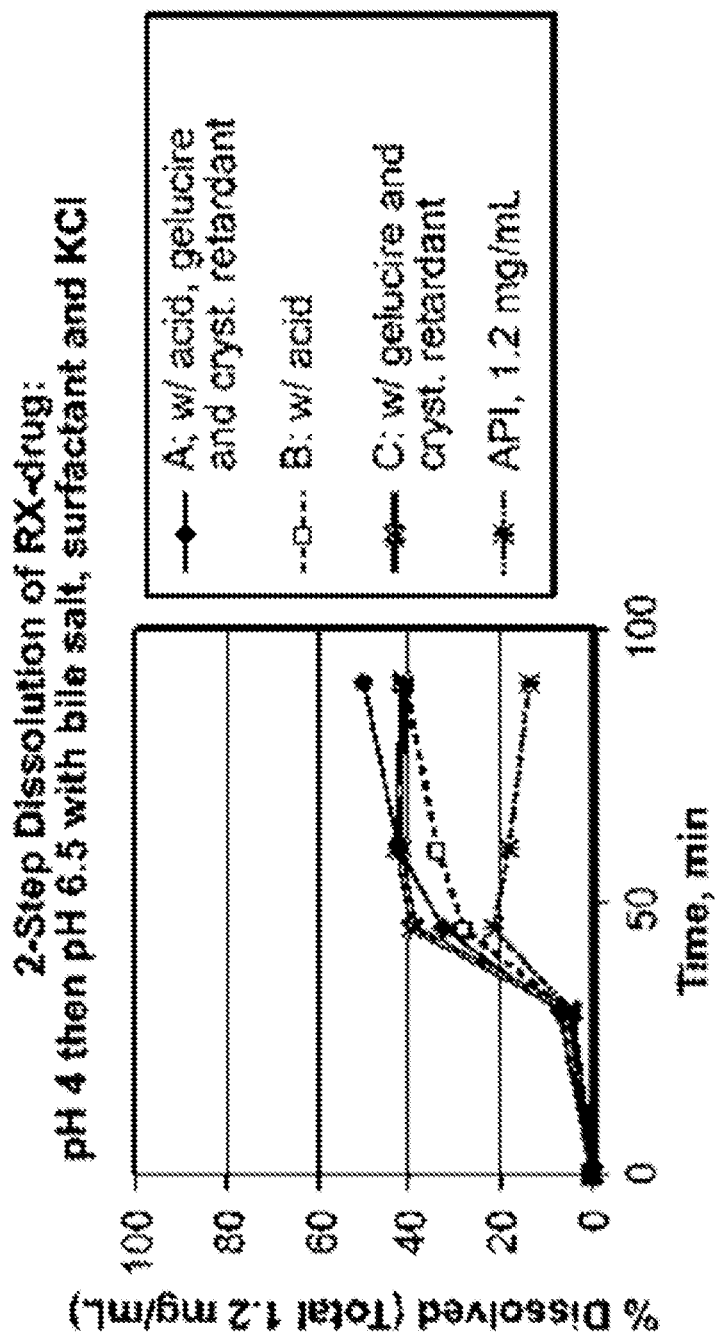
FIG. 8. shows the results of the 2-step dissolution test performed following Method 4. Dissolution of the radezolid formulation was tested in a buffer at pH 4 containing NaCl for 0-30 minutes, and then transferred to a buffer at pH 6.5 containing bile salt, surfactant and KC 1 for 30-90 minutes.
Figure 9:
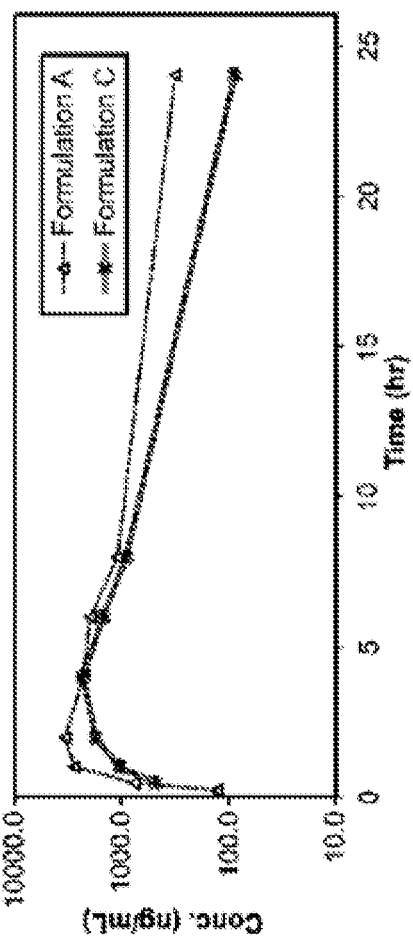
FIG. 9. shows the pharmacokinetic profiles of the radezolid formulations in beagle dogs (n=3).

FIG. 8 depicts the results of the 2-step dissolution test performed following Method 4. Dissolution of the radezolid formulation was tested in a buffer at pH 4 containing NaCl for 0-30 minutes, and then transferred to a buffer at pH 6.5 containing bile salt, surfactant and KC 1 for 30-90 minutes. Method 4 resulted in similar rank order as was observed under Method 3.

The 2-Step dissolution using simple buffer with sodium chloride presents an easy-to-use surrogate for the conventional 2-step dissolution system with bile-salts and surfactants. The dissolution in such medium enables the study of super-saturation and common ion effects for formulations of high dose hydrochloride salt drugs with microgram water solubility. The exposure in dog of the model compound is in agreement with the result of dissolution. On the other hand: The simple buffer system without chloride ion did not discriminate the formulations of a drug with a low chloride $K_{sp}$. The dissolution with bile salt and surfactant did not provide enough discriminating to rank order the formulations.

The results of the study also indicated that: inclusion of the polymer and surfactant in the formulations effectively improves dissolution and degree of super-saturation of the model compound, a basic salt, in dual pH media; and inclusion of a pH modifier in addition to the polymer and surfactant improved dissolution, super-saturation, and in vivo exposure of the compound further.

In Vivo Dog Study

An in-vivo dog study was conducted with beagle dogs (weight=12 kg, n=3). The dogs were dosed orally at 150 mg under fasting conditions. Serial of plasma samples were collected, extracted, and analyzed by LC/MS/MS. $C_{max}$ and AUC were estimated to evaluate the overall exposure from different formulations. Formulation A provided higher exposure than formulation C, which is in agreement with dissolution method C (described in Example 8). The Table in FIG. 9 lists the $C_{max}$, $T_{max}$, $T_{1/2}$, and AUC values for Formulations A and C, indicating that Formulation A showed superior bioavailability to Formulation C with respect to $C_{max}$, $T_{1/2}$ and AUC, though Formulation C showed a better $T_{max}$ than Formulation A.

Example 9

Use of Radezolid for Treating Skin Infections

Treatment with a variety of topical radezolid formulations can be used as a method to treat, prevent, or reduce the risk of various conditions caused or mediated by various radezolid-sensitive microbial pathogens. Conditions include skin and soft tissue infections (e.g., impetigo, rosacea, bacterial conjunctivitis, otitis externa, folliculitis, and local wound infections), acne, nosocomial or staph carrier nasal prophylaxis, and other bacterial infections such as bacterial vaginosis. Radezolid-sensitive microbial pathogens include *Propionibacterium acnes*, *Gardnerella vaginalis*, and *Staphylococcus aureus* (including Methicillin-resistant *Staphylococcus aureus*).

Proposed Formulations

For uncomplicated skin and soft tissues infections, nasal colonization and acne, radezolid will be formulated as a topical semi-solid dosage form (e.g., ointment, cream, lotion, solution, foam or gel) for topical cutaneous applications.

Radezolid will be formulated in ovules, soft-gel capsules, suppositories, creams, or foams for intravaginal application to treat bacterial vaginosis caused by *Gardnerella vaginalis*.

Typical compositions that can be used include from 0.1 to 1500 mg of radezolid.

Mode of Administration and Duration of Treatment (Anticipated Ranges Based on Possible Effectiveness)

For acne, topical application 1-2 times daily for 4-12 weeks is envisioned.

For uncomplicated skin and soft tissues infections caused by *S. aureus*/MRSA (e.g., impetigo, rosacea, bacterial conjunctivitis, otitis externa, folliculitis, and local wound infections), topical application 1-2 times daily for days to 2 weeks is envisioned.

For nosocomial or staph carrier nasal prophylaxis including MRSA, topical application 1-2 times daily for 3-7 days is envisioned.

For bacterial vaginosis/vaginitis, intravaginal administration 1-2 times daily for 3-7 days is envisioned.

Endpoint of Treatment

For acne, the endpoint will be clearance or material reduction of inflammatory and/or non-inflammatory lesions.

For uncomplicated skin and soft tissues, the endpoint will be resolution of all clinical signs and symptoms of infection (e.g., erythema, crusting, burning/stinging, pruritus etc.).

For nosocomial or staph carrier nasal prophylaxis including MRSA, the endpoint will be a negative culture.

For bacterial vaginosis/vaginitis, the endpoint will be resolution of all clinical signs and symptoms of infection (e.g., reversal of AMSEL criteria, vaginal discharge, odor, burning/stinging, pH≤4.5, and elimination of clue cell(s)).

The disclosed methods are sufficient to meet the proposed endpoints.

INCORPORATION BY REFERENCE

The entire disclosure of each of the patent documents, including certificates of correction, patent application documents, scientific articles, governmental reports, websites, and other references referred to herein is incorporated by reference in its entirety for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:

1. A method of treating a skin infection caused or mediated by *Propionibacterium acnes* or *Gardnerella vaginalis* in a patient, the method comprising administering a pharmaceutically effective amount of a compound having the formula:

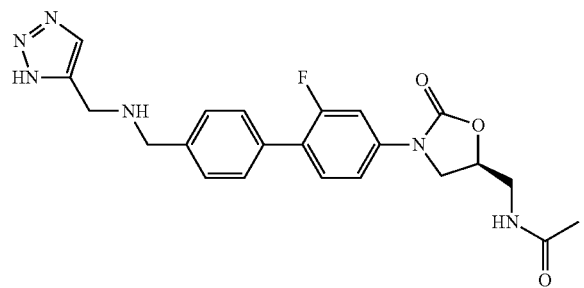 [SMILES: CC(=O)NC[C@H]1CN(c2ccc(-c3ccc(CNCc4cnn[nH]4)cc3)c(F)c2)C(=O)O1]

or a pharmaceutically acceptable tautomer, salt, ester, or prodrug thereof.

2. The method according to claim 1, wherein the compound is a pharmaceutically acceptable salt selected from the group consisting of acetate, ascorbate, benzoate, citrate, esylate, ethanedisulfonate, fumarate, hydrochloride, lactate, maleate, mesylate, phosphate, pyroglutamate, salicylate, succinate, sulfate, tartrate, and tosylate.

3. The method according to claim 1, wherein the skin infection is caused or mediated by *Propionibacterium acnes*.

4. The method according to claim 1, wherein the skin infection is caused or mediated by *Gardnerella vaginalis*.

5. The method according to claim 1, wherein the skin infection is selected from acne vulgaris, bacterial conjunctivitis, and bacterial vaginosis.

6. The method according to claim 1, wherein the skin infection is acne vulgaris.

7. The method according to claim 1, wherein the skin infection is bacterial vaginosis.

8. The method according to claim 1, wherein the compound is administered orally, parenterally, or topically.

9. The method according to claim 1, wherein the compound is administered topically.

10. The method according to claim 1, wherein the patient is a mammal or domestic animal.

11. The method according to claim 1, wherein the patient is a human.

12. The method according to claim 1, wherein the compound is administered once daily or twice daily.

13. The method according to claim 1, wherein the compound is administered once daily.

14. The method according to claim 1, wherein the compound is administered twice daily.

15. A method of treating a skin infection caused or mediated by *Propionibacterium acnes* or *Gardnerella vaginalis* in a patient, the method comprising administering a pharmaceutically effective amount of a topical formulation comprising one or more dermatologically acceptable carriers and a compound having the formula:

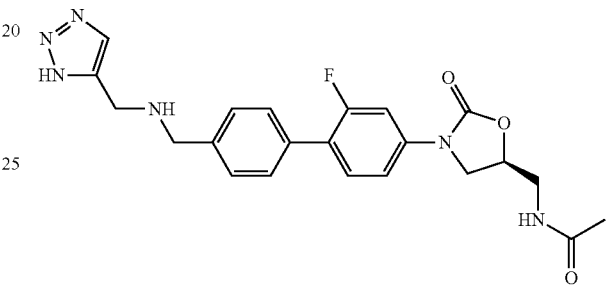

or a pharmaceutically acceptable tautomer, salt, ester, or prodrug thereof.

16. The method according to claim 15, wherein the skin infection is caused or mediated by *Propionibacterium acnes*.

17. The method according to claim 15, wherein the skin infection is caused or mediated by *Gardnerella vaginalis*.

18. The method according to claim 15, wherein the skin infection is selected from acne vulgaris, bacterial conjunctivitis, and bacterial vaginosis.

19. The method according to claim 15, wherein the skin infection is acne vulgaris.

20. The method according to claim 15, wherein the skin infection is bacterial vaginosis.

* * * * *

UNITED STATES PATENT AND TRADEMARK OFFICE
CERTIFICATE OF CORRECTION

PATENT NO. : 10,471,046 B2  
APPLICATION NO. : 14/942021  
DATED : November 12, 2019  
INVENTOR(S) : Erin M. Duffy Page 1 of 1

It is certified that error appears in the above-identified patent and that said Letters Patent is hereby corrected as shown below:

On the Title Page

Item (73) should read:  
(73) Assignee: MELINTA SUBSIDIARY CORP., Morristown, NJ (US)

Signed and Sealed this  
Twenty-eighth Day of January, 2020

Andrei Iancu  
*Director of the United States Patent and Trademark Office*